United States Patent
Magda et al.

(10) Patent No.: US 11,453,652 B2
(45) Date of Patent: Sep. 27, 2022

(54) DI-MACROCYCLES

(71) Applicant: LUMIPHORE, INC., Berkeley, CA (US)

(72) Inventors: Darren Magda, San Leandro, CA (US); Jide Xu, Richmond, CA (US); Nathaniel G. Butlin, Pacifica, CA (US)

(73) Assignee: LUMIPHORE, INC., Berkeley, CA (US)

( * ) Notice: Subject to any disclaimer, the term of this patent is extended or adjusted under 35 U.S.C. 154(b) by 0 days.

(21) Appl. No.: 14/443,310

(22) PCT Filed: Nov. 15, 2013

(86) PCT No.: PCT/US2013/070356
§ 371 (c)(1),
(2) Date: May 15, 2015

(87) PCT Pub. No.: WO2014/078690
PCT Pub. Date: May 22, 2014

(65) Prior Publication Data
US 2016/0221971 A1    Aug. 4, 2016

Related U.S. Application Data

(60) Provisional application No. 61/727,568, filed on Nov. 16, 2013, provisional application No. 61/793,265, filed on Mar. 15, 2013.

(51) Int. Cl.
| | | |
|---|---|---|
| *C07D 487/18* | (2006.01) | |
| *C07D 498/18* | (2006.01) | |
| *C07D 487/22* | (2006.01) | |
| *C07D 259/00* | (2006.01) | |
| *C07F 5/00* | (2006.01) | |
| *C07D 273/00* | (2006.01) | |
| *C07H 21/04* | (2006.01) | |
| *C07J 43/00* | (2006.01) | |
| *C07K 5/103* | (2006.01) | |

(52) U.S. Cl.
CPC ......... *C07D 259/00* (2013.01); *C07D 273/00* (2013.01); *C07D 487/18* (2013.01); *C07D 487/22* (2013.01); *C07D 498/18* (2013.01); *C07F 5/003* (2013.01); *C07H 21/04* (2013.01); *C07J 43/003* (2013.01); *C07K 5/1008* (2013.01)

(58) Field of Classification Search
CPC ... C07D 259/00; C07D 487/18; C07D 498/18
See application file for complete search history.

(56) References Cited

U.S. PATENT DOCUMENTS

| | | |
|---|---|---|
| 2,977,332 A | 3/1961 | Zumstein |
| 4,181,654 A | 1/1980 | Weitl et al. |
| 4,309,305 A | 1/1982 | Weitl et al. |
| 4,442,305 A | 4/1984 | Weitl et al. |
| 4,543,213 A | 9/1985 | Weitl et al. |
| 4,666,927 A | 5/1987 | Hider et al. |
| 4,698,431 A | 10/1987 | Raymond et al. |
| 4,748,184 A | 5/1988 | Stout et al. |
| 4,855,225 A | 8/1989 | Fung et al. |
| 4,868,103 A | 9/1989 | Stavrianopoulos et al. |
| 4,939,254 A | 7/1990 | McMurry et al. |
| 4,978,614 A | 12/1990 | Bronstein |
| 5,010,191 A | 4/1991 | Engelstad et al. |
| 5,047,519 A | 9/1991 | Hobbs, Jr. et al. |
| 5,049,280 A | 9/1991 | Raymond et al. |
| 5,252,462 A | 10/1993 | Drevin et al. |
| 5,435,990 A | 7/1995 | Cheng et al. |
| 5,470,896 A | 11/1995 | Wegmann et al. |
| 5,478,741 A | 12/1995 | Maret et al. |
| 5,482,698 A | 1/1996 | Griffiths |
| 5,601,800 A | 2/1997 | Katti et al. |
| 5,624,901 A | 4/1997 | Raymond et al. |
| 5,820,849 A | 10/1998 | Schmitt-Willich et al. |
| 5,892,029 A | 4/1999 | Raymond et al. |
| 5,989,823 A | 11/1999 | Jayasena et al. |
| 5,998,146 A | 12/1999 | Latva et al. |
| 6,221,476 B1 | 4/2001 | Bruening et al. |
| 6,406,297 B1 | 6/2002 | Raymond et al. |
| 6,515,113 B2 | 2/2003 | Raymond et al. |
| 6,846,915 B2 | 1/2005 | Raymond et al. |
| 6,864,103 B2 | 3/2005 | Raymond et al. |
| 7,018,850 B2 | 3/2006 | Raymond et al. |
| 7,404,912 B2 | 7/2008 | Raymond et al. |
| 7,442,558 B2 | 10/2008 | Raymond et al. |
| 7,718,781 B2 | 5/2010 | Raymond et al. |
| 7,794,691 B2 | 9/2010 | Morgenstern et al. |
| 8,173,800 B2 | 5/2012 | Raymond et al. |
| 8,507,199 B2 | 8/2013 | Butlin et al. |

(Continued)

FOREIGN PATENT DOCUMENTS

| | | |
|---|---|---|
| CA | 2099542 A1 | 1/1994 |
| EP | 0578067 A1 | 1/1994 |

(Continued)

OTHER PUBLICATIONS

Zhang (Chemistry and Biodiversity, 2005, 2, 1116-26).*
Atkinson. Australian Journal of Chemistry, 1999, 52(5), 351-58.*
Durbin. Human and Experimental Toxicology, 1996, 15(4), 352-360 (Year: 1996).*
Li. Journal of the American Chemical Society, 2014, 136, 14589-14597 (Year: 2014).*
Pandya. Chemical Communications, 2014, 51,2301-2303, published Dec. 18, 2014 (Year: 2014).*
Xu, J. et al., An Eight-Coordinate Cage: Synthesis and Structure of the First Macrotricyclic tetraterephthalamide ligand. Inorganic Chem., vol. 31, No. 24, p. 4903-4905 (1992).
Aime et al., Determination of the Prototropic Exchange Rate at the Water Molecule Coordinated to an Anionic Paramagnetic GdIII Chelate. Eur. J. Inorg. Chem. 1998, 1998 (9): 1283-1289.

(Continued)

*Primary Examiner* — Noble E Jarrell

(74) *Attorney, Agent, or Firm* — Jeffry S. Mann; Morgan, Lewis & Bockius LLP

(57) ABSTRACT

The invention relates to chemical compounds and complexes that can be used in therapeutic and diagnostic applications.

23 Claims, 3 Drawing Sheets

(56) References Cited

U.S. PATENT DOCUMENTS

| | | |
|---|---|---|
| 8,551,453 B2 | 10/2013 | Raymond et al. |
| 8,557,601 B2 | 10/2013 | Raymond et al. |
| 8,729,258 B2 | 5/2014 | Raymond et al. |
| 9,273,059 B2 | 3/2016 | Butlin et al. |
| 2002/0128451 A1 | 9/2002 | Raymond et al. |
| 2002/0188111 A1 | 12/2002 | Raymond et al. |
| 2003/0027189 A1 | 2/2003 | Raymond et al. |
| 2003/0095922 A1 | 5/2003 | Raymond et al. |
| 2003/0199688 A1 | 10/2003 | Kriesel et al. |
| 2004/0028611 A1 | 2/2004 | Frangioni |
| 2004/0249586 A1 | 12/2004 | Boge et al. |
| 2005/0008570 A1 | 1/2005 | Raymond et al. |
| 2005/0058604 A1 | 3/2005 | Raymond et al. |
| 2006/0135842 A1 | 6/2006 | Larsen et al. |
| 2006/0228297 A1 | 10/2006 | Larsen et al. |
| 2006/0286567 A1 | 12/2006 | Raymond et al. |
| 2007/0134160 A1 | 6/2007 | Leif et al. |
| 2008/0213780 A1 | 9/2008 | Butlin et al. |
| 2008/0213917 A1 | 9/2008 | Raymond et al. |
| 2008/0293155 A1 | 11/2008 | Raymond et al. |
| 2009/0023928 A1 | 1/2009 | Raymond et al. |
| 2009/0036537 A1 | 2/2009 | Raymond et al. |
| 2010/0015725 A1 | 1/2010 | Raymond et al. |
| 2010/0151591 A1 | 6/2010 | Butlin et al. |
| 2010/0167289 A1 | 7/2010 | Butlin et al. |
| 2011/0189088 A1 | 8/2011 | Xu et al. |
| 2012/0190012 A1 | 7/2012 | Butlin et al. |
| 2012/0214253 A1 | 8/2012 | Butlin et al. |
| 2012/0214843 A1 | 8/2012 | Durbin-Heavey et al. |
| 2012/0329174 A1 | 12/2012 | Raymond et al. |
| 2014/0039169 A1 | 2/2014 | Raymond et al. |

FOREIGN PATENT DOCUMENTS

| | | |
|---|---|---|
| EP | 2423201 A1 | 2/2012 |
| JP | 05-320147 A | 12/1993 |
| JP | 2003-535812 A | 12/2003 |
| JP | 2004-503331 A | 2/2004 |
| WO | WO 1989/011475 A1 | 11/1989 |
| WO | WO 1991/012530 A1 | 8/1991 |
| WO | WO 1992/011039 A1 | 7/1992 |
| WO | WO 1997/000245 A1 | 1/1997 |
| WO | WO 1997/045539 A1 | 12/1997 |
| WO | WO 2000/048990 A1 | 8/2000 |
| WO | WO 2000/048991 A1 | 8/2000 |
| WO | WO 2002/005859 A2 | 1/2002 |
| WO | WO 2003/016923 A2 | 2/2003 |
| WO | WO 2005/030711 A2 | 4/2005 |
| WO | WO 2005/030727 A1 | 4/2005 |
| WO | WO 2006/001835 A2 | 1/2006 |
| WO | WO 2007/121453 A2 | 10/2007 |
| WO | WO 2008/008797 A2 | 1/2008 |
| WO | WO 2008/063721 A2 | 5/2008 |
| WO | WO 2008/092120 A1 | 7/2008 |
| WO | WO 2010/034931 A1 | 4/2010 |
| WO | WO 2010/051544 A2 | 5/2010 |
| WO | WO 2011/025790 A1 | 3/2011 |
| WO | WO 2011/098611 A2 | 8/2011 |
| WO | WO 2013/167754 A1 | 11/2013 |
| WO | WO 2013/167755 A1 | 11/2013 |
| WO | WO 2013/167756 A1 | 11/2013 |

OTHER PUBLICATIONS

Aime et al., Paramagnetic GdIII[FeIII heterobimetallic complexes of DTPA-bis-salicylamide. Spectrochim. Acta A 1993, 49 (9), 1315-1322.

Alaverdian et al., A family of novel DNA sequencing instruments based on single-photon detection. Electrophoresis 2002, 23 (16): 2804-2817.

Allicotti et al., A time-resolved fluorescence immunoassay (DELFIA) increases the sensitivity of antigen-driven cytokine detection. J. Immunoassay Immunochem. 2003, 24 (4), 345-358.

Alpha et al., Luminescence Probes: The Eu3⊕- and Tb3⊕-Cryptates of Polypyridine Macrobicyclic Ligands. Angew. Chem. Int. Ed. Engl. 1987, 26 (12), 1266-1267.

Anderson and Welch, Radiometal-Labeled Agents (Non-Technetium) for Diagnostic Imaging. Chem. Rev. 1999, 99 (9), 2219-2234.

Arnaud et al., Synthesis of macrocyclic polyhydroxy tetralactams derived from L-tartaric acid and p-hydroxyglutaric acid. Tetrahedron 1997, 53 (40), 13757-13768.

Bai et al., Photocleavage of a 2-nitrobenzyl linker bridging a fluorophore to the 5' end of DNA. Proc. Natl. Acad. Sci. U.S.A. 2003, 100 (2), 409-413.

Bailly and Burgada, Nouvelle methode de synthesedu 3,4,3 LI 1,2 HOPO (1,5,10,14-tetra(1-hydroxy-2-pyridone-6 oyl) 1,5,10,14 tetraazatetradecane). C. R. Acad. Sci., Ser. IIc: Chim. 1998, 1 (4), 241-245.

Batard et al., Use of Phycoerythrin and Allophycocyanin for Fluorescence Resonance Energy Transfer Analyzed by Flow Cytometry: Advantages and Limitations. Cytometry 2002, 48 (2), 97-105.

Beeby et al., Luminescence imaging microscopy and lifetime mapping using kinetically stable lanthanide(III) complexes. J. Photochem. Photobiol. B 2000, 57 (2-3), 83-89.

Bergeron and Navratil, Catecholamide Chelators for Actinide Environmental and Human Decontamination. Chem. Abstr. 1986, 105, 221872z.

Blomberg et al., Terbium and rhodamine as labels in a homogeneous time-resolved fluorometric energy transfer assay of the beta subunit of human chorionic gonadotropin in serum. Clin Chem 1999, 45 (6 Pt 1), 855-861.

Bodanszky and Bodanszky, Activation and Coupling [excerpt]. In the Practice of Peptide Synthesis, 2nd ed.; Springer-Verlag Berlin Heidelberg, 1984; pp. 96-125.

Boswell and Brechbiel, Development of radioimmunotherapeutic and diagnostic antibodies: an inside-out view. Nucl. Med. Biol. 2007, 34 (7), 757-778.

Brooker et al., Figure-of-eight Shaped Metal-free Amide-containing Schiff-base Macrocycles and Two Dicobalt(III) Amide Complexes. Chemical Abstracts 2002, HCAplus Accession No. 2002:593344.

Bruchez et al., Semiconductor Nanocrystals as Fluorescent Biological Labels. Science 1998, 281 (5385), 2013-2016.

Brumley and Smith, Rapid DNA sequencing by horizontal ultrathin gel electrophoresis. Nucleic Acids Res. 1991, 19 (15), 4121-4126.

Brunet et al., Lanthanide complexes of polycarboxylate-bearing dipyrazolylpyridine ligands with near-unity luminescence quantum yields: the effect of pyridine substitution. Photochem. Photobiol. Sci. 2002, 1 (8), 613-618.

Bryant et al., Synthesis and relaxometry of high-generation {G=5, 7, 9, and 10} PAMAM dendrimer-DOTA-gadolinium chelates. J. Magn. Reson. Imaging 1999, 9 (2), 348-352.

Budimir et al., Study of metal complexes of a tripodal hydroxypyridinone ligand by electrospray tandem mass spectrometry, Rapid Commun. Mass Spectrom. 2005, 19 (13), 1822-1828.

Bulman et al., An examination of some complexing agents for ability to remove intracellularly deposited plutonium. Chem. Abstr. 1980, 92, 106582f.

Bunzli et al., Towards materials with planned properties : dinuclear f-f helicates and d-f non-convalent podates based on benzimidazole-pyridine binding units. J. Alloys Compd. 1997, 249 (1-2), 14-24.

Burgada et al., Synthesis of 3,4,3 LI 1,2 HOPO labelled with 14C. J. Label. Compd. Radiopharm. 2001, 44 (1), 13-19.

Cardullo et al., Detection of nucleic acid hybridization by nonradiative fluorescence resonance energy transfer. Proc. Natl. Acad. Sci. USA 1988, 85 (23), 8790-8794.

Chan and Nie, Quantum Dot Bioconjugates for Ultrasensitive Nonisotopic Detection. Science 1998, 281 (5385), 2016-2018.

Chen and Selvin, Lifetime- and color-tailored fluorophores in the micro- to millisecond time regime. J. Am. Chem. Soc. 2000, 122 (4), 657-660.

Chen and Selvin, Thiol-reactive luminescent chelates of terbium and europium. Bioconjug. Chem. 1999, 10(2), 311-315.

Choudhary et al., New compounds of tetradentate Schiff bases with vanadium (IV) and vanadium (V). J. Chem. Soc., Dalton Trans. 1999, 24, 4437-4446.

(56) References Cited

OTHER PUBLICATIONS

Clarke et al., Crystal structure of the tris 1,2-dimethyl-3-hydroxy-4-pyridinone (DMHP) complex with the Fe(III) ion. Inorg. Chim. Acta 1992, 196 (2), 177-183.
Cohen et al., A Novel Salicylate-Based Macrobicycle with a "Split Personality". Inorg. Chem. 1999, 38 (20), 4522-4529.
Cohen et al., Syntheses and relaxation properties of mixed gadolinium hydroxypyridinonate MRI contrast agents. Inorg. Chem. 2000, 39 (25), 5747-5756.
Collins et al., A vision for the future of genomics research. Nature 2003, 422 (6934), 835-847.
Comby et al., Stable 8-hydroxyquinolinate-based podates as efficient sensitizers of lanthanide near-infrared luminescence. Inorg. Chem. 2006, 45 (2), 732-743.
Curtet, C., In Vivo diagnosis and therapy of human tumors with monoclonal antibodies. Int. J. Radiat. Appl. Instrum., Part B, 1989, 16 (2), 180.
Dahlen, P., Detection of Biotinylated DNA Probes by Using Eu-Labeled Streptavidin and Time-Resolved Fluorometry. Anal. Biochem. 1987, 164 (1), 78-83.
De Sa et al., Spectroscopic properties and design of highly luminescent lanthanide coordination complexes. Coord. Chem. Rev. 2000, 196 (1), 165-195.
Demas and Crosby, Measurement of Photoluminescence Quantum Yields. A Review. J. Phys. Chem. 1971, 75 (8), 991-1024.
Dexter, D.L., A Theory of Sensitized Luminescence in Solids. J. Chem. Phys. 1953, 21 (5), 836-850.
Dickins et al., Synthesis, time-resolved luminescence, NMR spectroscopy, circular dichroism and circularly polarised luminescence studies of enantiopure macrocyclic lanthanide tetraamide complexes. Chem. Eur. J. 1999, 5 (3), 1095-1105.
Dickson et al., Time-resolved detection of lanthanide luminescence for ultrasensitive bioanalytical assays. J. Photochem. Photobiol. B. 1995, 27 (1), 3-19.
Doble et al., Toward optimized high-relaxivity MRI agents: the effect of ligand basicity on the thermodynamic stability of hexadentate hydroxypyridonate/catecholate gadolinium(III) complexes. Inorg. Chem. 2003, 42 (16), 4930-4937.
Durbin et al., In vivo chelation of Am(III), Pu(IV), Np(V) and U(VI) in mice by TREN-(Me-3,2-HOPO). Chem. Abstr. 1995, 122, 4449p.
Durbin et al., Specific sequestering agents for the actinides: 10. Enhancement of plutonium-238 elimination from mice by poly(catechoylamide) ligands. Chem. Abstr. 1984, 101, 125980e.
Eid et al., Real-Time DNA Sequencing from Single Polymerase Molecules. Science 2009, 323 (5910), 133-138.
Edelstein et al. Optical properties of Cm(III) in crystals and solutions and their application to Cm(III) speciation. Coord. Chem. Rev. 250, 2006, 948-973.
Farkas et al., Equilibrium studies on copper(II)- and iron(III)-monohydroxamates. Polyhedron 1998, 17 (19), 3331-3342.
Förster, T., Transfer Mechanisms of Electronic Excitation. Discuss. Faraday Soc. 1959, 27, 7-17.
Förster, T., Zwischenmolekulare Energiewanderung und Fluoreszenz. Ann. Phys. 1948, 437 (1-2), 55-75.
Frank et al., Detection of pulmonary emboli by using MR angiography with MPEG-PL-GdDTPA: an experimental study in rabbits. AJR Am. J. Roentgenol. 1994, 162 (5), 1041-1046.
Galaup et al., Mono(di)nuclear eropium(III) complexes of macrobi(tri)cyclic cryptands derived from diazatetralactams as luminophores in aqueous solution. Helv. Chim. Acta. 1999, 82 (4), 543-560.
Glazer, A. N., Light Harvesting by Phycobilisomes. Annu. Rev. Biophys. Biophys. Chem. 1985, 14, 47-77.
Gong, B., Crescent oligoamides: From acyclic "Macrocycles" to folding nanotubes. Chem Eur J 2001, 7 (20), 4336-4342.
Hajela et al., A tris-hydroxymethyl-substituted derivative of Gd-TREN-Me-3,2-HOPO: An MRI relaxation agent with improved efficiency. J. Am. Chem. Soc. 2000, 122 (45), 11228-11229.
Hajela et al., Synthesis of homochiral tris(2-alkyl-2-aminoethyl) amine derivatives from chiral a-amino aldehydes and their application in the synthesis of water soluble chelators. Inorg. Chem. 2001, 40 (13), 3208-3216.
Heid et al., Real time quantitative PCR. Genome Res. 1996, 6 (10), 986-994.
Hemmila et al., Development of luminescent lanthanide chelate labels for diagnostic assays. J. Alloys Compd. 1997, 249 (1-2), 158-162.
Hemmilä et al., Europium as a label in time-resolved immunofluorometric assays. Anal. Biochem. 1984, 137 (2), 335-343.
Hemmila, I. A. In Immunochemistry 1; Johnstone, A. P., Turner, M. W., Eds.; IRL Press: Oxford, U.K., 1997; pp. 193-214.
Hemmila, I., LANCE™: Homogeneous Assay Platform for HTS. J. Biomol. Screening 1999, 4 (6), 303-307.
Hemmilä, I., Luminescent lanthanide chelates—a way to more sensitive diagnostic methods. J. Alloys Compd. 1995, 225 (1-2), 480-485.
Higuchi. et al., Simultaneous Amplification and Detection of Specific DNA Sequences. Biotechnology (NY) 1992, 10 (4), 413-417.
Hochstrasser et al., Distance distribution in a dye-linked oligonucleotide determined by time-resolved fluorescence energy transfer. Biophys. Chem. 1992, 45 (2), 133-141.
Holland et al., Detection of specific polymerase chain reaction product by utilizing the 5'.fwdarw. 3' exonuclease activity of Thermus aquaticus DNA polymerase. Proc. Nat. Acad. Sci. USA 1991, 88 (16), 7276-7280.
Jaakkola et al., Solid-phase synthesis of oligonucleotides labeled with luminescent lanthanide(III) chelates. Bioconjug. Chem. 2005, 16 (3), 700-709.
Jagannathan and Soundararajan, "Complexes of lanthanide perchlorated with N,N,N'-tetra-amethyl-α-carboxamido-o-anisamide and N, N'-di-t-butyl-α-carboxamido-o-anisamide" Inorganica Chim. Acta 1979, 37, L449-L451.
Johansson et al., Time Gating Improves Sensitivity in Energy Transfer Assays with Terbium Chelate/Dark Quencher Oligonucleotide Probes. J. Am. Chem. Soc. 2004, 126 (50), 16451-16455.
Johnson et al., Synthesis of a ligand based upon a new entry into the 3-hydroxy-N-alkyl- 2(1H0-pyridinone ring system and thermodynamic evaluation of its gadolinium complex. Inorg. Chem. 2000, 39 (12), 2652-2660.
Ju et al., Fluorescence energy transfer dye-labeled primers for DNA sequencing and analysis. Proc. Natl. Acad. Sci. U.S.A. 1995, 92 (10), 4347-4351.
Karpishin et al., Stereoselectivity in chiral iron(III) and gallium(III) tris(catecholate) complexes effected by nonbonded weakly polar interactions. J. Am. Chem. Soc. 1993, 115 (14), 6115-6125.
Kelly and Lang, Total Synthesis of Dimethyl Sulfomycinamate. J. Org. Chem. 1996, 61 (14), 4623-4633.
Kheterpal et al., DNA sequencing using a four-color confocal fluorescence capillary array scanner. Electrophoresis 1996, 17 (12): 1852-1859.
Kling, J., Ultrafast DNA sequencing. Nat. Biotechnol. 2003, 21 (12), 1425-1427.
Knight, C.G., Fluorimetric Assays of Proteolytic Enzymes. Methods Enzymol. 1995, 248: 18-34.
Kostrikis et al., Spectral Genotyping of Human Alleles. Science 1998, 279 (5354), 1228-1229.
Kulmala et al., Electrochemiluminescent labels for applications in fully aqueous solutions at oxide-covered aluminium electrodes. Anal. Chim. Acta 1999, 386 (1-2), 1-6.
Kunkely and Vogler, Photoluminescence of thorium(IV) 2-methyl-8-quinolinolate. Chem. Phys. Lett. 304, 1999, 187-190.
Lassiter et al., Time-resolved fluorescence imaging of slab gels for lifetime base-calling in DNA sequencing applications. Anal. Chem. 2000, 72 (21), 5373-5382.
Law, G. et al., Circularly Polarized Luminescence of Curium: A New Characterization of the 5f Actinide Complexes. J. Am. Chem. Soc. 134, pp. 15545-15549 (2012).
Lee et al., Allelic discrimination by nick-translation PCR with fluorogenic probes. Nucleic Acids Res. 1993, 21 (16), 3761-3766.

(56) References Cited

OTHER PUBLICATIONS

Lee et al., New energy transfer dyes for DNA sequencing. Nucleic Acids Res. 1997, 25 (14), 2816-2822.
Lee et al., Seven-Color, Homogeneous Detection of Six PCR Products. Biotechniques 1999, 27 (2), 342-349.
Li et al., A photocleavable fluorescent nucleotide for DNA sequencing and analysis. Proc. Natl. Acad. Sci. U.S.A. 2003, 100 (2), 414-419.
Li et al., Shape-persistent aromatic amide oligomers: new tools for supramolecular chemistry, Chem. Asian J. 2006, 1 (6), 766-778.
Lichtenberger and Geyer, Cyanoethylation. II. Substituted β-phenoxypropionic acids. Bull. Soc. Chim. Fr. 1963, 275-282.
Lieberwirth et al., Multiplex dye DNA sequencing in capillary gel electrophoresis by diode laser-based time-resolved fluorescence detection. Anal. Chem. 1998, 70 (22), 4771-4779.
Margulies et al., Genome sequencing in microfabricated high-density picolitre reactors. Nature 2005, 437 (7057), 376-380.
Mathis, G., HTRF® Technology. J. Biomol. Screen. 1999, 4 (6), 309-314.
Mathis, G., Rare earth cryptates and homogeneous fluoroimmunoassays with human sera. Clin. Chem. 1993, 39 (9), 1953-1959.
Mattoussi et al., Self-Assembly of CdSe—ZnS Quantum Dot Bioconjugates Using an Engineered Recombinant Protein. J. Am. Chem. Soc. 2000, 122 (49), 12142-12150.
Metzker et al., Electrophoretically uniform fluorescent dyes for automated DNA sequencing. Science 1996, 271 (5254), 1420-1422.
Metzker, M. L., Emerging technologies in DNA sequencing. Genome Res. 2005, 15 (12), 1767-1776.
Mikola et al., Syntheses and properties of luminescent lanthanide chelate labels and labeled haptenic antigens for homogeneous immunoassays. Bioconjug. Chem. 1995, 6 (3), 235-241.
Momany et al. Crystal structure of dimeric HIV-1 capsid protein. Nat. Struct. Biol. 1996, 3 (9), 763-770.
Moore et al., "Cymothoe sangaris": An Extremely Stable and Highly Luminescent 1,2-Hydroxypyridinonate Chelate of Eu(III). J. Am. Chem. Soc. 2006, 128 (33), 10648-10649.
Moore et al., An octadentate luminescent Eu(III) 1,2-HOPO chelate with potent aqueous stability. Inorg. Chem. 2007, 46 (14), 5468-5470.
Moore et al., Eu (III) Complexes of Functionalized Octadentate 1-Hydroxypyridin-2-ones: Stability, Bioconjugation, and Luminescence Resonance Energy Transfer Studies. Inorg. Chem. 2010, 49, 9928-9939.
Moyer et al. Enhanced liquid-liquid anion exchange using macrocyclic anion receptors: effect of receptor structure on sulphate-nitrate exchange selectivity. Supra Molecular Chemistry. 2010 vol. 22, pp. 653-671.
Mugabe et al., Liposome-mediated gentamicin delivery: development and activity against resistant strains of Pseudomonas aeruginosa isolated from cystic fibrosis patients. J. Antimicrob. Chemother. 2005, 55 (2), 269-271.
Nazarenko et al., A closed tube format for amplification and detection of DNA based on energy transfer. Nucleic Acids Res. 1997, 25 (12), 2516-2521.
Nunnally et al., Characterization of visible dyes for four-decay fluorescence detection in DNA sequencing. Anal. Chem. 1997, 69 (13), 2392-2397.
Okawa et al., Binuclear metal complexes. V. Template synthesis of a binuclear copper(II) complex of a macrocycle containing amino groups. Chem. Lett. 1972, 10, 1027-1030.
Ost, H., Synthese mehrbasischer Sauren aus Salicylsäure und Kohlensäure. J. Prakt. Chem. 1876, 14 (1), 93-124.
Petoud et al., Stable Lanthanide Luminescence Agents Highly Emissive in Aqueous Solution: Multidentate 2-Hydroxyisophthalamide Complexes of Sm3+, Eu3+, Tb3+, Dy3+. J. Am. Chem. Soc. 2003, 125 (44), 13324-13325.
Pierre et al., Substituent effects on Gd(III)-based MRI contrast agents: optimizing the stability and selectivity of the complex and the number of coordinated water molecules. Inorg. Chem. 2006, 45 (20), 8355-8364.

Poole et al., Synthesis and characterisation of highly emissive and kinetically stable lanthanide complexes suitable for usage "in cellulo". Org. Biomol. Chem. 2005, 3 (6), 1013-1024.
Prober et al., A System for Rapid DNA Sequencing with Fluorescent Chain-Terminating Dideoxynucleotides. Science 1987, 238 (4825), 336-341.
Puerta et al., Tris(pyrone) Chelates of Gd(III) as High Solubility MRI-CA. J. Am. Chem. Soc. 2006, 128 (7), 2222-2223.
Rajapakse et al., Luminescent Terbium Protein Labels for Time-Resolved Microscopy and Screening. Angew. Chem. Int. Ed. Engl. 2009, 48 (27), 4990-4992.
Raymond and Pierre, Next Generation, High Relaxivity Gadolinium MRI Agents. Bioconjug. Chem. 2005, 16(1), 3-8.
Riehl and Richardson, Circularly Polarized Luminescence Spectroscopy. Chem. Rev. 1986, 86 (1), 1-16.
Ruparel et al., Design and synthesis of a 3'-O-allyl photocleavable fluorescent nucleotide as a reversible terminator for DNA sequencing by synthesis. Proc. Natl. Acad. Sci. U.S.A. 2005, 102 (17), 5932-5937.
Sabbatini et al., Luminescent lanthanide complexes as photochemical supramolecular devices. Coord. Chem. Rev. 1993, 123 (1), 201-228.
Saha et al., Time-resolved fluorescence new europium chelate complex: Demonstration of highly sensitive detection of protein and DNA samples. J. Am. Chem. Soc. 1993, 115 (23), 11032-11033.
Scarrow et al., Ferric ion sequestering agents. 14. 1-Hydroxy-2(1H)-pyridinone complexes: properties and structure of a novel iron-iron dimer. J. Am. Chem. Soc. 1985, 107 (23), 6540-6546.
Schoket et al., Increased sensitivity for determination of polycyclic aromatic hydrocarbon-DNA adducts in human DNA samples by dissociation-enhanced lanthanide fluoroimmunoassay (DELFIA). Cancer Epidemiol. Biomarkers Prev. 1993, 2 (4), 349-353.
Selvin, P. R., Principles and biophysical applications of lanthanide-based probes. Annu. Rev. Biophys. Biomol. Struct. 2002, 31, 275-302.
Selvin, P., Fluorescence Resonance Energy Transfer. Methods Enzymol. 1995, 246, 300-334.
Seo et al., Four-color DNA sequencing by synthesis on a chip using photocleavable fluorescent nucleotides. Proc. Natl. Acad. Sci. U.S.A. 2005. 102 (17), 5926-5931.
Sequoia, E., Complexes of Lanthanide Perchlorates. Inorganica Chim. Acta 1979, 37 (1), L-449-L451.
Smith et al., Fluorescence detection in automated DNA sequence analysis. Nature 1986, 321 (6071), 674-679.
Soini et al., Time-resolved fluorescence of lanthanide probes and applications in biotechnology. CRC Crit. Rev. Anal. Chem. 1987, 18 (2), 105-154.
Soulere et al., Selective Inhibition of Fe-versus Cu/Zn-Superoxide Dismutases by 2,3-Dihydrosybenzoic Acid Derivavtives. Chem. Pharm. Bull. (Tokyo) 2002, 50 (5), 578-582.
Southwood-Jones et al. Oxygen-17 NMR and EPR studies of water exchange from the first coordination sphere of gadolinium(III) aquoion and gadolinium(III) propylenediaminetetra-acetate. J. Chem. Phys. 1980, 73 (12), 5909-5918.
Stack et al. Rational reduction of the conformational space of a siderophore analog through nonbonded interactions: the role of entropy in enterobactin. J. Am. Chem. Soc. 1993, 115 (14), 6466-6467.
Steemers et al. Water-soluble neutral calix[4]arene-lanthanide complexes: Synthesis and luminescence properties. J. Org. Chem. 1997, 62 (13), 4229-4235.
Steinberg, I., Long-Range Nonradiative Transfer of Electronic Excitation Energy in Proteins and Polypeptides. Annu. Rev. Biochem. 1971, 40, 83-114.
Stenroos et al., Homogeneous time-resolved IL-21L-R.alpha. assay using fluorescence resonance energy transfer. Cytokine 1998, 10 (7), 495-499.
Streater et al., Novel 3-hydroxy-2(1H)-pyridinones. Synthesis, Iron(III)-Chelating Properties, and Biological Activity. J. Med. Chem. 1990, 33 (6), 1749-1755.
Stryer, L., Fluorescence Energy Transfer as a Spectroscopic Ruler. Ann. Rev. Biochem. 1978, 47, 819-846.

(56) References Cited

OTHER PUBLICATIONS

Sunderland et al., 6-Carboxamido-5, 4-Hydroxypyrimidinones: A New Class of Heterocyclic Ligands and Their Evaluation as Gadolinium Chelating Agents. Inorg. Chem. 2001, 40 (26), 6746-6756.
Syvanen et al., Time-resolved fluorometry: a sensitive method to quantify DNA-hybrids. Nucleic Acids Res. 1986, 14 (2), 1017-1028.
Takalo et al., Synthesis of europium(III) chelates suitable for labeling of bioactive molecules. Bioconjug. Chem. 1994, 5 (3), 278-282.
Tedeschi et al. A solid-state study of eight-coordinate lanthanide(III) complexes (Ln = Eu, Gd, Tb, Dy) with 1-hydroxy-2-pyridinone. Dalton Trans. 2003, 9, 1738-1745.
Tsien, R. Y., The Green Fluorescent Protein. Annu. Rev. Biochem. 1998, 67, 509-544.
Tyagi et al., Molecular Beacons: Probes that Fluoresce upon Hybridization. Nat. Biotechnol. 1996, 14 (3), 303-308.
Tyagi et al., Multicolor molecular beacons for allele discrimination. Nat. Biotechnol. 1998, 16 (1), 49-53.
Uhlir et al., Specific Agents for the Actinides. 21. Synthesis and Initial Biological Testing of Octadentate Mixed Catecholate-Hydroxypridinoate Ligands. J. Med. Chem. 1993, 36 (4), 504-509.
Uhlir, L. C., Mixed Functionality Actinide Sequestering Agents. Ph.D. Thesis, University of California, Berkeley, CA, 1992.
Ullman et al., Fluorescent excitation transfer immunoassay. A general method for determination of antigens. J. Biol. Chem. 1976, 251 (14), 4172-4178.
Unger et al., Gadolinium-containing copolymeric chelates-a new potential MR contrast agent. Magn. Reson. Mater. Phys., Biol. Med. 1999, 8 (3), 154-162.
Vander Elst et al., Stereospecific binding of MRI contrast agents to human serum albumin: the case of Gd-(S)- EOB-DTPA (Eovist) and its (R) isomer. J. Biol. Inorg. Chem. 2001, 6 (2), 196-200.
Veiopoulou et al., Comparative study of fluorescent ternary terbium complexes. Application in enzyme amplified fluorimetric immunoassay for .alpha.-fetoprotein. Anal. Chim. Acta 1996, 335 (1-2), 177-184.
Vereb et al., Temporally and Spectrally Resolved Imaging Microscopy of Lanthanide Chelates. Biophys. J. 1998, 74 (5), 2210-2222.
Vicentini et al., Luminescence and structure of europium compounds. Coord. Chem. Rev. 2000, 196 (1), 353-382.
Villa et al., Force Field Parametrization for Gadolinium Complexes Based on ab Initio Potential Energy Surface Calculations. J. Phys. Chem. A 2000, 104 (15), 3421-3429.
Voss et al., Direct genomic fluorescent on-line sequencing and analysis using in vivo amplification of DNA. Nucleic Acids Res. 1989, 17 (7), 2517-2527.
Wagnon and Jackels, Synthesis, characterization, and aqueous proton relaxation enhancement of a manganese(II) heptaaza macrocyclic complex having pendant arms. Inorg. Chem. 1989, 28 (10), 1923-1927.
Wang et al., Design and Synthesis of New Fluorogenic HIV Protease Substrates Based on Resonance Energy Transfer. Tetrahedron Lett. 1990, 31 (45), 6493-6496.

Wang et al., Rapid Sizing of Short Tandem Repeat Alleles Using Capillary Array Electrophoresis and Energy-Transfer Fluorescent Primers. Anal. Chem. 1995, 67 (7), 1197-1203.
Wang et al., Unnatural Amino Acid Mutagenesis of Green Fluorescent Protein. J. Org. Chem. 2003, 68 (1), 174-176.
Weibel et al., Engineering of highly luminescent lanthanide tags suitable for protein labeling and time-resolved luminescence imaging. J. Am. Chem. Soc. 2004, 126 (15), 4888-4896.
Werner et al., Highly Soluble Tris-hydroxypyridonate Gd(III) Complexes with Increased Hydration Number Fast Water Exchange, Slow Electronic Relaxation, and High Relaxivity. J. Am. Chem. Soc. 2007, 129 (7), 1870-1871.
Whitcombe et al., Detection of PCR products using self-probing amplicons and fluorescence. Nat. Biotechnol. 1999, 17 (8), 804-807.
White et al., Specific Sequestering Agents for the Actinides. 16. Synthesis and Initial Bioiological Testing of Polydentate Oxohydroxypyridinecarboxylate Ligands. J. Med. Chem. 1988, 31 (1), 11-18.
Xiao and Selvin, Quantum yields of luminescent lanthanide chelates and far-red dyes measured by resonance energy transfer. J. Am. Chem. Soc. 2001, 123 (29), 7067-7073.
Xu et al., Gadolinium (III) 1,2-hydroxypyridonate-based complexes: toward MRI contrast agents of high relaxivity. Inorg. Chem. 2004, 43 (18), 5492-5494.
Xu et al., Gadolinium complex of tris[(3-hydroxy-1-methyl-2-oxo-1,2-didehydropyridine-4-carboxamidojethyl]—amine: A new class of gadolinium magnetic resonance relaxation agents. J. Am. Chem. Soc. 1995, 117 (27), 7245-7246.
Xu et al., Plutonium(IV) Sequestration: Structural and Thermodynamic Evaluation of the Extraordinarily Stable Cerium(IV) Hydroxypyridinonate Complexes. Inorg. Chem. 2000, 39 (18), 4156-4164.
Xu et al., Specific Sequestering Agents for the Actinides. 28. Synthesis and Initial Evaluation of Multidentate 4-Carbamoyl-3-hydroxy-1-methyl-2-(1H)-pyridinone Ligands for in Vivo Plutonium (IV) Chelation. J. Med. Chem. 1995, 38 (14), 2606-2614.
Xu et al. Octadentate Cages of Tb(III) 2-Hydroxyisophthalamides: A New Standard for Luminescent Lanthanide Labels. J. Am. Chem. Soc., 133, pp. 19900-10 (2011).
Yamada et al., Selective Modification of Asparatic Acid-101 in Lysozyme by Carbodiimide Reaction. Biochemistry. 1981, 20, 4836-4842.
Yue et al., Potentiometric and spectrophotometric determination of stabilities of the 1-hydroxy-2-pyridinone complexes of trivalent and divalent metal ions. Inorg. Chim. Acta 1993, 214 (1-2), 103-111.
Cohen et al., Mixed Hydroxypyridonate Ligands as Iron Chelators. Inorg. Chem., 2000, 39, 4339-4346.
Xu et al., Thorium(IV) Complexes of Bidentate Hydroxypyridinonates, Inorganic Chemistry, 2003, 42, 2605-2674.
Zhao et al., Extractino of Plutonium by Chelating Hydroxppyridinone and Cathecholamide Resins. Solvent Extraction and Ion Exchange, 1999, 17(5), 1327-1353.

* cited by examiner

DI-MACROCYCLES

CROSS-REFERENCE TO RELATED APPLICATIONS

This application is a 371 National Stage entry of PCT International Application No. PCT/US2013/070356 filed Nov. 15, 2013 which claims the benefit under 35 U.S.C. § 119(e) of U.S. Provisional Application No. 61/793,265, filed Mar. 15, 2013, and U.S. Provisional Application No. 61/727,568, filed Nov. 16, 2012, all of which are incorporated herein by reference in their entirety for all purposes.

STATEMENT REGARDING FEDERALLY SPONSORED RESEARCH OR DEVELOPMENT

This invention was made with Government support under SBIR Phase I grant No. IIP-1215462 awarded by the National Science Foundation. The Government has certain rights in the invention.

FIELD OF THE INVENTION

The invention relates to chemical compounds and complexes that can be used in therapeutic and diagnostic applications.

BRIEF DESCRIPTION OF THE DRAWINGS

FIG. 3A shows absorption and emission spectra of di-macrocyclic chelator 12 with europium (III). FIG. 3B shows absorption and emission spectra of di-macrocyclic chelator 12 with terbium(III).

DESCRIPTION OF EMBODIMENTS

1. Definitions

Figure 1:
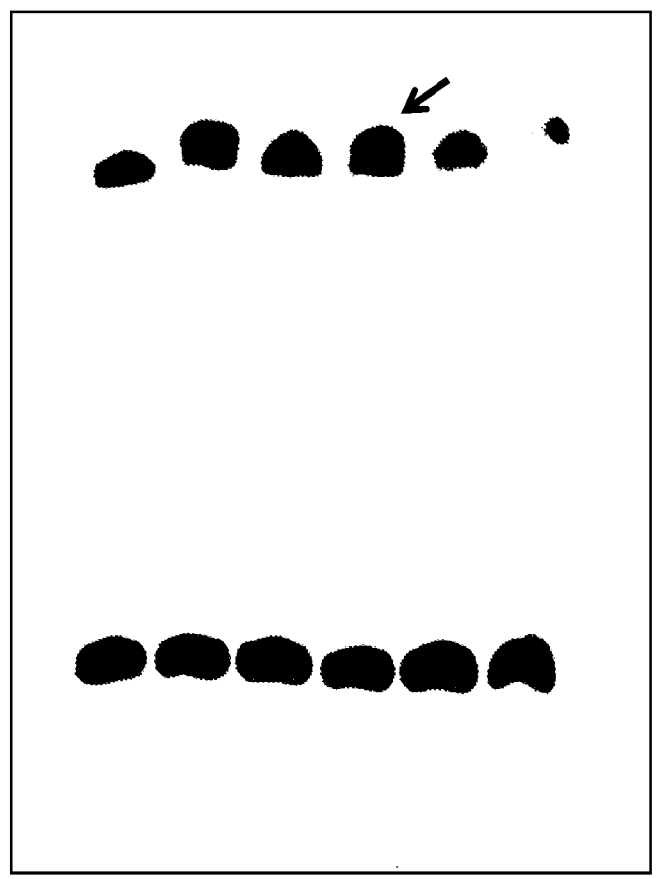
FIG. 1 shows the electrophoretic mobility of DNA oligonucleotide conjugate 15 (upper band) or DNA oligonucleotide 14 (lower band) in the absence or presence of metal cations.

Where substituent groups are specified by their conventional chemical formulae, written from left to right, they optionally equally encompass the chemically identical substituents, which would result from writing the structure from right to left, e.g., —CH$_2$O— is intended to also recite —OCH$_2$—.

The term "alkyl", by itself or as part of another substituent, means a straight or branched chain hydrocarbon, which may be fully saturated, mono- or polyunsaturated and includes mono-, di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds (i.e., alkenyl and alkynyl moieties). Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl" can refer to "alkylene", which by itself or as part of another substituent means a divalent radical derived from an alkane, as exemplified, but not limited, by —CH$_2$CH$_2$CH$_2$CH$_2$—. Typically, an alkyl (or alkylene) group will have from 1 to 30 carbon atoms. A "lower alkyl" or "lower alkylene" is a shorter chain alkyl or alkylene group, generally having eight or fewer carbon atoms. In some embodiments, alkyl refers to an alkyl or combination of alkyls selected from $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$ and $C_{30}$ alkyl. In some embodiments, alkyl refers to $C_1$-$C_{25}$ alkyl. In some embodiments, alkyl refers to $C_1$-$C_{20}$ alkyl. In some embodiments, alkyl refers to $C_1$-$C_{15}$ alkyl. In some embodiments, alkyl refers to $C_1$-$C_{10}$ alkyl. In some embodiments, alkyl refers to $C_1$-$C_6$ alkyl.

The term "heteroalkyl," by itself or in combination with another term, means an alkyl in which one or more carbons are replaced with one or more heteroatoms selected from the group consisting of O, N, Si and S, (preferably 0, N and 5), wherein the nitrogen and sulfur atoms may optionally be oxidized and the nitrogen heteroatom may optionally be quaternized. The heteroatoms 0, N, Si and S may be placed at any interior position of the heteroalkyl group or at the position at which the alkyl group is attached to the remainder of the molecule. In some embodiments, depending on whether a heteroatom terminates a chain or is in an interior position, the heteroatom may be bonded to one or more H or substituents such as ($C_1$, $C_2$, $C_3$, $C_4$, $C_5$ or $C_6$) alkyl according to the valence of the heteroatom. Examples of heteroalkyl groups include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. No more than two heteroatoms may be consecutive, as in, for example, —CH$_2$—NH—OCH$_3$ and —CH$_2$—O—Si(CH$_3$)$_3$, and in some instances, this may place a limit on the number of heteroatom substitutions. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. The designated number of carbons in heteroforms of alkyl, alkenyl and alkynyl includes the heteroatom count. For example, a ($C_1$, $C_2$, $C_3$, $C_4$, $C_5$ or $C_6$) heteroalkyl will contain, respectively, 1, 2, 3, 4, 5 or 6 atoms selected from C, N, O, Si and S such that the heteroalkyl contains at least one C atom and at least one heteroatom, for example 1-5 C and 1 N or 1-4 C and 2 N. Further, a heteroalkyl may also contain one or more carbonyl groups. In some embodiments, a heteroalkyl is any $C_2$-$C_{30}$ alkyl, $C_2$-$C_{25}$ alkyl, $C_2$-$C_{20}$ alkyl, $C_2$-$C_{15}$ alkyl, $C_2$-$C_{10}$ alkyl or $C_2$-$C_6$ alkyl in any of which one or more carbons are replaced by one or more heteroatoms selected from O, N, Si and S (or from 0, N and S). In some embodiments, each of 1, 2, 3, 4 or 5 carbons is replaced with a heteroatom. The terms "alkoxy," "alkylamino" and "alkylthio" (or thioalkoxy) are used in their conventional sense, and refer to those alkyl and heteroalkyl groups attached to the remainder of the molecule via an oxygen atom, a nitrogen atom (e.g., an amine group), or a sulfur atom, respectively.

The terms "cycloalkyl" and "heterocycloalkyl", by themselves or in combination with other terms, refer to cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means a polyunsaturated, aromatic substituent that can be a single ring or optionally multiple rings (preferably 1, 2 or 3 rings) that are fused together or linked covalently. In some embodiments, aryl is a 3, 4, 5, 6, 7 or 8 membered ring, which is optionally fused to one or two other 3, 4, 5, 6, 7 or 8 membered rings. The term "heteroaryl" refers to aryl groups (or rings) that contain 1, 2, 3 or 4 heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

In some embodiments, any of alkyl, heteroalkyl, cycloalkyl, heterocycloalkyl, aryl and heteroaryl is optionally substituted. That is, in some embodiments, any of these groups is substituted or unsubstituted. In some embodiments, substituents for each type of radical are selected from those provided below.

Substituents for the alkyl, heteroalkyl, cycloalkyl and heterocycloalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents". In some embodiments, an alkyl group substituent is selected from -halogen, —OR', =O, =NR', =N—OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. In one embodiment, R', R", R'" and R' are each independently selected from hydrogen, alkyl (e.g., $C_1$, $C_2$, $C_3$, $C_4$, $C_5$ and $C_6$ alkyl). In one embodiment, R', R", R'" and R' each independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. In one embodiment, R', R", R'" and R' are each independently selected from hydrogen, alkyl, heteroalkyl, cycloalkyl, heterocycloalkyl, aryl, heteroaryl, alkoxy, thioalkoxy groups, and arylalkyl. When R' and R" are attached to the same nitrogen atom, they can be combined with the nitrogen atom to form a 5-, 6-, or 7-membered ring. For example, —NR'R" can include 1-pyrrolidinyl and 4-morpholinyl. In some embodiments, an alkyl group substituent is selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

Similar to the substituents described for the alkyl radical, substituents for the aryl and heteroaryl groups are generically referred to as "aryl group substituents". In some embodiments, an aryl group substituent is selected from -halogen, —OR', =O, =NR', =N—OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system. In some embodiments, R', R", R'" and R"" are independently selected from hydrogen and alkyl (e.g., $C_1$, $C_2$, $C_3$, $C_4$, $C_5$ and $C_6$ alkyl). In some embodiments, R', R", R'" and R"" are independently selected from hydrogen, substituted or unsubstituted alkyl, substituted or unsubstituted heteroalkyl, substituted or unsubstituted aryl and substituted or unsubstituted heteroaryl. In some embodiments, R', R", R'" and R"" are independently selected from hydrogen, alkyl, heteroalkyl, aryl and heteroaryl. In some embodiments, an aryl group substituent is selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted ($C_1$-$C_6$)alkyl.

The term "acyl" refers to a species that includes the moiety C(O)R, where R has the meaning defined herein. Exemplary species for R include H, halogen, substituted or unsubstituted alkyl, substituted or unsubstituted aryl, substituted or unsubstituted heteroaryl, and substituted or unsubstituted heterocycloalkyl. In some embodiments, R is selected from H and ($C_1$-$C_6$)alkyl.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like. In some embodiments, halogen refers to an atom selected from F, Cl and Br.

The term "heteroatom" includes oxygen (O), nitrogen (N), sulfur (S) and silicon (Si). In some embodiments, a heteroatom is selected from N and S. In some embodiments, the heteroatom is O.

Unless otherwise specified, the symbol "R" is a general abbreviation that represents a substituent group that is selected from acyl, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound includes more than one R, R', R", R''' and R"" group, they are each independently selected.

For groups with solvent exchangeable protons, the ionized form is equally contemplated. For example, —COOH also refers to —COO⁻ and —OH also refers to —O⁻.

Any of the compounds disclosed herein can be made into a pharmaceutically acceptable salt. The term "pharmaceutically acceptable salts" includes salts of compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science,* 66: 1-19 (1977)). Certain specific compounds of the present invention contain both basic and acidic functionalities that allow the compounds to be converted into either base or acid addition salts. The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides any of the compounds disclosed herein in a prodrug form. Prodrugs of the compounds described herein are those compounds that readily undergo chemical changes under physiological conditions to provide the compounds of the present invention.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The compounds of the present invention may also contain unnatural proportions of atomic isotopes at one or more of the atoms that constitute such compounds. For example, the compounds may be labeled with deuterium ($^2$H) or radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The symbol , displayed perpendicular to a bond, indicates the point at which the displayed moiety is attached to the remainder of the molecule.

In some embodiments, the definition of terms used herein is according to IUPAC.

2. Compositions

The invention provides numerous chelators and metal ion complexes thereof. Generally, a chelator comprises a plurality of chelating agents that are linked together by way of three or more scaffold moieties.

There are several factors to be considered in the design for an alpha chelating agent for anticancer therapy. Some of the key issues apart from the kinetics will be the high affinity for the target metal (such as Th) which at the same time needs to have a low exchange rate for other biologically significant metal ions. So, in our ligand design, the electronic properties of the target metal and ligand are considered and matched. The chelate should also be able to assume the appropriate coordination cavity size and geometry for the desired metal. In this case, Th, an actinide ion, is a "hard" cation and has a large charge-to-radius ratio. Hence, Th prefers "hard" electron donors and negatively charged oxygen donors. A coordination number of 8 or greater is generally preferred by actinide ions as they have a tendency to form stable complexes with ligands of high denticity; however, the selectivity towards the binding of the thorium will be determined by our design of the chelating unit. The effective but nonselective amino-carboxylic acid ligands such as DTPA can deplete essential biological metal ions from patients, thus causing serious health problems. Selecting the correct type of chelating unit, therefore, is an important factor in achieving high selectivity toward the specific metal ion.

A chelator can comprise numerous chelating moieties. Particularly useful chelators contain a number of chelating moieties sufficient to provide, for example, 6, 8 or 10 heteroatoms such as oxygen that coordinate with a metal ion to form a complex. The heteroatoms such as oxygen provide electron density for forming coordinate bonds with a positively charged ion, and such heteroatoms can thus be considered "donors". In some embodiments, the plurality of chelating moieties of a chelator comprises a plurality of oxygen donors and a metal ion (such as a radionuclide) is chelated to the chelator via at least one of the oxygen donors. In some embodiments, a chelator comprises a plurality of oxygen donors and a metal ion (such as a radionuclide) is chelated to the chelator via a plurality or all of the oxygen donors.

Accordingly, in one aspect, the invention provides a complex comprising (a) a metal ion and (b) a di-macrocycle comprising (i) a plurality of chelating moieties, (ii) a linker, (iii) a first scaffold moiety, (iv) a second scaffold moiety, and (v) a third scaffold moiety, wherein each of the chelating moieties is attached to the first scaffold moiety and either the second or the third scaffold moiety. In some embodiments, the di-macrocycle comprises 4 or 5 chelating moieties. In some embodiments, the metal is a radionuclide.

Also provided herein are uncomplexed forms of any chelator described herein. Thus, in one aspect, the invention provides a di-macrocycle comprising (i) a plurality of chelating moieties, (ii) a linker, (iii) a first scaffold moiety, (iv) a second scaffold moiety, and (v) a third scaffold moiety, wherein each of the chelating moieties is attached to the first scaffold moiety and either the second or the third scaffold moiety.

In exemplary embodiments, the di-macrocycle comprises chelating moieties independently selected from

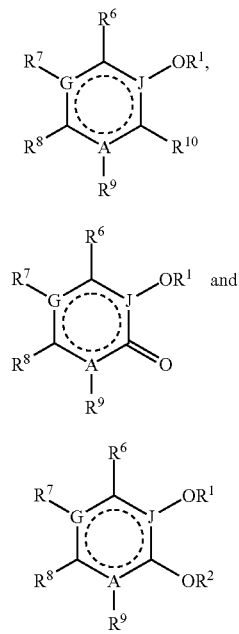

wherein $R^6$, $R^7$, $R^8$, $R^9$ and $R^{10}$ in each chelating moiety are independently selected from a bond to the first, second or third scaffold moiety, H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, halogen, CN, $CF_3$, —C(O)$R^{17}$, —$SO_2NR^{17}R^{18}$, —$NR^{17}R^{18}$, —$OR^{17}$, —S(O)$_2R^{17}$, —COO$R^{17}$, —S(O)$_2OR^{17}$, —OC(O)$R^{17}$, —C(O)N$R^{17}R^{18}$, —$NR^{17}$C(O)$R^{18}$, —$NR^{17}SO_2R^{18}$ and —$NO_2$;

$R^{17}$ and $R^{18}$ are each independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{17}$ and $R^{18}$, together with the atoms to which they are attached, are optionally joined to form a 5-, 6- or 7-membered ring;

at least two of $R^6$, $R^7$, $R^8$, $R^9$ and $R^{10}$ are optionally joined to form a ring system which is a member selected from substituted or unsubstituted cycloalkyl, substituted or unsubstituted heterocycloalkyl, substituted or unsubstituted aryl and substituted or unsubstituted heteroaryl;

$R^1$ and $R^2$ are each independently selected from H, a negative charge, an enzymatically labile group, a hydrolytically labile group, a metabolically labile group, and a photolytically labile group;

A and G are independently selected from carbon, nitrogen and oxygen; and

J is selected from carbon and nitrogen;

wherein one of $R^6$, $R^7$, $R^8$, $R^9$ and $R^{10}$ comprises a bond to the first scaffold moiety; and one of $R^6$, $R^7$, $R^8$, $R^9$ and $R^{10}$ comprises a bond to the second or the third scaffold moiety;

when A is oxygen, $R^9$ is not present; and
when G is oxygen, $R^7$ is not present.

In some embodiments, one of $R^6$ and $R^9$ in (II) or (III) or one of $R^6$ and $R^{10}$ in (I) comprises a bond to the first scaffold moiety, with the other of $R^6$ and $R^9$ in (II) or (III) and the other of $R^6$ and $R^{10}$ in (I) comprising a bond to the second or the third scaffold moiety.

In some embodiments, $R^1$ and $R^2$ are independently selected from H and a negative charge.

In some embodiments, $R^7$ and $R^8$ are selected from H, halogen, substituted or unsubstituted alkyl, haloalkyl, substituted or unsubstituted heteroalkyl, substituted or unsubstituted aryl, substituted or unsubstituted heteroaryl, —C(O)$R^{17}$, —$SO_2NR^{17}R^{18}$, —$NR^{17}R^{18}$, —$OR^{17}$, —S(O)$_2R^{17}$, —COO$R^{17}$, —S(O)$_2OR^{17}$, —OC(O)$R^{17}$, —C(O)N$R^{17}R^{18}$, —$NR^{17}$C(O)$R^{18}$, —$NR^{17}SO_2R^{18}$, wherein $R^{17}$ and $R^{18}$ are selected from H and alkyl. In some embodiments, $R^7$ and $R^8$ are selected from H and ($C_1$, $C_2$, $C_3$, $C_4$, $C_5$ or $C_6$) alkyl. In exemplary embodiments, $R^7$ and $R^8$ are H.

In exemplary embodiments, $R^{17}$ and $R^{18}$ are selected from H and ($C_1$, $C_2$, $C_3$, $C_4$, $C_5$ or $C_6$) alkyl.

In exemplary embodiments, in structure (I), A, G and J are carbon. In some embodiments, in structure (II), A is nitrogen and G and J are carbon. In some embodiments, in structure (II), J is nitrogen and A and G are carbon. In some embodiments, in structure (III), A, G and J are carbon.

In one aspect, the invention provides a complex comprising (a) a metal ion and (b) a di-macrocycle comprising (i) a plurality of chelating moieties having the structure

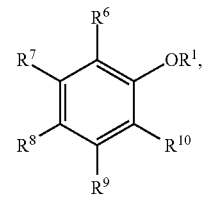

(ii) a linker, (iii) a first scaffold moiety, (iv) a second scaffold moiety, and (v) a third scaffold moiety, wherein each of the chelating moieties is attached to the first scaffold moiety and the second or the third scaffold moiety. $R^1$, $R^6$, $R^7$, $R^8$, $R^9$ and $R^{10}$ are as described herein. In exemplary embodiments, $R^7$, $R^8$ and $R^9$ are H. In one aspect, the invention provides the di-macrocycle itself, that is, the complex in the absence of the metal ion.

In one aspect, the invention provides a complex comprising (a) a metal ion and (b) a di-macrocycle comprising (i) a plurality of chelating moieties having the structure

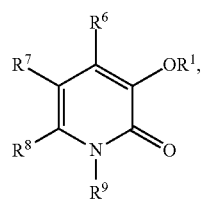

(ii) a linker, (iii) a first scaffold moiety, (iv) a second scaffold moiety, and (v) a third scaffold moiety, wherein each of the chelating moieties is attached to the first scaffold moiety and the second or the third scaffold moiety. R', $R^6$, $R^7$, $R^8$ and $R^9$ are as described herein. In exemplary embodiments, $R^7$ and $R^8$ are H. In one aspect, the invention provides the di-macrocycle itself, that is, the complex in the absence of the metal ion.

In one aspect, the invention provides a complex comprising (a) a metal ion and (b) a di-macrocycle comprising (i) a plurality of chelating moieties having the structure

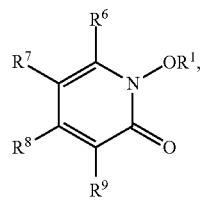

(ii) a linker, (iii) a first scaffold moiety, (iv) a second scaffold moiety, and (v) a third scaffold moiety, wherein each of the chelating moieties is attached to the first scaffold moiety and the second or the third scaffold moiety. $R^1$, $R^6$, $R^7$, $R^8$ and $R^9$ are as described herein. In exemplary embodiments, $R^7$ and $R^8$ are H. In one aspect, the invention provides the di-macrocycle itself, that is, the complex in the absence of the metal ion.

In one aspect, the invention provides a complex comprising (a) a metal ion and (b) a di-macrocycle comprising (i) a plurality of chelating moieties having the structure

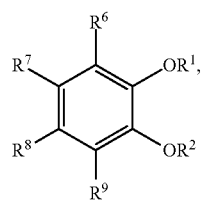

(ii) a linker, (iii) a first scaffold moiety, (iv) a second scaffold moiety, and (v) a third scaffold moiety, wherein each of the chelating moieties is attached to the first scaffold moiety and the second or the third scaffold moiety. $R^1$, $R^2$, $R^6$, $R^7$, $R^8$ and $R^9$ are as described herein. In exemplary embodiments, $R^7$ and $R^8$ are H. In one aspect, the invention provides the di-macrocycle itself, that is, the complex in the absence of the metal ion.

2.1. Di-Macrocycles

In one aspect, the invention provides a di-macrocycle of formula (DM1a), (DM1b), or (DM2):

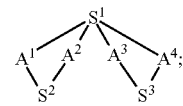

(DM1a)

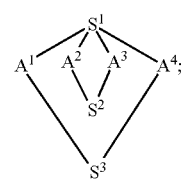

(DM1b)

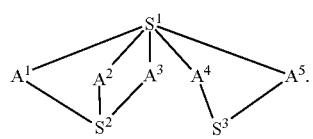

(DM2)

wherein $S^1$, $S^2$ and $S^3$ are independently selected scaffold moieties.

$A^1$, $A^2$, $A^3$, $A^4$, and $A^5$ are independently selected chelating moieties.

Scaffold moieties and chelating moieties are as defined herein.

Any of the combinations of $S^1$, $S^2$, $S^3$, $A^1$, $A^2$, $A^3$, $A^4$, and $A^5$ are encompassed by this disclosure and specifically provided by the invention.

In some embodiments, the di-macrocycle comprises a linker. In some embodiments, the linker is attached to a targeting moiety. In some embodiments, the di-macrocycle comprises a targeting moiety.

In some embodiments, the di-macrocycle comprises one, two or more modifying moieties. The modifying moieties can be the same or different.

2.1.1. Chelating Moieties $A^1$, $A^2$, $A^3$, $A^4$ and $A^5$ are chelating moieties having a structure independently selected from:

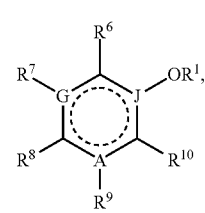

(I)

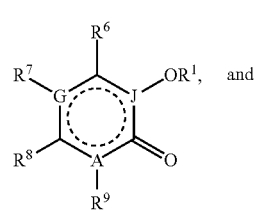

(II) and

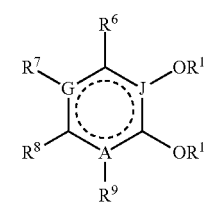

(III)

wherein
A and G are independently selected from carbon, nitrogen and oxygen;
wherein when A is oxygen, $R^9$ is not present; and when G is oxygen, $R^7$ is not present;
J is selected from carbon and nitrogen;
each $R^1$ and $R^2$ are independently selected from H, an enzymatically labile group, a hydrolytically labile group, a metabolically labile group, a photolytically labile group and a single negative charge;
each $R^6$, $R^7$, $R^8$, $R^9$, and $R^{10}$ are independently selected from a bond to $S^1$, $S^2$ or $S^3$, alkanediyl attached to $S^1$, $S^2$ or $S^3$, H, substituted or unsubstituted alkyl, substituted or unsubstituted heteroalkyl, halogen, CN, $CF_3$, $-C(O)R^{17}$, $-SO_2NR^{17}R^{18}$, $-NR^{17}R^{18}$, $-OR^{17}$, $-S(O)_2R^{17}$, $-COOR^{17}$, $-S(O)_2OR^{17}$, $-OC(O)R^{17}$, $-C(O)NR^{17}R^{18}$, $-NR^{17}C(O)R^{18}$, $-NR^{17}SO_2R^{18}$, and $-NO_2$,
wherein
at least two of $R^6$, $R^7$, $R^8$, $R^9$, and $R^{10}$ are optionally joined to form a ring system selected from substituted or unsubstituted cycloalkyl, substituted or unsubstituted heterocycloalkyl, substituted or unsubstituted aryl and substituted or unsubstituted heteroaryl;
$R^{17}$ and $R^{18}$ are independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl; and
$R^{17}$ and $R^{18}$, together with the atoms to which they are attached, are optionally joined to form a 5-, 6- or 7-membered ring;
wherein $A^1$, $A^2$, $A^3$, $A^4$ and $A^5$ are each attached to $S^1$ and $S^2$ or $S^1$ and $S^3$ through two members selected from $R^6$, $R^7$, $R^8$, $R^9$ and $R^{10}$.

In some embodiments, when any of $A^1$, $A^2$, $A^3$, $A^4$ and $A^5$ has a structure according to formula (I), the respective chelating moiety is attached to $S^1$ and $S^2$ or $S^1$ and $S^3$ through $R^6$ and $R^{10}$.

In some embodiments, when any of $A^1$, $A^2$, $A^3$, $A^4$ and $A^5$ has a structure according to formula (II) or (III), the respective chelating moiety is attached to $S^1$ and $S^2$ or $S^1$ and $S^3$ through $R^6$ and $R^9$.

In some embodiments, at least one of $R^6$ and $R^{10}$ in (I) is a bond attached to $S^1$, $S^2$, or $S^3$.

In some embodiments, $A^1$, $A^2$, $A^3$, $A^4$ and $A^5$ are chelating moieties having a structure independently selected from:

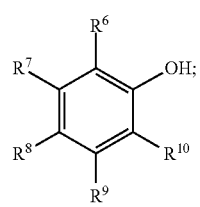
(1)

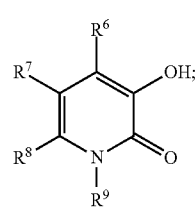
(2a)

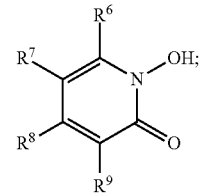
(2b)

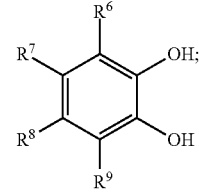
(3)

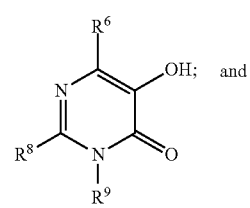
(4)

and

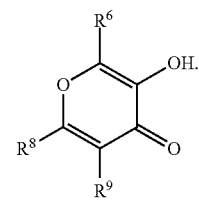
(5)

$R^6$, $R^7$, $R^8$, $R^9$, and $R^{10}$ are as defined herein.

In some embodiments, $A^1$, $A^2$, $A^3$, $A^4$ and $A^5$ are chelating moieties having a structure independently selected from:

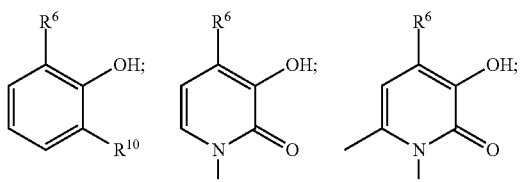

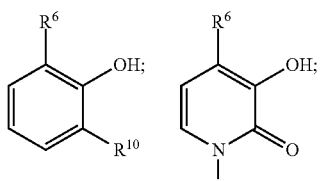 and 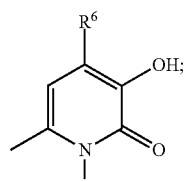

$R^6$, $R^9$, and $R^{10}$ are as defined herein.

2.1.2. Scaffold Moieties

A "scaffold moiety" is any moiety useful for covalently linking two or more chelating moieties in any of the chelators (di-macrocycles) disclosed herein. In exemplary embodiments, any two scaffold moieties disclosed herein are joined via a plurality of chelating moieties to form a macrocycle. In exemplary embodiments, one or more scaffold moieties of a chelator is substituted with a linker. In one embodiment, the scaffold moiety is selected from substituted or unsubstituted alkyl and substituted or unsubstituted heteroalkyl. Exemplary scaffold moieties include linear or branched ethers and amines. In some embodiments, the linker is attached to a targeting moiety. In some embodiments, the scaffold moiety comprises a targeting moiety.

Other exemplary scaffold moieties include, but are not limited to:

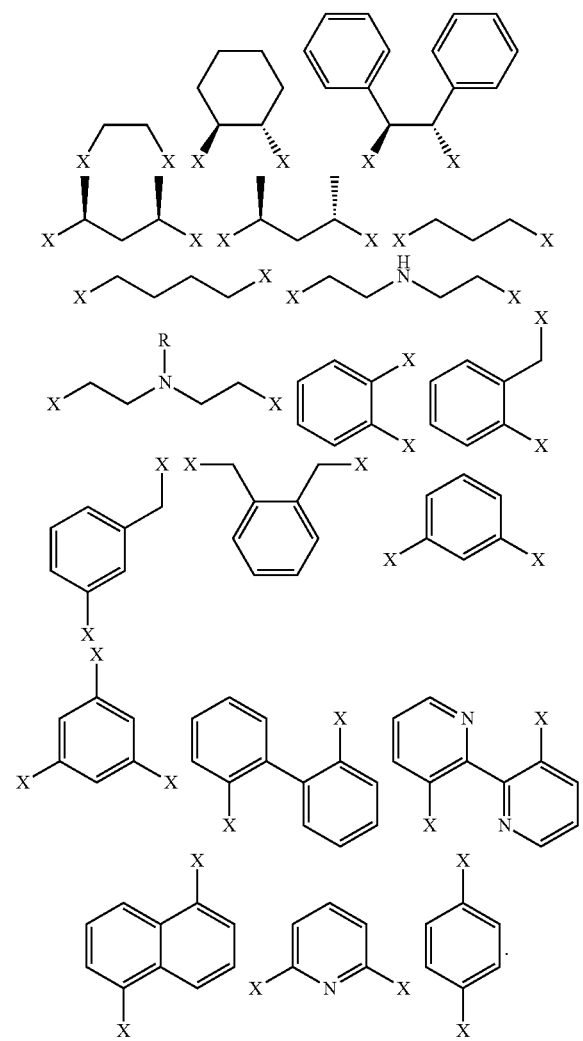

"X" represents a locus of attachment for a chelating moiety, and in exemplary embodiments includes a heteroatom such as nitrogen. Thus, in some embodiments, X is NR'R", wherein R' and R" are independently selected from substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, halogen, CN, $CF_3$, $-C(O)R^{17}$, $-SO_2NR^{17}R^{18}$, $-NR^{17}R^{18}$, $-OR^{17}$, $-S(O)_2R^{17}$, $-COOR^{17}$, $-S(O)_2OR^{17}$, $-OC(O)R^{17}$, $-C(O)NR^{17}R^{18}$, $-NR^{17}C(O)R^{18}$, $-NR^{17}SO_2R^{18}$, $-NO_2$; and $-NO_2$, and $R^{17}$ and $R^{18}$ are each independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; wherein at least one R' or R" comprises a bond to a chelating moiety. The chelating moiety can be attached to a scaffold via any appropriate linker.

In some embodiments, a scaffold moiety is linear. One exemplary scaffold moiety is $X-(CH_2)_3-X-(CH_2)_4-X-(CH_2)_3-X$, which is preferably substituted (e.g. with a linker) at at least one of the alkyl moieties. That is, one exemplary scaffold moiety is spermine based. Other exemplary scaffold moieties include

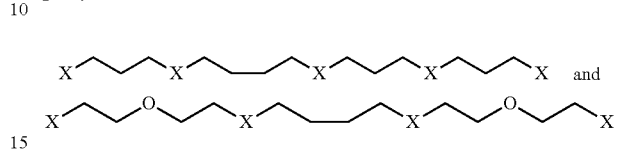

any of which is preferably substituted (e.g. with a linker) at at least one of the alkyl moieties. X is as given in the previous paragraph.

One preferred moiety for at least one of the X moieties is the 1,2-HOPO amide moiety, but those of skill in the art will appreciate that other chelating moieties in any used in any combination. In each of the scaffold structures, an aryl moiety or alkyl moiety can be substituted with one or more "aryl group substituent" or "alkyl group substituent" as defined herein.

A particularly useful scaffold moiety for any chelator described herein has the structure

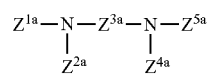

wherein $Z^{1a}$, $Z^{2a}$, $Z^{3a}$, $Z^{4a}$ and $Z^{5a}$ are selected from substituted or unsubstituted alkyl and substituted or unsubstituted heteroalkyl; and $Z^{1a}$, $Z^{2a}$, $Z^{4a}$ and $Z^{5a}$ comprise a bond to one of the chelating moieties.

In some embodiments, $Z^{3a}$ is substituted or unsubstituted ($C_1$, $C_2$, $C_3$, $C_4$, $C_5$ or $C_6$) alkyl. In some embodiments, $Z^{3a}$ is substituted or unsubstituted $-(CH_2)_m(CH_2CH_2O)_n(CH_2)_p-$, wherein m, n and p are integers independently selected from 1, 2, 3, 4, 5 and 6. In some embodiments, $Z^{3a}$ is ethyl. In some embodiments, $Z^{3a}$ is ethyl substituted with =O.

In some embodiments, $Z^{1a}$, $Z^{2a}$, $Z^{4a}$ and $Z^{5a}$ have a structure selected from Z'R$^{20a}$N(H)C(O)Z", Z'R$^{20a}$N(H)C(O)R$^{21a}$Z" and Z'R$^{21a}$Z" wherein Z' is a bond to the second scaffold moiety, Z" is a bond to one of the plurality of chelating moieties, R$^{20a}$ is selected from substituted or unsubstituted alkyl and substituted or unsubstituted heteroalkyl, and R$^{21a}$ is selected from substituted or unsubstituted alkyl and substituted or unsubstituted heteroalkyl. In some embodiments, R$^{20a}$ is selected from substituted or unsubstituted ($C_1$, $C_2$, $C_3$, $C_4$, $C_5$ or $C_6$) alkyl and substituted or unsubstituted ($C_1$, $C_2$, $C_3$, $C_4$, $C_5$ or $C_6$) heteroalkyl. In some embodiments, R$^{20a}$ is selected from substituted or unsubstituted ethyl. In some embodiments, R$^{21a}$ is from substituted or unsubstituted $-(CH_2)_wO-$ wherein w is selected from 1, 2, 3, 4, 5 and 6. In exemplary embodiments, w is 1 or 3.

In some embodiments, at least one of $Z^{1a}$, $Z^{2a}$, $Z^{3a}$, $Z^{4a}$ and $Z^{5a}$ is substituted with a linker.

Another particularly useful scaffold moiety for any chelator herein has the structure

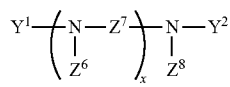

x is selected from 1, 2, 3 and 4. In exemplary embodiments, x is 1. In exemplary embodiments, x is 2. In exemplary embodiments, x is 3. In exemplary embodiments, x is 4.

$Y^1$ and $Y^2$ are each independently selected from H, substituted or unsubstituted alkyl and substituted or unsubstituted heteroalkyl. In exemplary embodiments, $Y^1$ and $Y^2$ are H.

$Z^7$ is selected from substituted or unsubstituted alkyl and substituted or unsubstituted heteroalkyl. In exemplary embodiments, at least one $Z^7$ is substituted with a linker. In some embodiments, each $Z^7$ is independently substituted or unsubstituted ($C_1$, $C_2$, $C_3$, $C_4$, $C_5$ or $C_6$) alkyl. In exemplary embodiments, each $Z^7$ is independently substituted or unsubstituted propyl or butyl. In some embodiments, each $Z^7$ is independently substituted or unsubstituted heteroalkyl.

In exemplary embodiments, each $Z^7$ is independently substituted or unsubstituted $-(CH_2)_m(CH_2CH_2O)_n(CH_2)_p-$, wherein m, n and p are integers independently selected from 1, 2, 3, 4, 5 and 6. In exemplary embodiments, each $Z^7$ is substituted or unsubstituted $-(CH_2)_2O(CH_2)_2-$.

$Z^6$ and $Z^8$ are independently selected from $-C(O)-$, substituted or unsubstituted alkyl, and substituted or unsubstituted heteroalkyl; and each of $Z^6$ and $Z^8$ comprises a bond to one of the chelating moieties.

In exemplary embodiments, $Z^6$ and $Z^8$ are $-C(O)-$.

Another useful scaffold moiety has the structure:

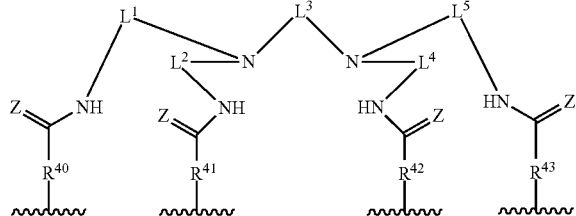

in which each Z is independently selected from O and S. In some embodiments, $L^3$ comprises $-(CH_2CH_2O)_mR^{31}-$ wherein m is an integer selected from 0, 1, 2, 3, 4, 5, 6, 7, 8 and 9. In some embodiments, m is 0. In some embodiments, m is 1. In some embodiments, $L^3$ is $-CH_2CH_2OCH_2CH_2-$. $L^1$, $L^2$, $L^4$, $L^5$ and $R^{31}$ are independently selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In exemplary embodiments, $L^1$, $L^2$, $L^4$, $L^5$ are independently selected substituted or unsubstituted ($C_1$, $C_2$, $C_3$, $C_4$, $C_5$ or $C_6$) alkyl. In some embodiments, $R^{31}$ is substituted or unsubstituted ($C_1$, $C_2$, $C_3$, $C_4$, $C_5$ or $C_6$) alkyl. In exemplary embodiments, $L^1$, $L^2$, $L^4$, $L^5$ are independently selected substituted or unsubstituted ethyl. In some embodiments, $R^{31}$ is substituted or unsubstituted ethyl. In exemplary embodiments, $L^1$, $L^2$, $L^4$, $L^5$ are ethyl, one or more of which is substituted with a linker. In some embodiments, $L^1$ is substituted with a linker. In some embodiments, $L^2$ is substituted with a linker. In some embodiments, $L^3$ is substituted with a linker. In some embodiments, $L^4$ is substituted with a linker. In some embodiments, $L^5$ is substituted with a linker. In some embodiments, $L^1$ is ethyl substituted with a linker. In some embodiments, $L^2$ is ethyl substituted with a linker. In some embodiments, $L^3$ is ethyl substituted with a linker. In some embodiments, $L^4$ is ethyl substituted with a linker. In some embodiments, $L^5$ is ethyl substituted with a linker. In some embodiments, $R^{40}$, $R^{41}$, $R^{42}$ and $R^{43}$ are bonds. In some embodiments, $R^{40}$, $R^{41}$, $R^{42}$ and $R^{43}$ are $-(CH_2)_wO-$, wherein w is selected from 0, 1, 2, 3, 4, 5, 6, 7, 8, 9 and 10. In exemplary embodiments, w is 3.

Another useful scaffold has the structure

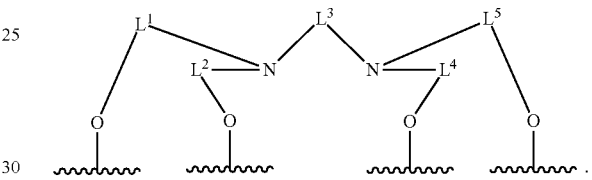

In some embodiments, $L^3$ comprises $-(CH_2CH_2O)_mR^{31}-$ wherein m is an integer selected from 0, 1, 2, 3, 4, 5, 6, 7, 8 and 9. In some embodiments, m is 0. In some embodiments, m is 1. In some embodiments, $L^3$ is $-CH_2CH_2OCH_2CH_2-$. In some embodiments, $L^3$ is $-C(O)C(O)-$. $L^1$, $L^2$, $L^4$, $L^5$ and $R^{31}$ are independently selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In exemplary embodiments, $L^1$, $L^2$, $L^4$, $L^5$ are independently selected substituted or unsubstituted ($C_1$, $C_2$, $C_3$, $C_4$, $C_5$ or $C_6$) alkyl. In some embodiments, $R^{31}$ is substituted or unsubstituted ($C_1$, $C_2$, $C_3$, $C_4$, $C_5$ or $C_6$) alkyl. In exemplary embodiments, $L^1$, $L^2$, $L^4$, $L^5$ independently selected substituted or unsubstituted ethyl. In exemplary embodiments, $L^1$, $L^2$, $L^4$, $L^5$ are independently selected substituted or unsubstituted propyl. In some embodiments, $R^{31}$ is substituted or unsubstituted ethyl. In exemplary embodiments, $L^1$, $L^2$, $L^4$, $L^5$ are ethyl, one or more of which is substituted with a linker. In some embodiments, $L^1$ is substituted with a linker. In some embodiments, $L^2$ is substituted with a linker. In some embodiments, $L^3$ is substituted with a linker. In some embodiments, $L^4$ is substituted with a linker. In some embodiments, $L^5$ is substituted with a linker. In some embodiments, $L^1$ is propyl substituted with a linker. In some embodiments, $L^2$ is propyl substituted with a linker. In some embodiments, $L^3$ is propyl substituted with a linker. In some embodiments, $L^4$ is propyl substituted with a linker. In some embodiments, $L^5$ is propyl substituted with a linker.

In some embodiments, a scaffold is selected from:
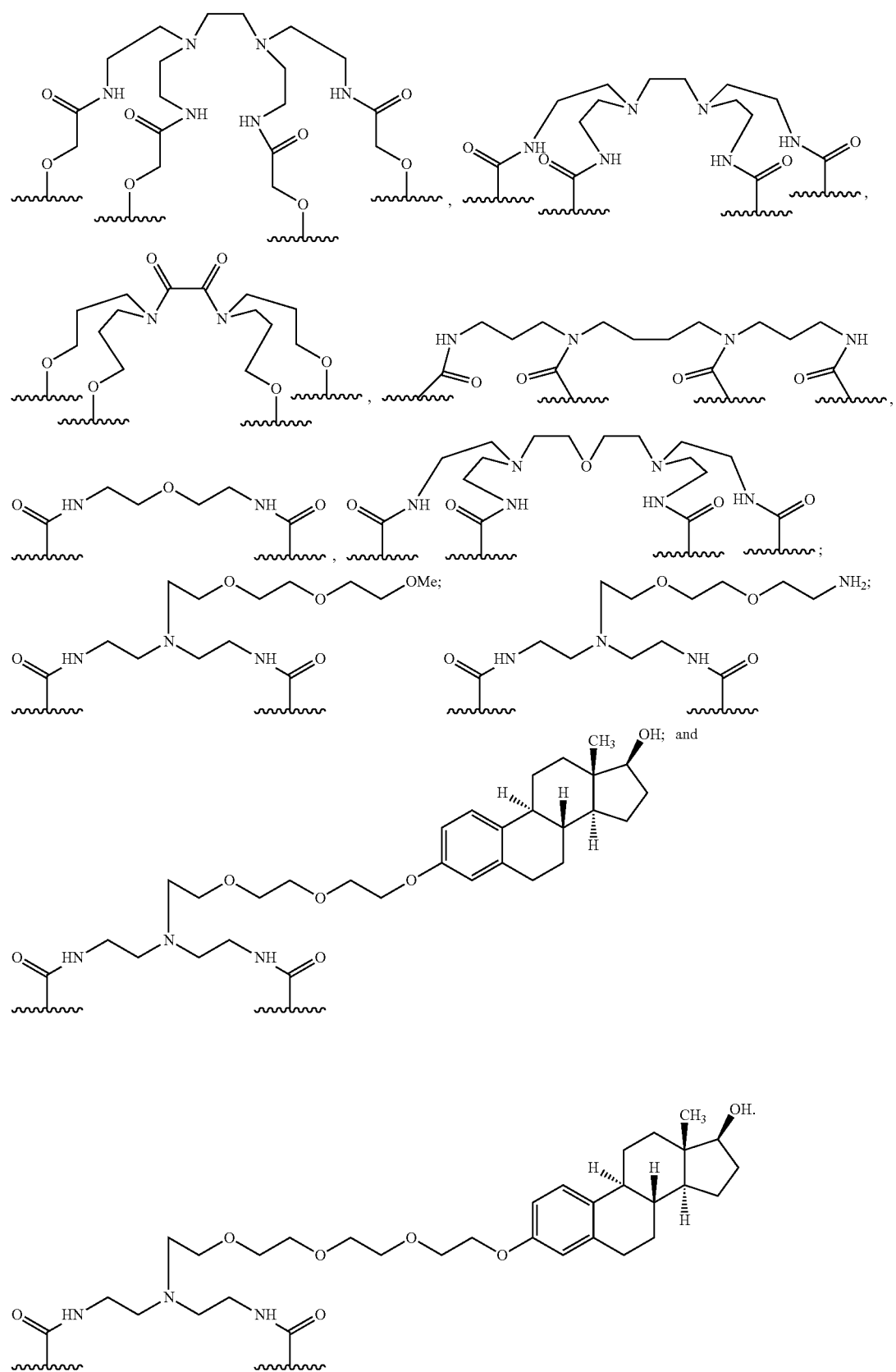

In any of these structures, one or more methyl, ethyl, propyl or butyl moieties can be substituted with one or more linkers. In some embodiments, two of these scaffold moieties, in which one or more methyl, ethyl, propyl or butyl moieties are optionally substituted with one or more linkers, are used to form a macrocycle.

In some embodiments, any one, two or all of the first, second and third scaffold moiety comprise a linker. In some embodiments, the linker is attached to a targeting moiety. In some embodiments, any one, two or all of the first, second and third scaffold moiety comprise a targeting moiety.

In some embodiments the first scaffold moiety is as defined for $S^1$ herein. In some embodiments, the second and third scaffold moieties are as defined for $S^2$ and $S^3$ herein.

In some embodiments, any one, two or all of $S^1$, $S^2$ and $S^3$ comprise a linker. In some embodiments, $S^1$ comprises a linker. In some embodiments, $S^2$ or $S^3$ comprises a linker. In some embodiments, the linker is attached to a targeting moiety. In some embodiments, any one, two or all of $S^1$, $S^2$ and $S^3$ comprise a targeting moiety. In some embodiments, $S^1$ comprises a targeting moiety. In some embodiments, $S^2$ or $S^3$ comprises a targeting moiety.

$S^1$

In some embodiments, $S^1$ has the structure:

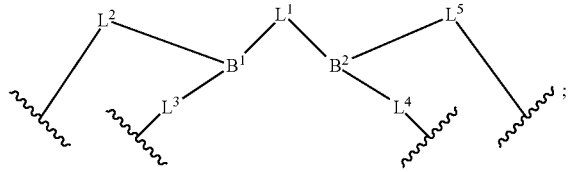

wherein
$L^1$, $L^2$, $L^3$, $L^4$, and $L^5$ are independently selected from substituted or unsubstituted alkyl, substituted or unsubstituted heteroalkyl, substituted or unsubstituted aryl, substituted or unsubstituted heteroaryl and substituted or unsubstituted heterocycloalkyl. In some embodiments, $L^1$, $L^2$, $L^3$, $L^4$, and $L^5$ are independently selected from substituted or unsubstituted alkyl and substituted or unsubstituted heteroalkyl.

In some embodiments, $L^1$ is

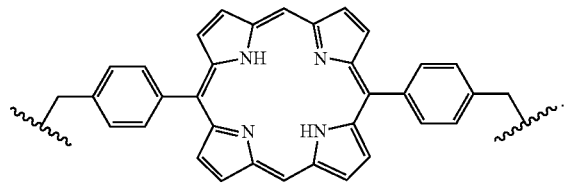 [SMILES: *Cc1ccc(-c2c3nc(cc4ccc([nH]4)c(-c4ccc(C*)cc4)c4nc(cc5ccc2[nH]5)C=C4)C=C3)cc1]

In some embodiments, one of $L^5$ and $L^1$ is substituted with a linker. In some embodiments, $L^5$ is substituted with a linker. Linkers are as defined herein.

$B^1$ and $B^2$ are independently selected from the elements capable of 3, 4, or 5 covalent bonds. In some embodiments, $B^1$ and $B^2$ are independently selected from N, C, B, Si, and P. In some embodiments, $B^1$ and $B^2$ are independently selected from N and C. In some embodiments, $B^1$ and $B^2$ are N.

In some embodiments, $S^1$ has the structure:

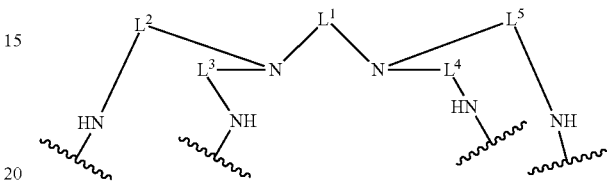

wherein $L^1$, $L^2$, $L^3$, $L^4$, and $L^5$ are as defined herein.

In some embodiments, $S^1$ has the structure:

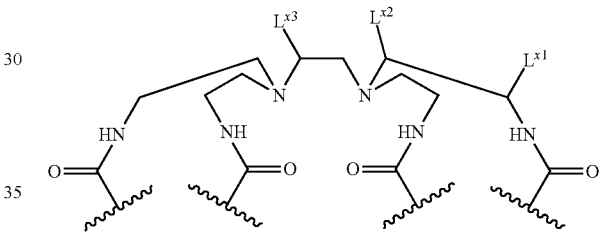

wherein $L^{x1}$, $L^{x2}$ and $L^{x3}$ are independently selected from H and a linker. In some embodiments, only one of $L^{x1}$, $L^{x2}$ and $L^{x3}$ is a linker. In some embodiments, $L^{x3}$ is a linker. Linkers are as defined herein. In some embodiments, $L^{x1}$, $L^{x2}$ and $L^{x3}$ are H.

In some embodiments, $S^1$ has the structure:

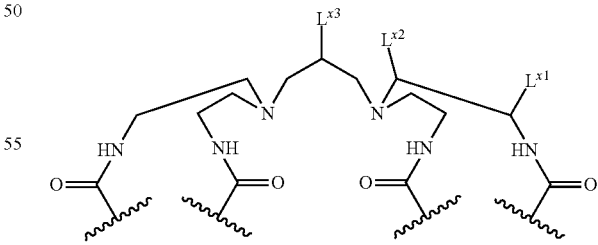

wherein $L^{x1}$, $L^{x2}$ and $L^{x3}$ are independently selected from H and a linker. In some embodiments, only one of $L^{x1}$, $L^{x2}$ and $L^{x3}$ is a linker. In some embodiments, $L^{x3}$ is a linker. Linkers are as defined herein. In some embodiments, $L^{x1}$, $L^{x2}$ and $L^{x3}$ are H.

In some embodiments, $S^1$ has the structure:

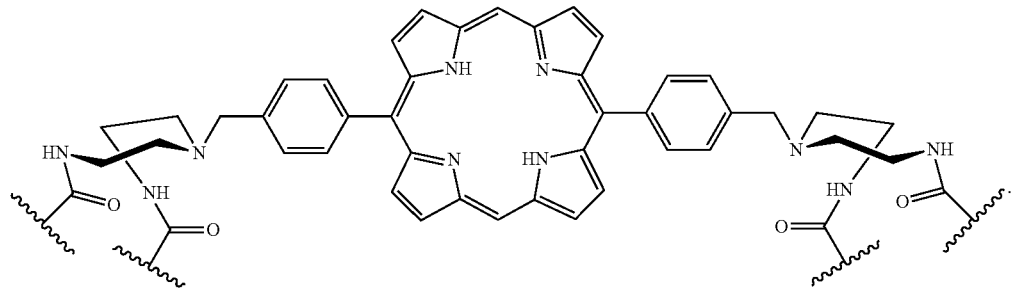

$S^2$ and $S^3$

In some embodiments, $S^2$ has the structure:

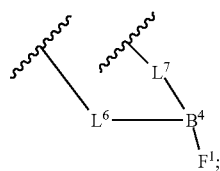

wherein $L^6$ and $L^7$ are independently selected from substituted or unsubstituted alkyl, substituted or unsubstituted heteroalkyl, substituted or unsubstituted aryl, substituted or unsubstituted heteroaryl and substituted or unsubstituted heterocycloalkyl. In some embodiments, $L^6$ and $L^7$ are independently selected from substituted or unsubstituted alkyl and substituted or unsubstituted heteroalkyl.

In some embodiments, one of $L^6$ and $L^7$ is substituted with a linker Linkers are as defined herein.

$B^4$ is selected from the elements capable of 3, 4, or 5 covalent bonds. In some embodiments, $B^4$ is selected from N, C, B, Si, and P. In some embodiments, $B^4$ is selected from N and C. In some embodiments, $B^4$ is N.

$F^1$ is selected from H, substituted or unsubstituted alkyl, substituted or unsubstituted heteroalkyl, substituted or unsubstituted aryl, substituted or unsubstituted heteroaryl and substituted or unsubstituted heterocycloalkyl. In some embodiments, $F^1$ is as defined herein.

In some embodiment $S^2$ has the structure:

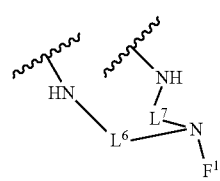

wherein $L^6$, $L^7$ and $F^1$ are as defined herein.

In some embodiment $S^2$ has the structure:

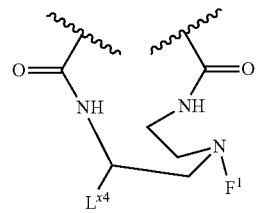

wherein $L^{x4}$ is H or a linker. $F^1$ is as defined herein. Linkers are as defined herein.

In some embodiments $S^2$ has the structure:

wherein $F^1$ is as defined herein.

In some embodiment $S^2$ has the structure:

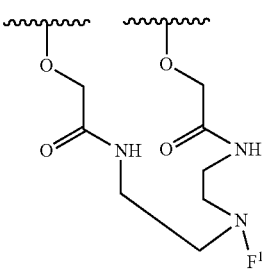

wherein $F^1$ is as defined herein.

In some embodiment $S^2$ has the structure:

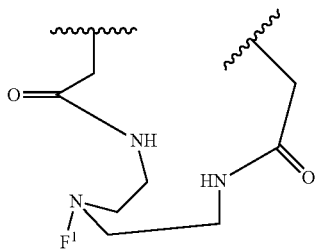

wherein $F^1$ is as defined herein.

In some embodiments, $S^3$ has the structure:

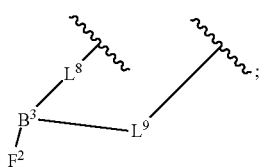

wherein
$L^8$ and $L^9$ are independently selected from substituted or unsubstituted alkyl, substituted or unsubstituted heteroalkyl, substituted or unsubstituted aryl, substituted or unsubstituted heteroaryl and substituted or unsubstituted heterocycloalkyl. In some embodiments, $L^8$ and $L^9$ are independently selected from substituted or unsubstituted alkyl and substituted or unsubstituted heteroalkyl.

In some embodiments, one of $L^8$ and $L^9$ is substituted with a linker Linkers are as defined herein.

$B^3$ is selected from the elements capable of 3, 4, or 5 covalent bonds. In some embodiments, $B^3$ is selected from N, C, B, Si, and P. In some embodiments, $B^3$ is selected from N and C. In some embodiments, $B^3$ is N.

$F^2$ is selected from H, substituted or unsubstituted alkyl, substituted or unsubstituted heteroalkyl, substituted or unsubstituted aryl, substituted or unsubstituted heteroaryl and substituted or unsubstituted heterocycloalkyl. In some embodiments, $F^2$ is as defined herein.

In some embodiment $S^3$ has the structure:

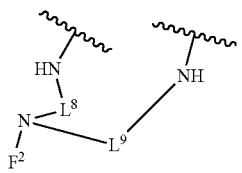

wherein $L^8$, $L^9$ and $F^2$ are as defined herein.

In some embodiment $S^3$ has the structure:

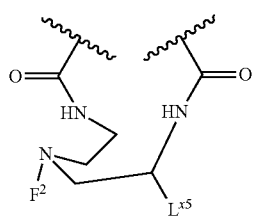

wherein $L^{x5}$ is H or a linker. $F^2$ is as defined herein. Linkers are as defined herein.

In some embodiment $S^3$ has the structure:

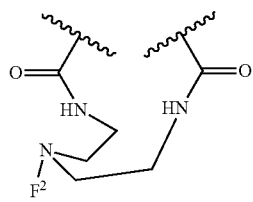

wherein $F^2$ is as defined herein.

In some embodiment $S^3$ has the structure:

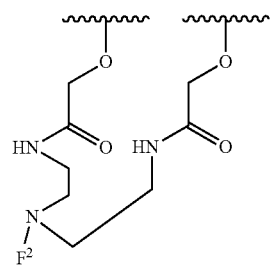

wherein $F^2$ is as defined herein.

In some embodiment $S^3$ has the structure:

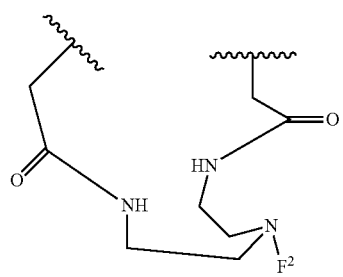

wherein $F^2$ is as defined herein.

In some embodiments, $S^2$ and $S^3$ have the same structure.

2.1.3. Linker to Functional/Targeting Moiety

A "linker", "linking member", or "linking moiety" as used herein is a moiety that joins or potentially joins, covalently or noncovalently, a first moiety to a second moiety. In particular, a linker attaches or could potentially attach a chelator described herein to another molecule, such as a targeting moiety. In some embodiments, a linker attaches or could potentially attach a chelator described herein to a solid support. A linker comprising a reactive functional group that can be further reacted with a reactive functional group on a structure of interest in order to attach the structure of interest to the linker is referred to as a "functionalized linker". In exemplary embodiments, a linker is a functionalized linker. In exemplary embodiments, a chelator comprises one or more functionalized linkers. In some embodiments, a linker comprises a targeting moiety. In some embodiments, a linker to a targeting moiety comprises a bond to the targeting moiety.

A linker can be any useful structure for that joins a chelator to a reactive functional group or a targeting moiety, such as an antibody. Examples of a linker include 0-order linkers (i.e., a bond), substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. Further exemplary linkers include substituted or unsubstituted ($C_1$, $C_2$, $C_3$, $C_4$, $C_5$, $C_6$, $C_7$, $C_8$, $C_9$ or $C_{10}$) alkyl, substituted or unsubstituted heteroalkyl, —C(O)NR'—, —C(O)O—, —C(O)S—, and —C(O)CR'R", wherein R' and R" are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. In some embodiments, a linker includes at least one heteroatom. Exemplary linkers also include —C(O)NH—, —C(O), —NH—, —S—, —O—, and the like. In an exemplary embodiment, a linker is a heteroalkyl substituted with a reactive functional group.

Reactive Functional Groups

In one embodiment, a linker comprises a reactive functional group (or a "reactive functional moiety", used synonymously), which can be further reacted to covalently attach the linker to a targeting moiety. Reactive functional groups and classes of reactions useful in practicing the present invention are generally those that are well known in the art of bioconjugate chemistry. Currently favored classes of reactions available with reactive functional groups of the invention are those which proceed under relatively mild conditions. These include, but are not limited to nucleophilic substitutions (e.g., reactions of amines and alcohols with acyl halides and activated esters), electrophilic substitutions (e.g., enamine reactions) and additions to carbon-carbon and carbon-heteroatom multiple bonds (e.g., Michael reactions and Diels-Alder reactions). These and other useful reactions are discussed, for example, in March, Advanced Organic Chemistry (3rd Ed., John Wiley & Sons, New York, 1985); Hermanson, Bioconjugate Techniques (Academic Press, San Diego, 1996); and Feeney et al., Modification of Proteins, Advances in Chemistry Series, Vol. 198 (American Chemical Society, Washington, D.C., 1982).

In some embodiments, a reactive functional group refers to a group selected from olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application or modification for a particular purpose is within the ability of one of skill in the art (see, for example, Sandler and Karo, eds., Organic Functional Group Preparations, (Academic Press, San Diego, 1989)).

A reactive functional group can be chosen according to a selected reaction partner. As an example, an activated ester, such as an NHS ester will be useful to label a protein via lysine residues. Sulfhydryl reactive groups, such as maleimides can be used to label proteins via amino acid residues carrying an SH-group (e.g., cystein). Antibodies may be labeled by first oxidizing their carbohydrate moieties (e.g., with periodate) and reacting resulting aldehyde groups with a hydrazine containing ligand.

The reactive functional groups can be chosen such that they do not participate in, or interfere with, the reactions necessary to assemble the reactive ligand. Alternatively, a reactive functional group can be protected from participating in the reaction by means of a protecting group. Those of skill in the art understand how to protect a particular functional group so that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

Amines and Amino-Reactive Groups

In one embodiment, a reactive functional group is selected from an amine, (such as a primary or secondary amine), hydrazine, hydrazide and sulfonylhydrazide. Amines can, for example, be acylated, alkylated or oxidized. Useful non-limiting examples of amino-reactive groups include N-hydroxysuccinimide (NHS) esters, sulfur-NHS esters, imidoesters, isocyanates, isothiocyanates, acylhalides, arylazides, p-nitrophenyl esters, aldehydes, sulfonyl chlorides, thiazolides and carboxyl groups.

NHS esters and sulfur-NHS esters react preferentially with a primary (including aromatic) amino groups of a reaction partner. The imidazole groups of histidines are known to compete with primary amines for reaction, but the reaction products are unstable and readily hydrolyzed. The reaction involves the nucleophilic attack of an amine on the acid carboxyl of an NHS ester to form an amide, releasing the N-hydroxysuccinimide.

Imidoesters are the most specific acylating reagents for reaction with amine groups of a molecule such as a protein. At a pH between 7 and 10, imidoesters react only with primary amines. Primary amines attack imidates nucleophilically to produce an intermediate that breaks down to amidine at high pH or to a new imidate at low pH. The new imidate can react with another primary amine, thus cross-linking two amino groups, a case of a putatively monofunctional imidate reacting bifunctionally. The principal product of reaction with primary amines is an amidine that is a stronger base than the original amine. The positive charge of the original amino group is therefore retained. As a result, imidoesters do not affect the overall charge of the conjugate.

Isocyanates (and isothiocyanates) react with the primary amines of the conjugate components to form stable bonds. Their reactions with sulfhydryl, imidazole, and tyrosyl groups give relatively unstable products.

Acylazides are also used as amino-specific reagents in which nucleophilic amines of the reaction partner attack acidic carboxyl groups under slightly alkaline conditions, e.g. pH 8.5.

Arylhalides such as 1,5-difluoro-2,4-dinitrobenzene react preferentially with the amino groups and tyrosine phenolic groups of the conjugate components, but also with its sulfhydryl and imidazole groups.

p-Nitrophenyl esters of carboxylic acids are also useful amino-reactive groups. Although the reagent specificity is not very high, α- and ε-amino groups appear to react most rapidly.

Aldehydes react with primary amines of the conjugate components (e.g., 8-amino group of lysine residues). Although unstable, Schiff bases are formed upon reaction of the protein amino groups with the aldehyde. Schiff bases, however, are stable, when conjugated to another double bond. The resonant interaction of both double bonds prevents hydrolysis of the Schiff linkage. Furthermore, amines at high local concentrations can attack the ethylenic double bond to form a stable Michael addition product. Alternatively, a stable bond may be formed by reductive amination.

Aromatic sulfonyl chlorides react with a variety of sites of the conjugate components, but reaction with the amino groups is the most important, resulting in a stable sulfonamide linkage.

Free carboxyl groups react with carbodiimides, soluble in both water and organic solvents, forming pseudoureas that can then couple to available amines yielding an amide linkage. Yamada et al., Biochemistry, 1981, 20: 4836-4842, e.g., teach how to modify a protein with carbodiimides.

Sulfhydryl and Sulfhydryl-Reactive Groups

In another embodiment, a reactive functional group is selected from a sulfhydryl group (which can be converted to disulfides) and sulfhydryl-reactive group. Useful non-limiting examples of sulfhydryl-reactive groups include maleimides, alkyl halides, acyl halides (including bromoacetamide or chloroacetamide), pyridyl disulfides, and thiophthalimides.

Maleimides react preferentially with the sulfhydryl group of the conjugate components to form stable thioether bonds. They also react at a much slower rate with primary amino groups and the imidazole groups of histidines. However, at pH 7 the maleimide group can be considered a sulfhydryl-specific group, since at this pH the reaction rate of simple thiols is 1000-fold greater than that of the corresponding amine.

Alkyl halides react with sulfhydryl groups, sulfides, imidazoles, and amino groups. At neutral to slightly alkaline pH, however, alkyl halides react primarily with sulfhydryl groups to form stable thioether bonds. At higher pH, reaction with amino groups is favored.

Pyridyl disulfides react with free sulfhydryl groups via disulfide exchange to give mixed disulfides. As a result, pyridyl disulfides are relatively specific sulfhydryl-reactive groups.

Thiophthalimides react with free sulfhydryl groups to also form disulfides.

Other Reactive Functional Groups

Other exemplary reactive functional groups include:
(i) carboxyl groups and various derivatives thereof including, but not limited to, N-hydroxybenztriazole esters, acid halides, acyl imidazoles, thioesters, p-nitrophenyl esters, alkyl, alkenyl, alkynyl and aromatic esters;
(ii) hydroxyl groups, which can be converted to esters, ethers, aldehydes, etc.;
(iii) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;
(iv) dienophile groups, which are capable of participating in Diels-Alder reactions such as, for example, maleimido groups;
(v) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;
(vi) alkenes, which can undergo, for example, cycloadditions, acylation, Michael addition, etc;
(vii) epoxides, which can react with, for example, amines and hydroxyl groups;
(ix) phosphoramidites and other standard functional groups useful in nucleic acid synthesis and
(x) any other functional group useful to form a covalent bond between the functionalized ligand and a molecular entity or a surface.

Functional Groups with Non-Specific Reactivities

In addition to the use of site-specific reactive moieties, the present invention contemplates the use of non-specific reactive groups to link a chelator to a targeting moiety. Non-specific groups include photoactivatable groups, for example.

Photoactivatable groups are ideally inert in the dark and are converted to reactive species in the presence of light. In one embodiment, photoactivatable groups are selected from precursors of nitrenes generated upon heating or photolysis of azides. Electron-deficient nitrenes are extremely reactive and can react with a variety of chemical bonds including N—H, O—H, C—H, and C═C. Although three types of azides (aryl, alkyl, and acyl derivatives) may be employed, arylazides are presently preferred. The reactivity of arylazides upon photolysis is better with N—H and O—H than C—H bonds. Electron-deficient arylnitrenes rapidly ring-expand to form dehydroazepines, which tend to react with nucleophiles, rather than form C—H insertion products. The reactivity of arylazides can be increased by the presence of electron-withdrawing substituents such as nitro or hydroxyl groups in the ring. Such substituents push the absorption maximum of arylazides to longer wavelength. Unsubstituted arylazides have an absorption maximum in the range of 260-280 nm, while hydroxy and nitroarylazides absorb significant light beyond 305 nm. Therefore, hydroxy and nitroarylazides are most preferable since they allow to employ less harmful photolysis conditions for the affinity component than unsubstituted arylazides.

In another preferred embodiment, photoactivatable groups are selected from fluorinated arylazides. The photolysis products of fluorinated arylazides are arylnitrenes, all of which undergo the characteristic reactions of this group, including C—H bond insertion, with high efficiency (Keana et al., *J. Org. Chem.* 55: 3640-3647, 1990).

In another embodiment, photoactivatable groups are selected from benzophenone residues. Benzophenone reagents generally give higher crosslinking yields than arylazide reagents.

In another embodiment, photoactivatable groups are selected from diazo compounds, which form an electron-deficient carbene upon photolysis. These carbenes undergo a variety of reactions including insertion into C—H bonds, addition to double bonds (including aromatic systems), hydrogen attraction and coordination to nucleophilic centers to give carbon ions.

In still another embodiment, photoactivatable groups are selected from diazopyruvates. For example, the p-nitrophenyl ester of p-nitrophenyl diazopyruvate reacts with aliphatic amines to give diazopyruvic acid amides that undergo ultraviolet photolysis to form aldehydes. The photolyzed diazopyruvate-modified affinity component will react like formaldehyde or glutaraldehyde forming intraprotein crosslinks.

In exemplary embodiments, a linker joins a chelator to a targeting moiety. That is, in exemplary embodiments, a linker comprises a targeting moiety. In some embodiments, a chelator comprises a linker to a targeting moiety. Any linker described herein may be a linker comprising a reactive functional group that could react with a reactive functional group on a targeting moiety to join the linker to the targeting moiety. Any linker described herein may be a linker comprising a bond to a targeting moiety. The term "targeting moiety" refers to a moiety serves to target or direct the molecule to which it is attached (e.g., a chelator or a chelator complexed to a metal ion (such as a radionuclide)) to a particular location or molecule. Thus, for example, a targeting moiety may be used to target a molecule to a specific target protein or enzyme, or to a particular cellular location, to a particular cell type or to a diseased tissue. As will be appreciated by those in the art, the localization of proteins within a cell is a simple method for increasing effective concentration. For example, shuttling an imaging agent and/or therapeutic into the nucleus confines them to a smaller space thereby increasing concentration. Finally, the physiological target may simply be localized to a specific compartment, and the agents must be localized appropriately.

The targeting moiety can be a small molecule (e.g., MW<500D), which includes both non-peptides and peptides. Examples of a targeting moiety also include peptides, polypeptides (including proteins, and in particular antibodies, which includes antibody fragments), nucleic acids, oligonucleotides, carbohydrates, lipids, hormones (including proteinaceous and steroid hormones), growth factors, lectins, receptors, receptor ligands, cofactors and the like. Targets of a targeting moiety can include a complementary nucleic acid, a receptor, an antibody, an antigen or a lectin, for example.

In exemplary embodiments, a targeting moiety can bind to a target with high binding affinity. In other words, a targeting moiety with high binding affinity to a target has a high specificity for or specifically binds to the target. In some embodiments, a high binding affinity is given by a dissociation constant $K_d$ of about $10^{-7}$ M or less. In exemplary embodiments, a high binding affinity is given by a dissociation constant $K_d$ of about $10^{-8}$ M or less, about $10^{-9}$ M or less, about $10^{-10}$ M or less, about $10^{-11}$ M or less, about $10^{-12}$ M or less, about $10^{-13}$ M or less, about $10^{-14}$ M or less or about $10^{-15}$ M or less. A compound may have a high binding affinity for a target if the compound comprises a portion, such as a targeting moiety, that has a high binding affinity for the target.

In exemplary embodiments, a targeting moiety is an antibody. An "antibody" refers to a protein comprising one or more polypeptides substantially encoded by all or part of the recognized immunoglobulin genes. The recognized immunoglobulin genes, for example in humans, include the kappa (κ), lambda (λ) and heavy chain genetic loci, which together compose the myriad variable region genes, and the constant region genes mu (μ), delta (δ), gamma (γ), epsilon (ε) and alpha (α), which encode the IgM, IgD, IgG, IgE, and IgA isotypes respectively. Antibody herein is meant to include full length antibodies and antibody fragments, and may refer to a natural antibody from any organism, an engineered antibody or an antibody generated recombinantly for experimental, therapeutic or other purposes as further defined below. Antibody fragments include Fab, Fab', F(ab')$_2$, Fv, scFv or other antigen-binding subsequences of antibodies and can include those produced by the modification of whole antibodies or those synthesized de novo using recombinant DNA technologies. The term "antibody" refers to both monoclonal and polyclonal antibodies. Antibodies can be antagonists, agonists, neutralizing, inhibitory or stimulatory.

While a targeting moiety may be appended to a chelator in order to localize the compound to a specific region in an animal, certain chelators have a natural affinity for cells, tissue, organs or some other part of the animal. For example, a chelator disclosed herein might have a natural or intrinsic affinity for bone. Thus, in some embodiments, a chelator (di-macrocycle), does not comprise a targeting moiety or a linker to a targeting moiety. A chelator lacking a targeting moiety can be used in any method that does not require specific targeting.

In some embodiments, a chelator comprises a linker to a solid support. That is, any linker described herein may be a linker comprising a reactive functional group that could react with a reactive functional group on a solid support to join the linker to the solid support. Any linker described herein may be a linker comprising a bond to a solid support. A "solid support" is any material that can be modified to contain discrete individual sites suitable for the attachment or association of a chelator. Suitable substrates include biodegradable beads, non-biodegradable beads, silica beads, magnetic beads, latex beads, glass beads, quartz beads, metal beads, gold beads, mica beads, plastic beads, ceramic beads, or combinations thereof. Of particular use are biocompatible polymers, including biodegradable polymers that are slowly removed from the system by enzymatic degradation. Example biodegradable materials include starch, cross-linked starch, poly(ethylene glycol), polyvinylpyrrolidine, polylactides (PLA), polyglycolides (PGA), poly(lactide-co-glycolides) (PLGA), polyanhydrides, poly-orthoesters, poly(DTH iminocarbonate), poly(bisphenol A iminocarbonate), polycyanoacrylate, polyphosphazene, mixtures thereof and combinations thereof. Other suitable substances for forming the particles exist and can be used. In some embodiments, a solid support is a bead comprising a cross-linked starch, for example, cross-linked potato starch. Beads made from starch are completely biodegradable in the body, typically by serum amylase, a naturally occurring enzyme found in the body. In these embodiments, the chelator optionally further comprises a targeting moiety or a linker to a targeting moeity. In cases where a chelator that is attached to a solid support does not comprise a targeting moiety, the chealtor can be localized directly by the practitioner, for example, by direct surgical implantation.

In some embodiments, a linker has the structure -$L^{11}$-X, wherein $L^{11}$ is selected from a bond, acyl, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl; and X is a reactive functional group or a targeting moiety.

In some embodiments, $L^{11}$ is selected from substituted or unsubstituted alkyl and substituted or unsubstituted heteroalkyl. In some embodiments, $L^{11}$ is heteroalkyl. In some embodiments, $L^{11}$ is ($C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$ or $C_{20}$) alkyl in which 1, 2 or 3 atoms are replaced with a heteroatom, such as nitrogen or oxygen.

In some embodiments, X is selected from —NH$_2$ and —CO(O)H.

In some embodiments, -$L^{11}$-X is selected from

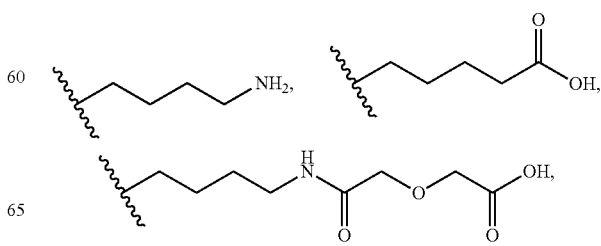

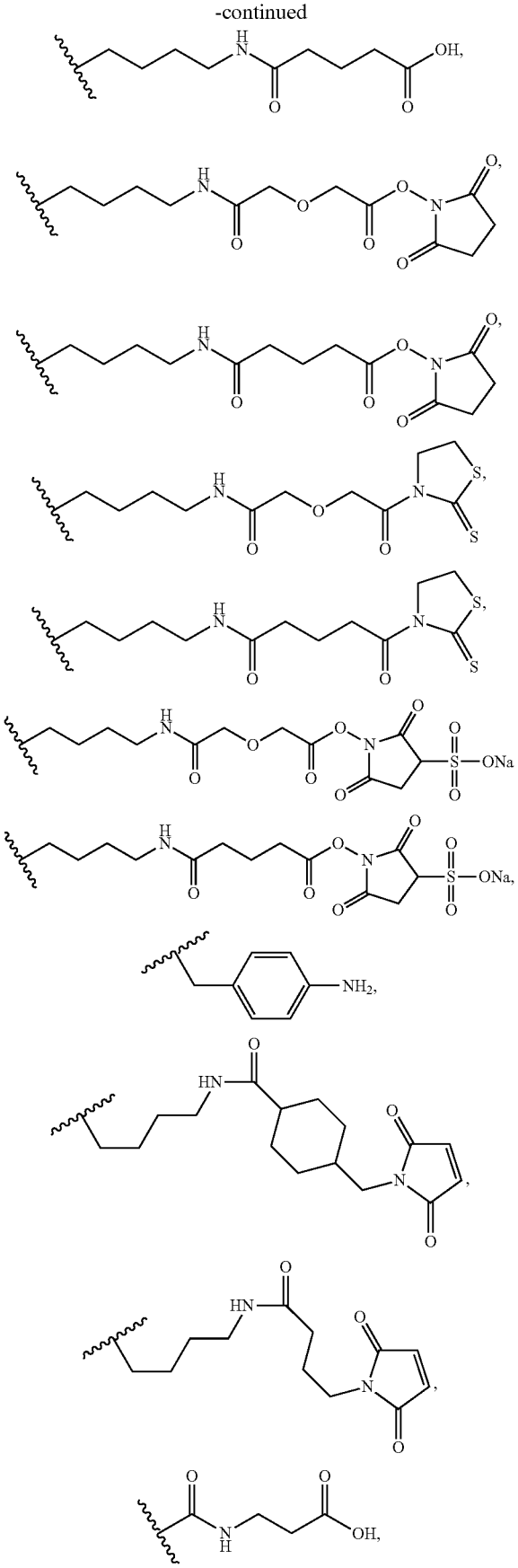

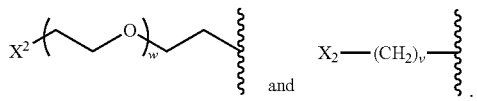

In exemplary embodiments, X is a targeting moiety.

In exemplary embodiments, a linker is a linker to a targeting moiety. In some embodiments, the targeting moiety is selected from a polypeptide, a nucleic acid, a lipid, a polysaccharide, a small molecule, a cofactor and a hormone. In exemplary embodiments, the targeting moiety is an antibody or antibody fragment.

In some embodiments, a linker includes an aliphatic carbon chain or a poly-ethyleneglycol (PEG) chain. Thus, a linker can comprise a structure selected from:

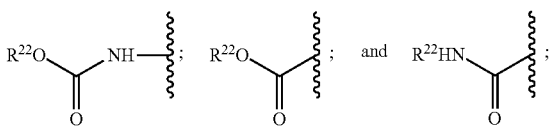

The integer v is selected from 1 to 20, and w is an integer from 1 to 1,000 or 1 to 500 or 1 to 100 or 1 to 50 or 1 to 10.

Exemplary $X^2$ groups include OH, alkoxy, and one of the following structures:

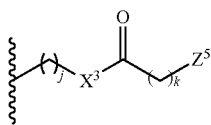

wherein $R^{22}$ is a member selected from H, substituted or unsubstituted alkyl, substituted or unsubstituted heteroalkyl, substituted or unsubstituted aryl, substituted or unsubstituted heteroaryl and substituted or unsubstituted heterocycloalkyl. The integer v is selected from 1 to 20, and w is an integer from 1 to 1,000 or 1 to 500 or 1 to 100 or 1 to 50 or 1 to 10.

In some embodiments, a linker has the structure:

wherein $Z^5$ is selected from H, $OR^{23}$, $SR^{23}$, $NHR^{23}$, $OCOR^{24}$, $OC(O)NHR^{24}$, $NHC(O)OR^{23}$, $OS(O)_2OR^{23}$, and C(O)R²⁴. R²³ is selected from H, substituted or unsubstituted alkyl, and substituted or unsubstituted heteroalkyl. R²⁴ is selected from H, OR²⁵, NR²⁵NH₂, SH, C(O)R²⁵, NR²⁵H, substituted or unsubstituted alkyl and substituted or unsubstituted heteroalkyl. R²⁵ is selected from H, substituted or unsubstituted alkyl and substituted or unsubstituted alkyl. X³ is selected from O, S and NR²⁶, wherein R²⁶ is a member selected from H, substituted or unsubstituted alkyl and substituted or unsubstituted heteroalkyl. The integers j and k are members independently selected from 1, 2, 3, 4, 5, 6, 7, In some embodiments, $F^1$, $F^2$ or both are modifying moieties. In some embodiments, $F^1$ and $F^2$ are modifying moieties.

In some embodiments, $F^1$, $F^2$ or both are substituted or unsubstituted heteroalkyl. In some embodiments, $F^1$, $F^2$ or both are a substituted or unsubstituted polyether. In some embodiments, $F^1$, $F^2$ or both comprise an estradiol-derived moiety. In some embodiments, $F^1$, $F^2$ or both are a polyether substituted with an estradiol-derived moiety.

In some embodiments, $F^1$, $F^2$ or both are members independently selected from:

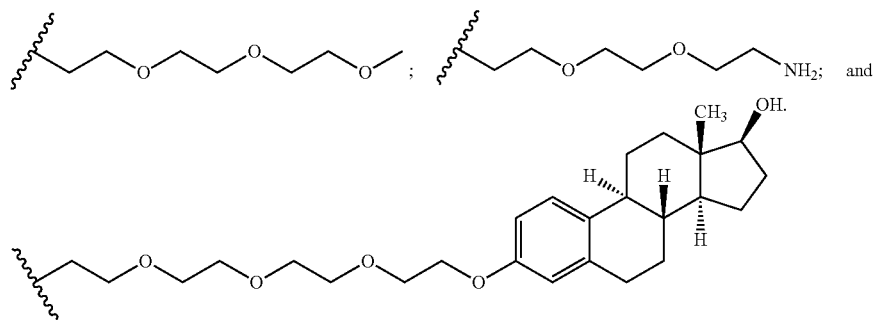

8, 9, 10, 11, 12, 13, 14, 15, 16, 17, 18, 19 and 20. In some embodiments, the integers j and k are members independently selected from 1, 2, 3, 4, 5, 6.

In a linker with multiple reactive functional groups, a particular functional group can be chosen such that it does not participate in, or interfere with, the reaction controlling the attachment of the functionalized spacer component to another ligand component. Alternatively, the reactive functional group can be protected from participating in the reaction by the presence of a protecting group. Those of skill in the art understand how to protect a particular functional group from interfering with a chosen set of reaction conditions. For examples of useful protecting groups, See Greene et al., PROTECTIVE GROUPS IN ORGANIC SYNTHESIS, John Wiley & Sons, New York, 1991.

2.1.4. Modifying Moiety

In some embodiments, one, two or all of $S^1$, $S^2$ and $S^3$ comprise a modifying moiety.

Each of the modifying moieties can be the same or different. The modifying moiety modifies various properties of the di-macrocycle and/or a complex formed between the di-macrocycle and a metal ion, such as solubility, charge, or affinity. In some embodiments, the modifying moiety does not interact with the metal when the di-macrocycle is complexed to a metal. In some embodiments, the modifying moiety is a solubilizing group, an estradiol-derived moiety, a prodrug moiety (for example, with a cleavable moiety), an oligonucleotide, ssDNA, dsDNA, RNA, or a peptide. The solubilizing group improves solubility of the di-macrocycle and/or a complex formed between the di-macrocycle and a metal ion in aqueous media.

In some embodiments, $S^2$ and $S^3$ comprise a modifying moiety. In some embodiments, $S^1$ comprises a linker; and $S^2$ and $S^3$ comprise a modifying moiety. In some embodiments, $S^2$ and $S^3$ comprise a modifying moiety; and $S^2$ or $S^3$ further comprises a linker.

In some embodiments, $F^1$, $F^2$ or both comprise a modifying moiety. In some embodiments, $F^1$ and $F^2$ comprise a modifying moiety.

In some embodiments, $F^1$, $F^2$ or both are a peptide. In some embodiments, $F^1$, $F^2$ or both are

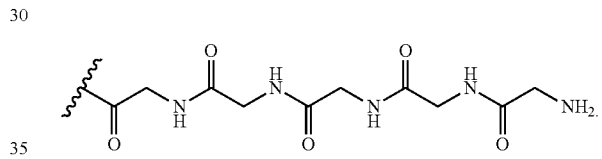

In some embodiments, $F^1$, $F^2$ or both comprise an olignucleotide. In some embodiments, $F^1$ and $F^2$ each comprise an oligonucleotide. In some embodiments, the oligonucleotide of $F^1$ is complementary to the oligonucleotide of $F^2$.

In some embodiments, $F^1$ and $F^2$ are the same.

In some embodiments, $F^1$, $F^2$ or both are a linker.

2.1.5. Exemplary Di-Macrocycles

In some embodiments, the invention provides a di-macrocycle having the structure:

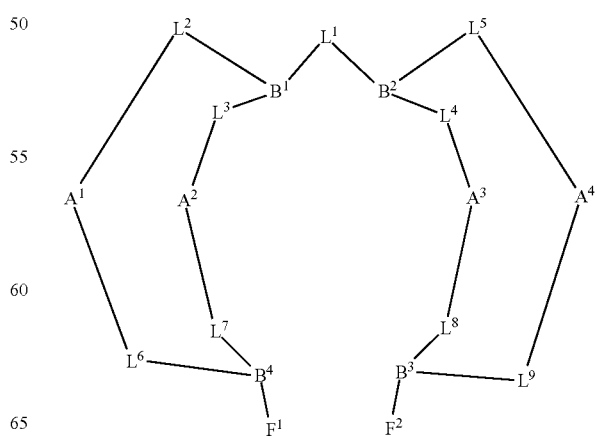

wherein

B$^1$, B$^2$, B$^3$, and B$^4$ are independently selected from N and C;

F$^1$ and F$^2$ are independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl;

L$^1$, L$^2$, L$^3$, L$^4$, L$^5$, L$^6$, L$^7$, L$^8$, and L$^9$ are independently selected from substituted or unsubstituted alkyl, and substituted or unsubstituted heteroalkyl;

A$^1$, A$^2$, A$^3$ and A$^4$ are members independently selected from:

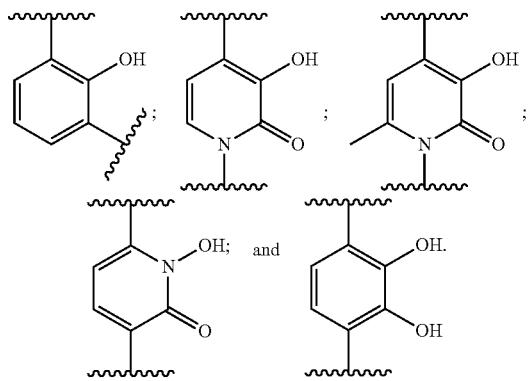

In some embodiments, F$^1$ and F$^2$ are modifying moieties. Modifying moieties are as defined herein.

In some embodiments, the di-macrocycle is covalently modified with at least one linker. In some embodiments, one of L$^1$, L$^2$, L$^3$, L$^4$, L$^5$, L$^6$, L$^7$, L$^8$, and L$^9$ is substituted with a linker. In some embodiments, L$^5$ is substituted with a linker. In some embodiments, L$^1$ is substituted with a linker. In some embodiments, one of L$^6$, L$^7$, L$^8$ and L$^9$ is substituted with a linker.

In some embodiments, the invention provides a di-macrocycle having the structure:

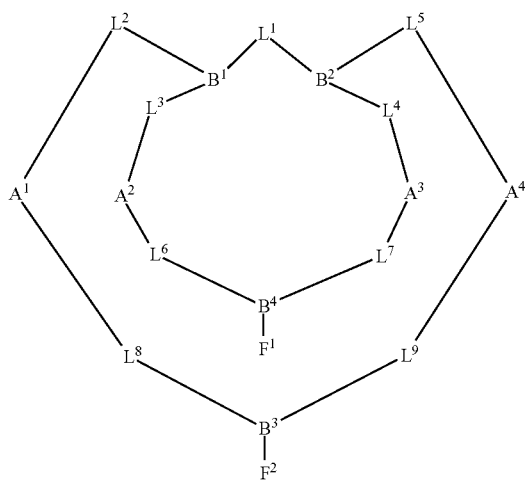

wherein

B$^1$, B$^2$, B$^3$, and B$^4$ are independently selected from N and C;

F$^1$ and F$^2$ are independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl;

L$^1$, L$^2$, L$^3$, L$^4$, L$^5$, L$^6$, L$^7$, L$^8$, and L$^9$ are independently selected from substituted or unsubstituted alkyl, and substituted or unsubstituted heteroalkyl;

A$^1$, A$^2$, A$^3$ and A$^4$ are members independently selected from:

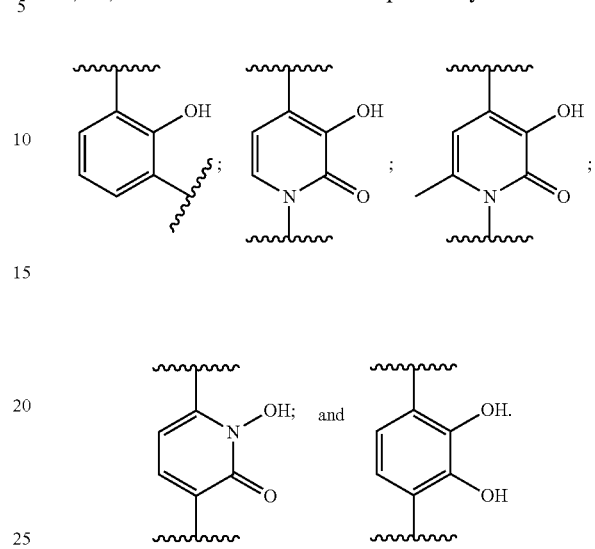

In some embodiments, F$^1$ and F$^2$ are modifying moieties. Modifying moieties are as defined herein.

In some embodiments, the di-macrocycle is covalently modified with at least one linker. In some embodiments, one of L$^1$, L$^2$, L$^3$, L$^4$, L$^5$, L$^6$, L$^7$, L$^8$, and L$^9$ is substituted with a linker. In some embodiments, L$^5$ is substituted with a linker. In some embodiments, L$^1$ is substituted with a linker. In some embodiments, one of L$^6$, L$^7$, L$^8$ and L$^9$ is substituted with a linker.

In some embodiments, the invention provides a di-macrocycle having the structure:

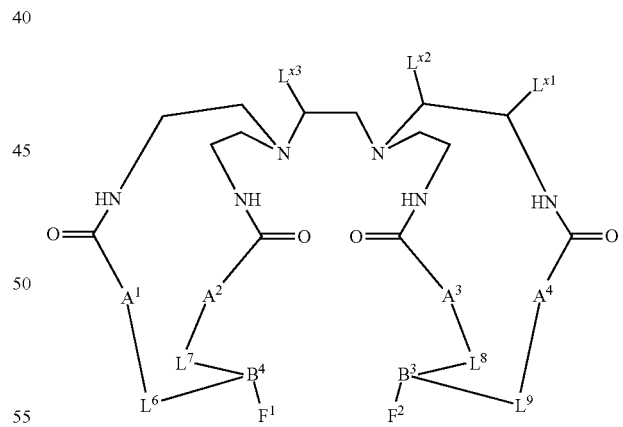

wherein

B$^3$ and B$^4$ are independently selected from N and C;

F$^1$ and F$^2$ are independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl;

L$^6$, L$^7$, L$^8$, and L$^9$ are independently selected from substituted or unsubstituted alkyl, and substituted or unsubstituted heteroalkyl;

$A^1$, $A^2$, $A^3$ and $A^4$ are members independently selected from:

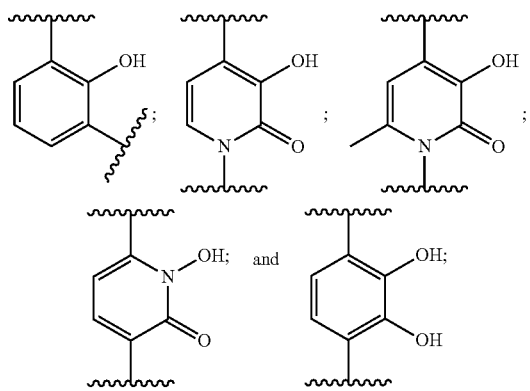

and $L^{x1}$, $L^{x2}$ and $L^{x3}$ are independently selected from H and a linker.

In some embodiments, $F^1$ and $F^2$ are modifying moieties. Modifying moieties are as defined herein.

In some embodiments, the di-macrocycle is covalently modified with at least one linker. In some embodiments, one of $L^{x1}$, $L^{x2}$, and $L^{x3}$ is a linker. In some embodiments, $L^{x1}$ is a linker. In some embodiments, one of $L^6$, $L^7$, $L^8$ and $L^9$ is substituted with a linker.

In some embodiments, the invention provides a di-macrocycle having the structure:

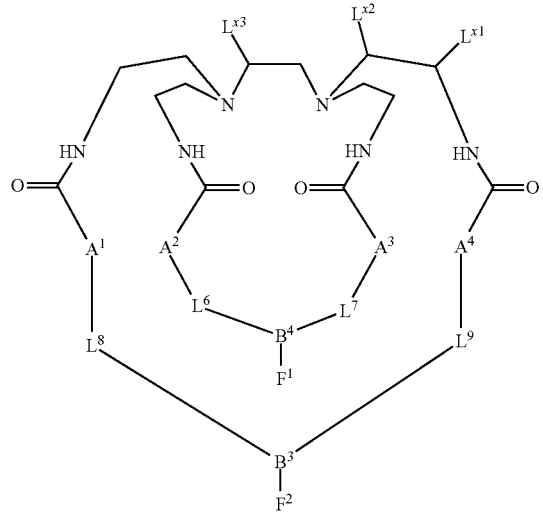

wherein $B^3$ and $B^4$ are independently selected from N and C;

$F^1$ and $F^2$ are independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl;

$L^6$, $L^7$, $L^8$, and $L^9$ are independently selected from substituted or unsubstituted alkyl, and substituted or unsubstituted heteroalkyl;

$A^1$, $A^2$, $A^3$ and $A^4$ are members independently selected from:

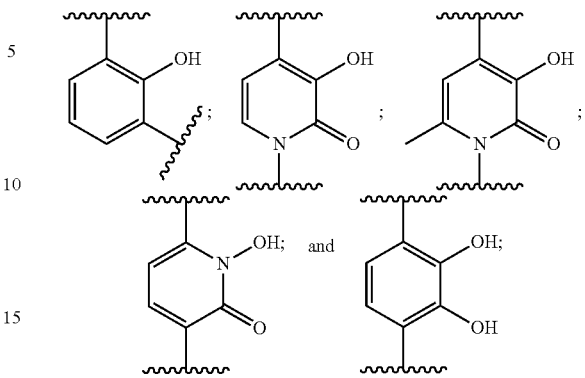

and $L^{x1}$, $L^{x2}$ and $L^{x3}$ are independently selected from H and a linker.

In some embodiments, $F^1$ and $F^2$ are modifying moieties. Modifying moieties are as defined herein.

In some embodiments, the di-macrocycle is covalently modified with at least one linker. In some embodiments, one of $L^{x1}$, $L^{x2}$, and $L^{x3}$ is a linker. In some embodiments, $L^{x1}$ is a linker. In some embodiments, one of $L^6$, $L^7$, $L^8$ and $L^9$ is substituted with a linker.

In some embodiments, the invention provides a di-macrocycle having the structure:

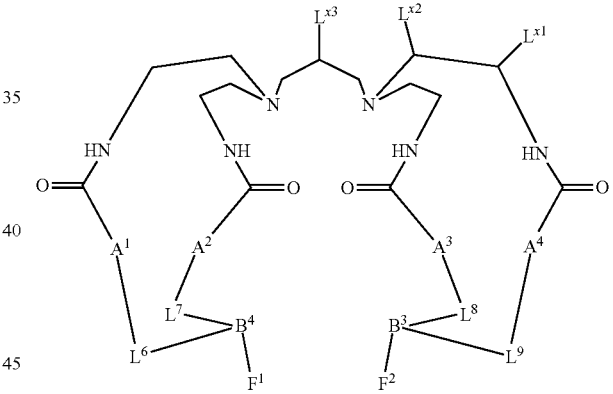

wherein $B^3$ and $B^4$ are independently selected from N and C;

$F^1$ and $F^2$ are independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl;

$L^6$, $L^7$, $L^8$, and $L^9$ are independently selected from substituted or unsubstituted alkyl, and substituted or unsubstituted heteroalkyl;

$A^1$, $A^2$, $A^3$ and $A^4$ are members independently selected from:

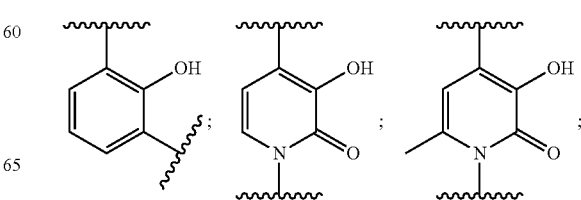

-continued

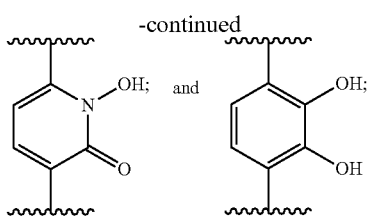

and
$L^{x1}$, $L^{x2}$ and $L^{x3}$ are independently selected from H and a linker.
In some embodiments, $F^1$ and $F^2$ are modifying moieties. Modifying moieties are as defined herein.
In some embodiments, the di-macrocycle is covalently modified with at least one linker. In some embodiments, one of $L^{x1}$, $L^{x2}$, and $L^{x3}$ is a linker. In some embodiments, $L^{x3}$ is a linker. In some embodiments, one of $L^6$, $L^7$, $L^8$ and $L^9$ is substituted with a linker.
In some embodiments, the invention provides a di-macrocycle having the structure:

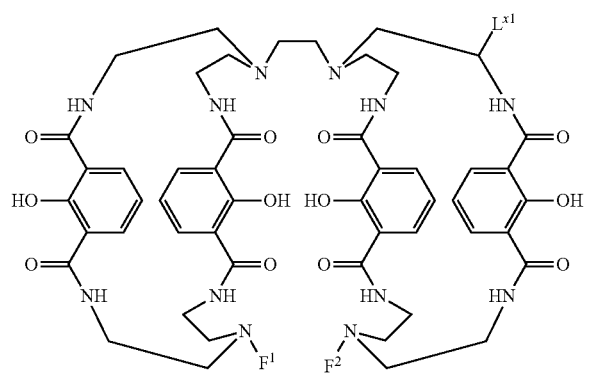

wherein $L^{x1}$ is H or a linker; and $F^1$ and $F^2$ are modifying moieties.
Linkers are as defined herein.
In some embodiments, $L^{x1}$ is H. In some embodiments, $L^{x1}$ is a linker.
In some embodiments, $F^1$ and $F^2$ are substituted or unsubstituted heteroalkyl. In some embodiments, $F^1$ and $F^2$ are a substituted or unsubstituted polyether. In some embodiments, $F^1$ and $F^2$ are a polyether substituted with an estradiol-derived moiety.
In some embodiments, $F^1$ and $F^2$ are members independently selected from:

In some embodiments, $F^1$ and $F^2$ are the same. In some embodiments, $F^1$ and $F^2$ are different.

In some embodiments, the invention provides a di-macrocycle having the structure:

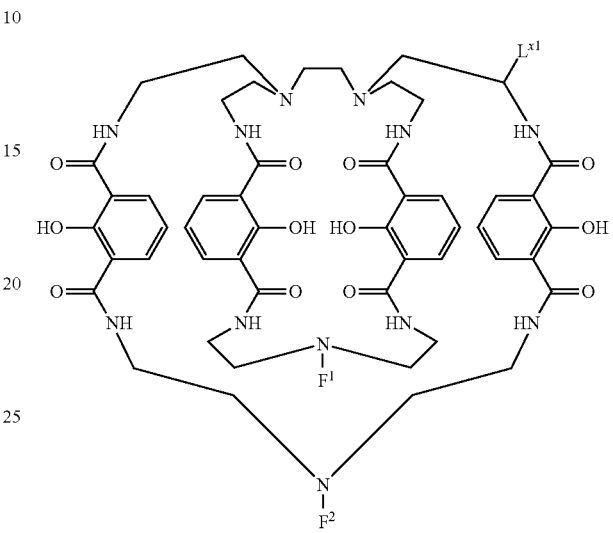

wherein $L^{x1}$ is H or a linker; and $F^1$ and $F^2$ are modifying moieties.

Linkers are as defined herein.

In some embodiments, $L^{x1}$ is H. In some embodiments, $L^{x1}$ is a linker.

In some embodiments, $F^1$ and $F^2$ are substituted or unsubstituted heteroalkyl. In some embodiments, $F^1$ and $F^2$ are a substituted or unsubstituted polyether. In some embodiments, $F^1$ and $F^2$ are a polyether substituted with an estradiol-derived moiety.

In some embodiments, $F^1$ and $F^2$ are members independently selected from:

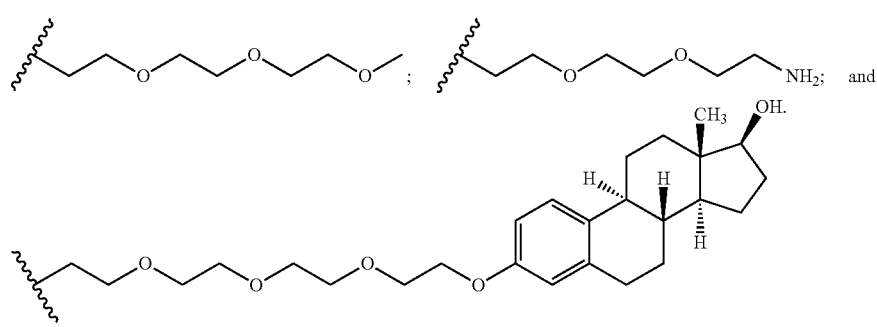

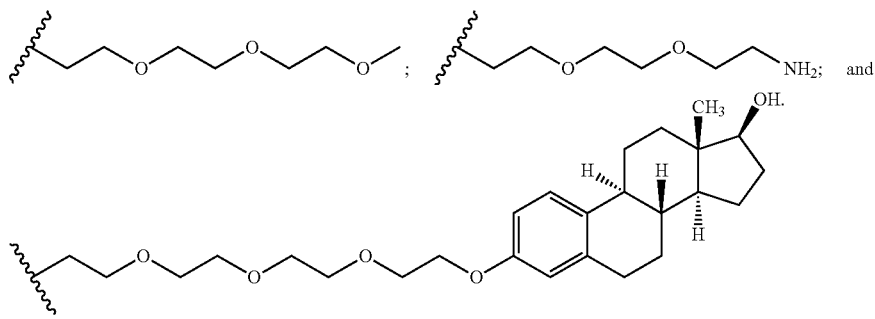

In some embodiments, $F^1$ and $F^2$ are the same. In some embodiments, $F^1$ and $F^2$ are different.

In some embodiments, the invention provides a di-macrocycle having the structure:

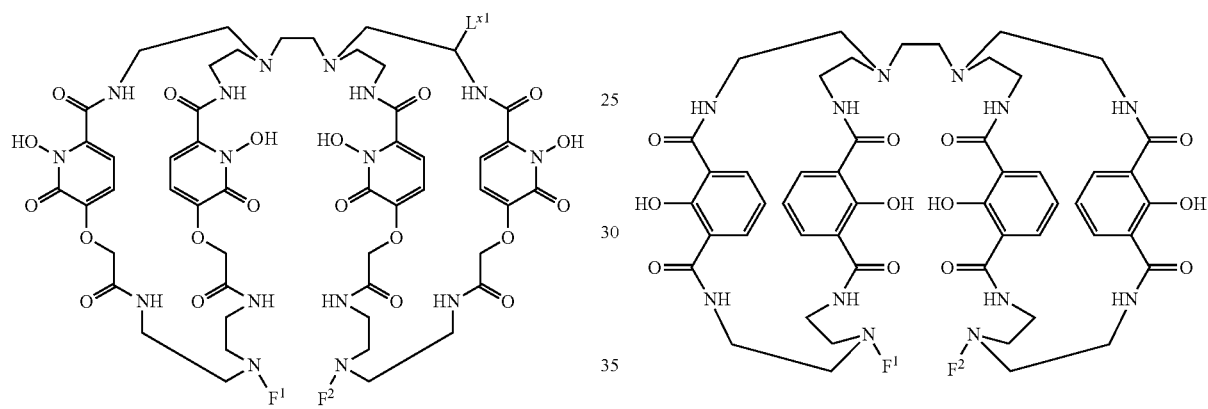

wherein $L^{x1}$ is H or a linker; and $F^1$ and $F^2$ are modifying moieties.
Linkers are as defined herein.
In some embodiments, $L^{x1}$ is H. In some embodiments, $L^{x1}$ is a linker.
In some embodiments, $F^1$ and $F^2$ are substituted or unsubstituted heteroalkyl. In some embodiments, $F^1$ and $F^2$ are a substituted or unsubstituted polyether. In some embodiments, $F^1$ and $F^2$ are a polyether substituted with an estradiol-derived moiety.
In some embodiments, $F^1$ and $F^2$ are members independently selected from:

In some embodiments, $F^1$ and $F^2$ are the same. In some embodiments, $F^1$ and $F^2$ are different.

In some embodiments, the invention provides a di-macrocycle having the structure:

wherein $F^1$ and $F^2$ are modifying moieties.

In some embodiments, $F^1$ and $F^2$ are peptides. In some embodiments, $F^1$ and $F^2$ are the same. In some embodiments, $F^1$ and $F^2$ are each

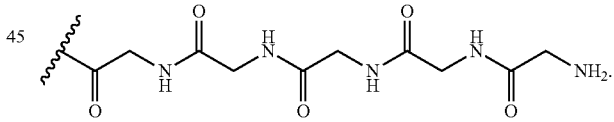

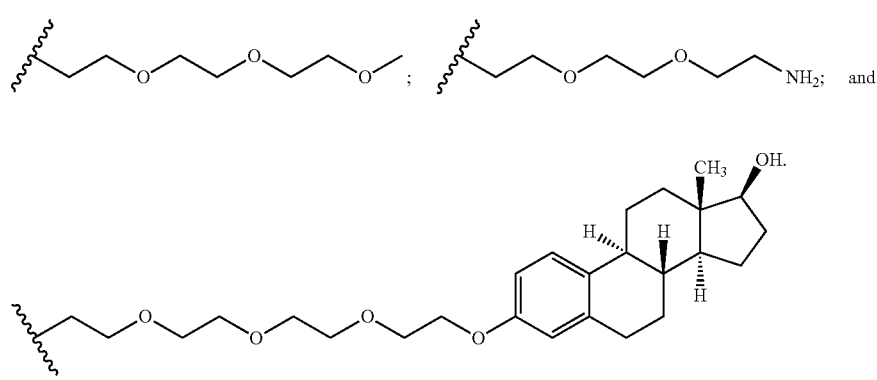

In some embodiments, $F^1$ and $F^2$ are different.

In some embodiments, $F^1$ and $F^2$ each comprise an oligonucleotide. In some embodiments, the oligonucleotide of $F^1$ is complementary to the oligonucleotide of $F^2$.

In some embodiments, the invention provides a di-macrocycle having the structure:

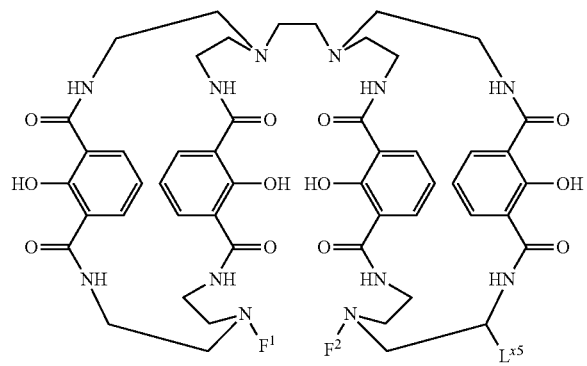

wherein $L^{x5}$ is a linker; and $F^1$ and $F^2$ are modifying moieties.

Linkers are as defined herein.

In some embodiments, $F^1$ and $F^2$ are substituted or unsubstituted heteroalkyl. In some embodiments, $F^1$ and $F^2$ are a substituted or unsubstituted polyether. In some embodiments, $F^1$ and $F^2$ are a polyether substituted with an estradiol-derived moiety.

In some embodiments, $F^1$ and $F^2$ are members independently selected from:

In some embodiments, $F^1$ and $F^2$ are the same. In some embodiments, $F^1$ and $F^2$ are different.

In some embodiments, the invention provides a di-macrocycle having the structure:

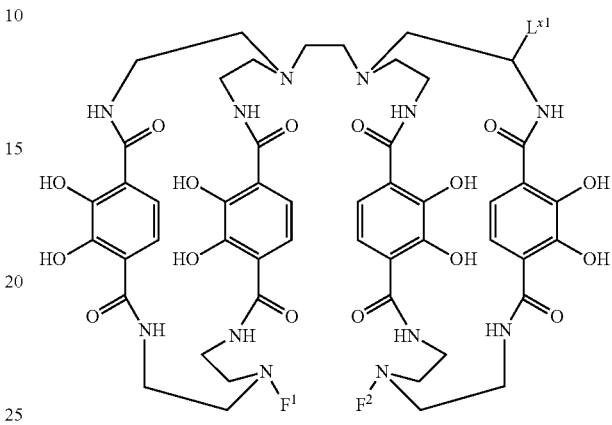

wherein $L^{x1}$ is H or a linker; and $F^1$ and $F^2$ are modifying moieties.

Linkers are as defined herein.

In some embodiments, $L^{x1}$ is H. In some embodiments, $L^{x1}$ is a linker.

In some embodiments, $F^1$ and $F^2$ are substituted or unsubstituted heteroalkyl. In some embodiments, $F^1$ and $F^2$ are a substituted or unsubstituted polyether. In some embodiments, $F^1$ and $F^2$ are a polyether substituted with an estradiol-derived moiety.

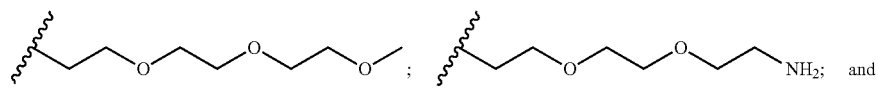

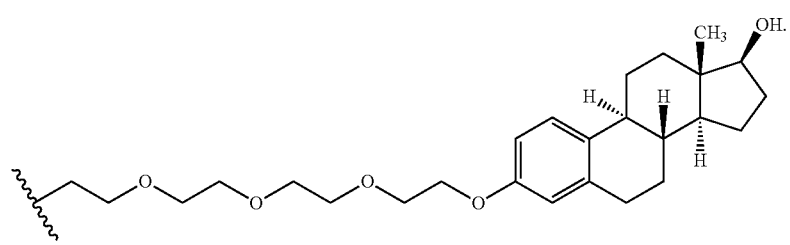

In some embodiments, $F^1$ and $F^2$ are members independently selected from:

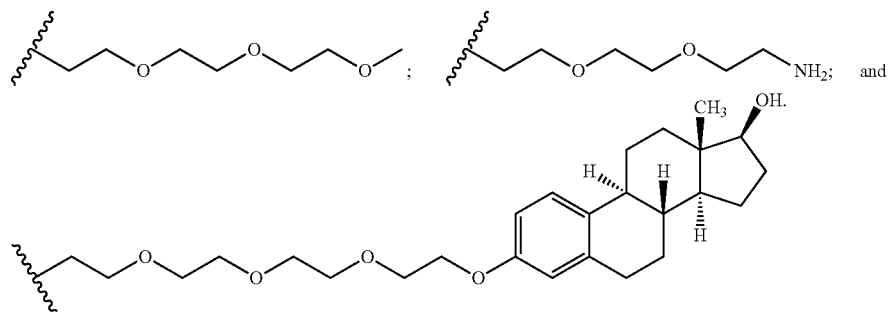

In some embodiments, $F^1$ and $F^2$ are the same. In some embodiments, $F^1$ and $F^2$ are different.

In some embodiments, the invention provides a di-macrocycle having the structure:

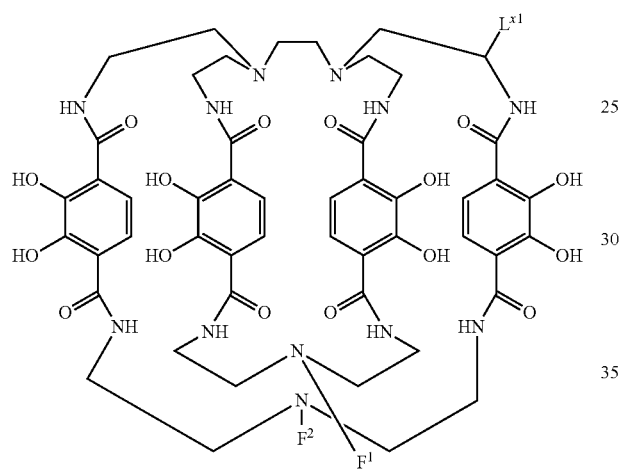

wherein $L^{x1}$ is H or a linker; and $F^1$ and $F^2$ are modifying moieties.

Linkers are as defined herein.

In some embodiments, $L^{x1}$ is H. In some embodiments, $L^{x1}$ is a linker.

In some embodiments, $F^1$ and $F^2$ are substituted or unsubstituted heteroalkyl. In some embodiments, $F^1$ and $F^2$ are a substituted or unsubstituted polyether. In some embodiments, $F^1$ and $F^2$ are a polyether substituted with an estradiol-derived moiety.

In some embodiments, $F^1$ and $F^2$ are members independently selected from:

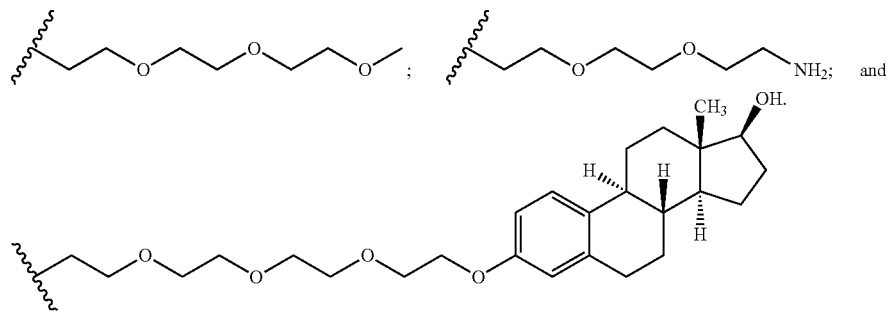

In some embodiments, $F^1$ and $F^2$ are the same. In some embodiments, $F^1$ and $F^2$ are different.

In some embodiments, the invention provides a di-macrocycle having the structure:

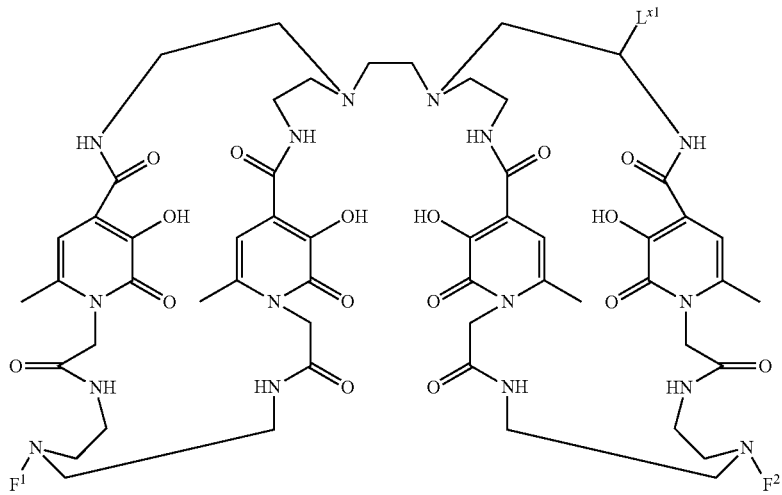

wherein $L^{x1}$ is H or a linker; and $F^1$ and $F^2$ are modifying moieties.

Linkers are as defined herein.

In some embodiments, $L^{x1}$ is H. In some embodiments, $L^{x1}$ is a linker.

In some embodiments, $F^1$ and $F^2$ are substituted or unsubstituted heteroalkyl. In some embodiments, $F^1$ and $F^2$ are a substituted or unsubstituted polyether. In some embodiments, $F^1$ and $F^2$ are a polyether substituted with an estradiol-derived moiety.

In some embodiments, $F^1$ and $F^2$ are members independently selected from:

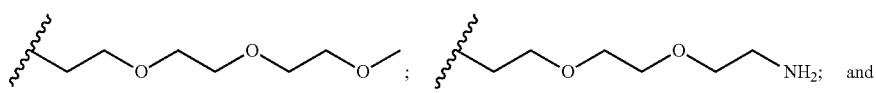

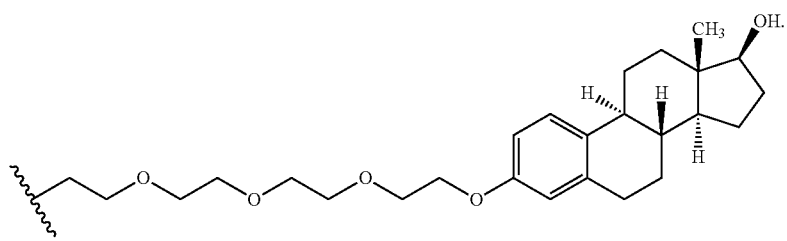

In some embodiments, $F^1$ and $F^2$ are the same. In some embodiments, $F^1$ and $F^2$ are different.

In some embodiments, the invention provides a di-macrocycle having the structure:

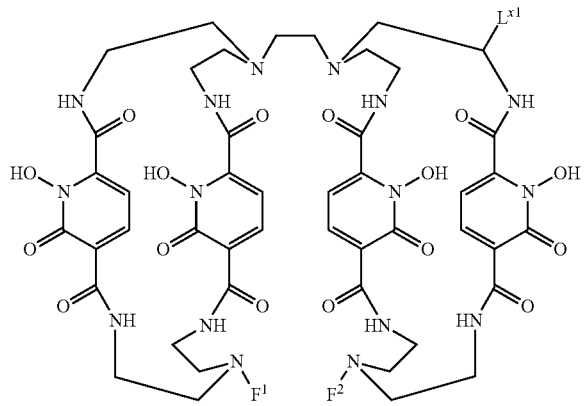

wherein $L^{x1}$ is H or a linker; and $F^1$ and $F^2$ are modifying moieties.

Linkers are as defined herein.

In some embodiments, $L^{x1}$ is H. In some embodiments, $L^{x1}$ is a linker.

In some embodiments, $F^1$ and $F^2$ are substituted or unsubstituted heteroalkyl. In some embodiments, $F^1$ and $F^2$ are a substituted or unsubstituted polyether. In some embodiments, $F^1$ and $F^2$ are a polyether substituted with an estradiol-derived moiety.

In some embodiments, $F^1$ and $F^2$ are members independently selected from:

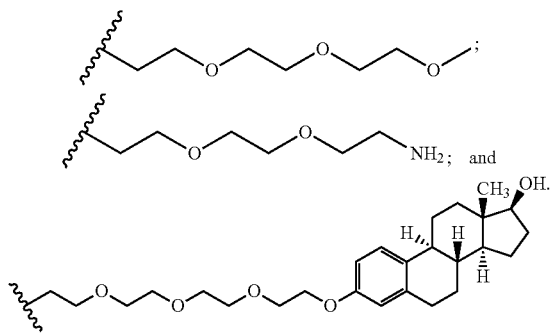

In some embodiments, $F^1$ and $F^2$ are the same. In some embodiments, $F^1$ and $F^2$ are different.

Additional exemplary di-macrocycles are shown in the Examples.

2.2. Complexes

In one aspect, the invention provides a complex of a di-macrocycle disclosed herein with a metal ion.

Any of the combinations of di-macrocycles disclosed herein and a metal ion disclosed herein are encompassed by this disclosure and specifically provided by the invention.

2.2.1. Metals

In some embodiments, the metal is an actinide. In some embodiments, the metal is a lanthanide. In some embodiments, the lanthanide is Tb. In some embodiments, the lanthanide is Eu.

In some embodiments, the metal ion is yttrium(III). In some embodiments, the metal ion is europium(III). In some embodiments, the metal ion is terbium(III). In some embodiments, the metal ion is zirconium(IV). In some embodiments, the metal ion is thorium(IV).

In some embodiments, the metal is a radionuclide. In some embodiments, the metal ion is $^{227}$Th(IV). In some embodiments, the metal ion is $^{89}$Zr(IV).

In some embodiments, the metal is $^{177}$Lu. In some embodiments, the metal is $^{166}$Ho. In some embodiments, the metal is $^{153}$Sm. In some embodiments, the metal is $^{90}$Y. In some embodiments, the metal is $^{86}$Y. In some embodiments, the metal is $^{166}$Dy. In some embodiments, the metal is $^{165}$Dy. In some embodiments, the metal is $^{169}$Er. In some embodiments, the metal is $^{175}$Yb. In some embodiments, the metal is $^{225}$AC. In some embodiments, the metal is $^{149}$Tb. In some embodiments, the metal is $^{153}$Gd. In some embodiments, the metal is $^{230}$U.

In some embodiments, the metal is $^{111}$In. In some embodiments, the metal is $^{67}$Ga. In some embodiments, the metal is $^{67}$Cu. In some embodiments, the metal is $^{64}$Cu. In some embodiments, the metal is $^{186}$Re. In some embodiments, the metal is $^{188}$Re. In some embodiments, the metal is $^{111}$Ag. In some embodiments, the metal is $^{109}$Pd. In some embodiments, the metal is $^{212}$Pb. In some embodiments, the metal is $^{203}$Pb. In some embodiments, the metal is $^{212}$Bi. In some embodiments, the metal is $^{213}$Bi. In some embodiments, the metal is $^{195m}$Pt. In some embodiments, the metal is $^{201}$Tl. In some embodiments, the metal is $^{55}$Co. In some embodiments, the metal is $^{99m}$Tc.

2.2.1.1. Radionuclides

The chelating moieties disclosed herein can be used to bind metal ions, in particular, a radionuclide. The term "radionuclide" or "radioisotope" refers to a radioactive isotope or element with an unstable nucleus that tends to undergo radioactive decay. Numerous decay modes are known in the art and include alpha decay, proton emission, neutron emission, double proton emission, spontaneous fission, cluster decay, β$^-$ decay, positron emission (β$^+$ decay), electron capture, bound state beta decay, double beta decay, double electron capture, electron capture with positron emission, double positron emission, isomeric transition and internal conversion.

Exemplary radionuclides include alpha-emitters, which emit alpha particles during decay. In some embodiments, a radionuclide is an emitter of a gamma ray or a particle selected from an alpha particle, an electron and a positron.

In some embodiments, the radionuclide is an actinide. In some embodiments, the radionuclide is a lanthanide. In some embodiments, the radionuclide is a 3$^+$ ion. In some embodiments, the radionuclide is a 4$^+$ ion. In some embodiments the radionuclide is a 2$^+$ ion.

Of particular use in the complexes provided herein are radionuclides selected from isotopes of U, Pu, Fe, Cu, Sm, Gd, Tb, Dy, Ho, Er, Yb, Lu, Y, Th, Zr, In, Ga, Bi, Ra, At and Ac. In some embodiments, a radionuclide is selected form radium-223, thorium-227, astatine-211, bismuth-213, Lutetium-177, and actinium-225. Other useful radioisotopes include bismuth-212, iodine-123, copper-64, iridium-192, osmium-194, rhodium-105, samarium-153, and yttrium-88, yttrium-90, and yttrium-91. In exemplary embodiments, the radionuclide is thorium, particularly selected from thorium-227 and thorium-232. In some embodiments, thorium-226 is excluded. In some embodiments, U is excluded. In some embodiments, uranium-230 is excluded. That is, in some embodiments, a radionuclide is not U, or a radionuclide is not uranium-230 or a radionuclide is not thorium-226.

$^{232}$Th exists in nature as an α-emitter with a half life of 1.4×10$^{10}$ yr. In aqueous solution, Th(IV) is the only oxidation state. Thorium(IV) ion is bigger than Pu(IV) and usually forms complexes with 9 or higher coordination number. For example, the crystal structure of both Th(IV) complexes of simple bidentate 1,2-HOPO and Me-3,2-HOPO have been determined as nine coordinated species.

Similar to other actinide ions, thorium(IV) prefers forming complexes with oxygen, especially negative oxygen donor ligands. Thorium(IV) also prefers octadentate or higher multidentate ligands:

| | Ligand | | | | | |
|---|---|---|---|---|---|---|
| | Acac | NTA | HEDTA* | EDTA** | DTPA | TTHA |
| Ligand Type | Bi-dentate | Tetra- | Hexa- | Hexa- | Octa- | Deca- |
| Log $K_1$ | 7.85 | 16.9 | 18.5 | 25.3 | 30.34 | 31.9 |

*with one alcoholic oxygen and three carboxyl groups;
**with four carboxyl groups.

Other radionuclides with diagnostic and therapeutic value that can be used with the compounds disclosed herein can be found, for example, in U.S. Pat. Nos. 5,482,698 and 5,601,800; and Boswell and Brechbiel, Nuclear Medicine and Biology, 2007 October, 34(7): 757-778 and the manuscript thereof made available in PMC 2008 Oct. 1.

3. Uses

The chelators and complexes disclosed herein can be used in a wide variety of therapeutic and diagnostic settings.

In one aspect, the invention provides a method of treating a disease in an animal comprising administering a complex disclosed herein to the animal, whereby the disease is ameliorated or eliminated.

In one aspect, the invention provides a method of diagnosing a disease in an animal comprising (a) administering a complex disclosed herein to the animal and (b) detecting the presence or absence of a signal emitted by the complex. In some embodiments, the detecting step comprises obtaining an image based on the signal.

In some embodiments, the disease is cancer.

In some embodiments, the complex comprises a linker to a targeting moiety and the method further comprises localizing the complex to a targeting site in the animal by binding the targeting moiety to the targeting site.

The compounds disclosed herein are particularly well suited for the preparation of stable, pre-labeled antibodies for use in the diagnosis and treatment of cancer and other diseases. For example, antibodies expressing affinity for specific tumors or tumor-associated antigens are labeled with a diagnostic radionuclide-complexed chelate, and the labeled antibodies can be further stabilized through lyophilization. Where a chelate is used, it generally is covalently attached to the antibody. The antibodies used can be polyclonal or monoclonal, and the radionuclide-labeled antibodies can be prepared according to methods known in the art. The method of preparation will depend upon the type of radionuclide and antibody used. A stable, lyophilized, radiolabeled antibody can be reconstituted with suitable diluent at the time of intended use, thus greatly simplifying the on site preparation process. The methods of the invention can be applied to stabilize many types of pre-labeled antibodies, including, but not limited to, polyclonal and monoclonal antibodies to tumors associated with melanoma, colon cancer, breast cancer, prostate cancer, etc. Such antibodies are known in the art and are readily available.

4. Synthesis

Any scaffold moiety can be derivatized with at least one linker, such as a functionalized linker. Thus, in one exemplary embodiment, a linker, such as a functionalized linker, can be attached to the scaffold moiety. In another exemplary embodiment, a linker, such as a functionalized linker, is attached to a chelating moiety. A functionalized linker can reacted to form a bond with a targeting moiety. The linker can also be attached to any other linker within a compound.

Scaffold moieties that include a linker can be prepared by the following exemplary methods.

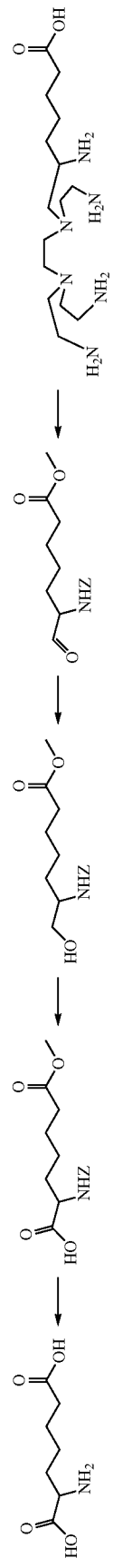
Scheme 1.1. Reverse synthetic scheme for carboxyl functionalized H22 cap-amine.

Other functionalize scaffolds include those in which the chiral carbon is placed on the central ethylene bridge of H22-amine. An exemplary route to such a scaffold initiates with 2,3-Diaminopropionic acid, as its carboxyl group is connected directly to the amine backbone to give a very rigid geometry, extended carboxyl chain is needed to provide flexibility for eventual protein conjugating. A synthetic scheme to the scaffold is shown in scheme 1.2.

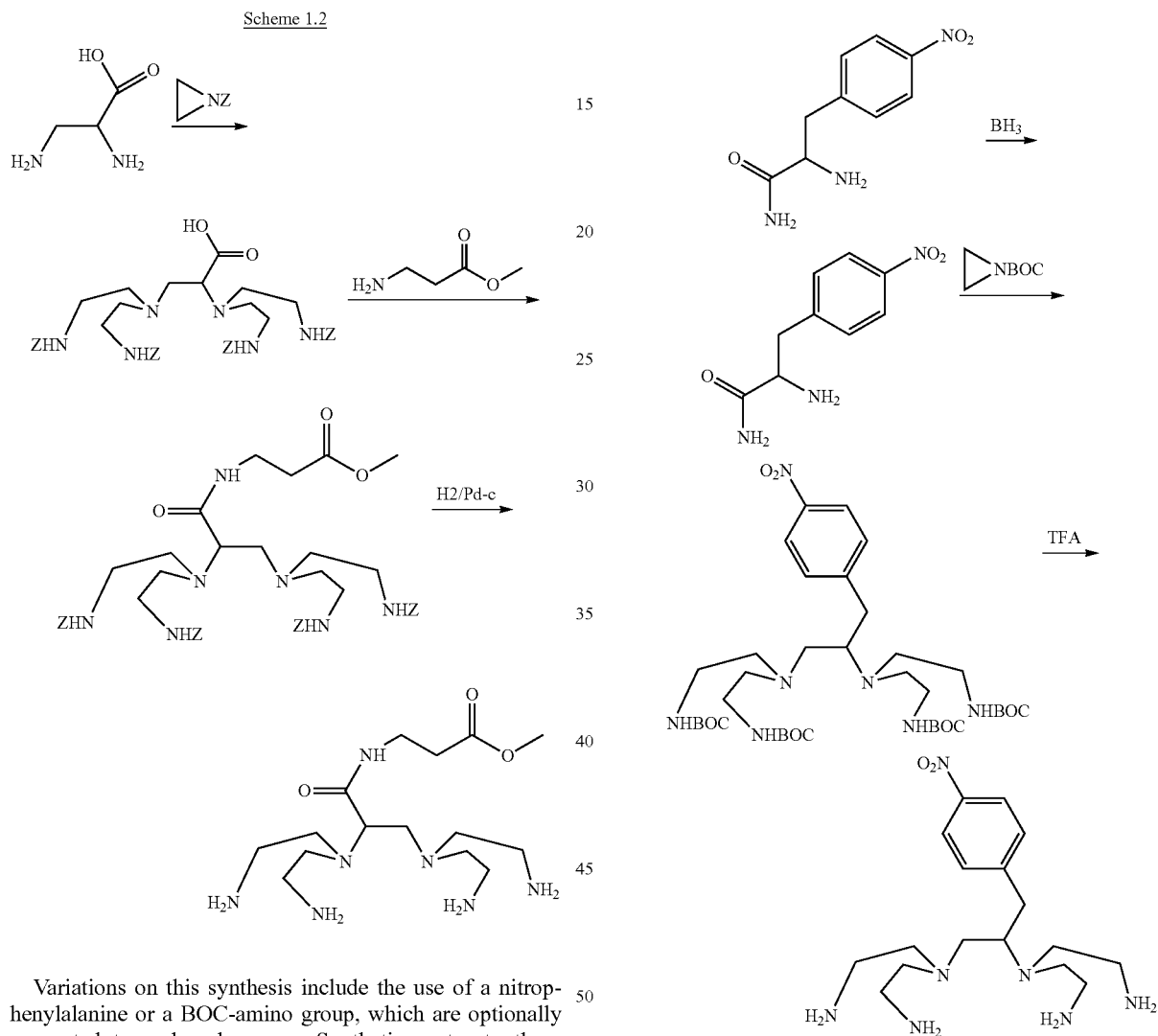

Variations on this synthesis include the use of a nitrophenylalanine or a BOC-amino group, which are optionally converted to carboxyl groups. Synthetic routes to these scaffolds are shown in Schemes 1.3 and 1.4.

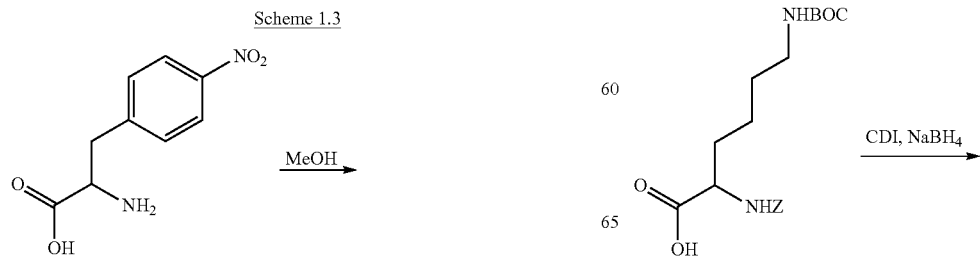

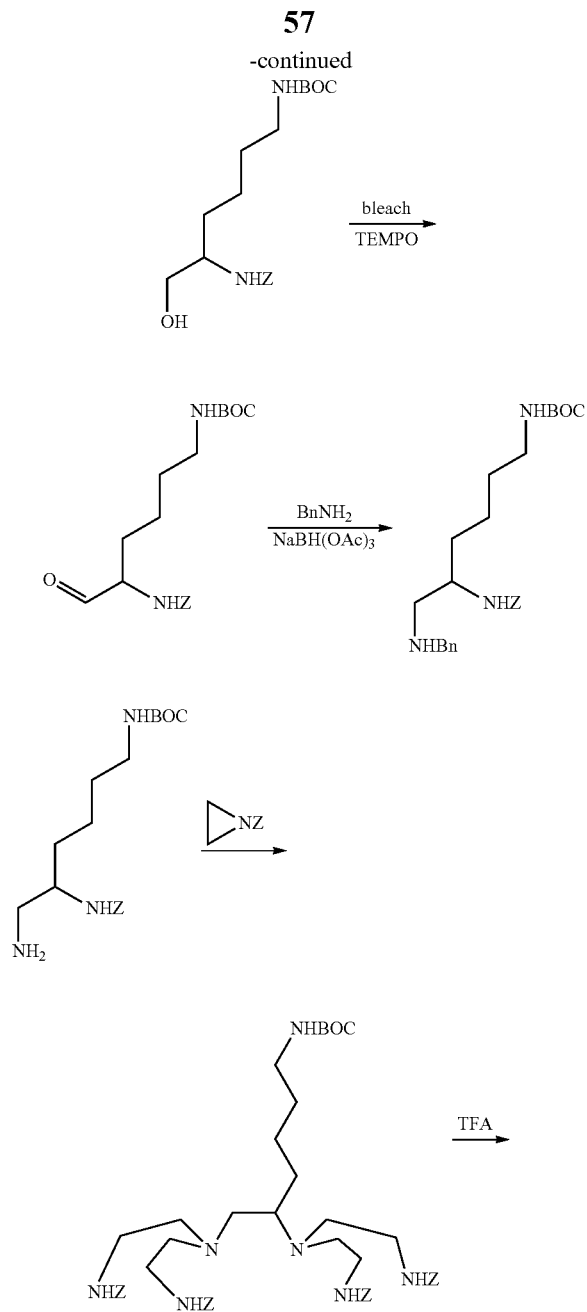

One concern with HOPO chelating moieties is that it might be difficult to couple these to a targeting moiety, such as an antibody, without protection in some form or another. One approach for HOPO chelating moiety protection/deprotection is to use a metal complex in the coupling reaction, then remove the metal from the metal complex-antibody conjugate after coupling to make room for the radionuclide (transmetalation). Another approach is to use ortho-nitrobenzyl in place of the benzyl protective group in the HOPO chelating moiety synthesis, and photodeprotect this after coupling the potential chelating moiety to the antibody.

Additional guidance for deprotecting, activating and attaching one or more chelating moieties to one or more scaffolds can be found, for example in U.S. Pat. Nos. 5,624,901; 6,406,297; 6,515,113 and 6,846,915; US Patent Application Publications 2008/0213780; 2008/0213917 and 2010/0015725; and PCT/US2010/046517.

Exemplary di-macrocycles, any of which can be derivatized with a linker (e.g., a functionalized linker or a linker comprising a targeting moiety) are disclosed throughout the application.

EXAMPLES

The compounds and complexes of the invention are synthesized by an appropriate combination of generally well-known synthetic methods. Techniques useful in synthesizing the compounds of the invention are both readily apparent and accessible to those of skill in the relevant art. The discussion below is offered to illustrate certain of the diverse methods available for use in assembling the compounds of the invention, it is not intended to limit the scope of reactions or reaction sequences that are useful in preparing the compounds of the present invention.

Example 1

Synthesis of an Octa-Coordinating Di-Macrocyclic Bifunctional Chelator (Scheme 1)

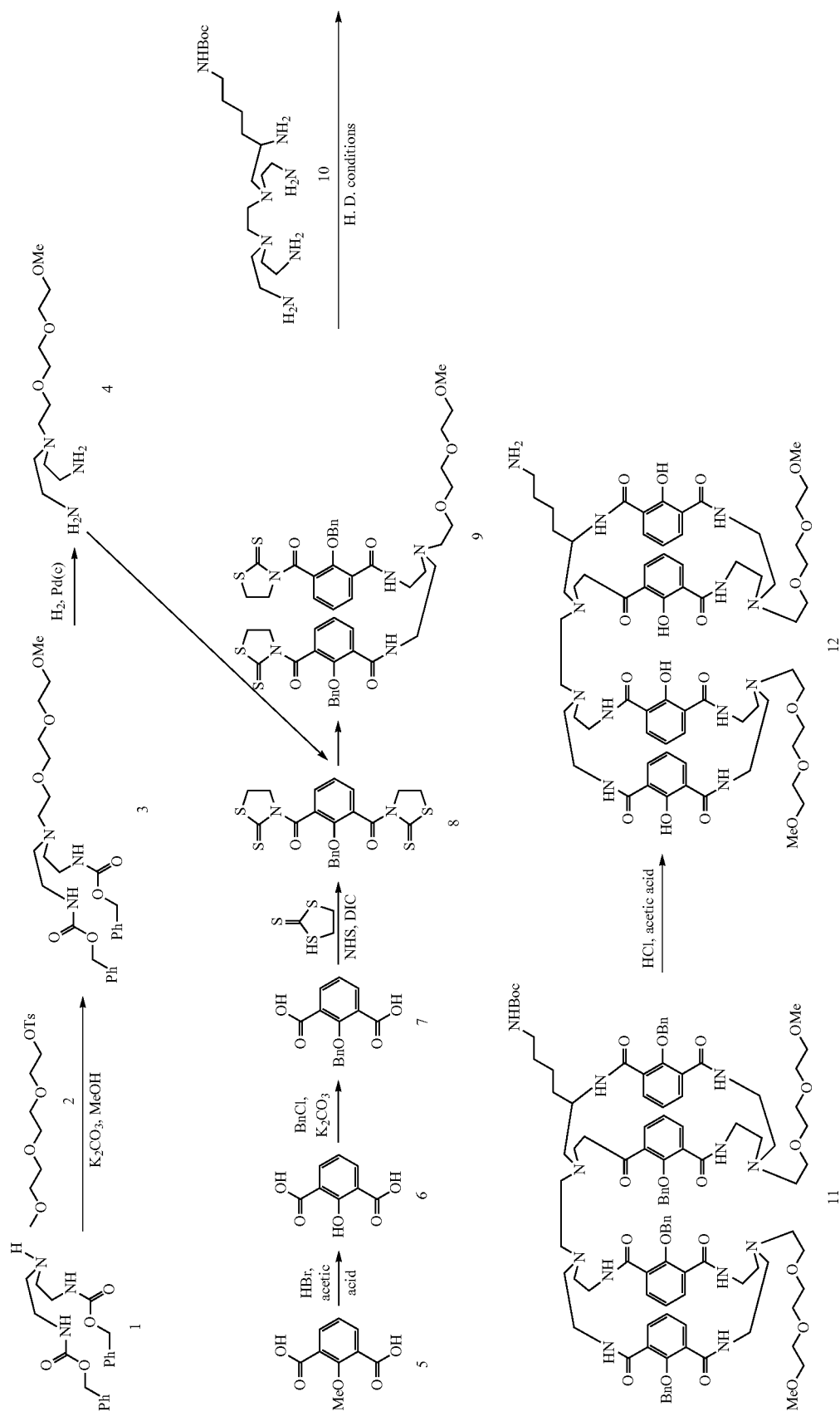
Scheme 1. Synthesis of di-macrocyclic bifunctional chelator 12.

Preparation of macrocyclic ligands began with di-Z-diethylenetriamine 1 as a starting material as shown in Scheme 1. Amine 1 was alkylated with [2-[2-(2-methoxyethoxy)ethoxy]ethoxy] p-toluene sulfonate 2 to provide the tertiary amine 3, which was deprotected under reducing conditions to provide triamine 4. In a separate sequence, 2-hydroxyisophthalic acid 6 was first protected as the benzyl ether 7, then condensed with 2-mercaptothiazole to form the amide 8. The activated amide 8 was reacted with triamine 4 under pseudo-first order conditions to provide the amide 9, which was reacted with amine 10 under high dilution conditions to form the di-macrocycle 11. Protective groups were removed from compound 11 using a solution of concentrated hydrochloric acid in acetic acid to provide di-macrocycle 12.

N,N''-Bis(carbobenzyloxy)-N'-[2-[2-(2-methoxyethoxy)ethoxy]ethoxy]-bis(2-aminoethyl)amine 3. N,N''-Di-Z-diethylenetriamine 1 (1.00 g, 2.69 mmol), [2-[2-(2-methoxyethoxy)ethoxy]ethoxy] p-toluene sulfonate 2 (1.529 g, 4.80 mmol), potassium carbonate (557 mg, 4.04 mmol), and sodium iodide (404 mg, 2.69 mmol) were dried together in vacuo. Anhydrous acetonitrile (15 mL) was added, and the resulting solution was heated at reflux for 28 hr. The residue was dissolved in dichloromethane (25 mL) and washed with 1 M sodium hydroxide (15 mL). The aqueous phase was extracted with dichloromethane (10 mL) and solvent was removed from the combined organic extracts under reduced pressure. The crude product was purified by silica gel chromatography using 1-2% methanol in dichloromethane as eluents. Fractions containing product were combined, solvent was removed under reduced pressure, and the residue dried in vacuo to provide N,N''-bis(carbobenzyloxy)-N'-[2-[2-(2-methoxyethoxy)ethoxy]ethoxy]-bis(2-aminoethyl)amine 3 (1.028 g, 73.8%). $^1$H NMR (300 MHz, CDCl$_3$): δ=7.30 (s, 10H, ArH), 5.05 (s, 4H, PhCH$_2$O), 3.50 (m, 4H, CH$_2$CH$_2$O), 3.42 (m, 6H, CH$_2$CH$_2$O), 3.29 (s, 3H, OMe), 3.21 (m, 4H, CH$_2$CH$_2$N), 2.62 (m, 6H, CH$_2$CH$_2$N). $^{13}$C NMR (400 MHz, CDCl$_3$): δ=156.8, 136.9, 128.4, 128.1, 128.0, 71.8, 70.5, 70.3, 70.2, 70.0, 66.5, 58.9, 54.3, 53.3, 39.2. FTMS pESI: calculated for C$_{27}$H$_{40}$N$_3$O$_7$ [MH]$^+$, 518.2861. found, 518.2857.

N'-[2-[2-(2-methoxyethoxy)ethoxy]ethoxy]-bis(2-aminoethyl)amine 4. N,N''-bis(carbobenzyloxy)-N'-[2-[2-(2-methoxyethoxy)ethoxy]ethoxy]-bis(2-aminoethyl)amine 3 (1.028 g, 1.99 mmol) was dissolved in ethyl alcohol (100 mL). Palladium on carbon (10% wet, 100 mg) was added, and the atmosphere was exchanged for hydrogen. After 19.5 hr, the solution was filtered through Celite® to remove catalyst, the Celite was washed with ethyl alcohol (100 mL), solvent was removed under reduced pressure, and the residue dried in vacuo to provide N'-[2-[2-(2-methoxyethoxy)ethoxy]ethoxy]-bis(2-aminoethyl)amine 4 (481 mg, 97.1%). $^1$H NMR (300 MHz, CDCl$_3$): δ=3.58 (m, 6H, CH$_2$CH$_2$O), 3.49 (m, 4H, CH$_2$CH$_2$O), 3.33 (s, 3H, OMe), 2.70 (t, 4H, CH$_2$CH$_2$N), 2.62 (t, 2H, CH$_2$CH$_2$N), 2.51 (t, 4H, CH$_2$CH$_2$N), 1.83 (br s, 4H, NH$_2$). $^{13}$C NMR (400 MHz, CDCl$_3$): δ=71.9, 70.6, 70.4, 70.3, 69.9, 59.0, 57.8, 53.7, 39.7. FTMS pESI: calculated for C$_{11}$H$_{28}$N$_3$O$_3$ [MH]$^+$, 250.2125. found, 250.2123.

2-Hydroxy-isophthalic Acid 6. 2-Methoxyisophthalic acid 5 (25 g, 0.127 mol) was dissolved in a 1:1 mixture of 48% HBr and glacial acetic acid (700 mL) in a 1 L round bottom flask. The mixture was heated at reflux for 48 hr, whereupon the 2-hydroxyisophthalic acid deposited after cooling as slight pink crystals. These were collected by filtration and dried in vacuo to provide 2-hydroxyisophthalic acid (20.5 g, 89%). $^1$H NMR (500 MHz, DMSO-d$_6$, 25° C.) δ: 6.942 (t, J=7.5, 1H, ArH), 7.950 (d, J=7.5, 1H, ArH), 10.51 (s, br, 1H, phenol H). $^{13}$C NMR (500 MHz, DMSO-d$_6$, 25° C.) δ: 117.19, 118.21, 135.66, 161.25, 169.24.

Dibenzyl 2-benzyloxyisophthalate 6A. 2-Hydroxyisophthalic acid 6 (75 g, 0.38 mol), benzyl chloride (158 g, 1.25 mol), and anhydrous K$_2$CO$_3$ (172 g, 1.25 mol) were added to 500 mL of dry dimethylformamide. The mixture was heated at 75° C. under nitrogen for 18 hr. The reaction mixture was cooled to ambient temperature and filtered, and the filtrate was evaporated to dryness under reduced pressure. The resulting residue was dissolved in dichloromethane (2 L) and filtered through a silica gel plug. Solvent was removed under reduced pressure and the residue was dried in vacuo to provide dibenzyl 2-(benzyloxy)benzene-1,3-dicarboxylate 6A as a thick pale yellow oil (158 g, 90%). $^1$H NMR (500 MHz, CDCl$_3$): δ 5.07 (s, 2H, CH2), 5.31 (s, 4H, CH2), 7.23 (t, 1H, ArH), 7.3-7.4 (m, 15H, ArH), 7.97 (d, 2H, ArH). $^{13}$C NMR (125 MHz, CDCl$_3$): δ 66.9, 77.7, 123.5, 127.1, 127.7, 128.0, 128.0, 128.1, 128.2, 128.3, 134.8, 135.3, 136.6, 157.8, 165.2 ppm; MS (FAB+): m/z 453 [MH]$^+$.

2-Benzyloxyisophthalic acid 7. To a solution of 6A (155 g, 0.34 mmol) in 2 L of a 1:4 mixture of MeOH:H$_2$O was added NaOH (40 g, 1.0 mol), and the reaction mixture was stirred at room temperature for 18 h. The solvents were removed under vacuum, and the resulting residue was dissolved in brine and washed with dichloromethane. The aqueous layer was acidified to pH 1 with conc. HCl, causing the product to form a precipitate. The product, a white solid, was collected by filtration and dried under vacuum to provide compound 7 (85.6 g, 92%). mp 235-237° C.; $^1$H NMR (500 MHz, CDCl$_3$): δ 5.23 (s, 2H, CH2), 7.39-7.41 (m, 3H, ArH), 7.425 (t, 1H, ArH), 7.48-7.51 (m, 2H, ArH), 8.35 (d, 2H, ArH). $^{13}$C NMR (125 MHz, D$_2$O-NaOD): δ 76.1, 123.4, 127.7, 128.0, 128.2, 128.5, 133.9, 136.2, 149.9, 176.6 ppm; MS (ESI−): m/z 271.1 [M−H]$^-$.

2-Benzyloxy-bis(2-mercaptothiazole)isophthalamide 8. To a solution of 2-benzyloxyisophthalic acid 7 (68 g, 0.25 mol) in anhydrous dichloromethane, oxalyl chloride (76 g, 0.6 mol) and a few drops of dimethylformamide were added with stirring. After 8 hours, volatiles were removed under reduced pressure and the residue dried overnight in vacuo. The intermediate diacid chloride was dissolved in anhydrous dichloromethane (500 mL) and added dropwise to a cooled solution of 2-mercaptothiazole (62 g, 0.52 mol) in triethylamine (90 mL) and dichloromethane (500 mL). After the addition was complete, the solution was allowed to warm to ambient temperature and stirred overnight. The solution was washed with 1N HCl (500 mL), brine (500 mL) and 1N NaOH (500 mL). Solvent was removed under reduced pressure, and the crude product was purified by silica gel chromatography using methanol in dichloromethane as eluents. Fractions containing product were combined, solvent was removed under reduced pressure, and the residue dried in vacuo to provide 2-benzyloxy-bis(2-mercaptothiazole)isophthalamide 8 (75 g, 63%). mp 149-151° C. $^1$H NMR (300 MHz, CDCl$_3$): δ=7.47 (d, 2H, ArH), 7.35 (m, 5H, ArH), 7.18 (t, 1H, ArH), 5.01 (s, 2H, OCH$_2$), 4.39 (t, 4H, CH$_2$), 3.02 (t, 4H, CH$_2$). $^{13}$C NMR (300 MHz, CDCl$_3$): δ=200.9, 167.2, 153.2, 136.6, 132.1, 128.7, 128.5, 128.3, 127.7, 123.7, 55.7, 28.8. FTMS pESI: calculated for C$_{21}$H$_{19}$N$_2$O$_3$S$_4$ [MH]$^+$, 475.0279. found, 475.0282.

N,N''-bis[1-benzyloxy-2-(2-mercaptothiazoleamido)-6-benzoyl]-N'-[2-[2-(2-methoxyethoxy)ethoxy]ethoxy]-bis(2-aminoethyl)amine 9. N'-[2-[2-(2-methoxyethoxy)ethoxy]ethoxy]-bis(2-aminoethyl)amine 4 (481 mg, 1.93 mmol) was dissolved in dichloromethane (50 mL) and added dropwise to a solution of 2-benzyloxy-bis(2-mercaptothiazole)isophthalamide 8 (10.515 g, 22.2 mmol) in dichloromethane (250 mL) over a period of 20 hrs. Solvent was removed under reduced pressure, and the crude product was purified by silica gel chromatography using 1-3.5% methanol in dichloromethane as eluents. Fractions containing product were combined, solvent was removed under reduced pressure, and the residue dried in vacuo to provide N,N''-bis[1-benzyloxy-2-(2-mercaptothiazoleamido)-6-benzoyl]-N'-[2-[2-(2-methoxyethoxy)ethoxy]ethoxy]-bis(2-aminoethyl)

amine 9 (1.209 g, 65.3%). $^1$NMR (300 MHz, CDCl$_3$): δ=8.05 (d, 2H, ArH), 7.47 (m, 2H, ArH), 7.30 (s, 10H, ArH), 7.25 (s, 2H, ArH), 4.98 (s, 4H, PhCH$_2$O), 4.44 (t, 4H, NCH$_2$CH$_2$S), 3.55 (m, 2H, CH$_2$CH$_2$O), 3.50 (m, 6H, CH$_2$CH$_2$O), 3.39 (m, 9H, CH$_2$CH$_2$O, CH$_2$CH$_2$N, OMe), 3.04 (t, 4H, NCH$_2$CH$_2$S), 2.60 (t, 2H, CH$_2$CH$_2$N), 2.51 (t, 4H, CH$_2$CH$_2$N). $^{13}$C NMR (400 MHz, CDCl$_3$): δ=167.4, 154.2, 136.2, 134.0, 132.3, 129.8, 128.8, 127.8, 124.8, 77.9, 71.9, 70.4, 55.7, 53.4, 37.8, 28.7. FTMS pESI: calculated for C$_{47}$H$_{54}$N$_5$O$_9$S$_4$ [MH]$^+$, 960.2799. found, 960.2791.

Benzyl and tert-butyloxycarbonyl-protected di-macrocycle 11. A solution of N,N″-bis[1-benzyloxy-2-(2-mercaptothiazoleamido)-6-benzoyl]-N′-[2-[2-(2-methoxyethoxy)ethoxy]ethoxy]-bis(2-aminoethyl)amine 9 (1.2 g, 1.25 mmol) in dichloromethane (1.0 L) and a solution of 5-amino-6-[(2-aminoethyl)-[2-[bis(2-aminoethyl)amino]ethyl]amino]hexylcarbamic acid tert-butyl ester 10 (0.5 g, 1.25 mmol) in dichloromethane (1.0 L) were added dropwise to dichloromethane (1.0 L) over a period of 5 days. Solvent was removed under reduced pressure, and the crude product was purified by silica gel chromatography using 0.1% triethylamine, 5-7.5% methanol in dichloromethane as eluents. The silica gel column was prepared so as to have a short section of aluminum oxide (basic, Brockmann I) on its top. Fractions containing product were combined, solvent was removed under reduced pressure, and the residue dried in vacuo to provide the protected di-macrocycle 11 (340 mg, 14.7%). $^1$H NMR (300 MHz, CDCl$_3$): δ=7.8-7.4 (m, 8H, ArH), 7.29 (s, 20H, ArH), 7.1-6.7 (m, 4H, ArH), 5.0-4.8 (m, 8H, PhCH$_2$O), 3.6-3.3 (m, 26H, CH$_2$CH$_2$O, OMe), 3.2-2.1 (m, 35H, CH$_2$CH$_2$N), 1.8 (br s, 4H, CH$_2$CH$_2$N), 1.4-1.2 (m, 15H, CH$_2$CH$_2$CH$_2$, C(CH$_3$)$_3$). $^{13}$C NMR (400 MHz, CDCl$_3$): δ=166.1, 166.0, 156.1, 154.1, 136.1, 135.8, 132.8, 132.5, 128.9, 128.8, 128.7, 128.3, 124.6, 124.4, 124.0, 71.9, 71.8, 70.5, 70.3, 70.1, 69.9, 69.7, 68.8, 58.9, 53.8, 53.1, 52.7, 52.3, 40.3, 38.5, 37.7, 37.5, 33.0, 29.7, 28.5, 23.3. FTMS pESI: calculated for C$_{101}$H$_{132}$N$_{13}$O$_{20}$ [MH]$^+$, 1846.9706. found, 1846.9722.

Di-macrocycle 12. Benzyl and tert-butyloxycarbonyl-protected di-macrocycle 11 (10 mg, 5.4 μmol) was dissolved in 12N hydrochloric acid (0.5 mL) and glacial acetic acid (0.5 mL). The solution was stirred under inert atmosphere for 24 hr, whereupon HCl was removed with a stream of inert gas. Solvents were removed under reduced pressure and the residue was dried in vacuo. The residue was dissolved in methanol (600 μL) and transferred to two O-ring microcentrifuge tubes. Ether (ca. 1.5 mL/tube) was added, and the tubes were placed at 4° C. for 30 minutes. The tubes were centrifuged at 12,000 rpm for 3 minutes, decanted, the pellets were washed with ether (ca. 1.5 mL/tube) and allowed to air dry. The pellets were dissolved in methanol (300 μL), transferred to a single microcentrifuge tube, and precipitated with ether as described above. The pellet was dried in vacuo to provide di-macrocycle 12, pentahydrochloride salt (8.0 mg, 94%). FTMS pESI: calculated for C$_{68}$H$_{100}$N$_{13}$O$_{18}$ [MH]$^+$, 1386.7304. found, 1386.7306.

During the synthesis of di-macrocycle 11, the regioisomer 11R is also formed. Regioisomer 11R can be deprotected to provide compound 12R:

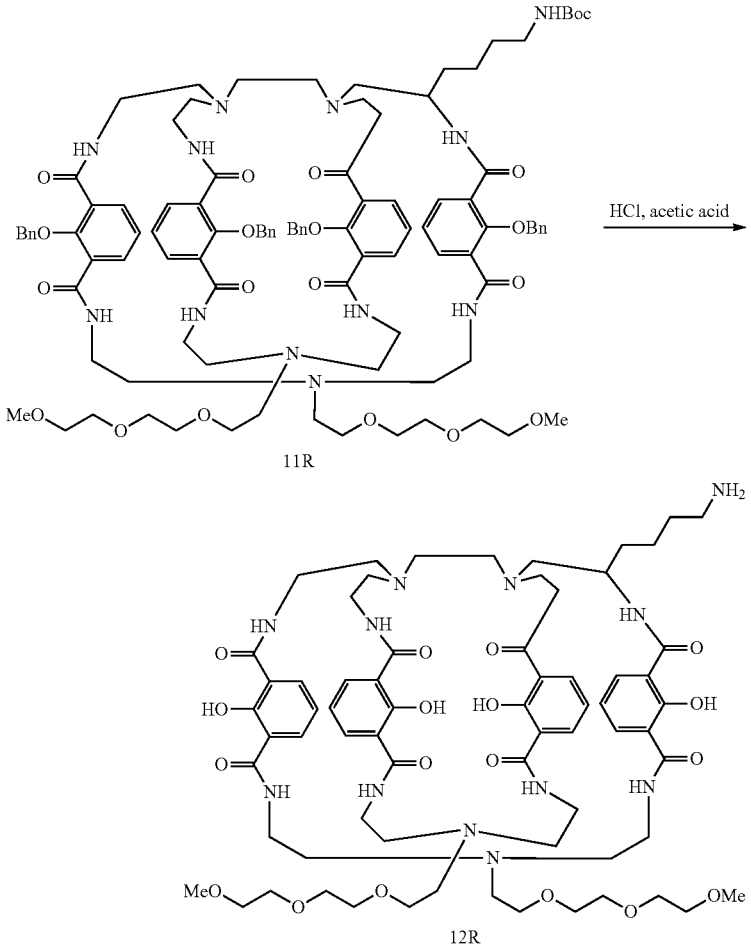

Example 2

Synthesis of an Octa-Coordinating Di-Macrocyclic Oligodeoxynucleotide Conjugate (Scheme 2)

Di-macrocycle, 4-isothiocyanatophenylthiourea derivative 13. Di-macrocycle 12 (5.1 mg, 3.3 μmol) was dissolved in dimethylformamide (250 μL) and triethylamine (10 μL). The solution was transferred to a microcentrifuge tube containing 1,4-phenyldiisothiocyanate (6.3 mg, 33 μmol) and mixed at 800 rpm under inert atmosphere for 1.5 hours. Ether (ca. 1.5 mL) was added, and the resulting suspension placed at 4° C. for 60 minutes. The tube was centrifuged at 12,000 rpm for 3 minutes, decanted, the pellet was washed with ether (ca. 1.5 mL) and allowed to air dry. The pellet was dissolved in methanol (250 μL) and precipitated and washed with ether as described above. The pellet was dissolved again in methanol (300 μL) and precipitated and washed with ether as described above. The pellet was dried in vacuo to provide di-macrocycle, 4-isothiocyanatophenylthiourea derivative 13 (1.4 mg, 27%). FTMS pESI: calculated for $C_{76}H_{104}N_{15}O_{18}S_2$ [MH]$^+$, 1578.7120. found, 1578.7125.

Scheme 2. Synthesis of octa-coordinating di-macrocycli-oligodeoxynucleotide conjugate 15.

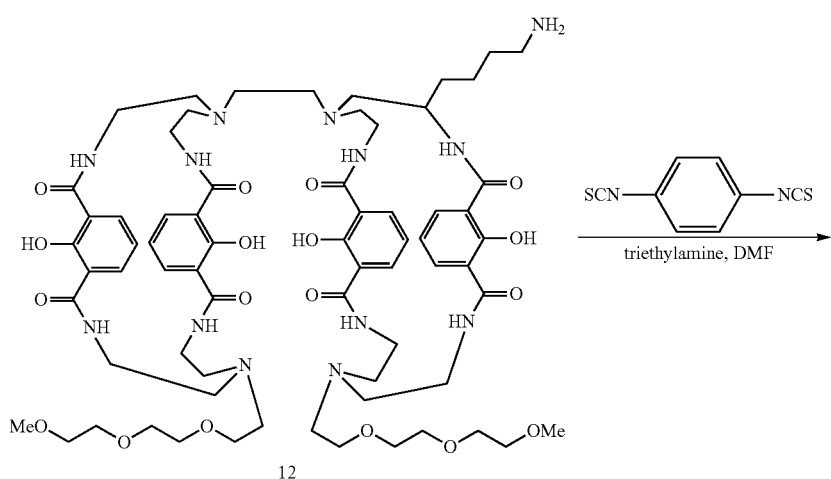

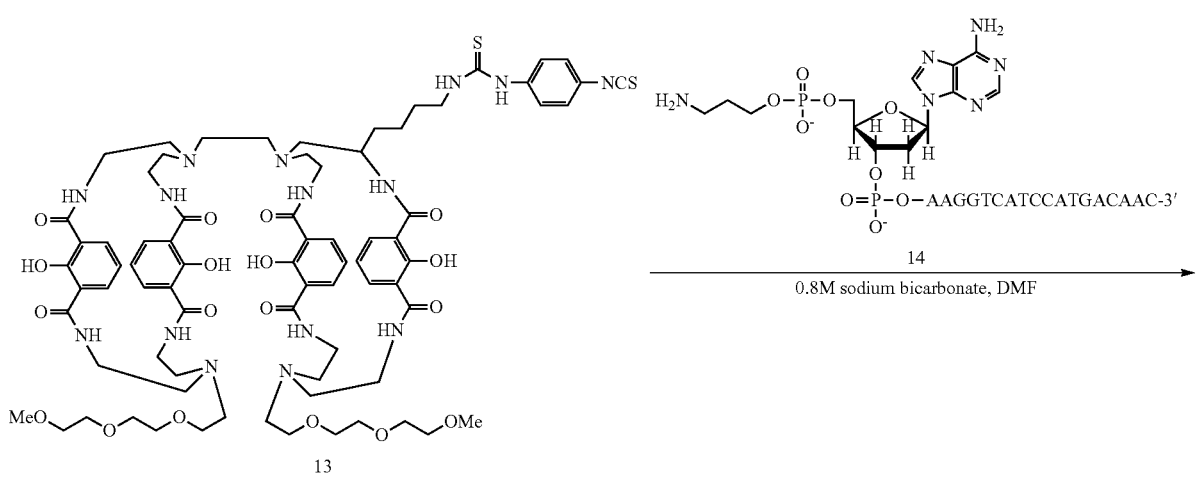

-continued

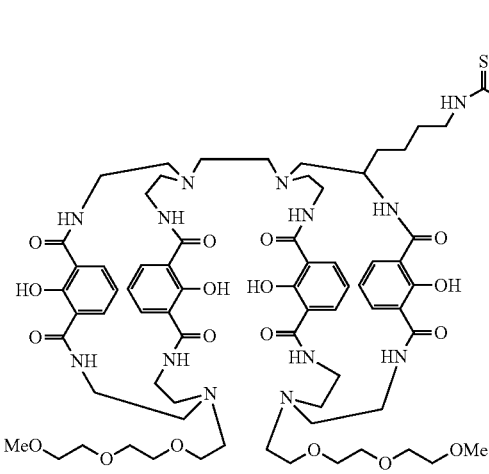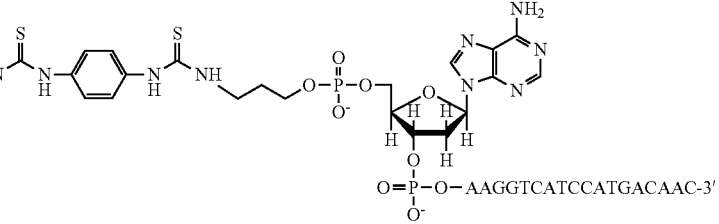

15

Dimacrocycle-oligodeoxynucleotide conjugate 15. A DNA 18-base oligonucleotide (14) with the sequence 5'-AAGGTCATCCATGACAAC-3' was purchased commercially (Eurogentec, Inc., Seraing, Belgium) and purified using reverse-phase HPLC. The oligonucleotide was modified during synthesis to possess an aminopropyl group attached at the 5'-terminus via a phosphodiester linkage. A solution of DNA oligomer in water (75 µL, 95 nmol) was diluted with sodium bicarbonate buffer (0.8 M, 100 µL) in an eppendorf tube. A solution of di-macrocycle, 4-isothiocyanatophenylthiourea derivative 13 (1 mg, 633 nmol) in anhydrous DMF (50 µL) was freshly prepared, added to the DNA oligomer and mixed at 1200 rpm using a commercial device (Eppendorf Mixmate®) at ambient temperature for 19.5 hours. A solution (45 µL) of glycogen (350 µg/mL) in 3M sodium acetate, pH 5.2 was added to the solution. The solution was mixed, absolute ethanol (1.1 mL) was added, the solution was mixed again, and the tube was stored at −20° C. for 1.5 hours. The eppendorf tube was centrifuged at 12,000 rpm for 20 minutes, the supernatant decanted, and the resulting pellet was washed with cold, 70% aqueous ethanol (1.1 mL). The supernatant was decanted, and the pellet was allowed to dry open to the air. The pellet was dissolved in sterile water (100 µL), and an aliquot (2 µL) was removed to quantify by UV-visible absorbance using the extinction coefficient at 260 nm of 181,600 $M^{-1}$ $cm^{-1}$. The resulting stock was found to have a concentration of 882 µM (88.2 nmol, 93% crude yield). There was ca. 40% conversion to conjugate, as estimated from analysis using 20% polyacrylamide gel electrophoresis. The conjugate was used without further purification.

Example 3

Complexation of a Dimacrocycle-Oligodeoxynucleotide Conjugate with Various Metal Cations as Demonstrated by Gel Electrophoresis For use in certain applications, such as acting as a bifunctional chelating agent to attach a radioisotope to a site-directing molecule, it is necessary that the chelator be able to coordinate to the metal ion of interest in a kinetically facile and thermodynamically stable manner. To demonstrate the utility of the di-macrocyclic chelator 12 for this type of application, its ability to coordinate to metal cations following conjugation with a site-directing molecule was assessed using a gel electrophoresis assay (FIG. 1). In this experiment, a conjugate of 12 with a small (18 base length) DNA oligomer, 15 was treated with a solution containing a metal cation. The electrophoretic mobility of the conjugate on a polyacrylamide gel was then compared with that of the conjugate which was not exposed to the solution of metal cation. Metal complexation in this format is indicated by a gel electrophoresis mobility shift, such that the heavier and more positively charged species formed upon metal complexation migrates more slowly. The gel electrophoretic mobility of the DNA oligomer 14 that was not conjugated to 12, present in the solution of 15, was also compared with and without exposure to the metal cation solution.

FIG. 1 shows the electrophoretic mobility of DNA oligonucleotide conjugate 15 (upper band) or DNA oligonucleotide 14 (lower band) in the absence or presence of metal cations. C=control, no metal cations. Y, Eu, Tb, Zr, Th=yttrium(III), europium(III), terbium(III), zirconium(IV), and thorium(IV), respectively. Arrow indicates luminescent band observed under hand held ultraviolet lamp.

In particular, a solution of DNA oligomer (3 µL, 33 µM, all concentrations final) was mixed with a solution of metal cation (2 µL, 625 µM) or an equal volume of water, additional water (2.5 µL) and a buffer solution (2.5 µL, 50 mM HEPES, pH 7.5). The solution was incubated at 55° C. for 15 minutes, whereupon the solution was allowed to cool to ambient temperature and a solution of 50% formamide (5 µL) was added. The solution was then applied to a 20% polyacrylamide gel containing 8M urea. Gel electrophoresis was conducted for about 7 hours using a commercial running buffer (Ambion AM9863) containing 89 mM tris (hydroxymethyl)aminomethane (TRIS), 89 mM borate, and 2 mM ethylenediaminetetraacetic acid (EDTA). Upon the completion of electrophoresis, the gel was removed from the glass plates and soaked in a 50% formamide solution containing 12.5 mg/mL Stains-All® (Sigma Chemicals). After staining, the gel was destained in de-ionized water for 2 hours and imaged using a commercial scanner (HP Officejet® J5750).

Inspection of the gel indicates that the oligonucleotide-di-macrocycle conjugate 15 migrates more slowly following treatment with the metal cation solution. In contrast, the gel mobility of the unmodified oligonucleotide is unaffected by metal cation treatment. These data indicate that the di-macrocyclic chelator 12, when conjugated to a DNA oligomer, coordinates with facility to the metal cations tested and forms a stable complex even upon electophoresis in the presence of the competing chelator EDTA. In summary, our findings suggest that di-macrocyclic chelator 12 when conjugated to a site-directing group coordinates readily with a variety of metal cations including those of the lanthanide series.

Preparation of metal ion stocks. In general, the chloride salts of metal cations were dissolved in 50 mM sodium citrate, pH 5, to provide primary stocks of 25 mM cation. These stocks were diluted to 2.5 mM in sterile water. Yttrium triflate was used instead of the chloride salt. In the case of Th(IV) nitrate, a 25 mM stock was prepared in methanol, and this was diluted to 2.5 mM using additional methanol. A saturated solution of zirconium oxalate in 5 mM sodium citrate, pH 5, was also used in these experiments.

Example 4

Synthesis of an Octa-Coordinating Di-Macrocyclic Chelator Peptide Conjugate (Scheme 3)

A related synthetic approach is used to prepare a symmetrical intermediate that is conjugated to a peptide, an oligonucleotide, or other biomolecules. In this approach, an orthogonal protective group, e.g., butyloxycarbonyl, is used to protect the secondary amine of diethylene triamine. Reaction with benzyl protected dithiazolide under pseudo-first order conditions yields the butyloxycarbonyl protected dithiazolide intermediate that is condensed with tetrakis(2-aminoethyl)-ethylenediamine under high dilution conditions to provide the fully protected dimacrocycle. The butyloxycarbonyl protective groups are removed using trifluoroacetic acid to provide the diamine. This diamine is reacted with two peptides sequentially, for example by using an excess of diamine to condense with the first peptide, then conjugating the resulting mono-peptide conjugate with a second peptide. The peptides may be identical or different. Following removal of benzyl protective groups under reducing conditions, the peptide protective groups are removed, for example, with trifluoroacetic acid. The resulting octa-coordinating di-macrocyclic chelator peptide conjugate is used to form a luminescent coordination complex with terbium(III). This compound can be used to assay for the presence of a protein, for example, that binds one or more of the peptide sequences, effecting terbium(III) release and loss of the luminescent signal.

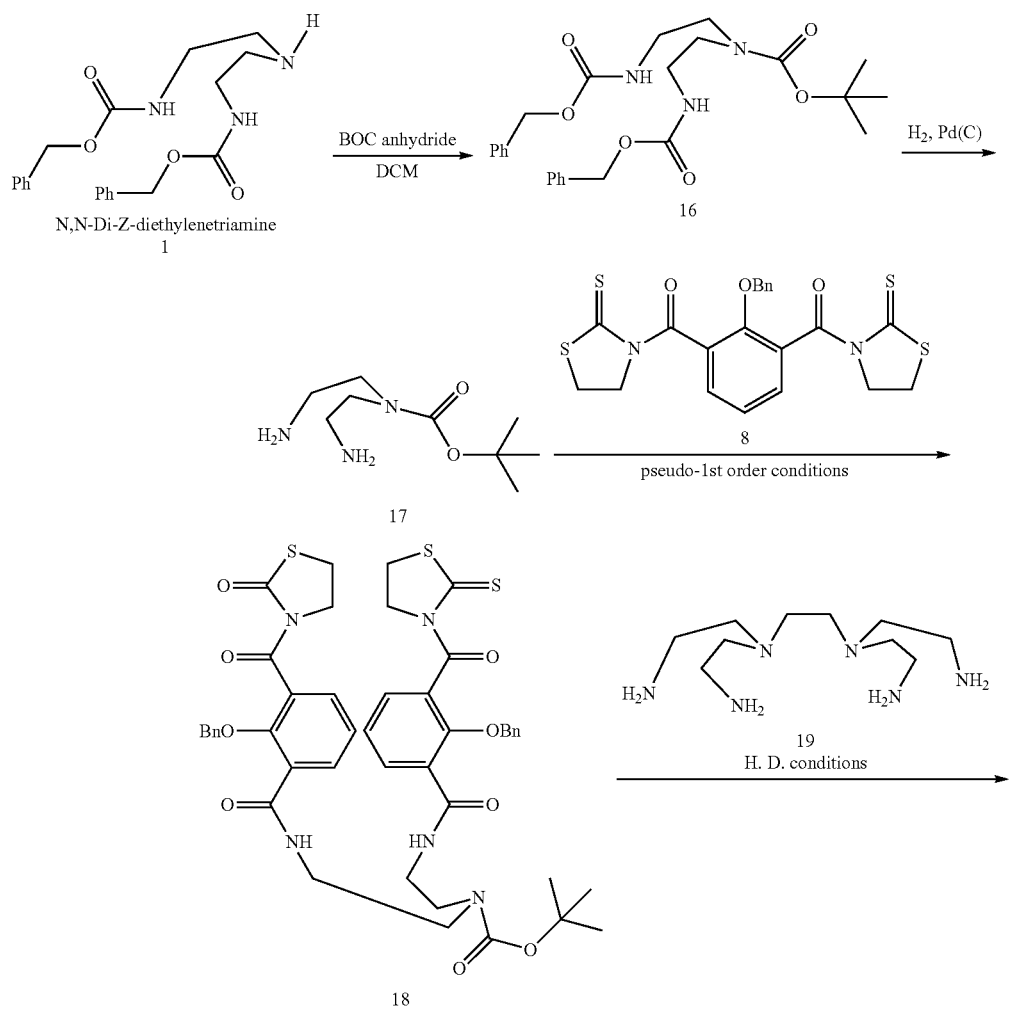

Scheme 3. Synthesis of an octa-coordinating di-macrocyclic chelator peptide conjugate.

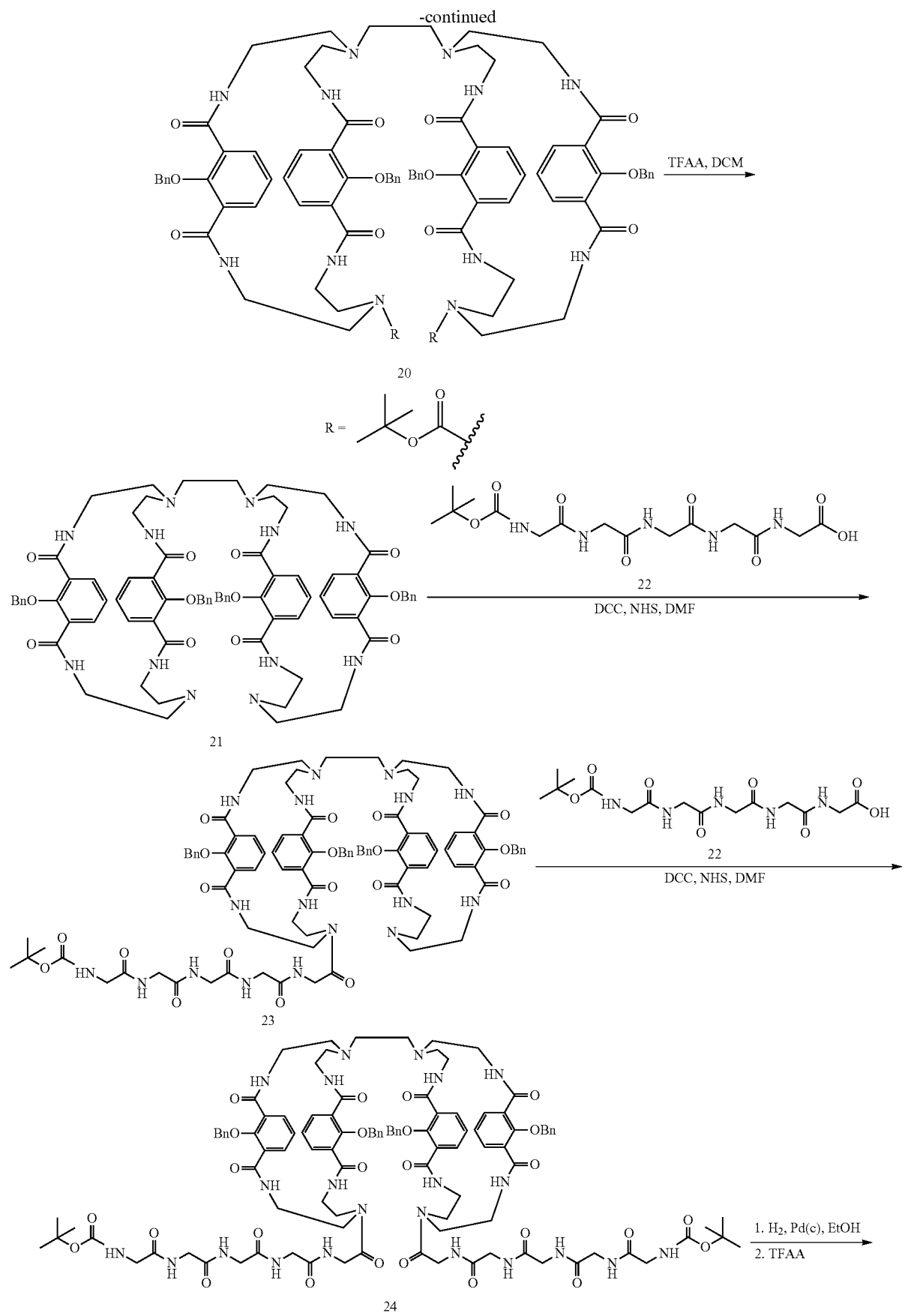

-continued

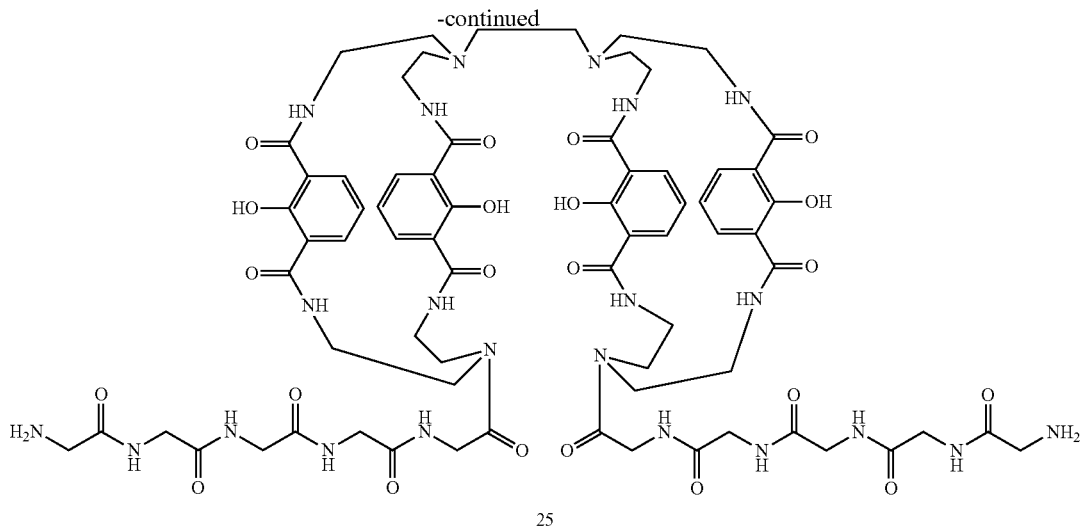

25

Example 5

Protein Detection Using a Luminescent Di-Macrocycle Peptide Conjugate

Figure 2:
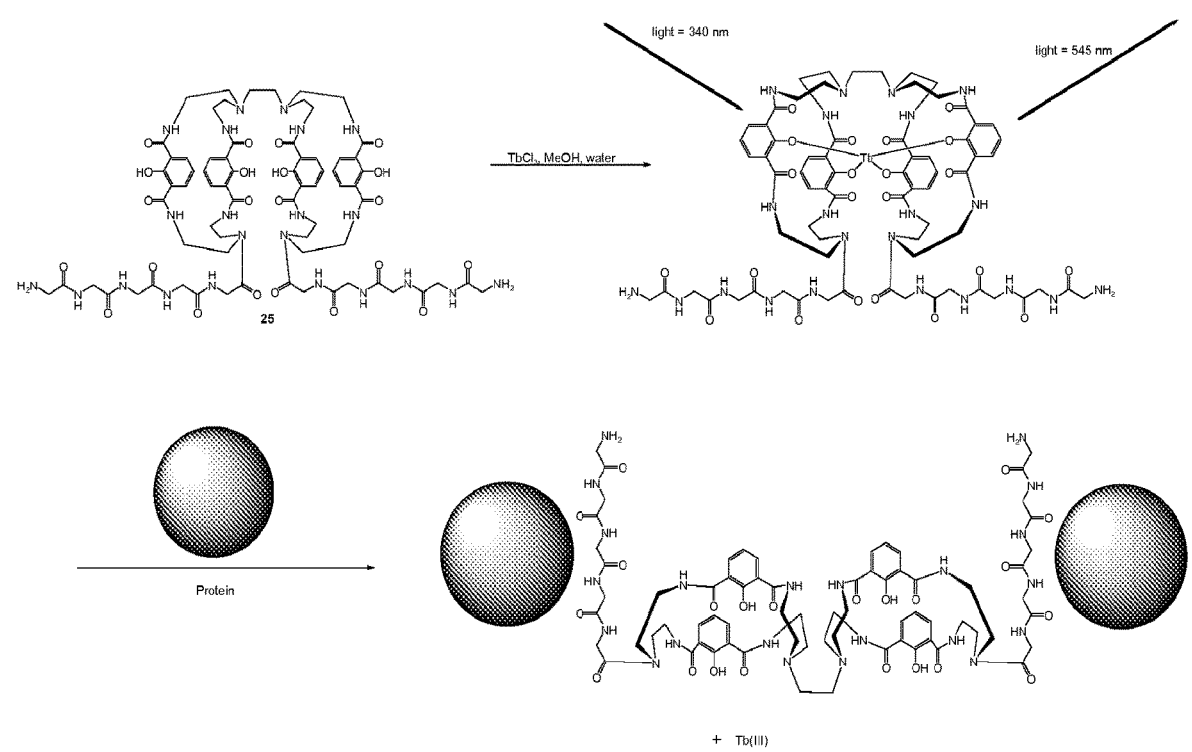
FIG. 2 is an illustration showing protein detection using a luminescent di-macrocycle peptide conjugate.

The octa-coordinating di-macrocyclic chelator peptide conjugate prepared above may be used to assay the presence of a protein that binds specifically to the peptide sequence(s) it contains. For example, addition of buffered terbium chloride solution to an aqueous or methanol solution of peptide conjugate 25 will result in formation of a metal complex (or chelate). The chelator in this instance shields the terbium cation from water and also acts as a photosensitizer, such that activation with light of approximately 340 nm results in long lived terbium luminescence at 545 nm (and other wavelengths). Specific association with a protein in an analytical specimen such as serum would be expected to induce a conformational change in the peptide conjugate such that terbium cation would be released into solution and thus lead to a loss of luminescence. A cartoon of this process is shown in FIG. 2.

Example 6

Synthesis of a Benzyl-Protected 1,2-Hydroxypyridinone Monoacid Monoester (Scheme 4)

Preparation of macrocyclic targets containing 3-pyridinol coordination groups began with 6-methyl-3-pyridinol 26 as a starting material as shown in Scheme 4. Following a literature procedure, 26 was elaborated to the key pyridinol 31, which was alkylated with bromoethylacetate to provide a suitable pyridine dicarboxylate system. Further standard synthetic transformation led to the protected pyridine diester 36. Selective saponification was necessary in order to assure regioisomeric purity of subsequent products. In this instance the selective hydrolysis of an aliphatic vs. aromatic ester provided the desired ester 37.

Methyl 2-bromo-3-[(ethylacetyl)oxy]-6-pyridinecarboxylate 32. Methyl 2-bromo-3-hydroxy-6-pyridinecarboxylate 31 was prepared as previously described (Kelly, T. R. and Lang, F. *J. Org. Chem.*, 1996, 61, 4623-4633). Compound 31 (4.732 g, 20.4 mmol) was treated with ethyl bromoacetate (3.39 mL, 30.6 mmol) and potassium carbonate (4.22 g, 30.6 mmol) in 125 mL anhydrous acetonitrile and heated at reflux for 6 hr. Solvent was removed under reduced pressure, and the residue was dissolved in dichloromethane (100 mL) and washed with water (50 mL). The aqueous wash was extracted with dichloromethane (25 mL) and the combined dichloromethane extracts were washed with water (25 mL). Solvent was removed under reduced pressure, and the residue was dried in vacuo. The crude product was purified by silica gel chromatography using neat dichloromethane and 1% methanol in dichloromethane as eluents. Fractions containing product were combined, solvent was removed under reduced pressure, and the residue dried in vacuo to provide methyl 2-bromo-3-[(ethylacetyl)oxy]-6-pyridinecarboxylate 32 (6.519 g, 100%). $^1$H NMR (300 MHz, CDCl$_3$): δ=8.06 (d, 1H, ArH), 7.08 (s, H, ArH), 4.79 (s, 2H, CH$_2$O), 4.27 (q, 2H, CH$_2$CH$_3$), 3.96 (s, 3H, CO$_2$CH$_3$), 1.29 (t, 3H, CH$_2$CH$_3$. $^{13}$C NMR (300 MHz, CDCl$_3$): δ=167.3, 164.5, 154.5, 141.0, 133.2, 126.0, 119.5, 66.2, 62.3, 53.2, 14.4. FTMS pESI: calculated for C$_{11}$H$_{13}$BrNO$_5$ [MH]$^+$, 317.9972. found, 317.9973.

2-Bromo-3-[(carboxymethyl)oxy]-6-pyridinecarboxylic acid 33. Compound 32 (6.519 g, 20.5 mmol) was dissolved in tetrahydrofuran (85 mL). Sodium hydroxide, 1 M solution (62 mL, 62 mmol) was added and the mixture was stirred for 5 hr. Tetrahydrofuran was removed under reduced pressure, and the solution was acidified to pH 2 using 6N hydrochloric acid (ca. 11 mL). The resulting solids were filtered, washed with water (2×10 mL), and dried in vacuo to provide 2-bromo-3-[(carboxymethyl)oxy]-6-pyridinecarboxylic acid 33 (5.657 g, 100%). $^1$H NMR (300 MHz, MeOD): δ=8.07 (d, 1H, ArH), 7.42 (d, 1H, ArH), 4.93 (s, 2H, CH$_2$O). $^{13}$C NMR (300 MHz, MeOD): δ=170.7, 166.5, 156.0, 141.7, 133.3, 127.0, 121.3, 66.5. FTMS–pESI: calculated for C$_8$H$_5$BrNO$_5$ [M]$^-$, 273.9357. found, 273.9365.

2-Bromo-3-[(carboxymethyl)oxy]-6-carboxypyridine-N-oxide 34. Compound 33 (5.657 g, 20.5 mmol) was dissolved in trifluoroacetic acid (113 mL) under inert atmosphere. Hydrogen peroxide, 30% aqueous solution (8.0 mL, 71 mmol) was added and the solution was heated to 80° C. for 3 hr. After cooling, water (25 mL) was added and solvents were removed under reduced pressure. Additional water (25 mL) was added, the resulting suspension was triturated for 0.5 hr, whereupon the solids were filtered using a fitted funnel, washed with water (3×5 mL) and dried in vacuo to provide 2-bromo-3-[(carboxymethyl)oxy]-6-carboxypyridine-N-oxide 34 (5.205 g, 87.0%). $^1$H NMR (300 MHz, MeOD): δ=8.29 (d, 1H, ArH), 7.43 (d, 1H, ArH), 5.05 (s, 2H, CH$_2$O). $^{13}$C NMR (400 MHz, DMSO, MeOD): δ=168.9, 160.7, 157.6, 131.7, 127.6, 125.8, 114.9, 66.7. FTMS pESI: calculated for C$_8$H$_7$BrNO$_6$ [MH]$^+$, 291.9451. found, 291.9449.

1-Hydroxy-2-oxo-3-[(carboxymethyl)oxy]-6-pyridinecarboxylic acid 35. Compound 34 (5.205 g, 17.8 mmol) was dissolved in 15% aqueous potassium hydroxide (83 mL) under inert atmosphere. The solution was heated to 80° C. for 36 hr. After cooling, concentrated hydrochloric acid (17 mL) was added, the resulting suspension was triturated for 0.5 hr, whereupon the solids were filtered using a fitted funnel, washed with water (3×5 mL) and dried in vacuo to provide crude 1-hydroxy-2-oxo-3-[(carboxymethyl)oxy]-6-pyridinecarboxylic acid 35 (4.667 g, 114%) that was used in the next step without further purification. $^1$H NMR (300 MHz, D2O, NaOD): δ=6.60 (d, 1H, ArH), 6.15 (d, 1H, ArH), 4.30 (s, 2H, CH$_2$O). $^{13}$C NMR (400 MHz, D2O, NaOD): δ=176.3, 170.5, 156.2, 145.9, 140.1, 111.9, 102.8, 67.4. FTMS–pESI: calculated for C$_8$H$_6$NO$_7$ $_{[M]}^-$, 228.0150. found, 228.0149.

1-Benzyloxy-2-oxo-3-[(carboxymethyl)oxy]-6-pyridinecarboxylic acid dimethyl ester 36. Compound 35 (2.340 g, 10.2 mmol) was suspended in methanol (80 mL) under inert atmosphere. Chlorotrimethylsilane (13 mL, 102 mmol) was added, and the suspension was stirred for 44 hr. Solvents were removed under reduced pressure, potassium carbonate (2.819 g, 20.4 mmol) was added, and the residue was dried in vacuo overnight. The mixture was suspended in anhydrous acetonitrile (100 mL), benzyl bromide (2.43 mL, 20.4 mmol) was added, and the suspension was heated at reflux for 6 hr. After cooling, solvents were removed under reduced pressure, the residue was dissolved in dichloromethane (75 mL), and washed with water (50 mL). The aqueous layer was washed with dichloromethane (20 mL), and the combined dichloromethane extracts were washed with water (25 mL). Solvent was removed under reduced pressure and the product was purified by silica gel chromatography using 2% methanol in dichloromethane as eluent. Purified product was dried in vacuo to provide 1-benzyloxy-2-oxo-3-[(carboxymethyl)oxy]-6-pyridinecarboxylic acid dimethyl ester 36 (2.883 g, 81.3%). $^1$H NMR (300 MHz, CDCl3): δ=7.57 (m, 2H, ArH), 7.37 (m, 3H, ArH), 6.64 (s, 2H, ArH), 5.40 (s, 2H, CH2Ph), 4.82 (s, 2H, CH$_2$O), 3.85 (s, 3H, CH3), 3.79 (s, 3H, CH3). $^{13}$C NMR (400 MHz, CDCl3): δ=168.4, 160.1, 154.8, 152.1, 133.8, 131.1, 130.2, 129.2, 128.6, 114.4, 108.4, 78.6, 66.2, 53.0, 52.4. FTMS+pESI: calculated for C$_{17}$H$_{18}$NO$_7$ [MH]$^+$, 348.1078. found, 348.1078.

Scheme 4. Synthesis of a benzy-protected 1,2-hydroxypyridinone monoacid monoester.

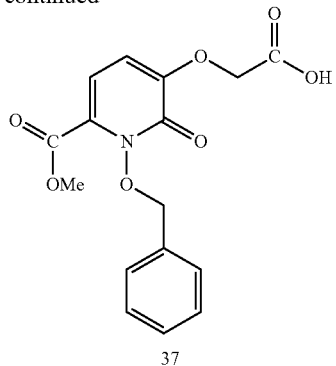

37

1-Benzyloxy-2-oxo-3-[(carboxymethyl)oxy]-6-pyridinecarboxylic acid 6-methyl ester 37. Compound 36 (2.348 g, 6.76 mmol) was dissolved in tetrahydrofuran (57 mL) and deionized water (14 mL). Sodium hydroxide (1M, 6.42 mL, 6.42 mmol) was added over the course of half an hour by addition funnel. The funnel was rinsed with water (0.5 mL), and the solution was allowed to stir overnight. Tetrahydrofuran was removed under reduced pressure, and the solution was transferred to a separatory funnel using dichloromethane (75 mL) and water (50 mL). The organic layer was removed and saved. The aqueous layer was washed with dichloromethane (3×75 mL), and the combined dichloromethane extracts were also saved (to recover unreacted starting material). Hydrochloric acid (1 M, 6.0 mL) was added to the aqueous phase to form a precipitate that was extracted with 20% ethyl acetate in dichloromethane (200 mL and 2×100 mL). The combined organic extracts were washed with water (2×100 mL) and solvents were removed under reduced pressure. Product was dried in vacuo to provide 1-benzyloxy-2-oxo-3-[(carboxymethyl)oxy]-6-pyridinecarboxylic acid 6-methyl ester 37 (1.764 g, 78.3%). Unreacted starting material (285 mg) was also recovered. $^1$H NMR (400 MHz, DMSO-d6): δ=7.50 (m, 2H, ArH), 7.42 (m, 3H, ArH), 6.78 (d, 1H, ArH), 6.64 (d, 1H, ArH), 5.27 (s, 2H, CH2Ph), 4.39 (s, 2H, CH$_2$O), 3.81 (s, 3H, CH3). $^{13}$C NMR (400 MHz, DMSO-d6): δ=160.3, 154.4, 153.0, 134.3, 130.2, 130.0, 129.0, 128.7, 112.1, 110.0, 78.2, 67.5, 53.4. FTMS+pESI: calculated for $C_{16}H_{16}NO_7$ [MH]$^+$, 334.0921. found, 334.0917.

Example 7

Synthesis of a 1,2-Hydroxypyridinone Octa-Coordinating Di-Macrocycle (Scheme 5)

Benzyl-protected 1,2-hydroxypyridinone monoacid monoester 37 is activated using diisopropylcarbodiimide and N-hydroxysuccinimide in dimethylformamide and reacted with diamine 4 to form the diamide 38. Ester groups are removed from the diamide by hydrolysis, whereupon the resulting diacid 39 is activated using diisopropylcarbodiimide and N-hydroxysuccinimide in dimethylformamide and condensed with tetra-amine 10 under high-dilution conditions to provide the benzyl and tert-butyloxycarbonyl protected di-macrocycle 40. Removal of protective groups using acidic conditions results in the 1,2-hydroxypyridinone octa-coordinating di-macrocycle 41.

N,N"-bis[1-Benzyloxy-2-oxo-3-[(carboxyamidomethyl)oxy]-6-(methoxycarbonyl)pyridine]-N'-[2-[2-(2-methoxyethoxy)ethoxy]ethoxy]-bis(2-aminoethyl)amine 38. 1-Benzyloxy-2-oxo-3-[(carboxymethyl)oxy]-6-pyridinecarboxylic acid 6-methyl ester 37 (821 mg, 2.46 mmol) and N-hydroxysuccinimide (340 mg, 2.95 mmol) were dried in vacuo overnight. Anhydrous dimethylformamide (5 mL) was added to form a solution, diisopropylcarbodiimide (458 µL, 2.95 mmol) was added, and the solution was stirred for 6 hr under nitrogen atmosphere. N'-[2-[2-(2-methoxyethoxy)ethoxy]ethoxy]-bis(2-aminoethyl)amine 4 (256 mg, 1.03 mmol) was dissolved in dimethylformamide (1 mL) and diisopropylethylamine (536 µL, 3.08 mmol) and added to the reaction mixture. After 22 hr, water (ca. 1 mL) was added, and solvents were removed under reduced pressure. The residue was dissolved in dichloromethane (20 mL), washed with water (15 mL), and the aqueous fraction was extracted with dichloromethane (2×10 mL). The combined dichloromethane extracts were concentrated and the crude product was purified by silica gel chromatography using 0.1% triethylamine, 5% methanol in dichloromethane as eluents. Fractions containing product were combined, solvent was removed under reduced pressure, and the residue dried in vacuo to provide compound 38 (389 mg, 43.1%). $^1$H NMR (300 MHz, CDCl$_3$): δ=7.99 (br t, 2H, NH), 7.52 (m, 4H, PhH), 7.36 (m, 6H, PhH), 6.58 (s, 4H, ArH), 5.33 (s, 4H, PhCH$_2$O), 4.50 (s, 4H, OCH$_2$C=O), 3.81 (6H, s, CO$_2$CH$_3$), 3.55-3.39 (m, 14H, CH$_2$O, CH$_2$NC=O), 3.32 (s, 3H, OCH$_3$), 2.74 (m, 6H, CH$_2$N). $^{13}$C NMR (600 MHz, CDCl$_3$): δ=166.6, 159.6, 154.7, 152.7, 133.7, 130.1, 129.6, 129.1, 129.0, 128.5, 112.4, 108.9, 78.4, 71.9, 71.8, 70.5, 70.3, 69.5, 68.4, 58.9, 53.9, 53.4, 52.8, 37.5. FTMS pESI: calculated for $C_{43}H_{54}N_5O_{15}$ [M+H]$^+$, 880.3611. found, 880.3608.

N,N"-bis[1-Benzyloxy-2-oxo-3-[(carboxyamidomethyl)oxy]-6-carbonyl(2-mercaptothiazolide) pyridine]-N'-[2-[2-(2-methoxyethoxy)ethoxy]ethoxy]-bis(2-aminoethyl)amine 39. Diester 38 (341 mg, 388 µmol) was dissolved in tetrahydrofuran (7 mL) and water (1 mL). One molar aqueous sodium hydroxide solution (1.356 mL, 1.356 mmol) was added and the solution was stirred for 23 hr. Hydrochloric acid (6N, 226 µL) was added, solvents were removed under reduced pressure, and the residue was dried in vacuo. A portion of the residue (281 mg, 316 µmol) was treated with TBTU (254 mg, 791 µmol) and 2-mercaptothiazoline (94 mg, 789 µmol), and the flask was dried further in vacuo Anhydrous dichloromethane (10 mL) was added to form a suspension, whereupon diisopropylethylamine (500 uL, 2.87 mmol) was added to form a solution. After 18 hours, solvent was removed under reduced pressure and the residue was purified by silica gel chromatography to provide compound 39 (136 mg, 40.8%). FTMS pESI: calculated for $C_{47}H_{56}N_7O_{13}S_4$ [M+H]$^+$, 1054.2813. found, 1054.2797.

Benzyl and tert-butyloxycarbonyl-protected di-macrocycle 40. A solution of compound 39 (ca. 1 g) in dichloromethane (49.5 mL) and triethylamine (0.5 mL) and a solution of 5-amino-6-[(2-aminoethyl)-[2-[bis(2-aminoethyl)amino]ethyl]amino]hexylcarbamic acid tert-butyl ester 10 (one molar equivalent) in dichloromethane, isopropyl alcohol (ca. 5%), and diisopropylethylamine (ca. 3%) (50 mL) are added dropwise to dichloromethane (2 L) over a period of four days using two syringe pumps at a rate of 0.5 mL/hr. After an additional two days of reaction, solvent is removed under reduced pressure, and the crude product is purified by silica gel chromatography. The silica gel column is prepared so as to have a short section (ca. 1.25") of aluminum oxide (basic, Brockmann I) on its bottom. Fractions containing product are combined, solvent is removed under reduced pressure, and the residue dried in vacuo to provide the protected di-macrocycle 40.

Di-macrocycle 41. Benzyl and tert-butyloxycarbonyl-protected di-macrocycle 40 (ca. 50 mg) is dissolved in 12N hydrochloric acid (1.0 mL) and glacial acetic acid (1.0 mL). The solution is stirred under inert atmosphere for ca. one day, whereupon HCl is removed with a stream of inert gas. Solvents are removed under reduced pressure and the residue is dried in vacuo. The residue is dissolved in methanol (600+300 μL) and transferred to two O-ring microcentrifuge tubes. Ether (ca. 1.5 mL) is added, and the tubes are placed at 4° C. for 1 hr. The tubes are centrifuged at 12,000 rpm for 3 minutes, decanted, the pellets are washed with ether (ca. 1.5 mL) and allowed to air dry. The pellets are dried in vacuo to provide di-macrocycle 41, pentahydrochloride salt.

Scheme 5. Synthesis of a 1,2-hydroxypyridinone octa-coordinating di-macrocycle.

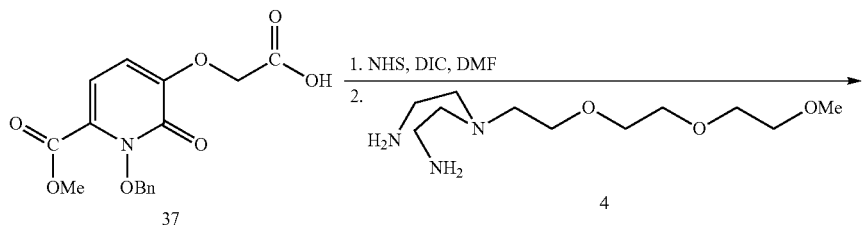

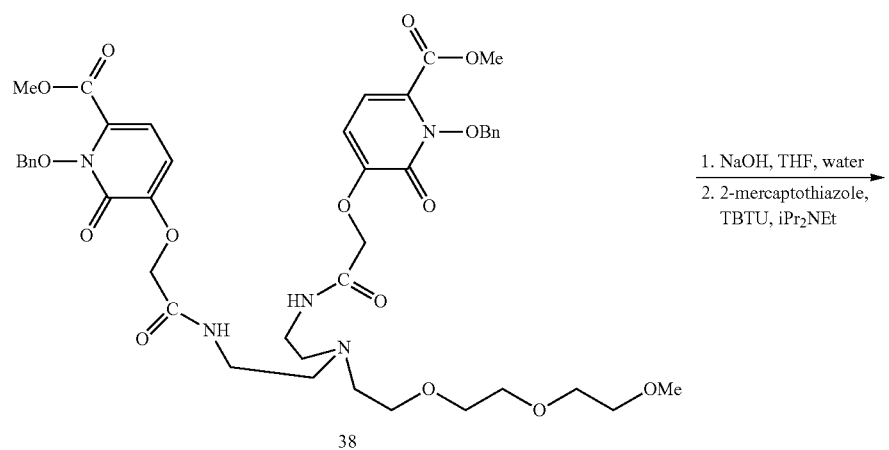

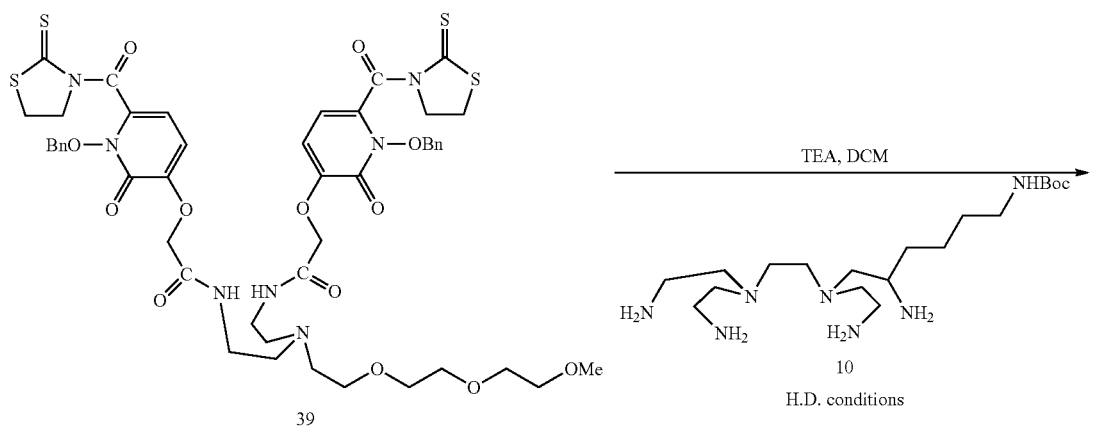

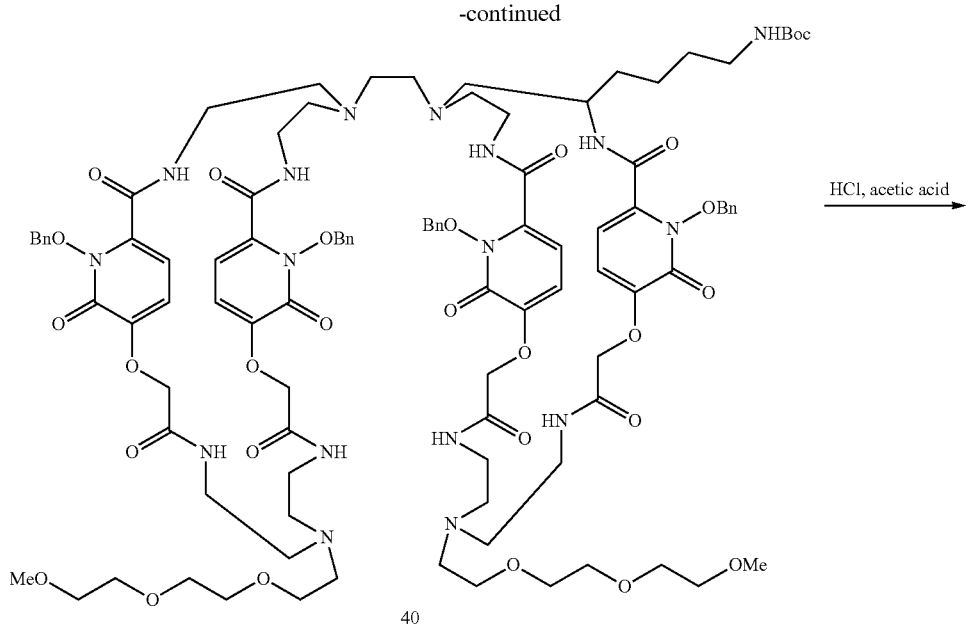

40

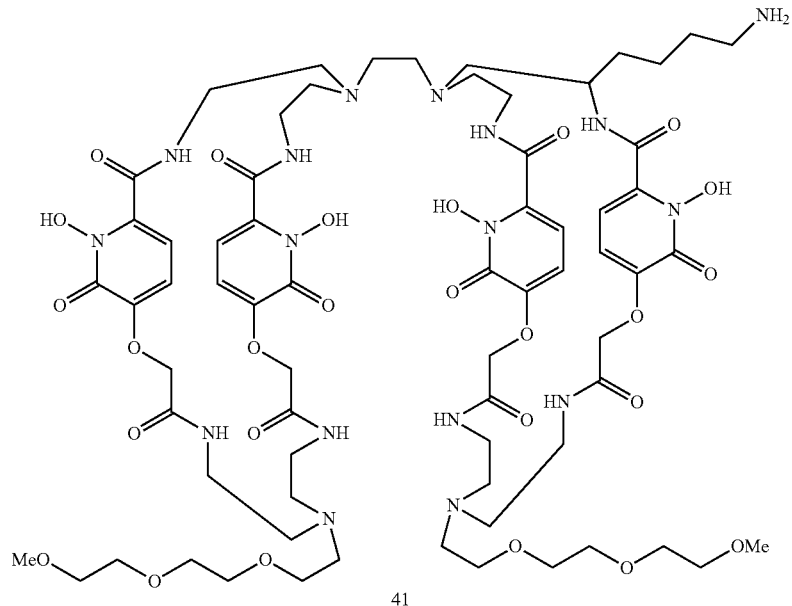

41

Example 8

Compound Stabilization Using Complementary DNA Oligonucleotides

Utilizing complimentary oligonucleotides on endocyclic amines allows for complimentary pairing in aqueous solution. The synthetic method is versatile in that it allows for the coupling of different entities on the two free amines during synthesis, prior to formation of the macromolecule.

In yet another approach, the two covalently attached oligonucleotides need not be complementary, such that a third, free oligonucleotide in solution, of appropriate sequence, could be used to stabilize the reported structure. Additionally, if the solution based oligo is from a specimen under investigation, a properly prepared reporter could serve to prime various polymerase chain reactions that would replicate the template DNA.

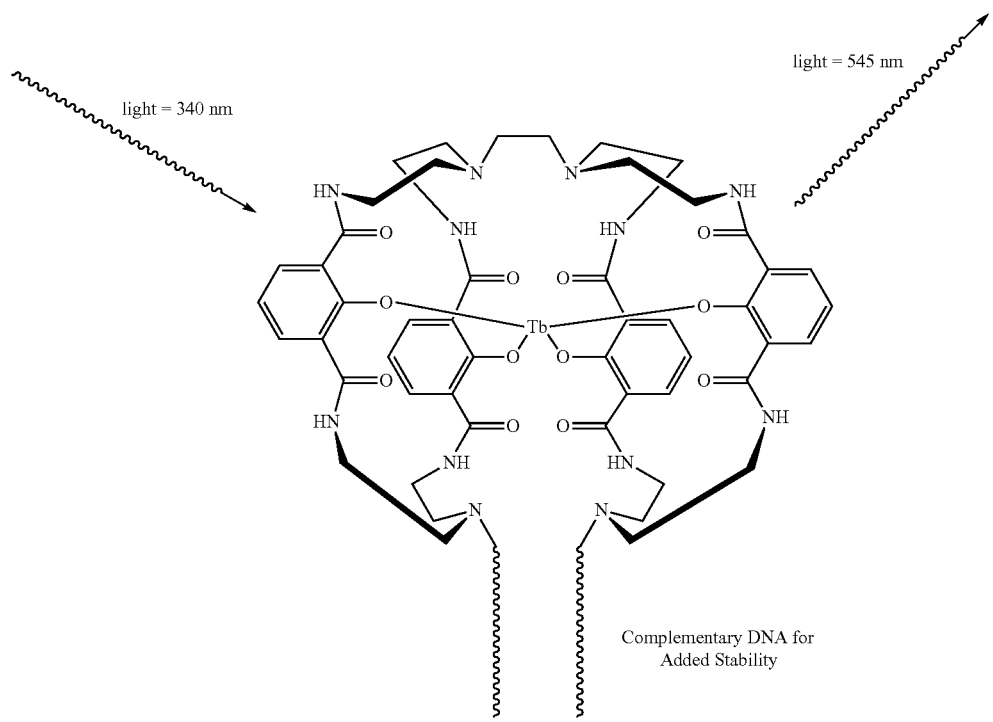

Complementary DNA for Added Stability

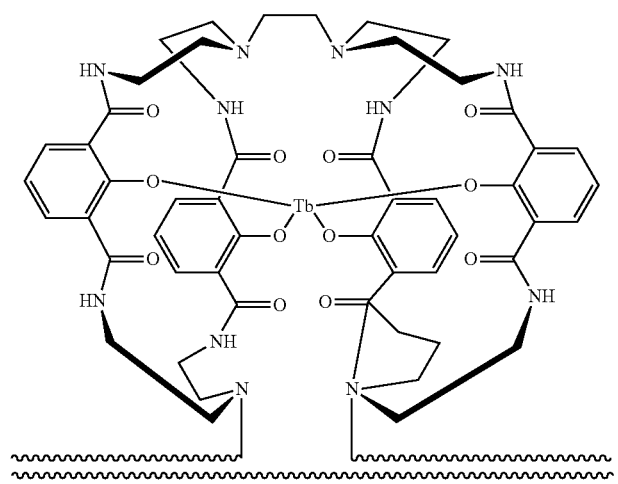

Example 9

Formation of dsDNA Results in Reporter Attenuation Via Structural Disruption of Chelate and Tb Loss In yet another example, a properly designed chelate is provided with covalently attached oligos that are bound to their compliment sections of a hybridized oligo spanning both segments. An intermediate sequence that lacks complementarity to the reporter, is designed with complementarity with a sequence that is of interest in biological samples. Upon mixing, the loop section hybridizes with the target sequence and the rigid double-stranded oligo forces the reporter open, releasing the Tb and resulting in a subsequent loss of fluorescent signal.

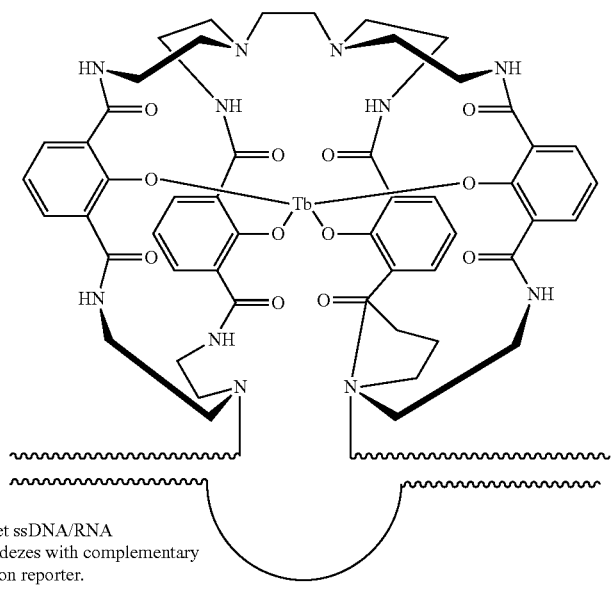

Target ssDNA/RNA hybridezes with complementary loop on reporter.

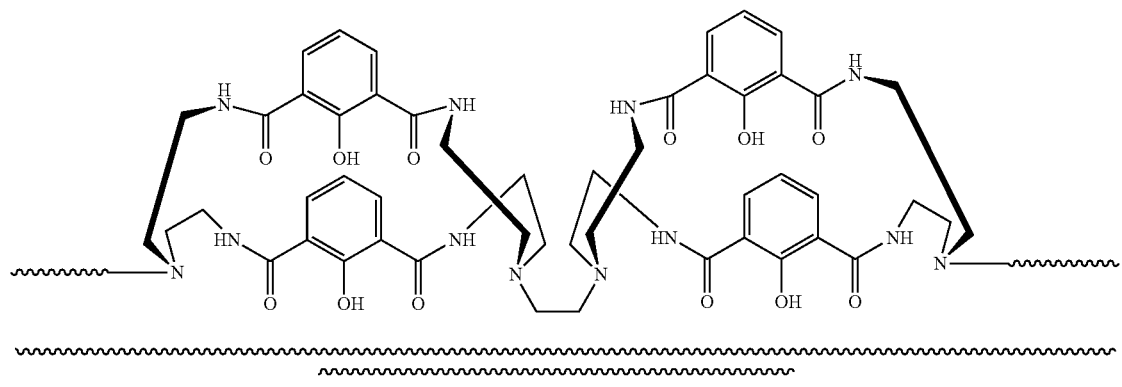

Target ssDNA/RNA in sample hybridizes forcing the reporter reporter open, losing Tb and reducing eliminating reporter signal.

Example 10

Stepwise Synthesis of Di-Macrocycle (Scheme 6)

Alternative approaches may be used for the large scale manufacture of di-macrocyclic compounds. tert-Butyloxycarbonyl protected diethylenetriamine 17 is condensed with 2-benzyloxy-bis(2-mercaptothiazole)isophthalamide 8, using pseudo-first order conditions as shown in Scheme 6. Condensation of 18 with diamine 4 under high dilution conditions leads to formation of the mono-macrocycle 42. Removal of the tert-butyloxycarbonyl protective group with trifluoroacetic acid produces the macrocycle 43. Alkylation of 43 with 1,2-dibromoethane using pseudo-first order conditions produces alkyl halide 44. Reaction between benzyloxycarbonyl protected ethylene diamine 45 and the aldehyde prepared from tert-butyloxycarbonyl and benzyloxycarbonyl protected lysine 46 forms a secondary amine 47, that is protected as the formamide 48 using triethylorthoformate. Removal of the benzyloxycarbonyl protective groups from 48 under reducing conditions provides the diamine 49, which is condensed with dithiazolide intermediate 9 under high dilution conditions. This leads to formation of the mono-macrocycle 50. Removal of the formamide protective group with hydrazine produces the macrocycle 51. Macrocyclic amine 55 is condensed with macrocyclic bromide 44 to form the protected di-macrocycle 11. Di-macrocycle 11 is deprotected as shown above in Scheme 1 to form di-macrocycle 12.

Scheme 6. Stepwise synthesis of di-macrocycle.
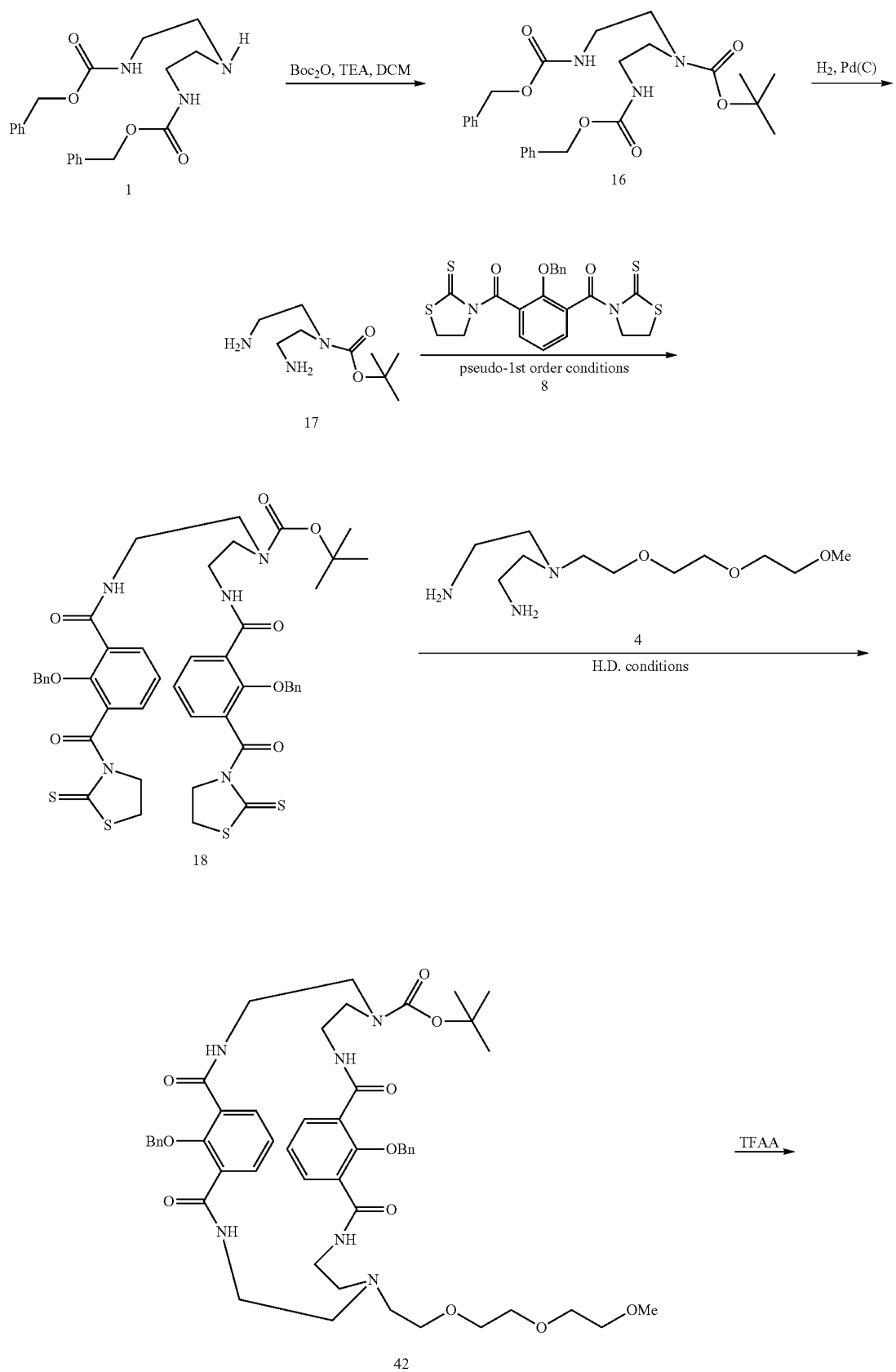

-continued
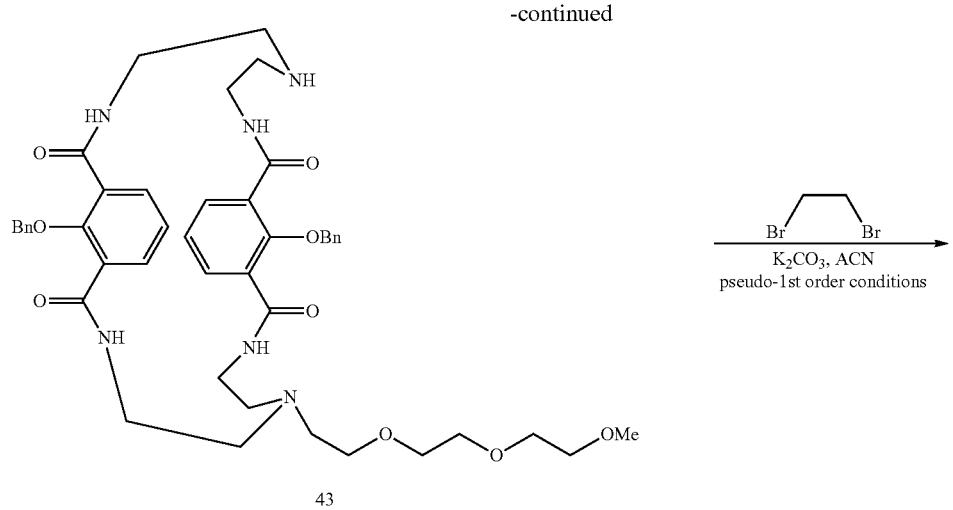
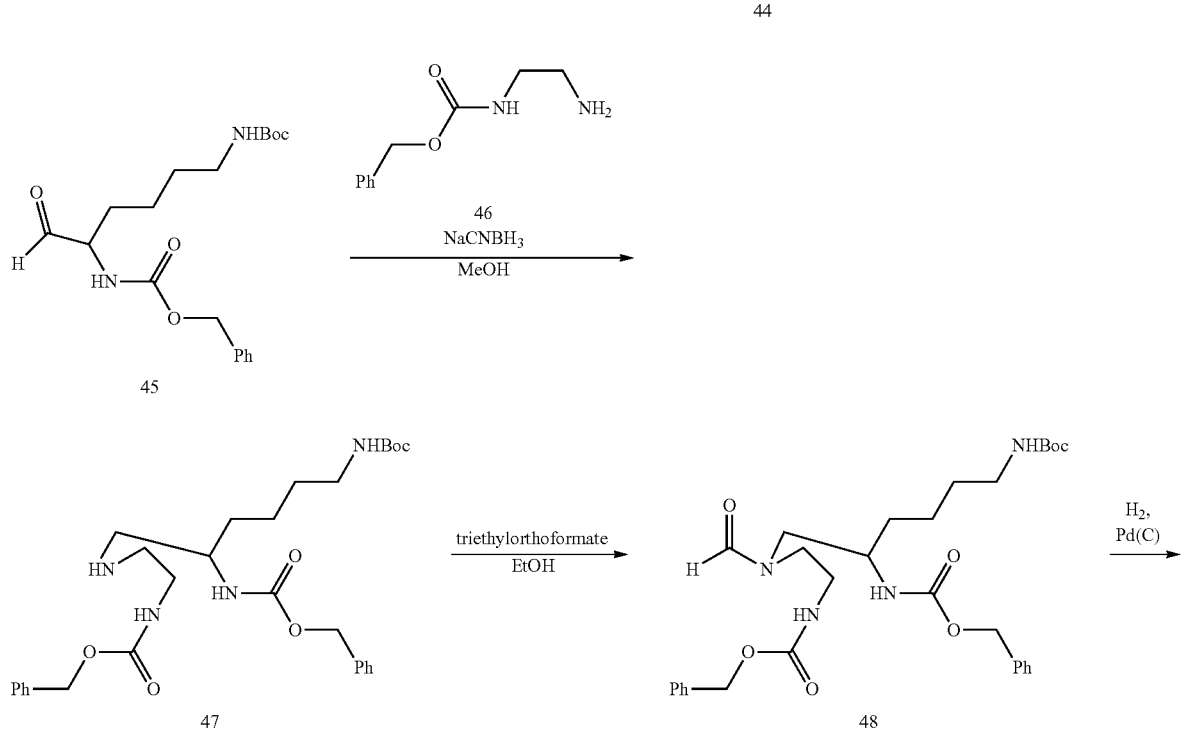

-continued
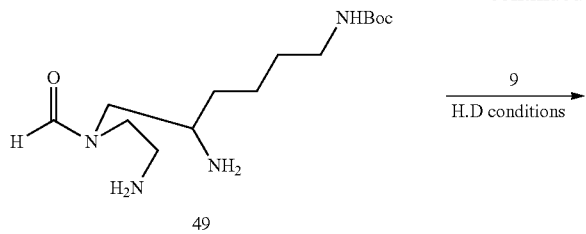
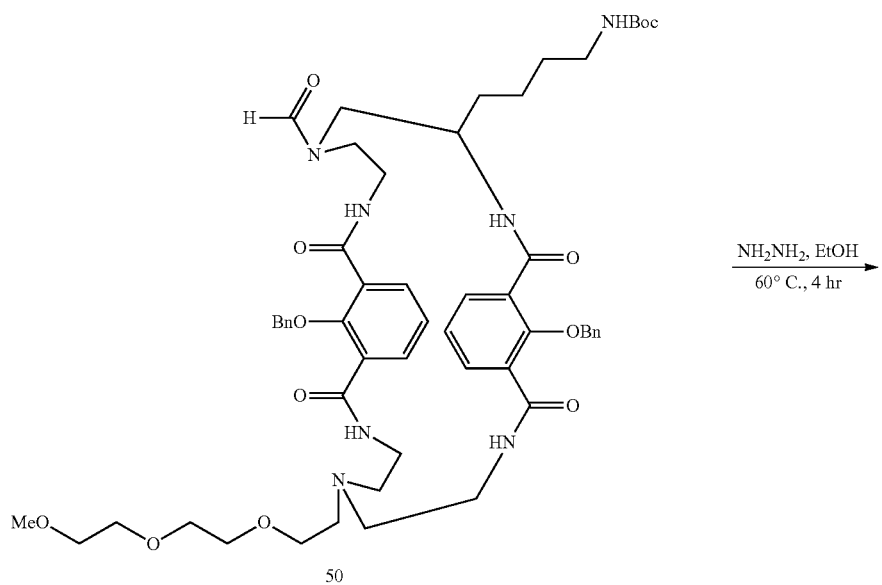
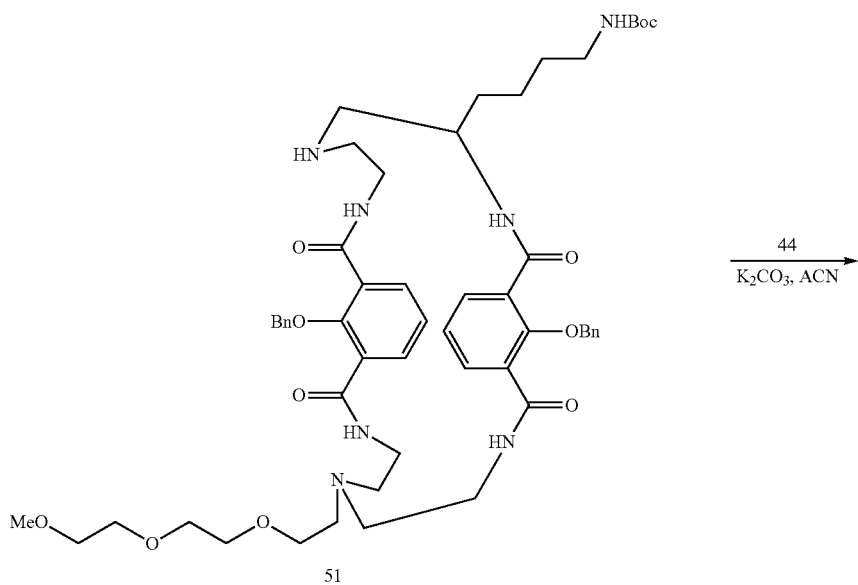

-continued

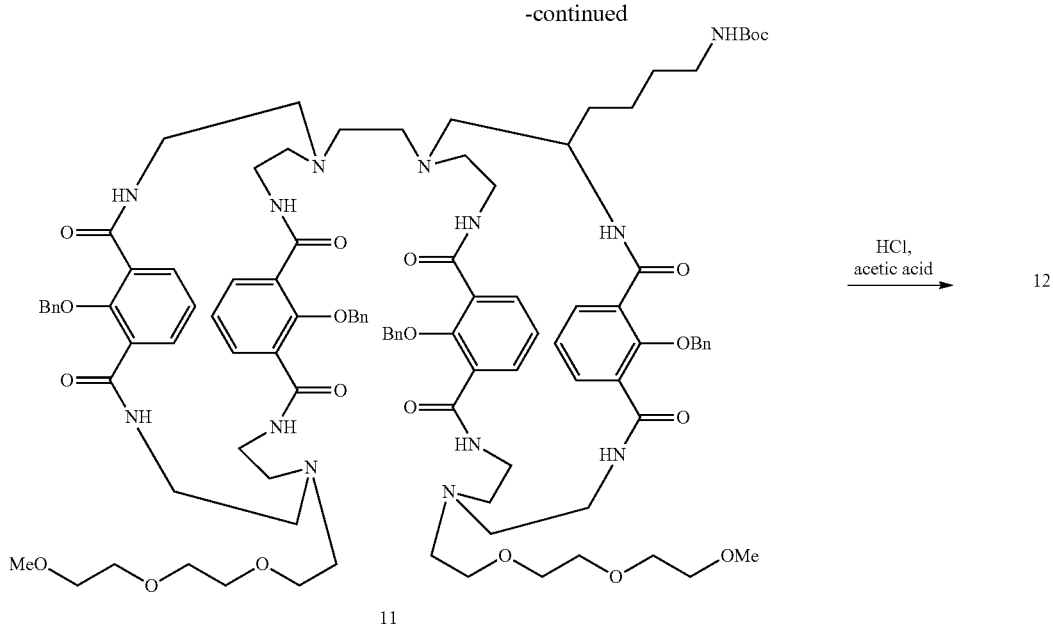

11

HCl,
acetic acid
⟶ 12

Example 11

Stepwise Synthesis of Di-Macrocycle (Scheme 7)

Alternative approaches may be used for the large scale manufacture of di-macrocyclic compounds. Reaction between benzyloxycarbonyl protected ethylene diamine 45 and the aldehyde prepared from tert-butyloxycarbonyl and benzyloxycarbonyl protected lysine 46 forms a secondary amine 47. As an alternative approach, this amine is reacted with 2-bromoethanol to form the alcohol 52. Removal of the benzyloxycarbonyl protective groups from 52 under reducing conditions provides the diamine 53, which is condensed with dithiazolide intermediate 9 under high dilution conditions. This leads to formation of the mono-macrocycle 54. Activation of the alcohol using p-toluenesulfonyl chloride produces the macrocycle 55. Macrocyclic amine 55 is used to alkylate macrocyclic amine 43 to form the protected di-macrocycle 11. Di-macrocycle 11 is deprotected as shown above in Scheme 1 to form di-macrocycle 12.

Scheme 7. Stepwise synthesis of di-macrocycle.

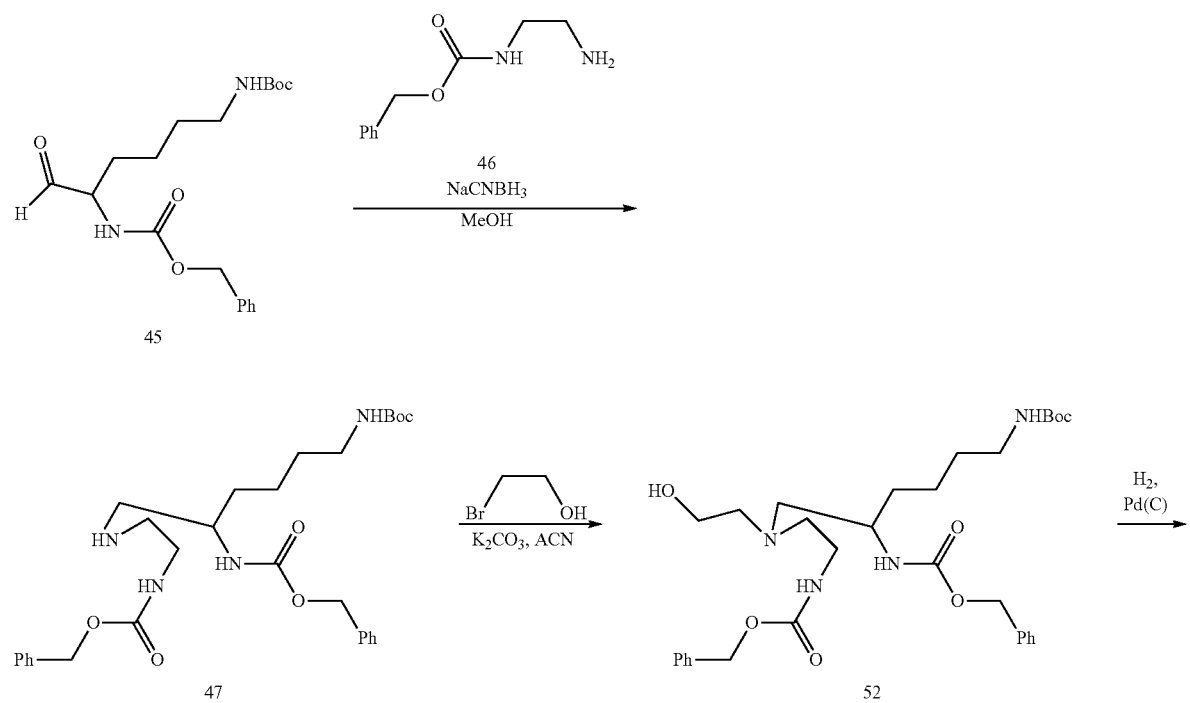

-continued
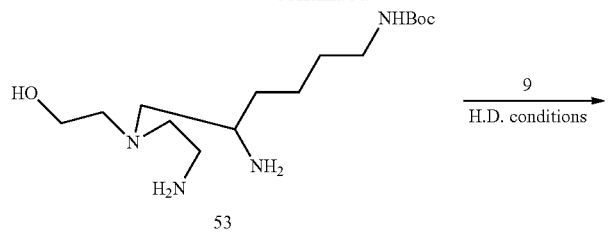
53
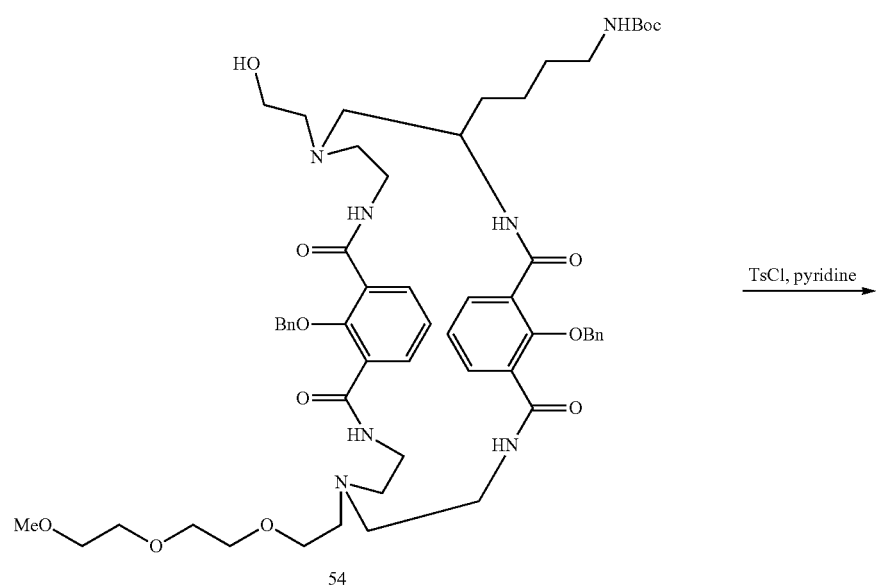
54
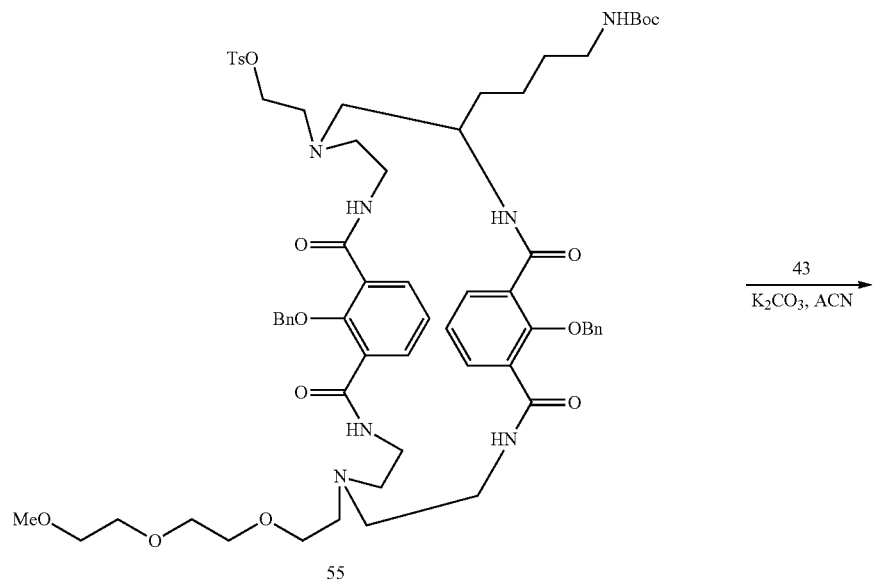
55

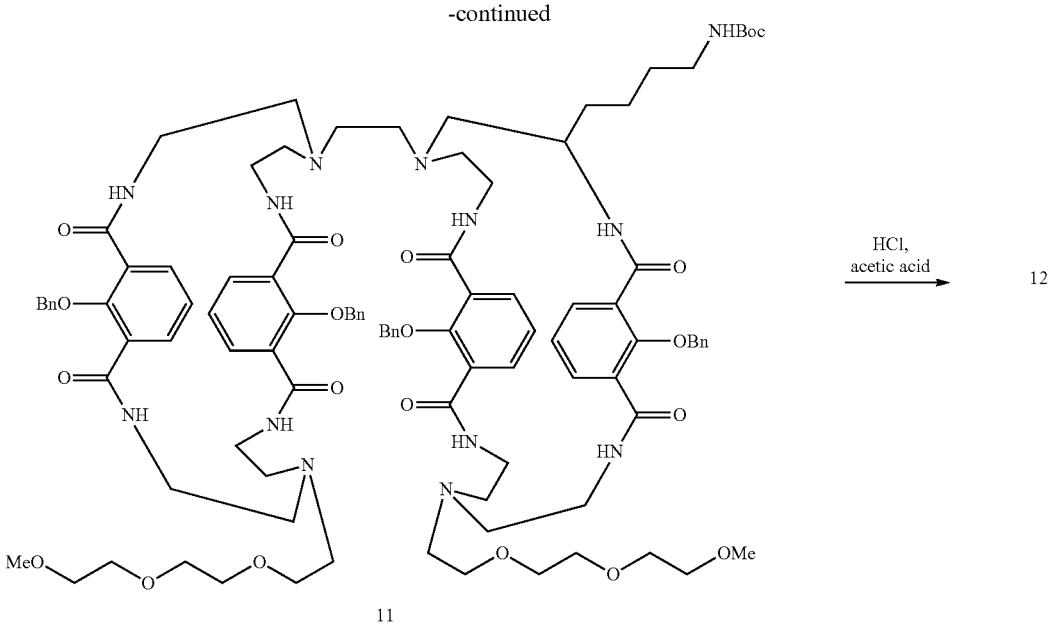

Example 12

Stepwise Synthesis of Di-Macrocycle (Scheme 8)

Alternative approaches may be used to alter the position of the linker arm in di-macrocyclic compounds. Formamide protected diethylenetriamine 57 is condensed with 8 under pseudo-first order conditions to form dithiazolide 58. The secondary amine 47 is alkylated to form tertiary amine 59, which is deprotected under reducing conditions to provide diamine 60. The dithiazolide 58 is condensed with diamine 60 under high dilution conditions to form macrocycle 61. The formamide group is removed using hydrazine to form the macrocyclic amine 62, which is alkylated with the macrocyclic bromide 44 to form the protected di-macrocycle 63. Di-macrocycle 63 is deprotected under acidic conditions to form di-macrocycle 64.

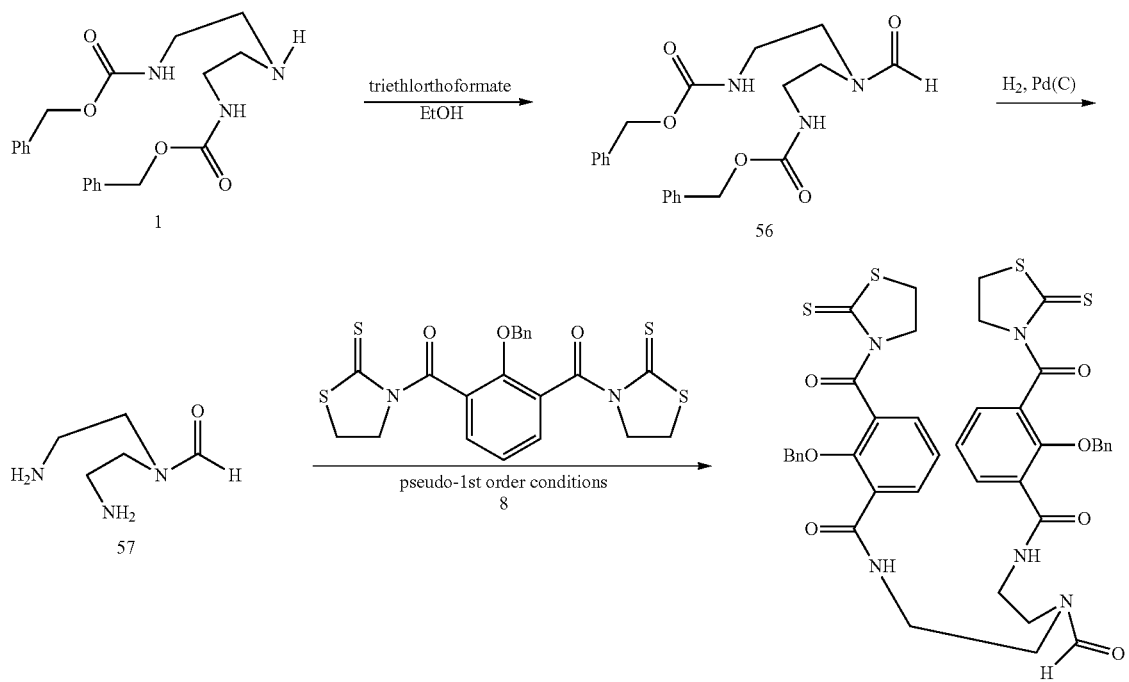

Scheme 8. Stepwise synthesis of di-macrocycle.

-continued
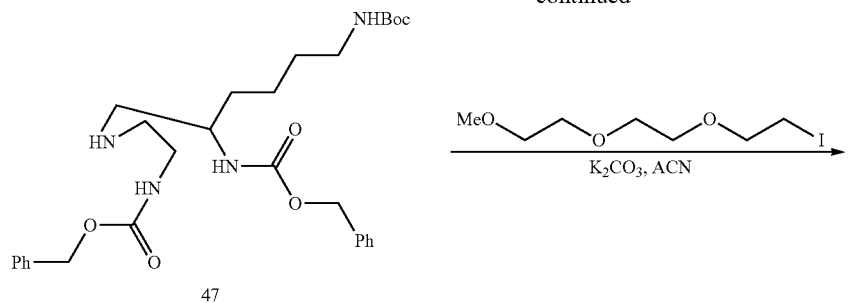
47
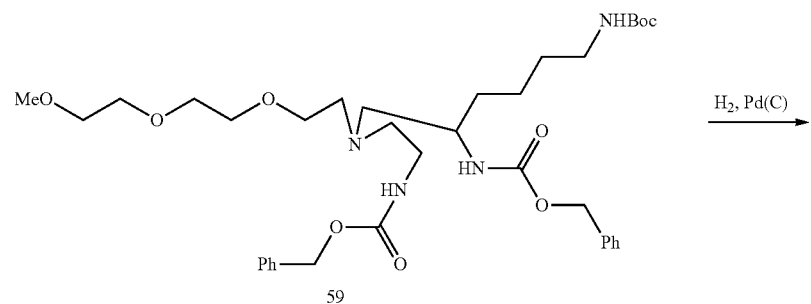
59
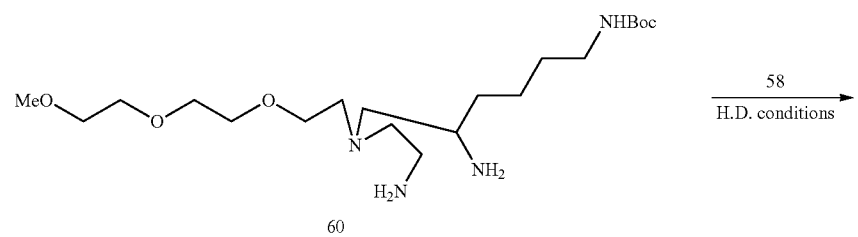
60
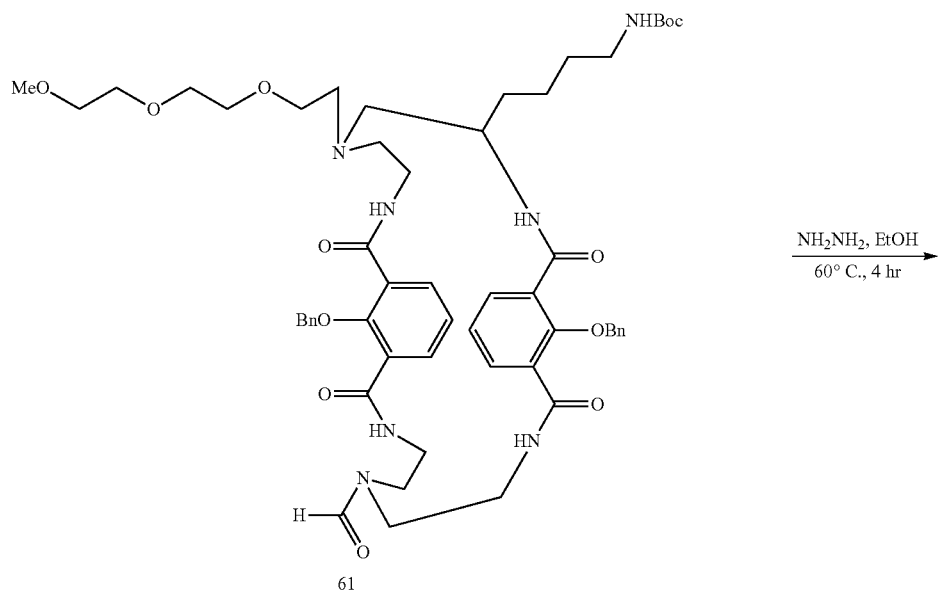
61

-continued
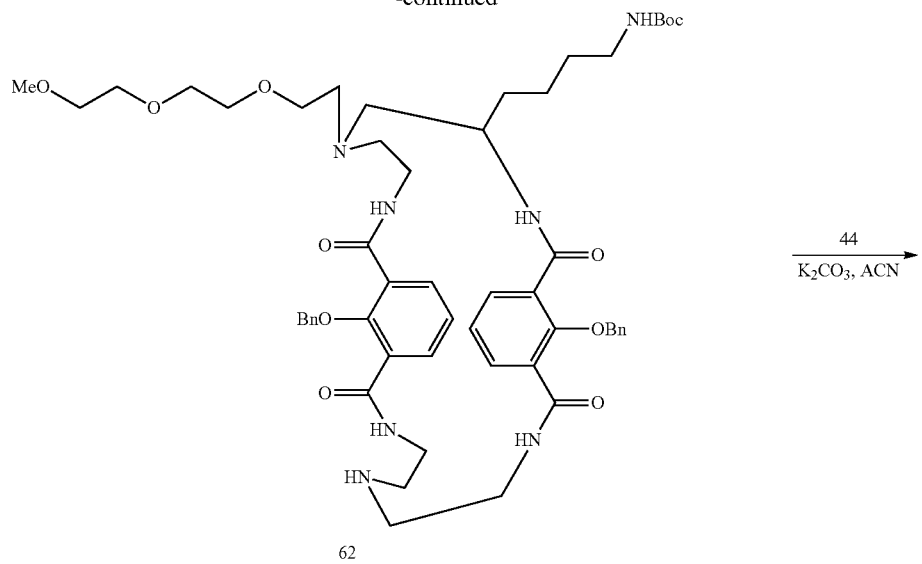
62
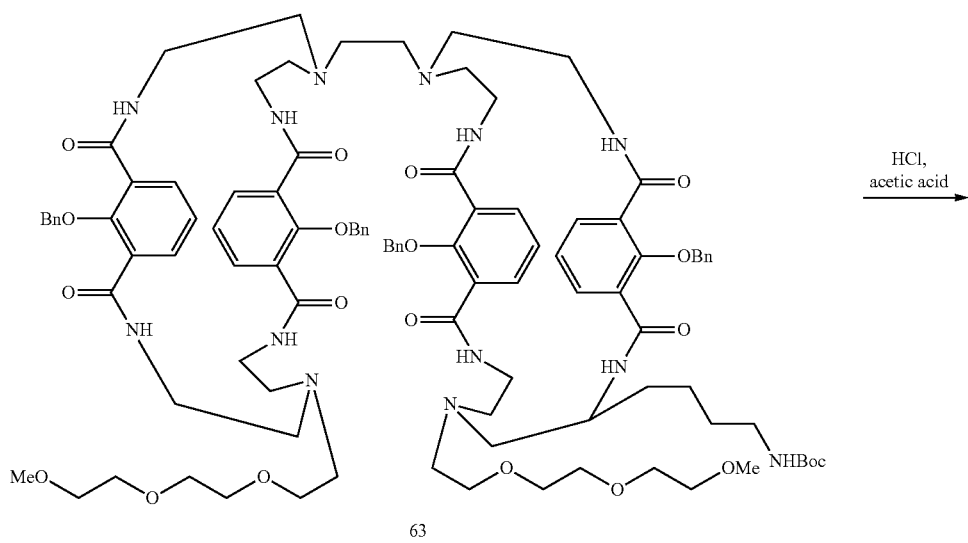
63
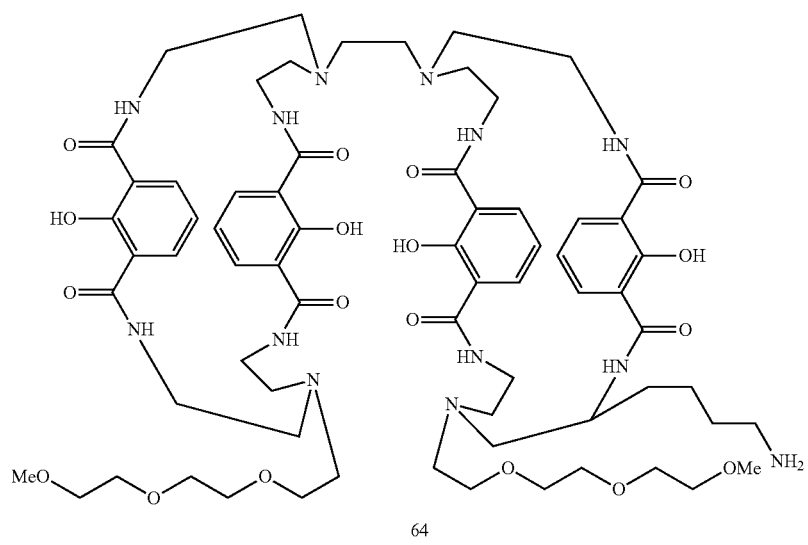
64

Example 13

Stepwise Synthesis of Di-Macrocycle (Scheme 9)

Alternative approaches may be used to change the substituents present on the di-macrocycles. Formamide protected dithiazolide 58 is condensed with tetra-amine 10 to form the di-macrocycle 65. Deprotection of the formamide groups using hydrazine affords the macrocyclic diamine 66. Alkylation of diamine 66 with a tosylate derived from estradiol, 67, produces the protected di-macrocycle 68. Di-macrocycle 68 is deprotected under acidic conditions to form di-macrocycle 69. The presence of the estradiol-derived moieties on the bifunctional chelator may serve to alter the pharmacokinetics of the derived site-directing molecule, for example by binding to human serum albumin.

Scheme 9. Stepwise synthesis of di-macrocycle.

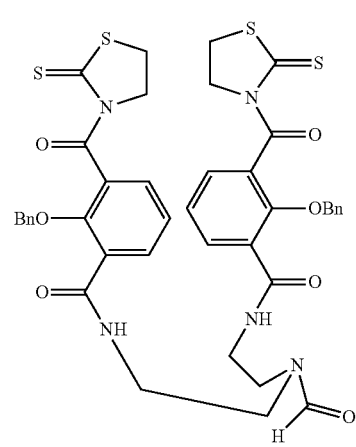

58

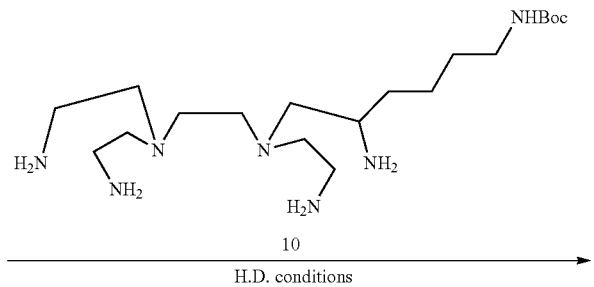

10

H.D. conditions

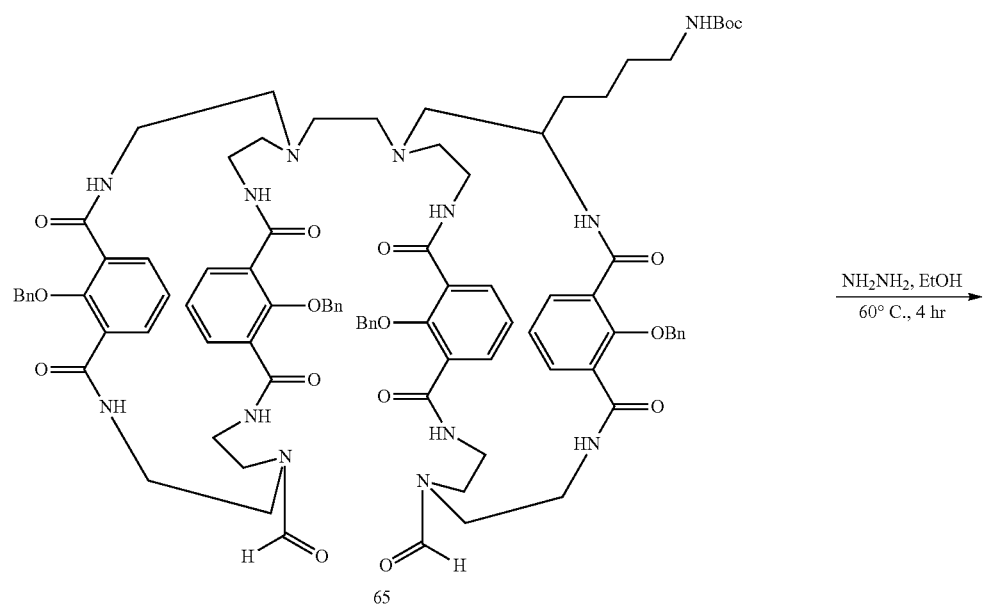

65

NH₂NH₂, EtOH
60° C., 4 hr

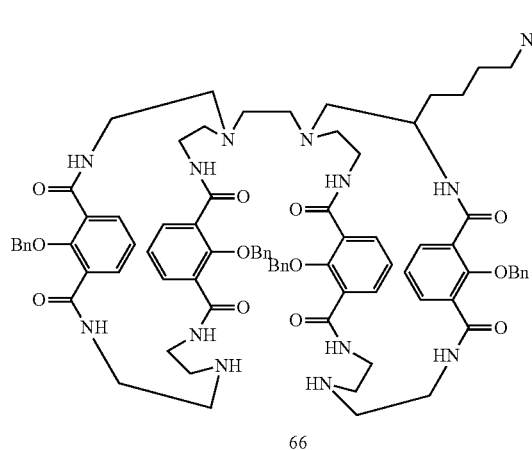

66

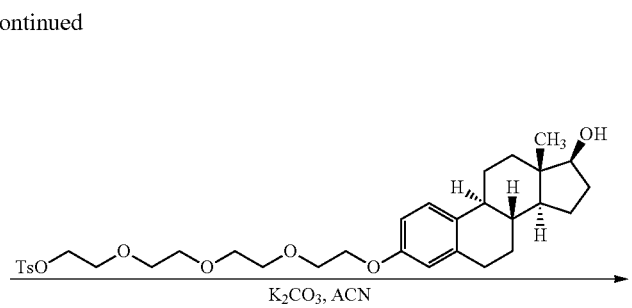

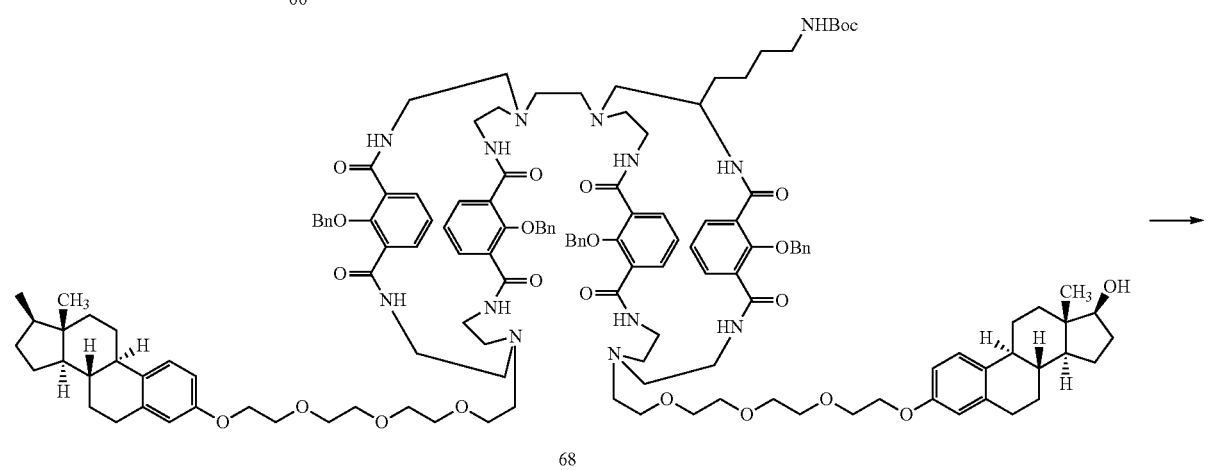

68

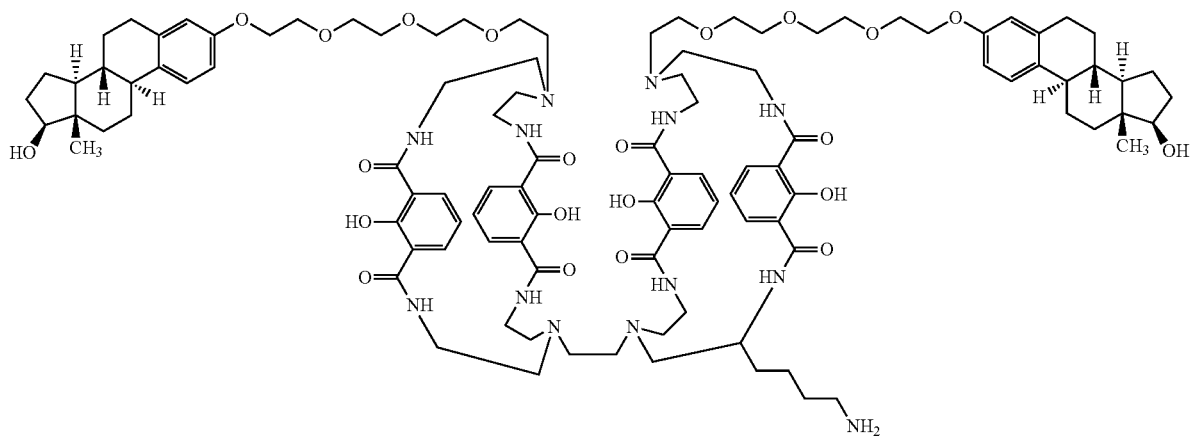

69

Example 14

Templated Synthesis of Di-Macrocycle (Scheme 10)

Alternative approaches may be used to manufacture di-macrocycles. Macrocyclic amine 43 is alkylated with 2-bromoethanol to form alcohol 70. Protective groups are removed under acidic conditions to form macrocycle 71, which is activated using p-toluenesufonyl chloride in pyridine to afford tosylate 72. Macrocyclic amine 43 is deprotected under acidic conditions to form macrocycle 73. Macrocycle 73 and macrocycle 72 are mixed together in an aqueous buffer containing a metal cation such as terbium chloride. Upon metal complexation, the terbium complex 74 is formed. The proximity of the amine and the tosylate increases the rate of reaction to form di-macrocyclic metal complex 75 in improved yield. The metal cation can be removed under acidic conditions. The di-macrocyclic chelator formed from 75 and mono-macrocyclic compounds such as 73 could display utility to sequester metal cations from ores, mining slags, tailings, nuclear waste, or biological systems.

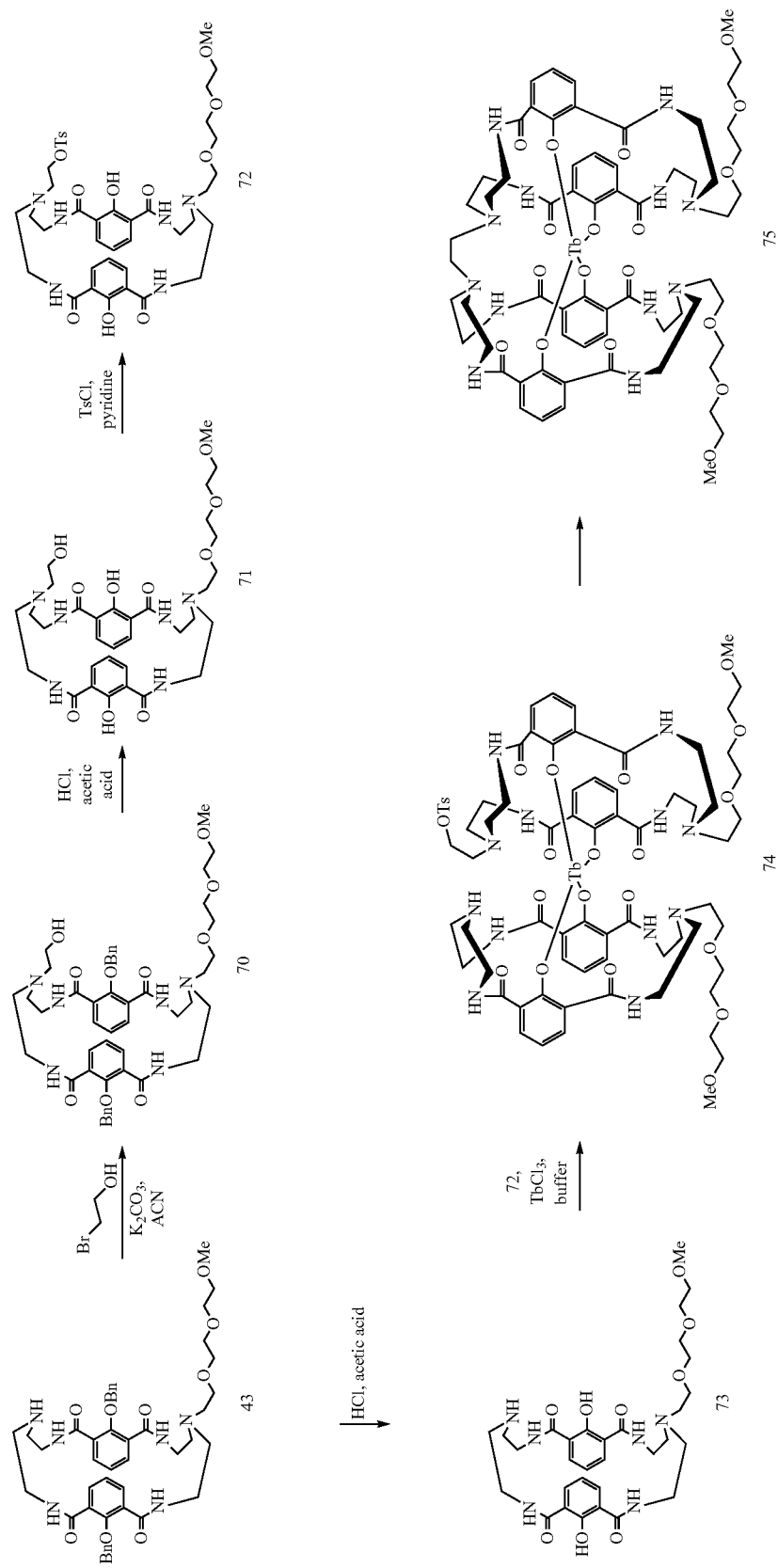

Example 15

Stepwise Synthesis of Di-Macrocycle (Scheme 11)

Alternative approaches may be used to change the position of the linker arm present on the di-macrocycles. Removal of protective groups from compound 76 under reducing conditions yields the diamine 77. Removal of protective groups from compound 78 under reducing conditions yields the diamine 79. Reaction of diamine 79 with di-thiazolide 8 under pseudo-first order conditions forms dithiazolide 80. This is condensed with diamine 77 under high dilution conditions to form protected macrocycle 81. Activation of the alcohol moiety present in macrocycle 81 using p-toluenesulfonyl chloride in pyridine forms the tosylate 82. Macrocylic amine 43 is alkylated with tosylate 82 to provide the protected di-macrocycle 83. Di-macrocycle 83 is deprotected under acidic conditions to form di-macrocycle 84.

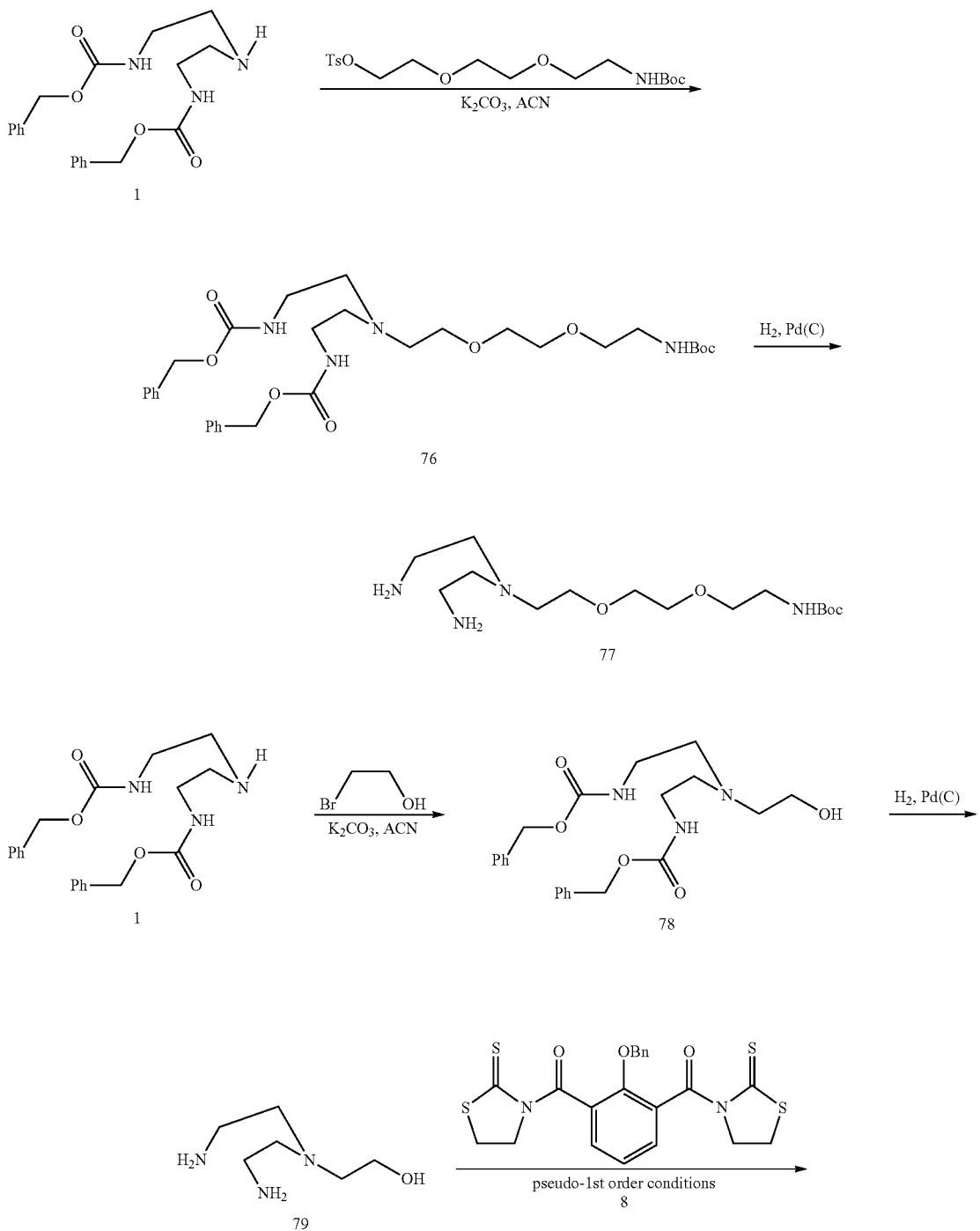

Scheme 11. Stepwise synthesis of di-macrocycle.

-continued
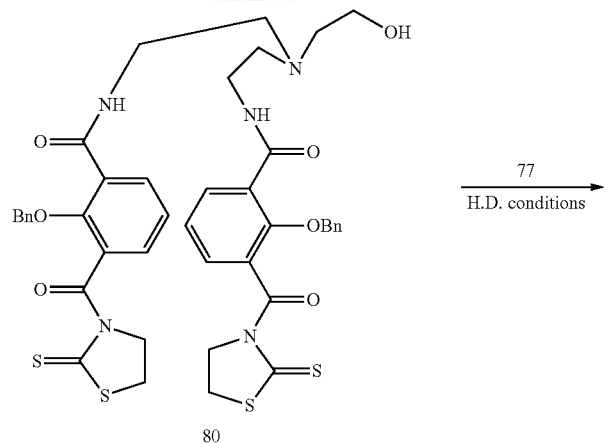
80
$\xrightarrow{\text{77}}$
H.D. conditions
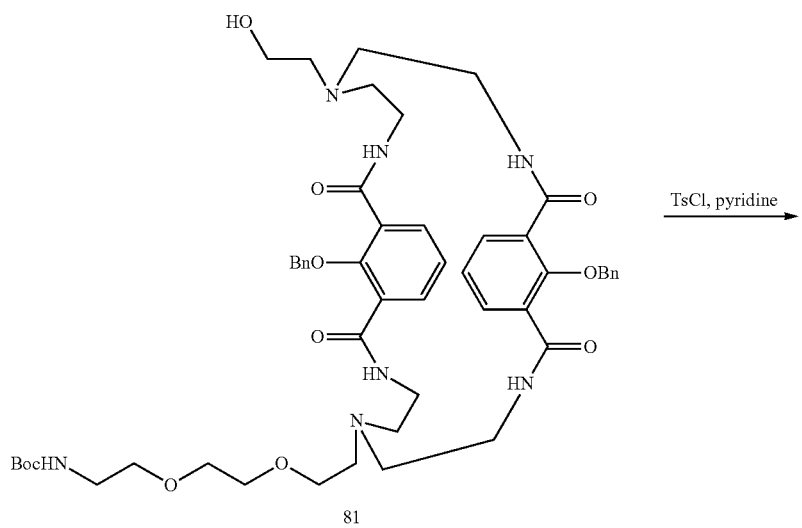
81
$\xrightarrow{\text{TsCl, pyridine}}$
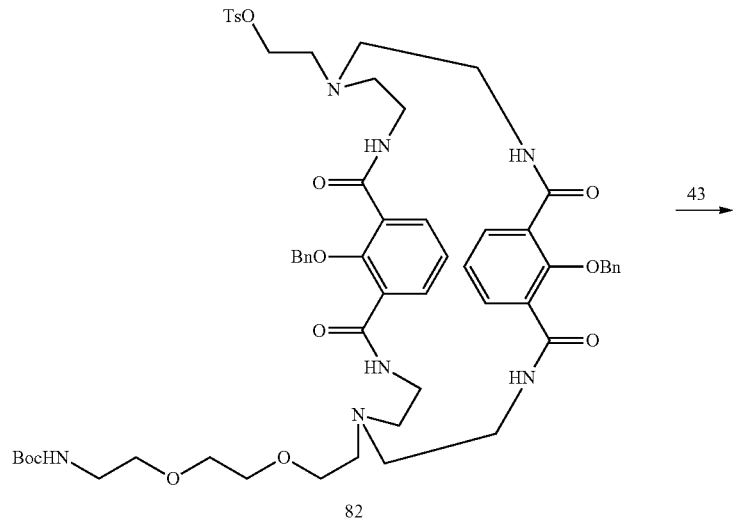
82
$\xrightarrow{\text{43}}$ -continued

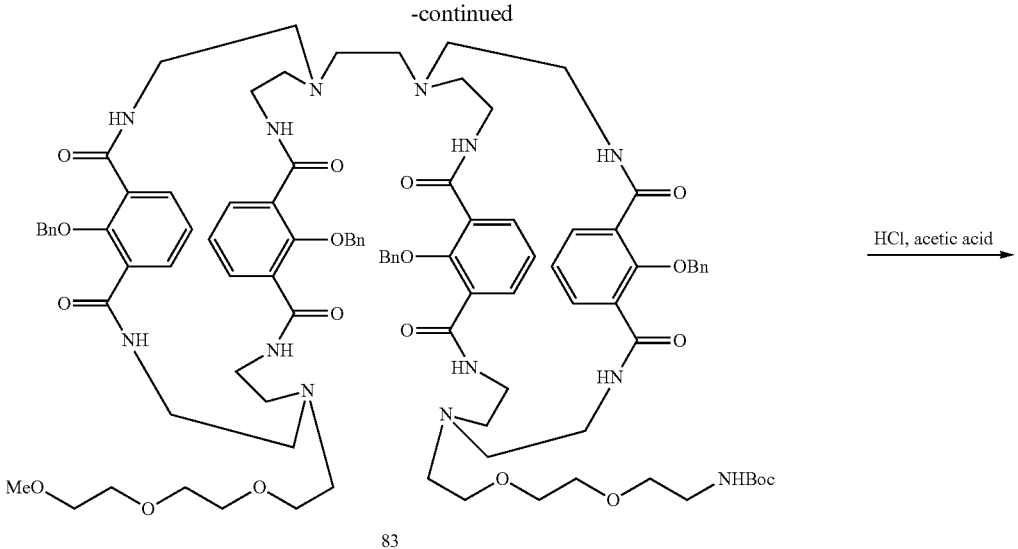

83

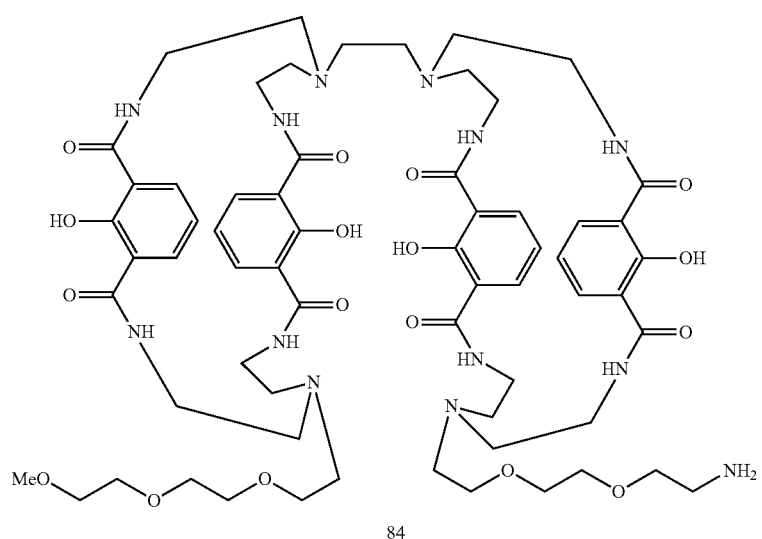 [SMILES: COCCOCCOCCN1CCNC(=O)c2cccc(c2O)C(=O)NCCN(CCN2CCNC(=O)c3cccc(c3O)C(=O)NCCN(CCOCCOCCN)CCNC(=O)c3cccc(c3O)C(=O)NCC2)CCNC(=O)c2cccc(c2O)C(=O)NCC1]

84

Example 16

Synthesis of Multimeric Di-Macrocycle Species (Scheme 12)

Alternative compositions may be derived by judicious selection of the structural element joining the macrocyclic subunits in di-macrocyclic species. Alkylation of macrocyclic amine 43 with bis-bromomethyl substituted porphyrin 85 yields protected di-macrocycle 86. Di-macrocycle 86 is deprotected under acidic conditions to form di-macrocycle 87. Complexation with a metal cation such as terbium(III) in aqueous buffered solution forms a dimer or higher order species such as the coordination polymer 88. Such supramolecular compositions may display light harvesting properties that are of value for photovoltaic cells, for example.

Scheme 12. Synthesis of multimeric di-macrocycle species.
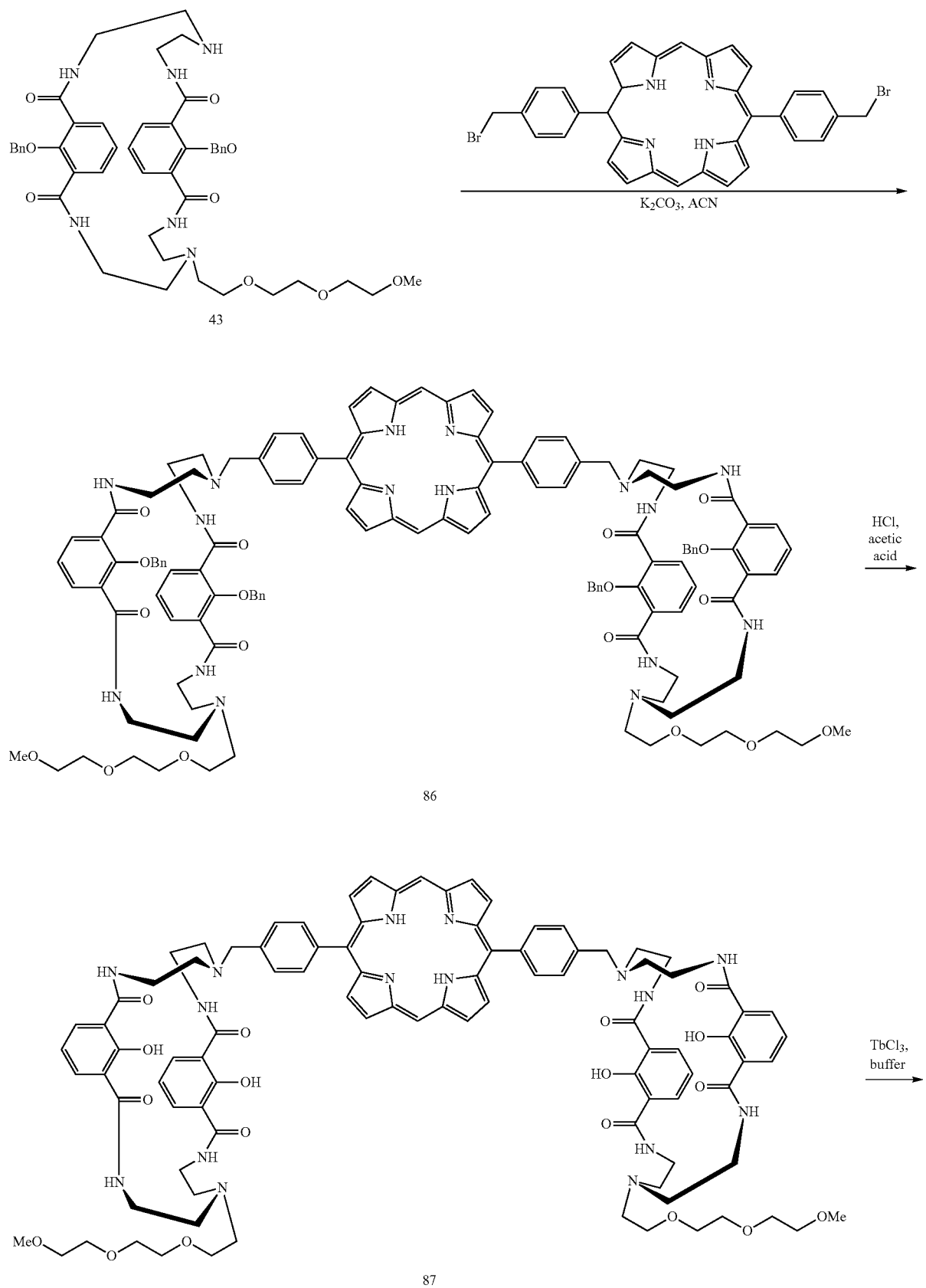

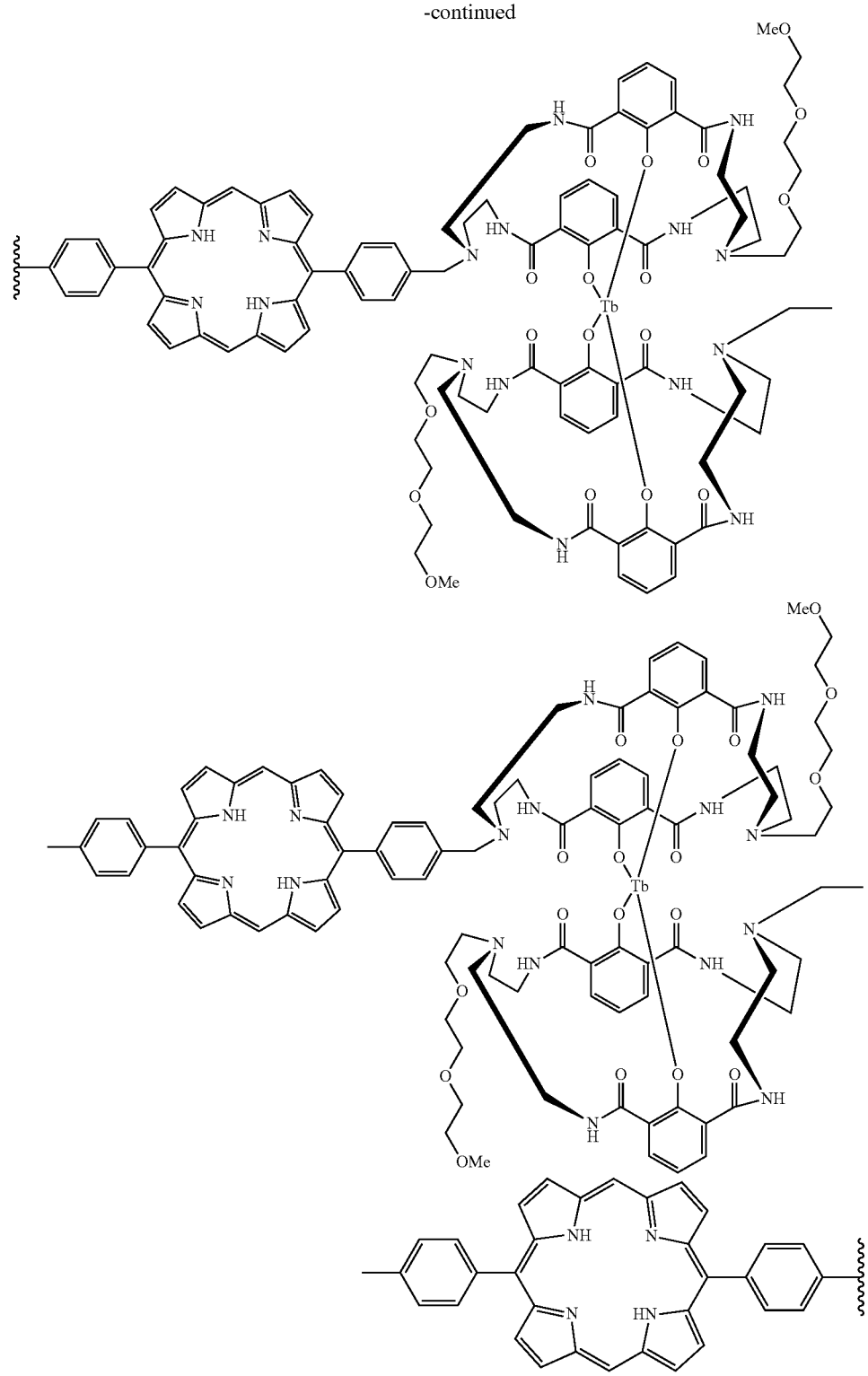
Example 17
Bifunctional Chelators (Scheme 13)
Synthesis of Octa-Coordinating Di-Macrocyclic

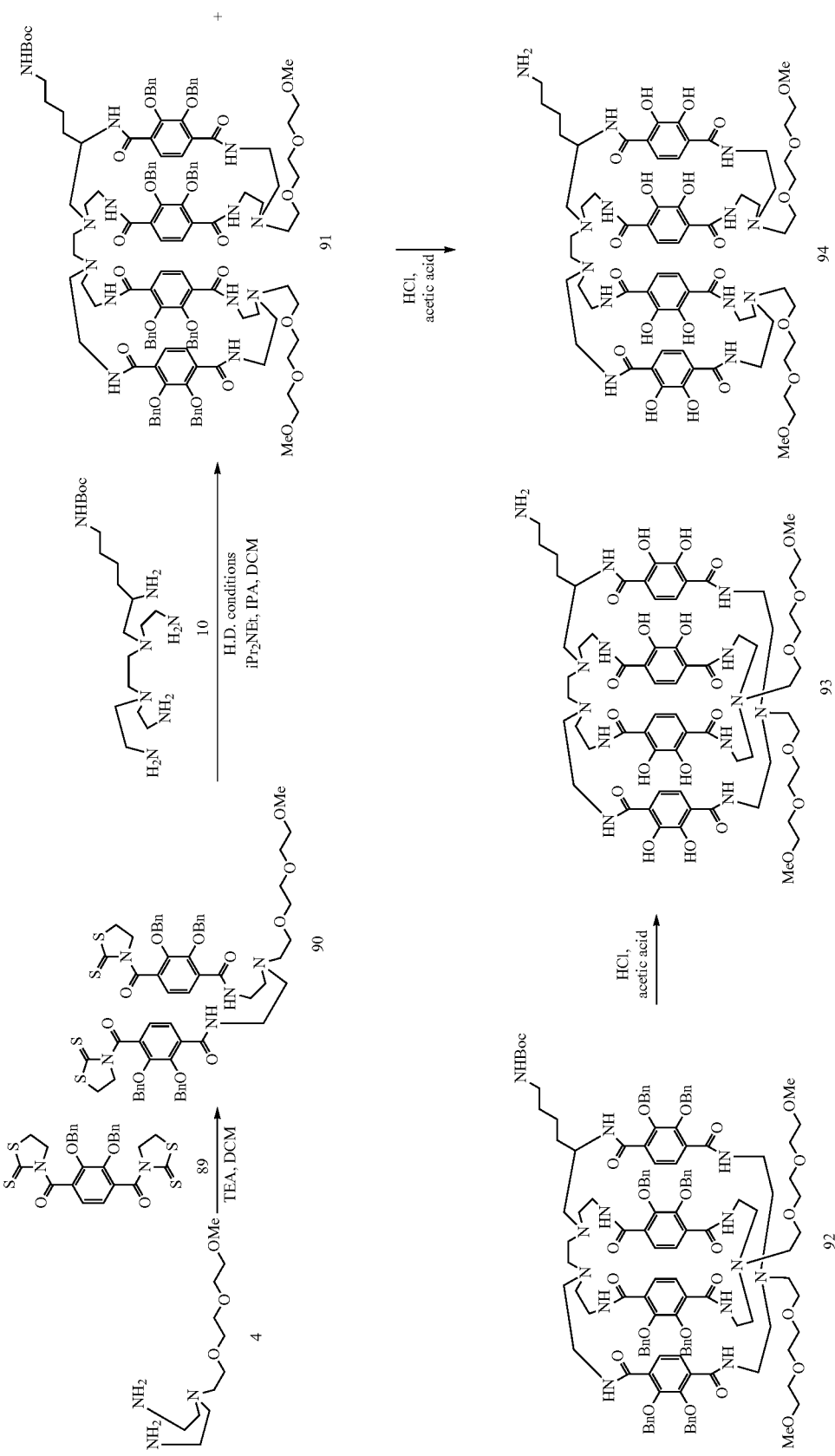
Scheme 13. Synthesis of di-macrocyclic bifunctional chelators 93 and 94.

Preparation of terephthalamide macrocyclic ligands began with [2-[2-(2-methoxyethoxy)ethoxy]ethoxy] diethylenetriamine 4, which was condensed with 2-mercaptothiazole activated amide 89 under pseudo-first order conditions to provide the amide 90, which was reacted with amine 10 under high dilution conditions to form the di-macrocycles 91 and 92. Following separation of the two regioisomers by silica gel chromatography, protective groups were removed using a solution of concentrated hydrochloric acid in acetic acid to provide di-macrocycles 93 and 94. Structural assignment of the regioisomers was performed using tandem mass spectrometry.

2,3-Dibenzyloxy-bis(2-mercaptothiazolide)terephthalamide 89 was synthesized as described (Doble, D. M. J., et al., *Inorg. Chem.* 2003, 42, 4930-4937.

N,N''-bis[2,3-dibenzyloxy-1-(2-mercaptothiazoleamido)-4-terephthalamido]-N'-[2-[2-(2-methoxyethoxy)ethoxy]ethoxy]-bis(2-aminoethyl)amine 90. N'-[2-[2-(2-methoxyethoxy)ethoxy]ethoxy]-bis(2-aminoethyl)amine 4 (371 mg, 1.49 mmol) was dissolved in dichloromethane (30 mL) and added using a syringe pump (NE1000) to a solution of 2,3-dibenzyloxy-bis(2-mercaptothiazole)terephthalamide 89 (7.80 g, 13.4 mmol) in dichloromethane (75 mL) over a period of 20 hrs at a rate of 1.50 mL/hr. After a further 22 hr, solvent was removed under reduced pressure, and the crude product was purified by silica gel chromatography using 1-2% methanol in dichloromethane as eluents. Fractions containing product were combined, solvent was removed under reduced pressure, and the residue dried in vacuo to provide compound 90 (1.134 g, 65.0%). $^1$H NMR (300 MHz, CDCl$_3$): δ=7.77 (d, 2H, ArH), 7.35-7.31 (m, 20H, ArH), 7.18 (d, 2H, ArH), 5.07 (s, 8H, PhCH$_2$O), 4.36 (t, 4H, NCH$_2$CH$_2$S), 3.56-3.46 (m, 8H, CH$_2$CH$_2$O), 3.38 (t, 2H, CH$_2$CH$_2$O), 3.31-3.26 (m, 7H, CH$_2$CH$_2$N, OMe), 2.92 (t, 4H, NCH$_2$CH$_2$S), 2.59 (t, 2H, CH$_2$CH$_2$N), 2.47 (t, 4H, CH$_2$CH$_2$N). $^{13}$C NMR (300 MHz, CDCl$_3$): δ=201.6, 167.1, 164.6, 150.3, 149.6, 137.3, 136.2, 133.5, 131.0, 129.1, 129.0, 128.9, 128.6, 128.2, 126.8, 124.7, 77.2, 76.4, 72.1, 70.8, 70.7, 70.6, 69.9, 59.3, 55.8, 53.7, 53.5, 38.1, 29.0. FTMS pESI: calculated for C$_{61}$H$_{66}$N$_5$O$_{11}$S$_4$ [MH]$^+$, 1172.3636. found, 1172.3621.

Benzyl and tert-butyloxycarbonyl-protected di-macrocycles 91 and 92. A solution of N,N''-bis[2,3-dibenzyloxy-1-(2-mercaptothiazoleamido)-4-terephthalamido]-N'-[2-[2-(2-methoxyethoxy)ethoxy]ethoxy]-bis(2-aminoethyl)amine 90 (1.085 g, 925 μmol) in dichloromethane (50 mL) and a solution of 5-amino-6-[(2-aminoethyl)-[2-[bis(2-aminoethyl)amino]ethyl]amino]hexylcarbamic acid tert-butyl ester 10 (187 mg, 463 μmol) in dichloromethane, isopropyl alcohol (ca. 5%), and diisopropylethylamine (ca. 3%) (50 mL) were added dropwise to dichloromethane (2 L) over a period of four days using two syringe pumps at a rate of 0.5 mL/hr. After an additional two days of reaction, solvent was removed under reduced pressure, and the crude product was purified by silica gel chromatography using 0.1% triethylamine, 5-7.5% methanol in dichloromethane as eluents. The silica gel column was prepared so as to have a short section (ca. 1.25") of aluminum oxide (basic, Brockmann I) on its bottom. Di-macrocycle 91 eluted first, with 5% MeOH in dichloromethane. Fractions containing each product were combined, solvent was removed under reduced pressure, and the residues dried in vacuo to provide the protected di-macrocycles 91 and 92 (264 mg and 242 mg, respectively, 24.1%). Di-macrocycle 91: $^1$H NMR (300 MHz, CDCl$_3$): δ=7.67 (m, 4H, ArH), 7.29-7.25 (m, 40H, ArH), 7.12-7.00 (m, 4H, ArH), 5.04-4.90 (m, 16H, PhCH$_2$O), 3.54-3.29 (m, 26H, CH$_2$CH$_2$O, OMe), 2.98-2.14 (m, 39H, CH$_2$CH$_2$N), 1.67 (m, 4H, CH$_2$), 1.38 (s, 9H, CH$_3$), 1.24 (m, 5H, CH, CH$_2$). $^{13}$C NMR (600 MHz, CDCl$_3$): δ=166.0, 165.8, 155.9, 150.3, 150.2, 136.5, 136.4, 131.8, 128.7, 128.6, 128.4, 128.3, 128.2, 127.8, 125.0, 124.8, 76.7, 76.5, 71.8, 70.5, 70.4, 70.2, 68.8, 68.7, 58.9, 52.4, 51.8, 47.1, 40.3, 37.1, 37.0, 33.6, 29.8, 28.4, 23.4. FTMS pESI: calculated for C$_{129}$H$_{157}$N$_{13}$O$_{24}$ [M+2H]$^{2+}$, 1136.0727. found, 1136.0709. Di-macrocycle 92: $^1$H NMR (300 MHz, CDCl$_3$): δ=8.17-7.57 (m, 4H, ArH), 7.33-7.25 (m, 40H, ArH), 7.20-6.96 (m, 4H, ArH), 5.29-4.93 (m, 16H, PhCH$_2$O), 3.66-3.27 (m, 26H, CH$_2$CH$_2$O, OMe), 2.92-2.51 (m, 39H, CH$_2$CH$_2$N), 1.95-1.81 (m, 4H, CH$_2$), 1.38 (s, 9H, CH$_3$), 1.24 (m, 5H, CH, CH$_2$). $^{13}$C NMR (600 MHz, CDCl$_3$): δ=165.7, 165.6, 165.5, 155.9, 150.3, 150.2, 149.9, 136.5, 136.4, 132.1, 128.7, 128.6, 128.5, 128.4, 128.3, 128.0, 124.8, 124.6, 76.7, 76.6, 76.5, 76.3, 71.8, 70.5, 70.3, 70.1, 69.3, 58.9, 54.1, 53.9, 53.5, 53.4, 52.9, 52.3, 52.2, 37.8, 37.7, 37.6, 37.5, 29.6, 28.4, 23.4. FTMS pESI: calculated for C$_{129}$H$_{157}$N$_{13}$O$_{24}$ [M+2H]$^{2+}$, 1136.0727. found, 1136.0705.

Di-macrocycle 94. Benzyl and tert-butyloxycarbonyl-protected di-macrocycle 91 (10 mg, 4.4 μmol) was dissolved in 12N hydrochloric acid (0.5 mL) and glacial acetic acid (0.5 mL). The solution was stirred under inert atmosphere for 44 hr, whereupon HCl was removed with a stream of inert gas. Solvents were removed under reduced pressure and the residue was dried in vacuo. The residue was dissolved in methanol (2×200 μL) and transferred to an O-ring microcentrifuge tube. Ether (ca. 1.5 mL) was added, and the tube was placed at 4° C. overnight. The tube was centrifuged at 12,000 rpm for 3 minutes, decanted, the pellet was washed with ether (ca. 1.5 mL) and allowed to air dry. The pellet was dried in vacuo to provide di-macrocycle 94, pentahydrochloride salt (6.75 mg, 94%). FTMS pESI: calculated for C$_{68}$H$_{101}$N$_{13}$O$_{22}$ [M+2H]$^2$, 725.8587. found, 725.8583. Di-macrocycle 93 was formed from compound 92 following a similar procedure. FTMS pESI: calculated for C$_{68}$H$_{101}$N$_{13}$O$_{22}$ [M+2H]$^{2+}$, 725.8587. found, 725.8590. Tandem mass spectrometry performed on compound 94, 484.33 MS1 peak [M+3H]$^{3+}$, revealed peaks at mass 352.1688 [M+2H]$^{2+}$, 387.7056 [M+2H]$^{2+}$, 677.3151 [M+H]$^+$, and 748.3884 [M+H]$^+$, consistent with fragmentation across the ethylene diamine bridge. Similar fragmentation was not observed upon analysis of compound 93.

Example 18

Synthesis of an Octa-Coordinating Di-Macrocyclic-Oligodeoxynucleotide Conjugate (Scheme 14)

Di-macrocycle, 4-isothiocyanatophenylthiourea derivative 95. To di-macrocycle 94 (5.98 mg, 3.7 μmol), dissolved in dimethylformamide (75 μL) and triethylamine (10.2 μL), was added a solution of 1,4-phenyldiisothiocyanate (7.7 mg, 40 μmol) in dimethylformamide (75 μL). The resulting solution was mixed at 800 rpm under inert atmosphere for 1.5 hours. Ether (ca. 1.5 mL) was added, and the resulting suspension placed at 4° C. for 60 minutes. The tube was centrifuged at 12,000 rpm for 3 minutes, decanted, the pellet was washed with ether (ca. 1.5 mL) and allowed to air dry. The pellet was dissolved in methanol (350 μL) and transferred to a new microtube, then precipitated and washed with ether as described above. The pellet was dried in vacuo to provide di-macrocycle, 4-isothiocyanatophenylthiourea derivative 95 (4.71 mg, 78.3%). FTMS pESI: calculated for C$_{76}$H$_{105}$N$_{15}$O$_{22}$S$_2$ [M+2H]$^{2+}$, 821.8495. found, 821.8492.

Scheme 14. Synthesis of octa-coordinating di-macrocyclic chelator-oligodeoxynucleotide conjugate 96.
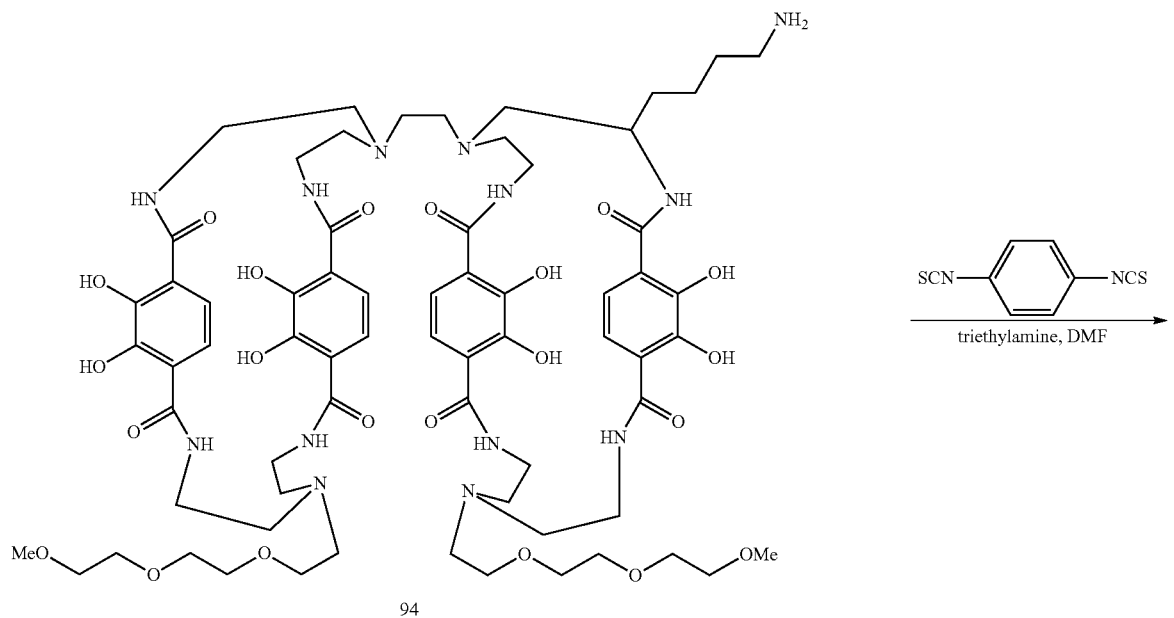
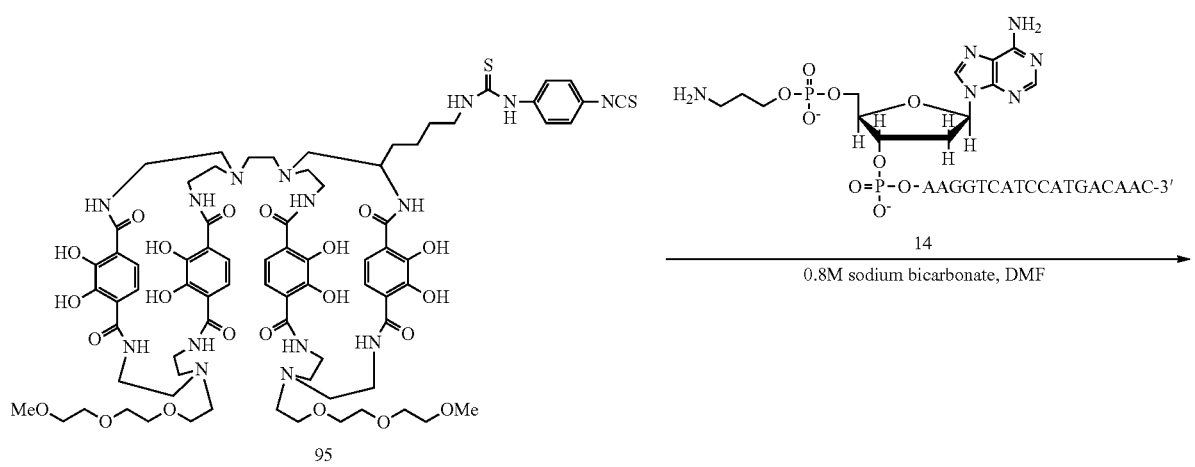

-continued

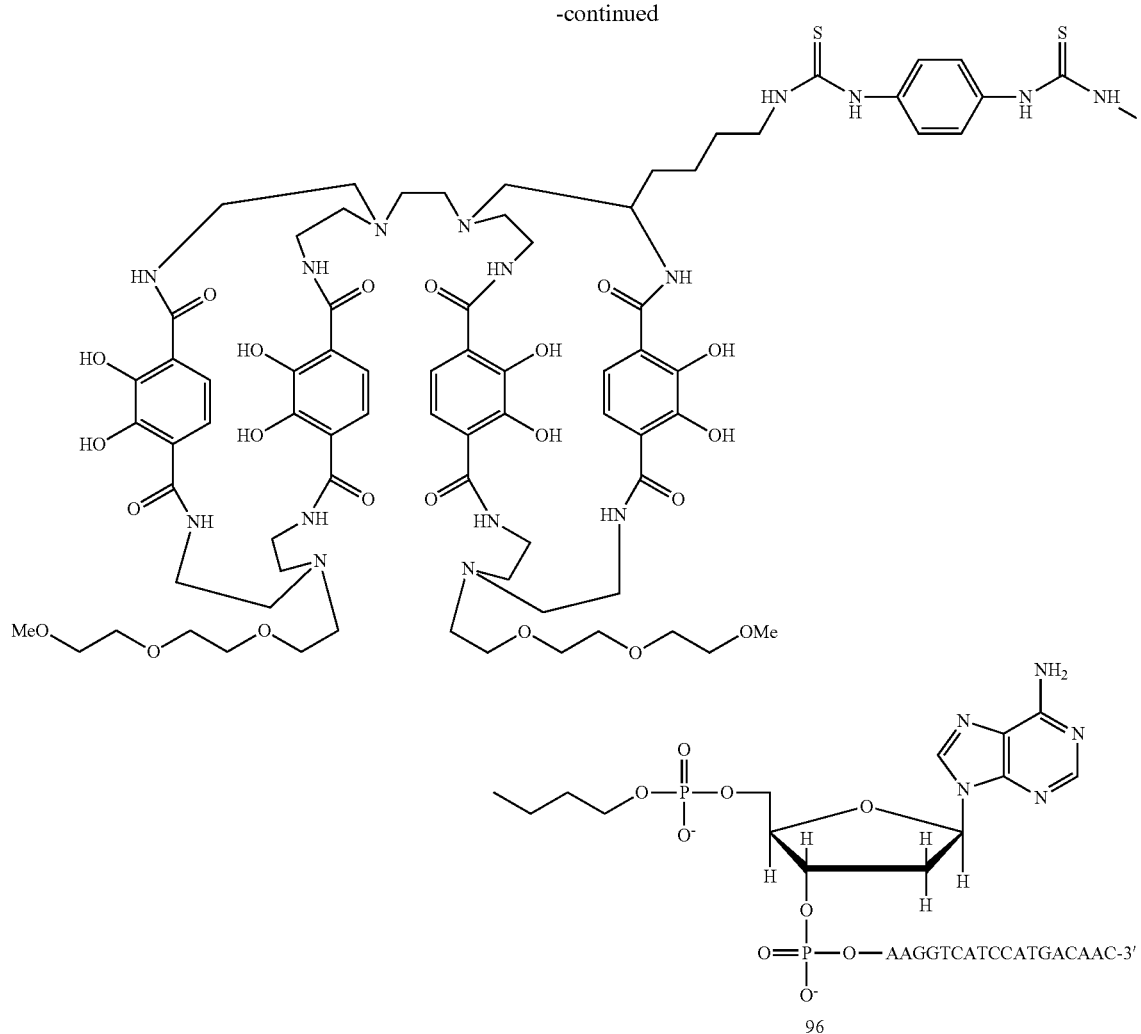

96

Dimacrocycle-oligodeoxynucleotide conjugate 96. A DNA 18-base oligonucleotide (14) with the sequence 5'-AAGGTCATCCATGACAAC-3' was purchased commercially (Eurogentec, Inc., Seraing, Belgium) and purified using reverse-phase HPLC. The oligonucleotide was modified during synthesis to possess an aminopropyl group attached at the 5'-terminus via a phosphodiester linkage. A solution of DNA oligomer in water (75 µL, 102 nmol) was diluted with sodium bicarbonate buffer (0.8 M, 100 µL) in an eppendorf tube. A solution of di-macrocycle, 4-isothiocyanatophenylthiourea derivative 95 (1.65 mg, 1.00 µmol) in anhydrous DMF (50 µL) was freshly prepared, added to the DNA oligomer and mixed at 1200 rpm using a commercial device (Eppendorf Mixmate®) at ambient temperature for 18 hours. A solution (45 µL) of glycogen (350 µg/mL) in 3M sodium acetate, pH 5.2 was added to the solution. The solution was mixed, absolute ethanol (1.1 mL) was added, the solution was mixed again, and the tube was stored at −20° C. for 1.5 hours. The eppendorf tube was centrifuged at 12,000 rpm for 20 minutes, the supernatant decanted, and the resulting pellet was washed with cold, 70% aqueous ethanol (1.1 mL). The supernatant was decanted, and the pellet was allowed to dry open to the air. The pellet was dissolved in sterile water (100 µL), and an aliquot (2 µL) was removed to quantify by UV-visible absorbance using the extinction coefficient at 260 nm of 181,600 $M^{-1}$ $cm^{-1}$. The resulting stock was found to have a concentration of 881 µM (88 nmol, 86% crude yield). There was ca. 70% conversion to conjugate, as estimated from analysis using 20% polyacrylamide gel electrophoresis. The conjugate was used without further purification.

Di-macrocycle 93 was converted to the corresponding isothiocyanate derivative 97 using a protocol similar to that above. Isothiocyanate 97 was coupled with oligonucleotide 14 to provide the corresponding di-macrocycle oligodeoxynucleotide conjugate 98.

Example 19

Synthesis of an Octacoordinating Di-Macrocyclic Chelator Maleimide Derivative

As an alternative to amine-reactive isothiocyanate functionality, a thiol-reactive maleimide bifunctional chelator may be prepared from di-macrocyclic chelators as illustrated in the example below:

Di-macrocycle, 3-maleimidopropyl derivative 99. Di-macrocycle 12 (10.12 mg, 6.45 µmol), was dissolved in dimethylformamide (100 µL) and triethylamine (10 µL), and added to 3-maleimidoproprionic acid, N-hydroxysuccinimide ester (3.4 mg, 13 µmol). The resulting solution was mixed at 800 rpm under inert atmosphere for 1 hour. Ether (ca. 1.5 mL) was added, and the resulting suspension placed at 4° C. for 60 minutes. The tube was centrifuged at 12,000 rpm for 3 minutes, decanted, the pellet was washed with ether (ca. 1.5 mL) and allowed to air dry. The pellet was dissolved in methanol (300 µL) then precipitated and washed with ether as described above. The pellet was dried in vacuo to provide di-macrocycle, 3-maleimidopropyl derivative 99 (7.42 mg, 74.8%). FTMS pESI: calculated for $C_{75}H_{105}N_{14}O_{21}$ [M+H]$^1$, 1537.7573. found, 1537.7561.

Scheme 15. Synthesis of octa-coordinating di-macrocyclic chelator-maleimide derivative 99.

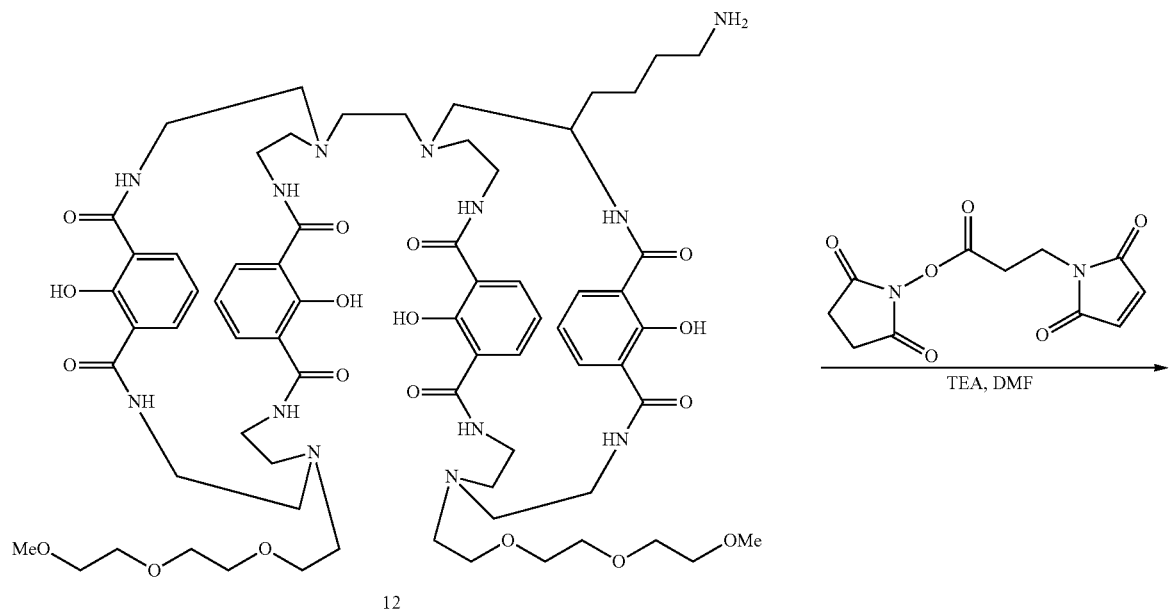

12

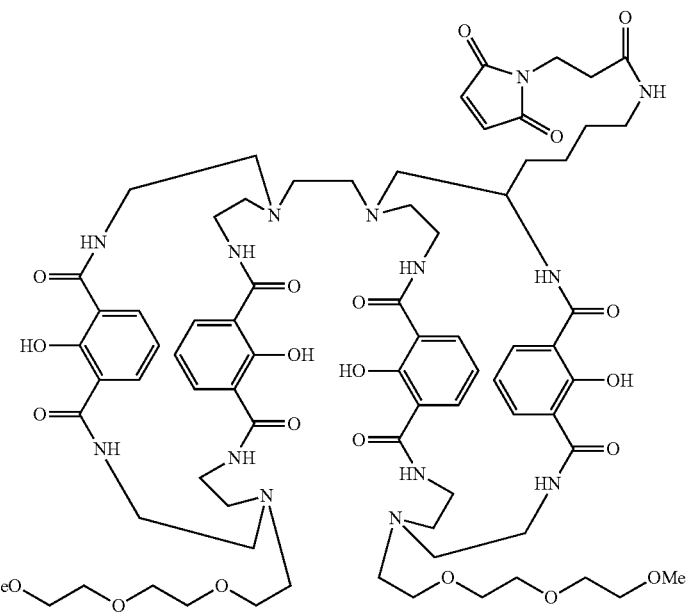

99

Example 20
Synthesis of an Octa-Coordinating Di-Macrocyclic Bifunctional Chelator (Scheme 16)
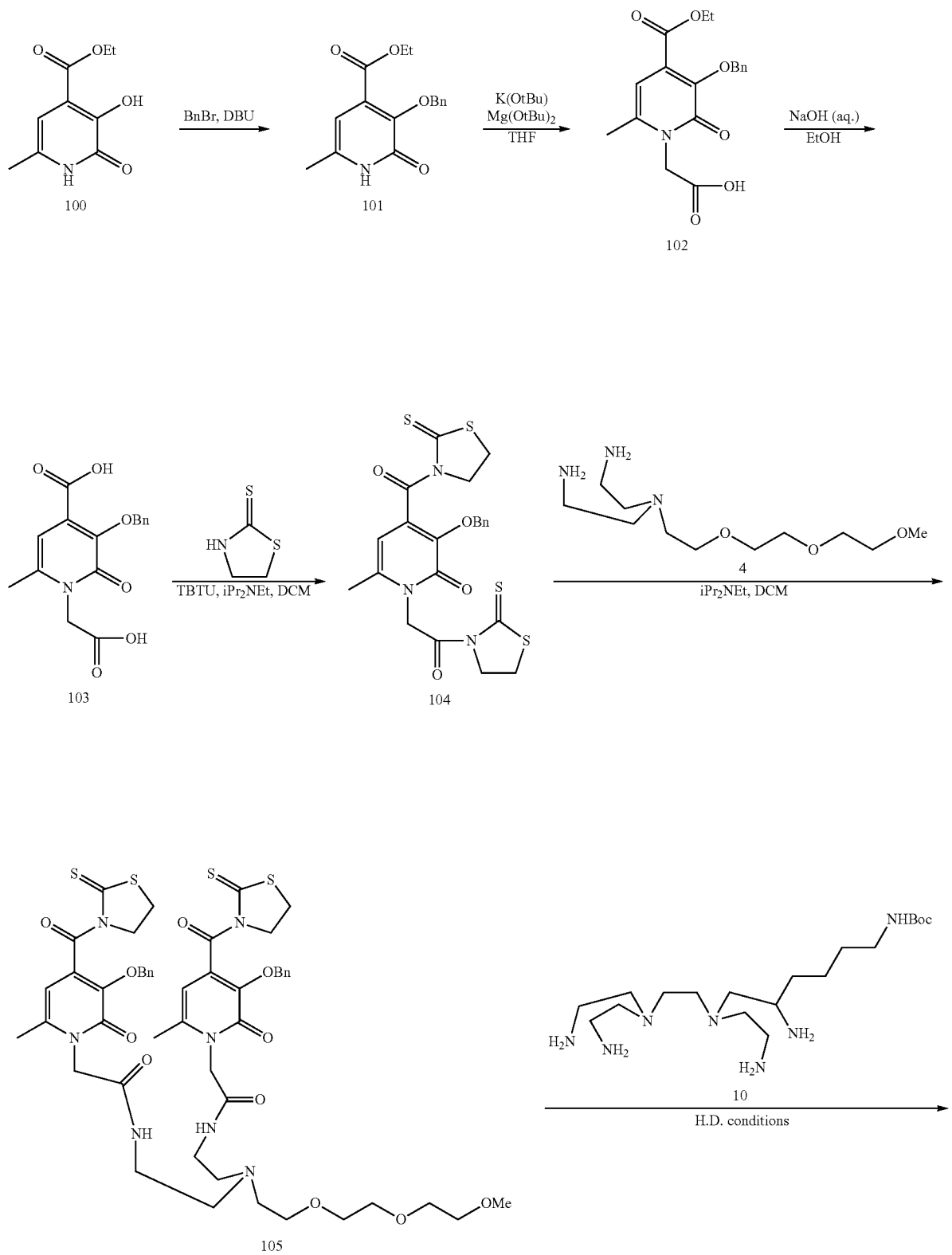
Scheme 16. Synthesis of di-macrocyclic bifunctional chelator 107.

-continued

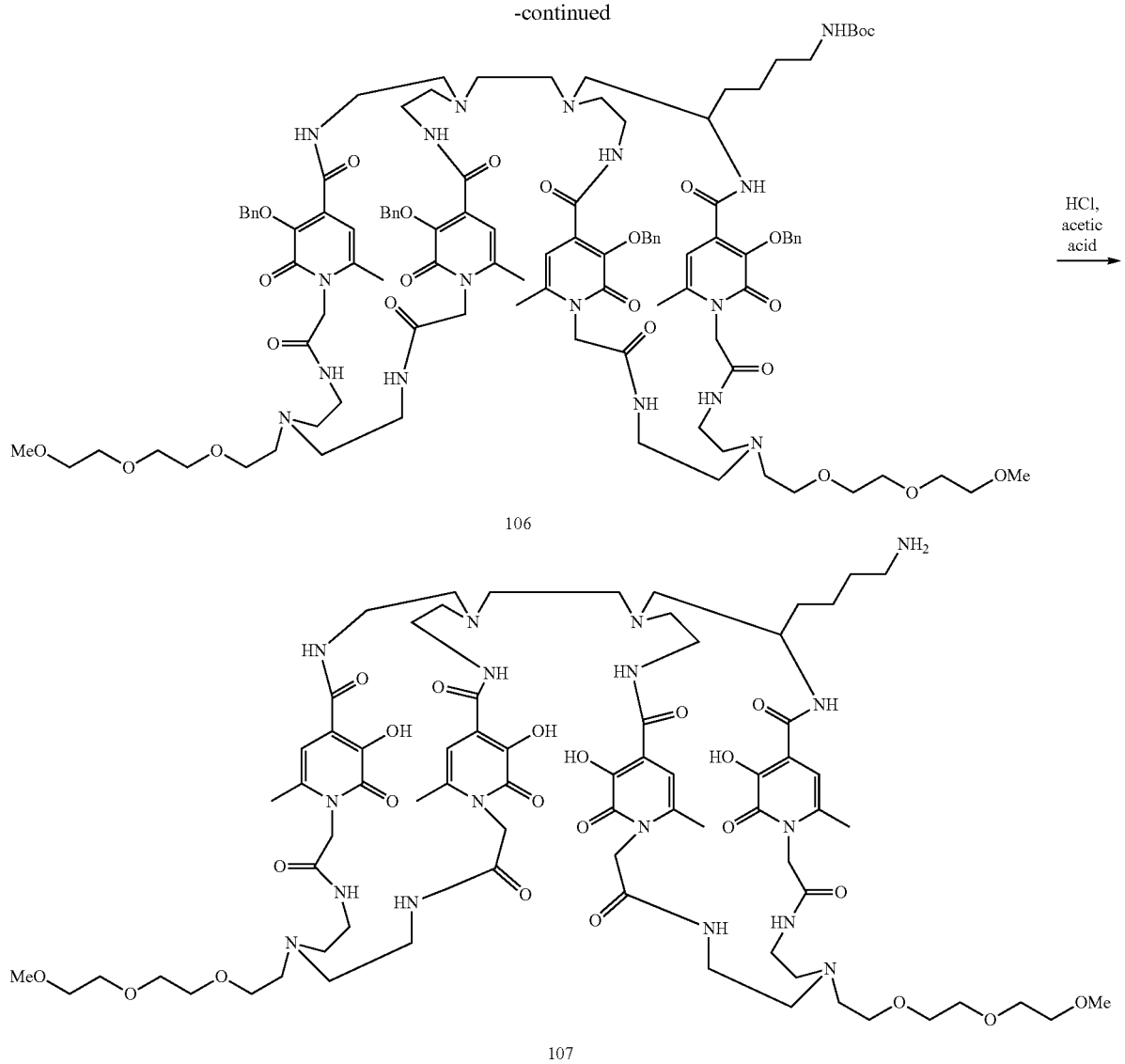

Preparation of a 3,2-HOPO macrocyclic ligand began with 3-hydroxy-6-methyl-2-oxo-1,2-dihydropyridine-4-carboxylic acid ethyl ester 100, which was alkylated with benzyl bromide to provide benzyl ether 101. Alkylation of 101 with bromoacetic acid provided monoester 102, which was saponified to provide diacid 103. Diacid 103 was activated with 0-(benzotriazol-1-yl)-N,N,N',N'-tetramethyluronium tetrafluoroborate (TBTU) in the presence of 2-mercaptothiazole to provide di-thiazolide 104. Di-thiazolide 104 was condensed with [2-[2-(2-methoxyethoxy)ethoxy]ethoxy] diethylenetriamine 4 under pseudo-first order conditions to provide the activated di-amide 105, which was reacted with amine 10 under high dilution conditions to form the di-macrocycle 106. Protective groups were removed using a solution of concentrated hydrochloric acid in acetic acid to provide di-macrocycle 107.

3-Hydroxy-6-methyl-2-oxo-1,2-dihydropyridine-4-carboxylic acid ethyl ester 100 was synthesized as described (Doble, D. M. J., et al., *Inorg. Chem.* 2003, 42, 4930-4937.

3-Benzyloxy-6-methyl-2-oxo-1,2-dihydropyridine-4-carboxylic acid ethyl ester 101. Compound 100 (24.59 g, 124.8 mmol) and 1,8-diazabicycloundec-7-ene (DBU, 28.32 g, 186.0 mmol) were mixed together in isopropyl alcohol (400 mL). The mixture was stirred under $N_2(g)$ and heated to slow reflux. Benzyl bromide (25.60 g, 149.7 mmol) was added dropwise to the isopropyl alcohol mixture under $N_2(g)$. The mixture was stirred under reflux (82-83° C.) for 4 hr. The reaction was allowed to cool to ambient temperature, resulting in a dark brown solution. Solvent was removed under reduced pressure, the residue was dissolved in dichloromethane (40 mL) and the resulting solution was washed with 3M aqueous HCl (2×60 mL) to remove DBU. The organic phase was then washed with Millipore water (3×60 mL). The solution was dried over magnesium sulfate, filtered, and dried in vacuo to produce a dark brown oil. The product was precipitated by addition of diisopropyl ether (50 mL) and stirred overnight. The precipitate was filtered and dried in vacuo to provide 101 (20.56 g, 57%). $^1$H NMR ($CDCl_3$+TMS, 300 MHz): δ=1.28 (t, 3H, $CH_3$, J=7.2), 2.33 (s, 3H, $CH_3$), 4.28 (q, 2H, $CH_2$, J=7.2), 5.26 (s, 2H, $CH_2$), 6.16 (s, 1H, CH), 7.30-7.37 (m, 3H, Ph), 7.49-7.51 (m, 3H, Ph), 12.66 (s, 1H, NH); $^{13}$C NMR ($CDCl_3$+TMS, 400 MHz):

δ=165.3, 162.0, 144.6, 139.4, 137.3, 133.2, 128.57, 128.29, 128.06, 104.3, 74.0, 61.7, 18.61, 14.4, ESI-MS (+), [M+H]$^+$ m/z=288.1232 ($C_{16}H_{18}NO_4$, expected 288.1238). [M+H]$^+$ calculated for $C_{16}H_{18}NO_4$ 288.1236, [M+Na]$^+$ calculated for $C_{16}H_{17}NO_4Na$ 310.1055. found 310.1055 m/z, mp:232.4-235.7° C.

3-Benzyloxy-1-carboxymethyl-6-methyl-2-oxo-1,2-dihydropyridine-4-carboxylic acid ethyl ester 102. Compound 101 (8.15 g, 28 mmol), magnesium tert-butoxide (9.68 g, 56 mmol), and potassium tert-butoxide (3.35 g, 29 mmol) were purged with $N_2$ then dissolved in anhydrous tetrahydrofuran (28 mL). Bromoacetic acid (9.86 g, 71.0 mmol) was dissolved in anhydrous tetrahydrofuran (5 mL) and added dropwise to the previous mixture under $N_2$. The mixture was stirred at room temperature for 4 hours, whereupon 3M HCl (30 mL) was added. Organic material was extracted with dichloromethane (20 mL×3) and the combined organic extracts were dried over magnesium sulfate, filtered, and solvent removed under reduced pressure. Diisopropyl ether was added to the residue to form a precipitate that was filtered and dried in vacuo to provide compound 102 (7.43 g, 75%). IR (cm$^{-1}$): 2981 (s), 2511 (w), 1733 (s), 1716 (vs), 1645 (s), 1545 (vs), 1471 (s), 1455 (s), 1404 (vs), 1385 (s), 1365 (s), 1337 (s), 1250 (vs), 1200 (vs), 1097 (s), 1050 (s), 1016 (s), 953 (s), 916 (s), 881 (w), 865 (vw), 846 (s), 765 (s). $^1$H NMR (CDCl$_3$+TMS, 400 MHz): δ=1.29 (t, 3H, CH$_3$, J=7.1 Hz), 2.28 (s, 3H, CH$_3$), 4.30 (q, 2H, CH$_2$, J=7.1 Hz), 4.78 (s, 2H, CH$_2$), 5.21 (s, 2H, CH$_2$), 6.28 (s, 1H, CH), 7.27-7.35 (m, 3H, Ph), 7.45-7.53 (m, 2H, Ph), 8.17 (s, 1H, COOH). $^{13}$C NMR (CDCl$_3$+TMS, 400 MHz): δ=170.1, 164.9, 161.0, 145.0, 140.1, 136.8, 131.4, 128.6, 128.3, 128.1, 105.5, 74.3, 61.8, 46.5, 20.2, 14.1. ESI-MS (−): m/z 344.1149 [M−H]$^-$ ($C_{18}H_{18}NO_6$, expected 344.1134). mp: 242.9-245.7° C.

3-Benzyloxy-1-carboxymethyl-6-methyl-2-oxo-1,2-dihydropyridine-4-carboxylic acid 103. Sodium hydroxide (0.2 g, 4 mmol) was dissolved in water (5 mL) and added slowly to a solution of compound 102 (865 mg, 2.5 mmol) in ethanol (30 mL). The solution was stirred at ambient temperature overnight, whereupon solvent was removed under reduced pressure. The residue was dissolved in water and the mixture was cooled in an ice bath and acidified. The white precipitate which formed was filtered and dried in vacuo to provide compound 103. $^1$H NMR (DMSO-d$^6$, 300 MHz): δ=7.42-7.26 (m, 5H), 6.19 (s, 1H), 5.01 (s, 2H), 4.70 (s, 2H), 2.19 (s, 3H).

3-Benzyloxy-1-carbonyl(2-mercaptothiazolide)methyl-6-methyl-2-oxo-1,2-dihydropyridine-4-carbonyl(2-mercaptothiazolide) 104. Diacid 103 (1.00 g, 3.15 mmol), TBTU (2.4 g, 7.57 mmol), 4-dimethylaminopyridine (DMAP, 35 mg, 28 μmol, 0.09 eq.), and 2-mercaptothiazoline (789 mg, 6.62 mmol) were suspended in anhydrous dichloromethane (20 mL). Diisopropylethylamine (1.63 g, 12.6 mmol) was added dropwise to form a solution. After one hour, solvent was removed under reduced pressure and the residue was purified by silica gel chromatography to provide compound 104 (1.228 g, 75%). $^1$H NMR (CDCl$_3$, 300 MHz): δ=7.41-7.31 (m, 5H), 6.01 (s, 1H), 5.62 (s, 2H), 5.25 (s, 2H), 4.6 (t, 2H, 7.5 Hz), 4.29, t, 2H, 7.5), 3.41 (t, 2H, 7.5 Hz), 2.87 (t, 2H, 7.5 Hz), 2.28 (s, 3H). $^{13}$C NMR (CDCl$_3$, 400 MHz): δ=202.1, 200.8, 168.2, 166.4, 159.3, 141.5, 140.5, 137.6, 133.0, 128.4, 128.4, 128.1, 104.3, 73.9, 55.9, 55.1, 51.3, 29.4, 29.2, 20.5. FTMS pESI: calculated for $C_{22}H_{21}N_3O_4S_4$ [M+H]$^+$, 520.0493. found, 520.0484.

N,N''-bis[3-benzyloxy-1-carbamidomethyl-6-methyl-2-oxo-1,2-dihydropyridine-4-carbonyl(2-mercaptothiazolide)]-N'-[2-[2-(2-methoxyethoxy)ethoxy]ethoxy]-bis(2-aminoethyl)amine 105. N'-[2-[2-(2-methoxyethoxy)ethoxy]ethoxy]-bis(2-aminoethyl)amine 4 (382 mg, 1.54 mmol) was dissolved in dichloromethane (33 mL) and diisopropylethylamine (0.8 mL) and added using a syringe pump (NE1000) to a solution of 3-benzyloxy-1-carbonyl(2-mercaptothiazolide)methyl-6-methyl-2-oxo-1,2-dihydropyridine-4-carbonyl(2-mercaptothiazolide) 104 (1.99 g, 38.3 mmol) in dichloromethane (50 mL) over a period of 23 hrs at a rate of 1.50 mL/hr. After a further 24 hr, solvent was removed under reduced pressure, and the crude product was purified by silica gel chromatography using 0.1% triethylamine, 2-3.5% methanol in dichloromethane as eluents. Fractions containing product were combined, solvent was removed under reduced pressure, and the residue dried in vacuo to provide compound 105 (997 mg, 60.7%). $^1$H NMR (600 MHz, CDCl$_3$): δ=7.45-7.30 (m, 10H, PhH), 6.21 (s, 2H, ArH), 5.19 (s, 4H, PhCH$_2$O), 4.76 (4H, s, CH$_2$C=O), 4.29 (t, 4H, NCH$_2$CH$_2$S), 3.61-3.51 (m, 10H, CH$_2$O), 3.35 (s, 3H, OCH$_3$), 3.30 (m, 4H, CH$_2$NC=O), 2.89 (t, 4H, NCH$_2$CH$_2$S), 2.66 (m, 6H, CH$_2$N), 2.36 (s, 6H, CH$_3$). $^{13}$C NMR (600 MHz, CDCl$_3$): δ=200.7, 167.0, 165.9, 159.6, 141.8, 141.3, 137.7, 133.2, 128.4, 128.2, 128.1, 104.1, 73.8, 71.8, 70.6, 70.4, 70.2, 58.9, 55.1, 54.4, 52.9, 48.2, 38.0, 29.1, 20.5. FTMS pESI: calculated for $C_{49}H_{60}N_7O_{11}S_4$ [M+H]$^+$, 1050.3228. found, 1050.3223.

Benzyl and tert-butyloxycarbonyl-protected di-macrocycle 106. A solution of N,N''-bis[3-benzyloxy-1-carbamidomethyl-6-methyl-2-oxo-1,2-dihydropyridine-4-carbonyl(2-mercaptothiazolide)]-N'-[2-[2-(2-methoxyethoxy)ethoxy]ethoxy]-bis(2-aminoethyl)amine 105 (924 mg, 880 μmol) in dichloromethane (49.5 mL) and triethylamine (0.5 mL) and a solution of 5-amino-6-[(2-aminoethyl)-[2-[bis(2-aminoethyl)amino]ethyl]amino]hexylcarbamic acid tert-butyl ester 10 (213 mg, 528 μmol) in dichloromethane, isopropyl alcohol (ca. 5%), and diisopropylethylamine (ca. 3%) (50 mL) were added dropwise to dichloromethane (2 L) over a period of four days using two syringe pumps at a rate of 0.5 mL/hr. After an additional two days of reaction, solvent was removed under reduced pressure, and the crude product was purified by silica gel chromatography using 0.1% triethylamine, 5-7.5% methanol in dichloromethane as eluents. The silica gel column was prepared so as to have a short section (ca. 1.25") of aluminum oxide (basic, Brockmann I) on its bottom. Fractions containing product were combined, solvent was removed under reduced pressure, and the residue dried in vacuo to provide the protected di-macrocycle 106 (202 mg, 22.7%). $^1$H NMR (300 MHz, CDCl$_3$): δ=7.45-7.29 (m, 20H, PhH), 6.48-6.37 (m, 4H, ArH), 5.56-4.78 (m, 8H, PhCH$_2$O), 4.77 (8H, br s, CH$_2$C=O), 3.76-3.57 (m, 20H, CH$_2$O), 3.36 (s, 6H, OCH$_3$), 2.90 (m, 17H, CH$_2$NC=O, CHNC=O), 2.65-2.33 (m, 24H, CH$_2$N), 2.18 (m, 12H, CH$_3$), 1.39 (s, 9H, CH$_3$), 1.03-0.98 (m, 6H, CH$_2$). $^{13}$C NMR (600 MHz, CDCl$_3$): δ=167.5, 163.5, 160.4, 155.9, 128.9, 128.6, 128.5, 128.4, 128.3, 74.5, 74.4, 71.9, 71.0, 70.5, 58.9, 52.9, 46.2, 40.4, 38.9, 28.4, 23.1, 20.3, 20.1, 20.0, 19.9, 11.6, 8.0. FTMS pESI: calculated for $C_{105}H_{145}N_{17}O_{24}$ [M+2H]$^{2+}$, 1014.0319. found, 1014.0342.

Di-macrocycle 107. Benzyl and tert-butyloxycarbonyl-protected di-macrocycle 106 (51 mg, 25 μmol) was dissolved in 12N hydrochloric acid (1.0 mL) and glacial acetic acid (1.0 mL). The solution was stirred under inert atmosphere for 23 hr, whereupon HCl was removed with a stream of inert gas. Solvents were removed under reduced pressure and the residue was dried in vacuo. The residue was dissolved in methanol (600+300 μL) and transferred to two 0-ring microcentrifuge tubes. Ether (ca. 1.5 mL) was added, and the tubes were placed at 4° C. for 1 hr. The tubes were centrifuged at 12,000 rpm for 3 minutes, decanted, the pellets were washed with ether (ca. 1.5 mL) and allowed to air dry. The pellets were dried in vacuo to provide dimacrocycle 107, pentahydrochloride salt (39.8 mg, 90%). FTMS pESI: calculated for $C_{72}H_{113}N_{17}O_{22}$ $[M+2H]^{2+}$, 783.9118. found, 783.9140.

Example 21

Synthesis of Di-Macrocyclic Chelator Metal Cation Complexes (Scheme 17)

Metal cation complexes of di-macrocyclic chelators may be prepared readily, for example, by treatment with the metal cation as a solution in methanol in the presence of a tertiary amine as described below. Stock solutions of the pentahydrochloride salts of chelators 94, 12, and 107 were prepared at a concentration of 50 mg/mL in methanol (ca. 30 mM). Triethylamine (10 µL, ca. 12 molar equivalents) was added to each stock solution to free the base. Stock solutions of metal cation salts were prepared at a concentration of 5 mM in methanol. Chelator 94, 12, or 107 (20 µL was added to the metal cation salt solution (122.4 µL, ca. 1 molar equivalent) at ambient temperature in a 2 mL microcentrifuge tube. A precipitate formed immediately. After standing for 30 minutes, diethyl ether (ca. 1.8 mL) was added, and the samples were stored at 4° C. for 15 minutes. The samples were centrifuged for 3 minutes at 12,000 rpm, whereupon the supernatants were decanted and the pellets allowed to air dry. Samples were analyzed in methanol by mass spectrometry, with results reported below. The europium(III) and terbium(III) complexes of chelator 12 were noted to be luminescent when viewed using a long wavelength (365 nm) UV lamp. Absorption and emission spectra for these species were obtained. Metal cation salts tested include europium (III) chloride hexahydrate (99.99%), terbium chloride hexahydrate (99.9%), thorium nitrate hydrate (99.8%), zirconium acetate (16% solution in dilute acetic acid, diluted in methanol to 5 mM concentration), gadolinium nitrate hydrate (99.9%), lutetium chloride hydrate (99.99+%), yttrium chloride hydrate (99.99%), and dysprosium chloride hydrate (99.99%).

Results:

94•Eu: FTMS pESI: calculated for $C_{68}H_{98}N_{13}O_{22}Eu$ $[M]^{2+}$, 799.8069. found, 799.8087.

12•Eu: FTMS pESI: calculated for $C_{68}H_{98}N_{13}O_{18}Eu$ $[M]^{2+}$, 767.8170. found, 767.8195.

107•Eu: FTMS pESI: calculated for $C_{72}H_{110}N_{17}O_{22}Eu$ $[M]^{2+}$, 857.8599. found, 857.8622.

94•Tb: FTMS pESI: calculated for $C_{68}H_{98}N_{13}O_{22}Tb$ $[M]^{2+}$, 803.8096. found, 803.8129.

12•Tb: FTMS pESI: calculated for $C_{68}H_{98}N_{13}O_{18}Tb$ $[M]^{2+}$, 771.8198. found, 771.8224.

107•Tb: FTMS pESI: calculated for $C_{72}H_{110}N_{17}O_{22}Tb$ $[M]^{2+}$, 861.8627. found, 861.8643.

94•Th: FTMS–pESI: calculated for $C_{68}H_{93}N_{13}O_{22}Th$ $[M]^{2-}$, 837.8475. found, 837.8511.

12•Th: FTMS–pESI: calculated for $C_{68}H_{94}N_{13}O_{18}Th$ $[M]^{-}$, 1612.7226. found, 1612.7273.

107•Th: FTMS pESI: calculated for $C_{72}H_{109}N_{17}O_{22}Th$ $[M]^{2+}$, 897.9151. found, 897.9172.

94•Zr: FTMS–pESI: calculated for $C_{68}H_{92}N_{13}O_{22}Zr$ $[M]^{-}$, 1532.5532. found, 1532.5450.

94•Y: FTMS pESI: calculated for $C_{68}H_{98}N_{13}O_{22}Y$ $[M]^{2+}$, 768.7998. found, 768.8015.

12•Y: FTMS pESI: calculated for $C_{68}H_{98}N_{13}O_{18}Y$ $[M]^{2+}$, 736.8100. found, 736.8113.

107•Y: FTMS pESI: calculated for $C_{72}H_{110}N_{17}O_{22}Y$ $[M]^{2+}$, 826.8529. found, 826.8547.

94•Gd: FTMS pESI: calculated for $C_{68}H_{98}N_{13}O_{22}Gd$ $[M]^{2+}$, 803.3090. found, 803.3117.

12•Gd: FTMS pESI: calculated for $C_{68}H_{98}N_{13}O_{18}Gd$ $[M]^{2+}$, 771.3191. found, 771.3220.

107•Gd: FTMS pESI: calculated for $C_{72}H_{110}N_{17}O_{22}Gd$ $[M]^{2+}$, 861.3621. found, 861.3652.

94•Dy: FTMS pESI: calculated for $C_{68}H_{98}N_{13}O_{22}Dy$ $[M]^{2+}$, 806.3115. found, 806.3148.

12•Dy: FTMS pESI: calculated for $C_{68}H_{98}N_{13}O_{18}Dy$ $[M]^{2+}$, 774.3217. found, 774.3245.

107•Dy: FTMS pESI: calculated for $C_{72}H_{110}N_{17}O_{22}Dy$ $[M]^{2+}$, 864.3646. found, 864.3676.

94•Lu: FTMS pESI: calculated for $C_{68}H_{98}N_{13}O_{22}Lu$ $[M]^{2+}$, 811.8173. found, 811.8201.

12•Lu: FTMS pESI: calculated for $C_{68}H_{98}N_{13}O_{18}Lu$ $[M]^{2+}$, 779.8275. found, 779.8300.

107•Lu: FTMS pESI: calculated for $C_{72}H_{110}N_{17}O_{22}Lu$ $[M]^{2+}$, 869.8704. found, 869.8720.

Scheme 17. Synthesis of di-macrocyclic chelator metal cation complexes (formation of the europium (III) complexes as shown).

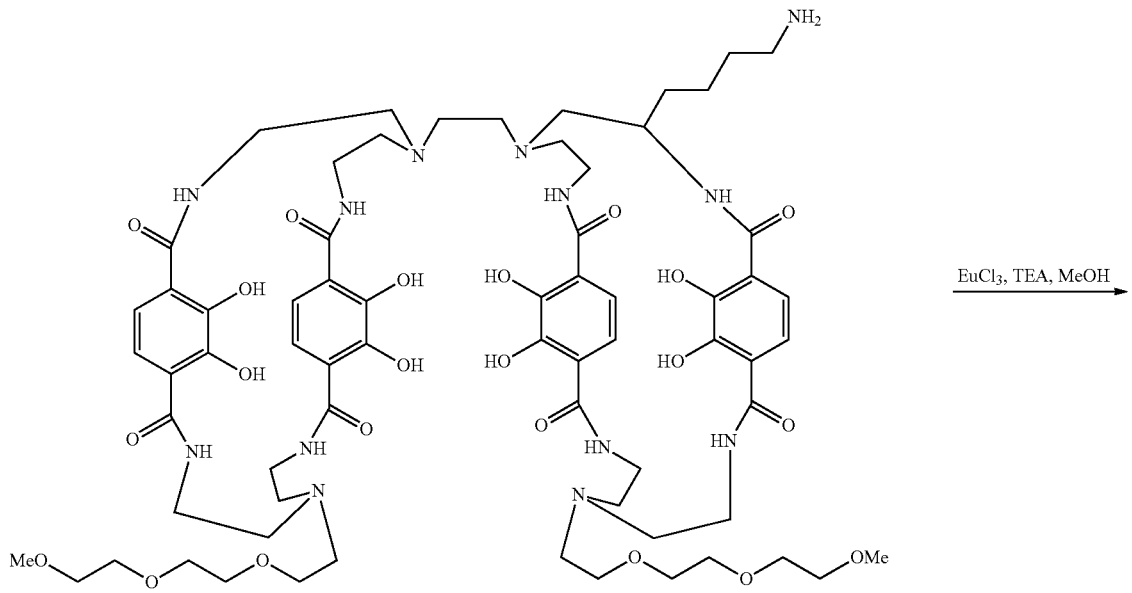

-continued
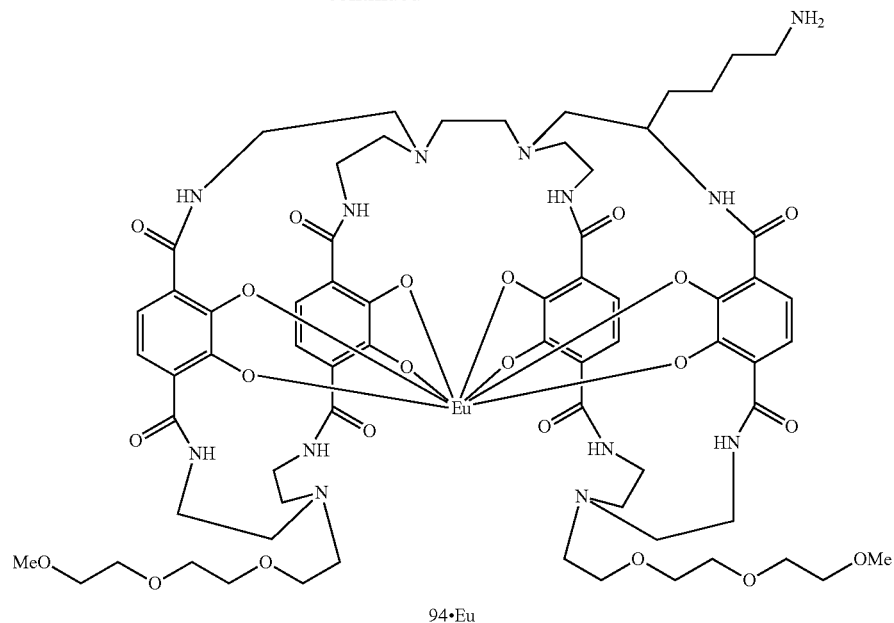
94•Eu
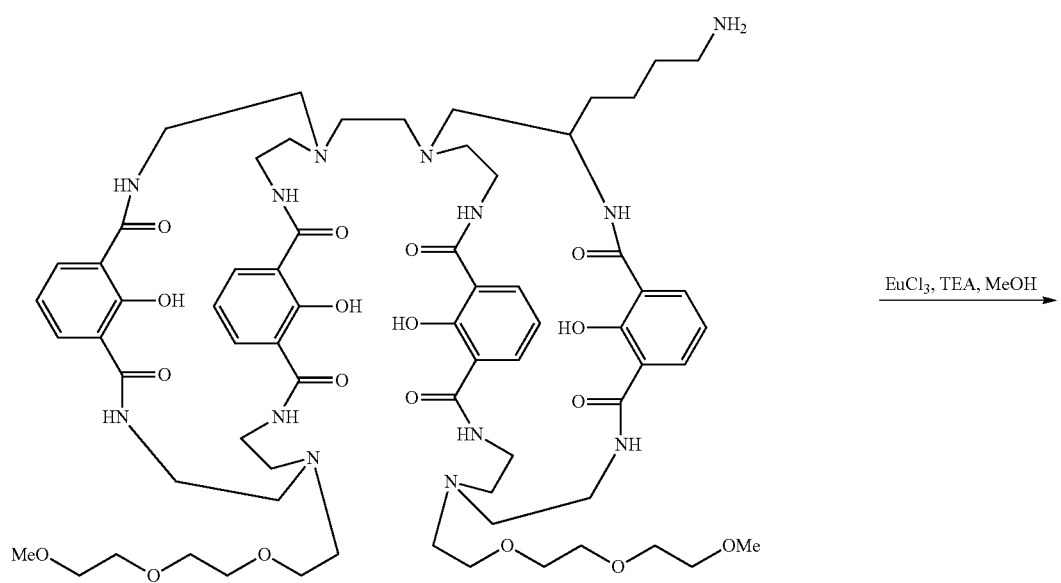
EuCl$_3$, TEA, MeOH

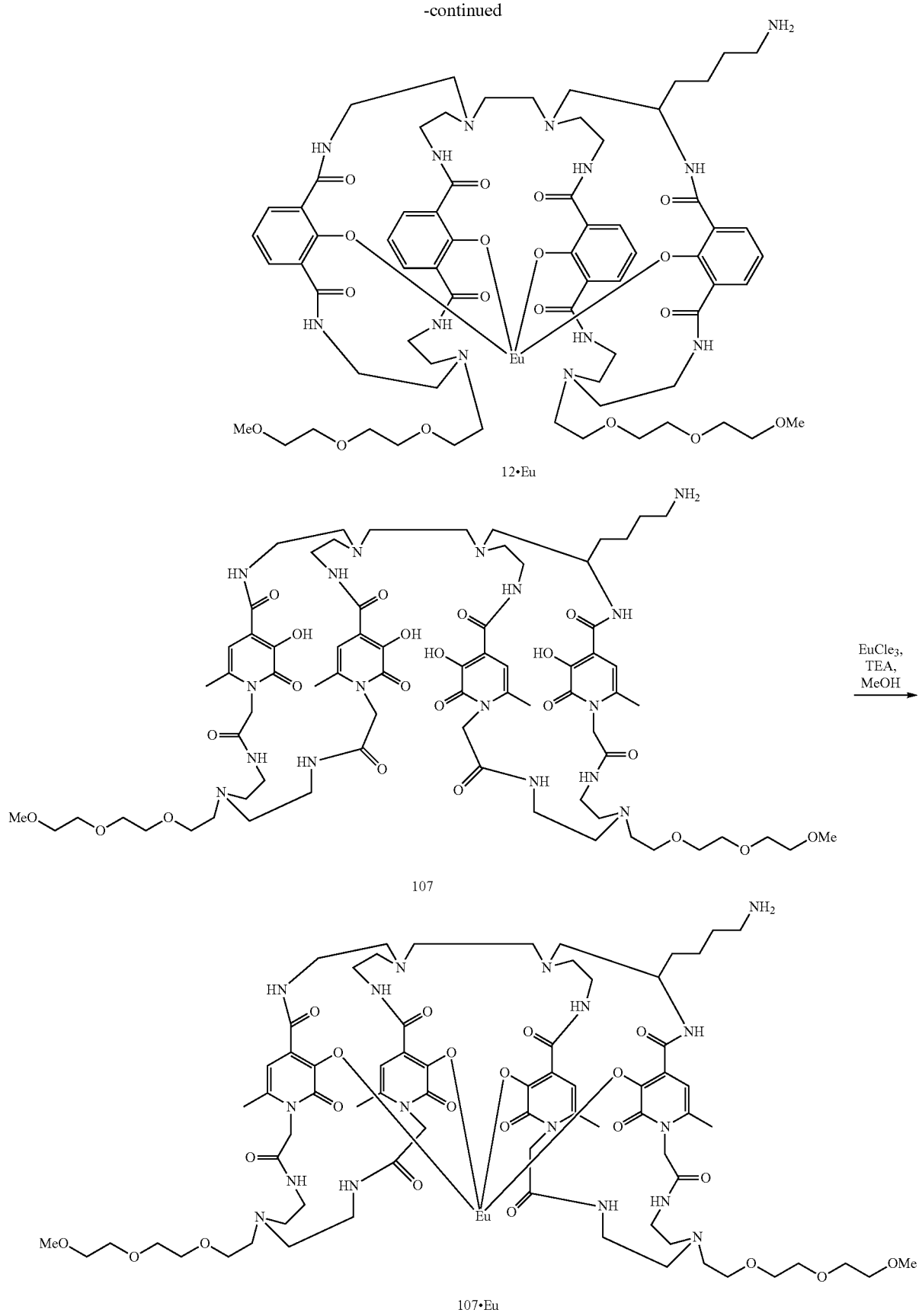

Figure 3A:
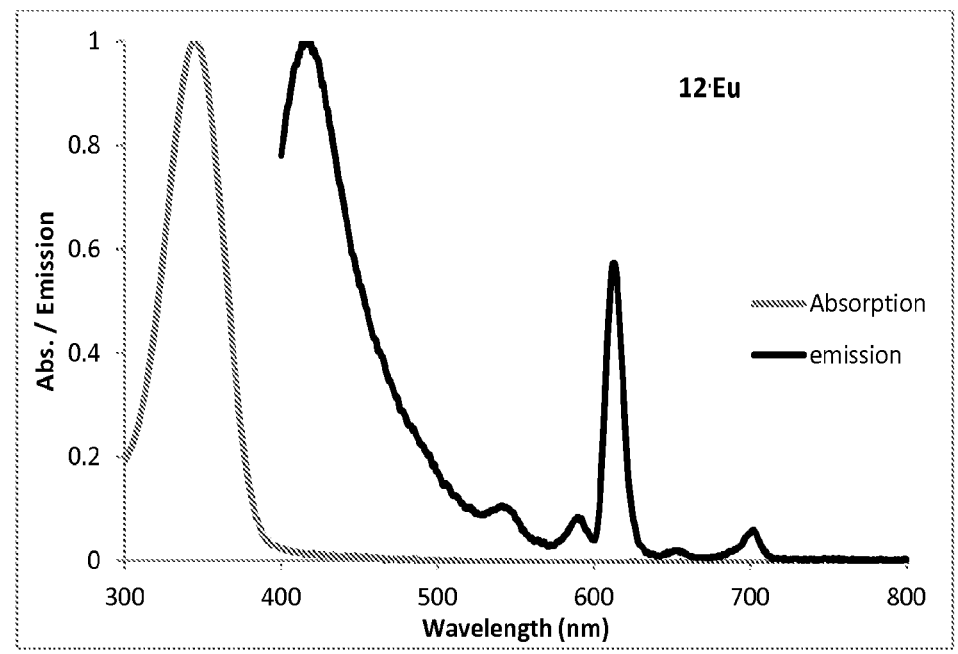
FIG. 3A-FIG. 3B.
Figure 3B:
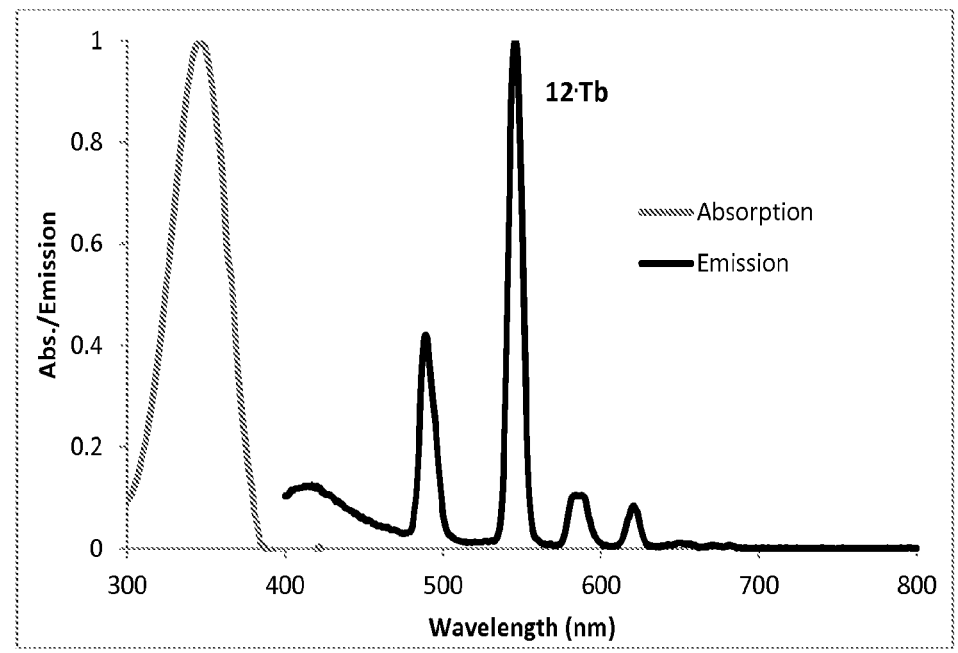

FIG. 3A shows absorption and emission spectra of di-macrocyclic chelator 12 with europium(III). FIG. 3B shows absorption and emission spectra of di-macrocyclic chelator 12 with terbium(III).
Example 22
Synthesis of an Octa-Coordinating Di-Macrocyclic Bifunctional Chelator (Scheme 18)
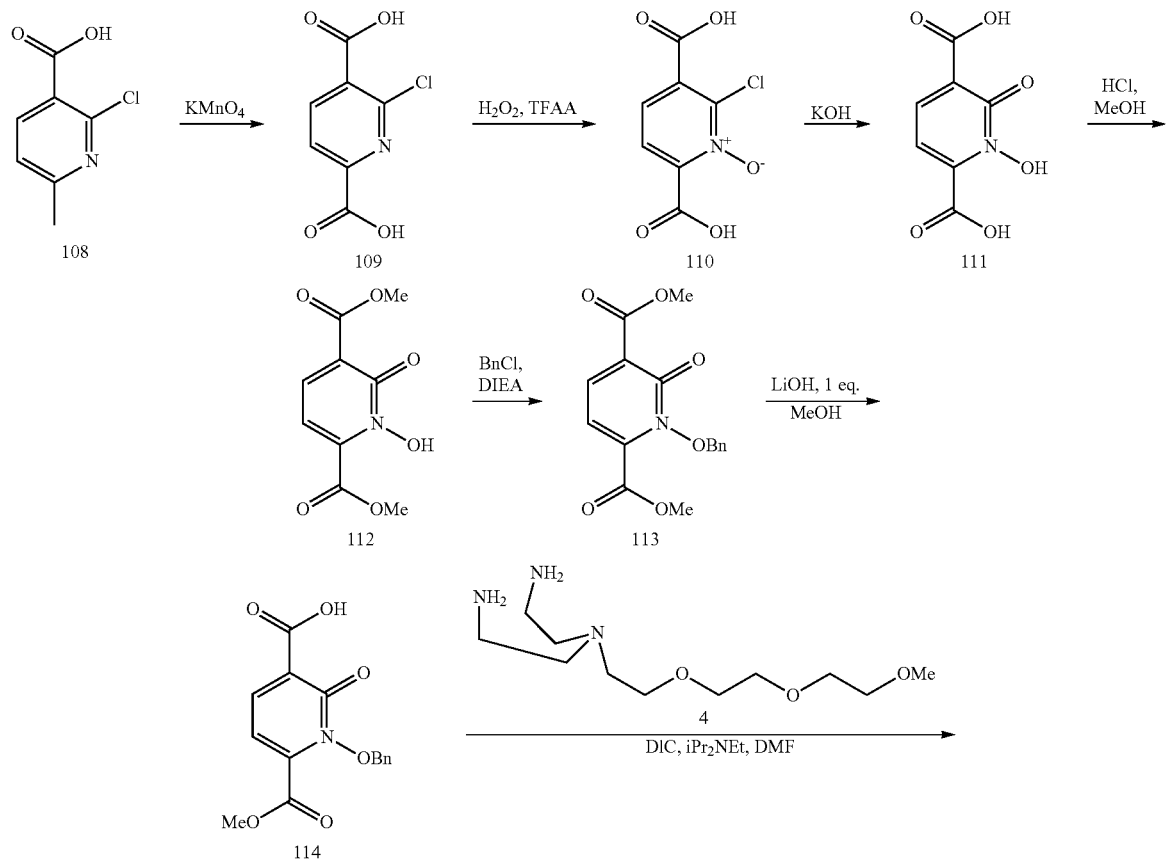
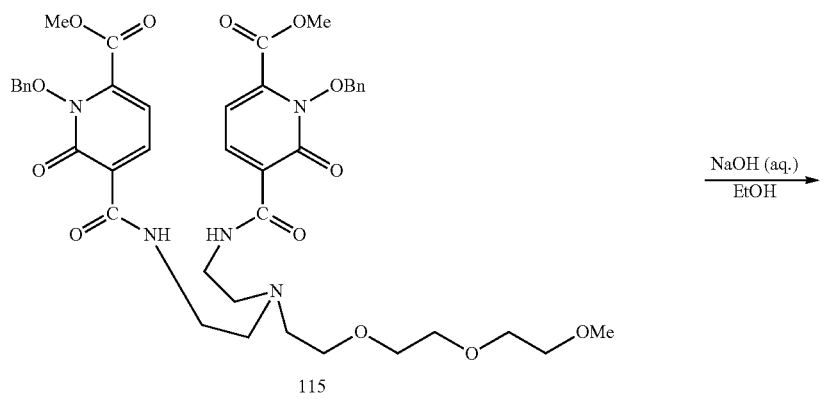

-continued
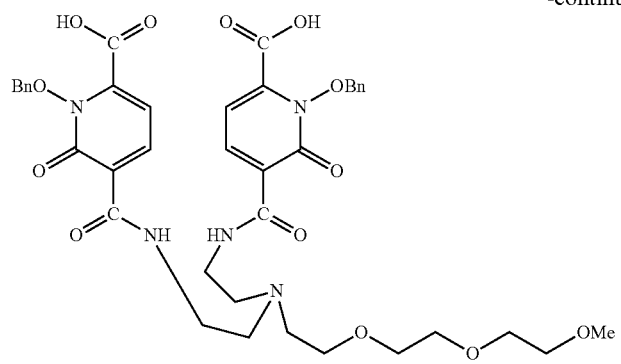
116
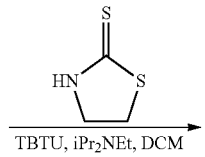
TBTU, iPr₂NEt, DCM
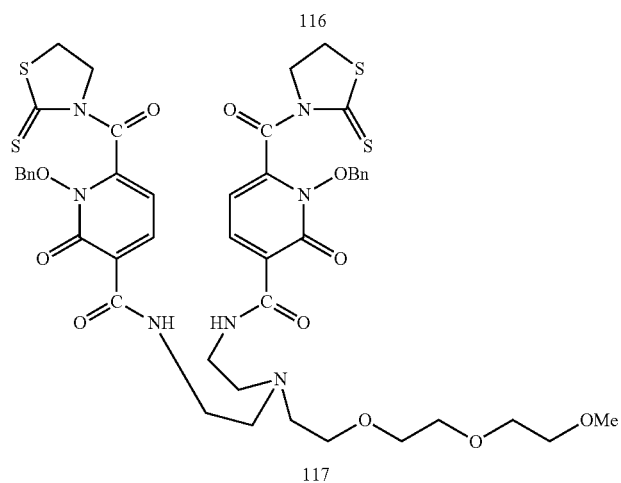
117
H.D. conditions
iPr₂NEt, IPA, DCM
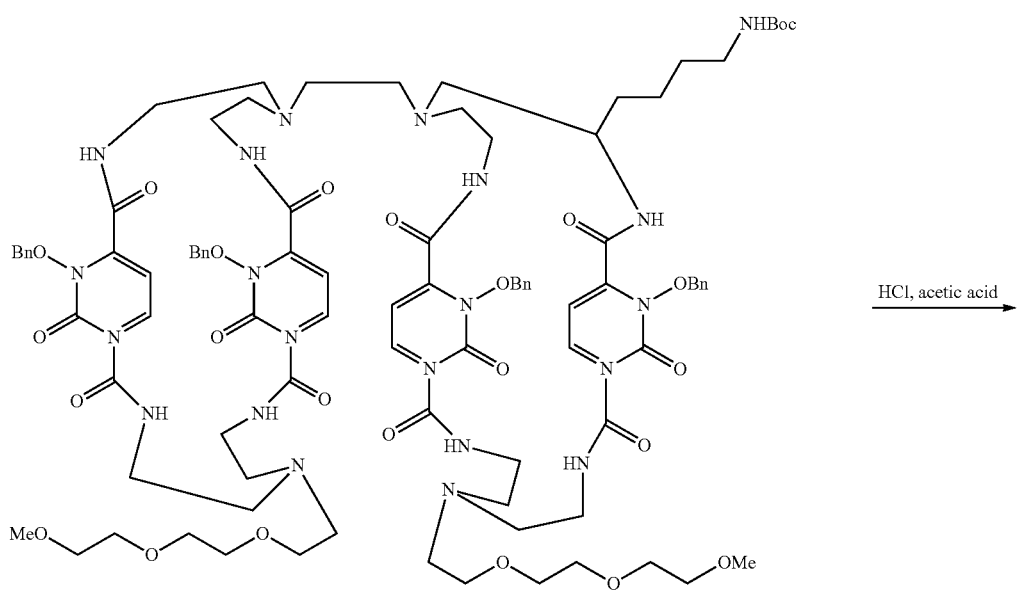
118
HCl, acetic acid -continued

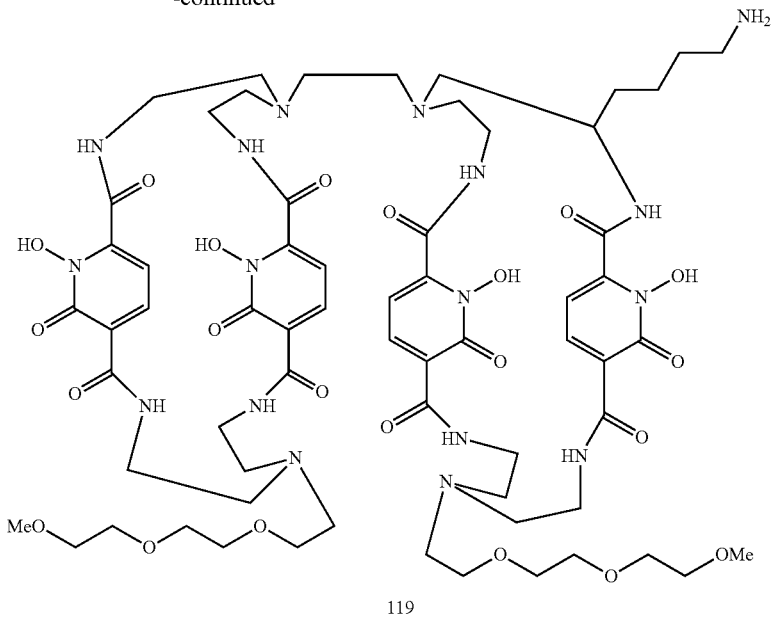

119

Preparation of a 1,2-HOPO macrocyclic ligand began with 2-chloro-6-methyl-nicotinic acid 108, which was oxidized with potassium permanganate to provide 2-chloro-pyridine-3,6-dicarboxylic acid 109. Oxidation of 109 with hydrogen peroxide under acidic conditions provided the pyridine-N-oxide 110, which was heated with sodium hydroxide to provide 1-hydroxy-3,6-dicarboxy-2(1H)pyridinone 111. Diacid 111 was treated with methanol under acidic conditions to provide methyl diester 112. Diester 112 was alkylated with benzyl chloride to provide the benzyl ether 113. Ether 113 was selectively saponified using lithium hydroxide to provide the lithium salt of mono-acid, monomethyl ester 114, which was condensed with [2-[2-(2-methoxyethoxy)ethoxy]ethoxy] diethylenetriamine 4 using diisopropylcarbodiimide to provide di-amide 115. Diamide 115 is saponified with sodium hydroxide to provide the diacid 116, which may be converted to the bis(2-mercaptothiazolide) derivative 117 by treatment with 2-mercaptothiazoline in the presence of a uronium salt such as TBTU in the presence of a tertiary amine. Active amide 117 is reacted with amine 10 under high dilution conditions to form the di-macrocycle 118. Protective groups are removed using a solution of concentrated hydrochloric acid in acetic acid to provide di-macrocycle 119.

2-Chloro-pyridine-3,6-dicarboxylic acid 109. To a mixture of 2-chloro-6-methyl-nicotinic acid 108 (25 g, 0.146 mol) and water (1.5 L) in a 3 liter flask equipped with a mechanical stirrer and a heating mantle, potassium hydroxide (15 g, 0.26 mol) was added to form a clear light brown solution. The solution was heated so that the temperature of the reaction mixture was kept in the range of 85-95° C. during the oxidation process. Potassium permanganate was added in 2-4 gram portions, with the successive portion added only after the pink color from last portion of potassium permanganate had disappeared. The oxidation was monitored by HPLC and proton NMR (in $D_2O$-NaOD). Additional potassium permanganate (70 g, 0.44 mol) was used to complete the reaction. The reaction mixture was filtered while it was hot to remove the large amount of $MnO_2$, and the $MnO_2$ filter cake washed with boiling water (0.5 L). The combined filtrates were acidified with conc. HCl. The white crystals that formed were collected by filtration and dried under reduced pressure to provide 109 (22 g, 75%). $^1$H NMR (500 MHz, DMSO-$d_6$): δ=8.12 (d, 1H, J=7.5 Hz), ArH), 8.34 (d, 1H, J=7.5 Hz, ArH), 13.85 (br s, 2H, COOH). $^{13}$C NMR (125 MHz, DMSO-$d_6$, 25° C.): δ=124.1, 131.4, 141.4, 147.7, 150.0, 164.6, 165.8. (−)-High resolution ESI MS: m/z: 199.9750 [M], calculated 199.9751.

2-Chloro-pyridine-N-oxide-3,6-dicarboxylic acid 110. 2-Chloro-pyridine-3,6-dicarboxylic acid (22 g, 0.109 mol) was dissolved in 300 mL of trifluoroacetic acid and 30% $H_2O_2$ (40 mL) was added to this solution while stirring. The solution was heated to 80° C., and the reaction progress was monitored by HPLC. After the reaction finished, the reaction mixture was concentrated to ca. 50 mL by rotary evaporation and then added to ice water (500 mL). The product immediately precipitated as a finely divided, white crystalline solid. It was isolated by filtration, washed with ice water, and dried in vacuum to provide compound 110 (20 g, 84%). $^1$H NMR (300 MHz, DMSO-$d_6$): δ=8.06 (d, 1H, J=7.4 Hz, ArH), 8.21 (d, 1H, J=7.4 Hz, ArH). $^{13}$C NMR (75 MHz, DMSO-$d_6$, 25° C.): δ=125.9, 130.6, 133.8, 139.9, 140.5, 160.3, 163.6.

1-Hydroxy-3,6-dicarboxy-2(1H)pyridinone 111. 2-Chloro-pyridine-N-oxide-3,6-dicarboxylic acid (20 g, 92 mmol) was dissolved in 25% aqueous KOH (250 mL), and the resulting solution was maintained at 80° C. overnight. Reaction progress was monitored by HPLC. Upon completion of the reaction, the solution was cooled in an ice bath and treated with concentrated hydrochloric acid until the acidity of solution reached about pH 2. The brown-yellow suspended solid was isolated by filtration, washed with dilute HCl and cold water (3×15 mL), and dried in vacuo to provide compound 111 (15.5 g, 80%). $^1$H NMR (300 MHz, DMSO-$d_6$): δ=7.19 (d, 1H, J=7.5 Hz, ArH), 8.06 (d, 1H, J=7.5 Hz, ArH), 15.35 (br s, 2H, COOH). $^{13}$C NMR (75 MHz, $D_2O$-NaOD, 25° C.): δ=102.6, 123.3, 133.3, 148.1, 160.8, 170.3, 175.2.

Dimethyl 1-hydroxy-6-oxo-1,6-dihydropyridine-2,5-dicarboxylate 112. Compound 111 (10 g, 50.2 mmol) was suspended in methanol (150 mL) in a 500 mL flask. The suspension was stirred while dry HCl gas was dispersed into the vessel for 15 minutes to form a partial solution. The reaction mixture was heated at reflux overnight, whereupon HPLC revealed that the esterification was finished. The solution was concentrated and the product deposited as crystalline material. This was collected by filtration and dried in a vacuum oven at 40° C. to provide compound 112 (10.3 g, 90%). $^1$H NMR (300 MHz, DMSO-$d_6$): δ=3.92 (s, 3H, CH$_3$), 3.99 (s, 3H, CH$_3$), 7.81 (d, 1H, J=8.4 Hz, ArH), 8.56 (d, 1H, J=8.4 Hz, ArH). $^{13}$C NMR (75 MHz, DMSO-$d_6$): δ=53.8, 54.8, 116.6, 117.9, 135.3, 142.3, 154.9, 157.9, 161.7.

Dimethyl 1-(benzyloxy)-6-oxo-1,6-dihydropyridine-2,5-dicarboxylate 113. Compound 112 (3 g, 13 mmol) and anhydrous potassium carbonate (4.5 g, 33 mmol) were mixed with benzyl chloride (2.5 g, 20 mmol) in DMF (250 mL). The mixture was heated for 20 h, filtered, and the filtrate evaporated to dryness under reduced pressure. The residue was partitioned in a mixture of 4 M aqueous potassium carbonate (50 mL) and dichloromethane (50 mL). The aqueous phase was extracted with dichloromethane (2×25 mL) and solvent was removed from the combined organic extracts under reduced pressure. The crude product was purified by silica gel chromatography using 0-3% methanol in dichloromethane as eluents. Fractions containing product were combined, solvent was removed under reduced pressure, and the residue dried in vacuo to provide compound 113 as a pale yellow oil (3.3 g, 80%). $^1$H NMR (300 MHz, DMSO-$d_6$): δ=3.58 (s, 3H, CH$_3$), 3.63 (s, 3H, CH$_3$), 5.12 (s, 2H, PhCH$_2$), 6.22 (d, 1H, J=7.5 Hz, ArH), 7.09 (s, br, 3H, PhH) 7.30 (m, br, 2H, PhH), 7.80 (d, 1H, J=7.5 Hz, ArH). $^{13}$C NMR (75 MHz, DMSO-$d_6$): δ=516, 52.7, 77.9, 104.5, 123.8, 127.7, 128.7, 129.2, 132.6, 141.6, 154.7, 158.9, 163.4.

Lithium 1-(benzyloxy)-6-(methoxycarbonyl)-2-oxo-1,2-dihydropyridine-3-carboxylate 114. To a solution of dimethyl 1-(benzyloxy)-6-oxo-1,6-dihydropyridine-2,5-dicarboxylate 113 (3.2 g, 10 mmol) in methanol (100 mL), cooled with an ice bath, a solution of lithium hydroxide (0.24 g) in a mixture of methanol (20 mL) and water (1 mL) was added under nitrogen. The mixture was allowed to warm to ambient temperature while stirring overnight. The reaction mixture was concentrated to dryness and the residue was recrystallized using methanol to provide compound 114, lithium salt as white crystals (2.5 g, 81%). $^1$H NMR (300 MHz, DMSO-$d_6$): δ=3.87 (s, 3H, CH$_3$), 5.39 (s, 2H, PhCH$_2$), 6.32 (d, 1H, J=7.5 Hz, ArH), 7.37 (m, br, 3H, PhH) 7.61 (m, br, 2H, PhH), 8.26 (d, 1H, J=7.8 Hz, ArH). $^{13}$C NMR (75 MHz, DMSO-$d_6$): δ=516, 77.7, 98.6, 115.7, 128.3, 128.8, 129.9, 134.5, 144.5, 155.1, 156.0, 161.1, 165.0.

N,N''-bis[1-benzyloxy-3-carbamido-2-oxo-1,2-dihydropyridine-4-methylcarboxy-N'-[2-[2-(2-methoxyethoxy)ethoxy]ethoxy]-bis(2-aminoethyl)amine 115. Lithium 1-(benzyloxy)-6-(methoxycarbonyl)-2-oxo-1,2-dihydropyridine-3-carboxylate 114 (496 mg, 1.60 mmol) was suspended in anhydrous methanol (25 mL) and concentrated hydrochloric acid (134 μL, 1.61 mmol) was added to form a solution. Solvents were removed under reduced pressure. N-hydroxysuccinimide (222 mg, 1.93 mmol) was added and the solids were dried in vacuo overnight Anhydrous dimethylformamide (4 mL) was added to form a solution, diisopropylcarbodiimide (348 μL, 2.25 mmol) was added, and the solution was stirred for 4.5 hr under nitrogen atmosphere. N'-[2-[2-(2-methoxyethoxy)ethoxy]ethoxy]-bis(2-aminoethyl)amine 4 (182 mg, 729 μmol) was dissolved in dimethylformamide (1 mL) and diisopropylethylamine (381 μL, 2.19 mmol) and added to the reaction mixture. After a further 15 hr, water (ca. 1 mL) was added, and solvents were removed under reduced pressure. The residue was dissolved in dichloromethane (15 mL), washed with water (5 mL), and the aqueous fraction was extracted with dichloromethane (2×10 mL). The combined dichloromethane extracts were concentrated and the crude product was purified by silica gel chromatography using 0.1% triethylamine, 2-5% methanol in dichloromethane as eluents. Fractions containing product were combined, solvent was removed under reduced pressure, and the residue dried in vacuo to provide compound 115 (190 mg, 31.7%). $^1$H NMR (600 MHz, CDCl$_3$): δ=8.13 (br t, 2H, NH), 8.06 (d, 2H, ArH), 7.54 (m, 4H, PhH), 7.34 (m, 6H, PhH), 6.22 (d, 2H, ArH), 5.32 (s, 4H, PhCH$_2$O), 3.90 (6H, s, CO$_2$CH$_3$), 3.32-3.16 (m, 12H, CH$_2$O, CH$_2$NC=O), 2.97 (s, 3H, OCH$_3$), 2.96 (m, 2H, CH$_2$O), 2.41 (m, 4H, CH$_2$N), 2.33 (m, 2H, CH$_2$N). $^{13}$C NMR (600 MHz, CDCl$_3$): δ=164.7, 160.3, 155.6, 148.1, 143.6, 133.5, 130.6, 129.4, 128.4, 122.3, 102.4, 79.5, 71.4, 70.0, 69.6, 69.5, 69.2, 58.4, 54.2, 53.5, 52.5, 37.6. FTMS pESI: calculated for C$_{41}$H$_{50}$N$_5$O$_{13}$ [M+H]$^+$, 820.3400. found, 820.3387.

N,N''-bis[1-benzyloxy-3-carbamido-2-oxo-1,2-dihydropyridine-4-carboxy-N'-[2-[2-(2-methoxyethoxy)ethoxy]ethoxy]-bis(2-aminoethyl)amine 116 disodium salt. Compound 115 is dissolved in methanol and treated with 1 M sodium hydroxide solution (2 molar equivalents) for one hour at ambient temperature. Solvents are removed under reduced pressure to provide compound 116 as the disodium salt.

N,N''-bis[1-benzyloxy-3-carbamido-2-oxo-1,2-dihydropyridine-4-carbonyl(2-mercaptothiazolide) —N'-[2-[2-(2-methoxyethoxy)ethoxy]ethoxy]-bis(2-aminoethyl)amine 117. Disodium salt 116 (1 molar equivalent), TBTU (2.2 molar equivalents), and 2-mercaptothiazoline (2.2 molar equivalents) are suspended in anhydrous dichloromethane (20 mL). Diisopropylethylamine (3 molar equivalents) is added dropwise to form a solution. After one hour, solvent is removed under reduced pressure and the residue is purified by silica gel chromatography to provide compound 117.

Benzyl and tert-butyloxycarbonyl-protected di-macrocycle 118. A solution of compound 117 (ca. 1 g) in dichloromethane (49.5 mL) and triethylamine (0.5 mL) and a solution of 5-amino-6-[(2-aminoethyl)-[2-[bis(2-aminoethyl)amino]ethyl]amino]hexylcarbamic acid tert-butyl ester 10 (one molar equivalent) in dichloromethane, isopropyl alcohol (ca. 5%), and diisopropylethylamine (ca. 3%) (50 mL) are added dropwise to dichloromethane (2 L) over a period of four days using two syringe pumps at a rate of 0.5 mL/hr. After an additional two days of reaction, solvent is removed under reduced pressure, and the crude product is purified by silica gel chromatography. The silica gel column is prepared so as to have a short section (ca. 1.25") of aluminum oxide (basic, Brockmann I) on its bottom. Fractions containing product are combined, solvent is removed under reduced pressure, and the residue dried in vacuo to provide the protected di-macrocycle 118.

Di-macrocycle 119. Benzyl and tert-butyloxycarbonyl-protected di-macrocycle 118 (ca. 50 mg) is dissolved in 12N hydrochloric acid (1.0 mL) and glacial acetic acid (1.0 mL). The solution is stirred under inert atmosphere for ca. one day, whereupon HCl is removed with a stream of inert gas. Solvents are removed under reduced pressure and the residue is dried in vacuo. The residue is dissolved in methanol (600+300 μL) and transferred to two O-ring microcentrifuge tubes. Ether (ca. 1.5 mL) is added, and the tubes are placed at 4° C. for 1 hr. The tubes are centrifuged at 12,000 rpm for 3 minutes, decanted, the pellets are washed with ether (ca. 1.5 mL) and allowed to air dry. The pellets are dried in vacuo to provide di-macrocycle 119, pentahydrochloride salt.

Example 23
Synthesis of an Octa-Coordinating Di-Macrocyclic Bifunctional Chelator (Scheme 19)
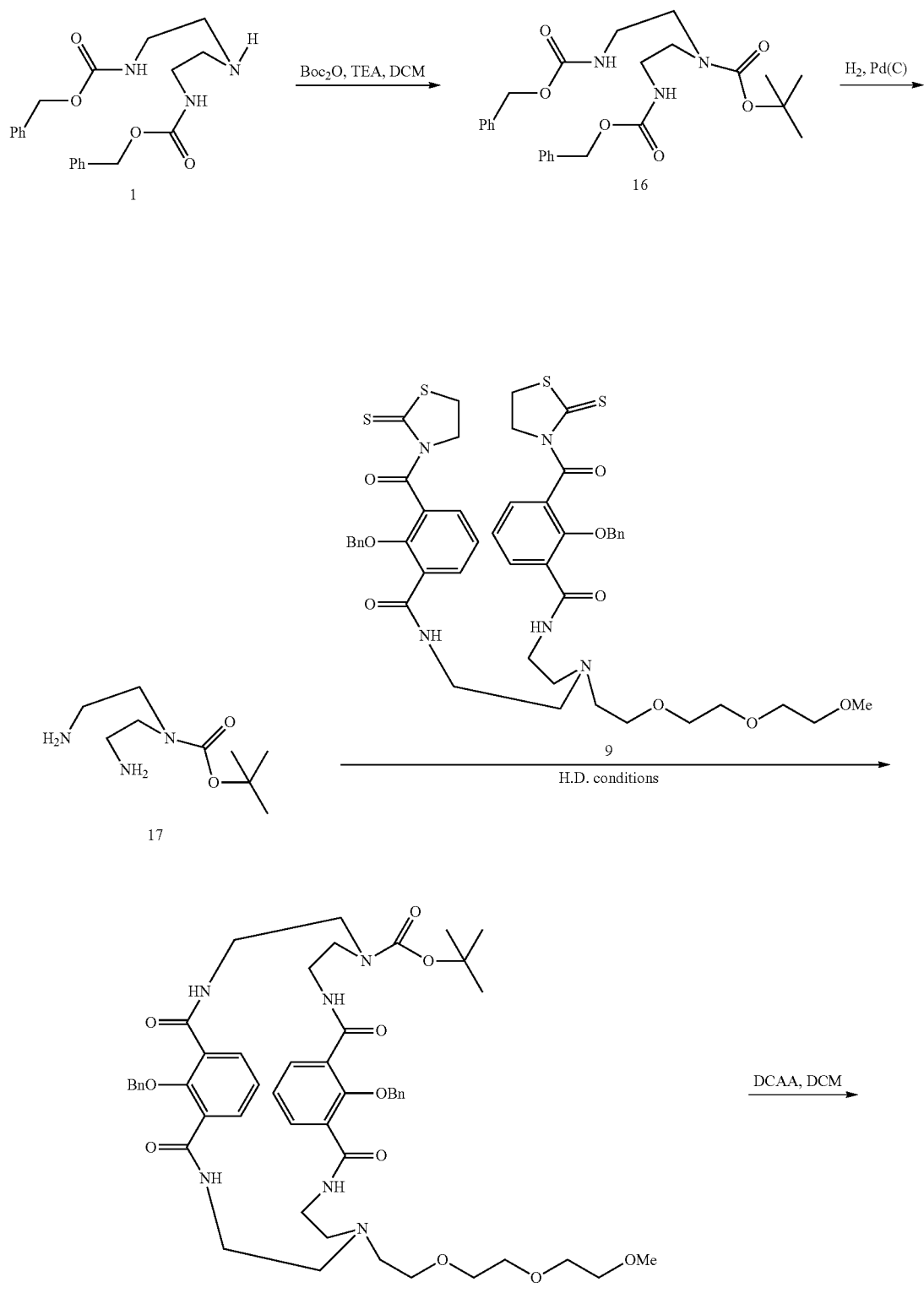

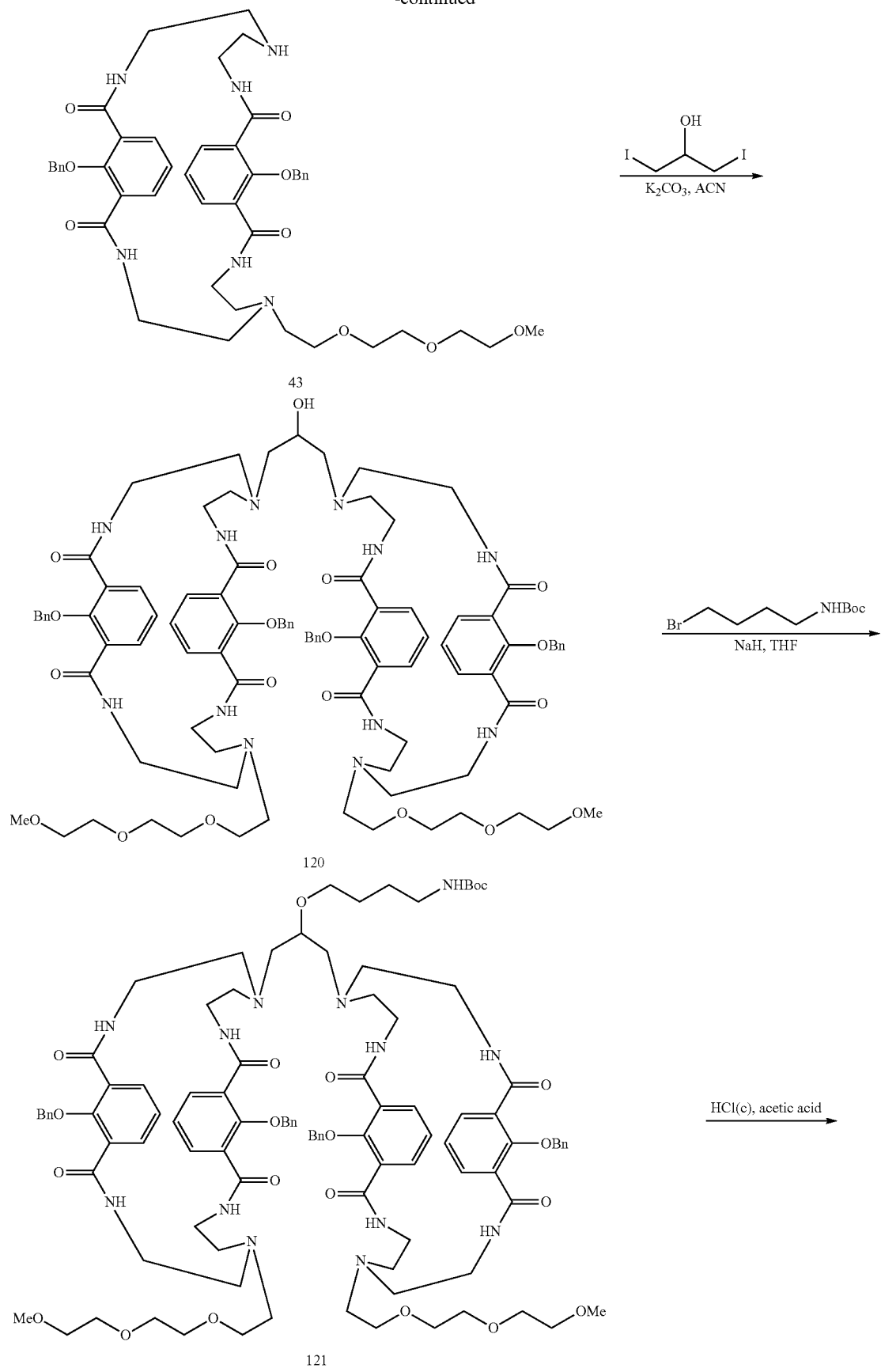

-continued

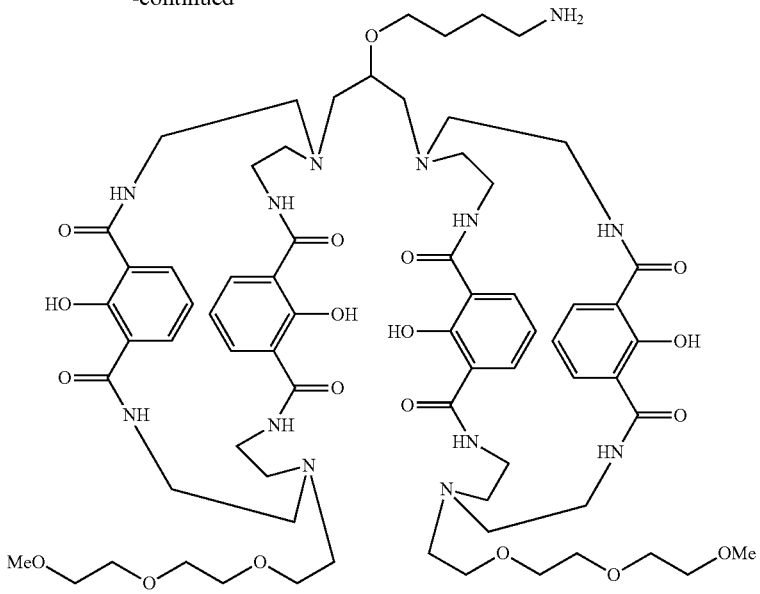

122

For ease of manufacture, it might be desirable to prepare di-macrocylic chelators using a convergent synthesis. One such approach, exemplified for a chelator containing four isophthalamide coordinating units, is shown is Scheme 19. Here, the mono-macrocyclic intermediate 42 is prepared by cyclization of dithiazolide 9 with diamine 17. Deprotection of 42 under acidic conditions provides secondary amine 43, which may be alkylated in one pot to provide the symmetrical di-macrocycle 120. Di-macrocycle 120 is further alkylated to provide ether 121. Deprotection of di-macrocycle 121 under acidic conditions forms the symmetric di-macrocyclic chelator 122. It is to be noted that only one regioisomer is formed using this approach.

N,N''-Bis(carbobenzyloxy)-N'-tert-butyloxycarbonyl-bis (2-aminoethyl)amine 16. N,N''-Di-Z-diethylenetriamine 1 (1.00 g, 2.69 mmol) was dried overnight in vacuo Anhydrous dichloromethane (25 mL) was added, and the resulting solution was treated with triethylamine (0.751 mL, 5.39 mmol) and Boc anhydride (0.928 mL, 4.04 mmol) for 27 hr. The solution was transferred to a separatory funnel using dichloromethane (25 mL) and washed with 1 M sodium hydroxide (50 mL). The aqueous phase was extracted with dichloromethane (2×25 mL) and solvent was removed from the combined organic extracts under reduced pressure. The crude product was purified by silica gel chromatography using 1-2% methanol in dichloromethane as eluents. Fractions containing product were combined, solvent was removed under reduced pressure, and the residue dried in vacuo to provide compound 16 (1.283 g, 100%). $^1$H NMR (300 MHz, CDCl$_3$): δ=7.32 (s, 10H, PhH), 5.07 (s, 4H, PhCH$_2$O), 3.32 (m, 8H, CH$_2$N), 1.41 (s, 9H, Me). $^{13}$C NMR (600 MHz, CDCl$_3$): δ=156.3, 136.9, 128.4, 128.0, 80.4, 66.6, 48.3, 47.4, 40.4, 40.0, 28.3.

N'-tert-butyloxycarbonyl-bis(2-aminoethyl)amine 17. N,N''-Bis(carbobenzyloxy)-N'-tert-butyloxycarbonyl-bis(2-aminoethyl)amine 16 (1.150 g, 2.44 mmol) was dissolved in ethyl alcohol (50 mL). Palladium on carbon (10% wet, 115 mg) was added, and the atmosphere was exchanged for hydrogen. After 15 hr, methanol (50 mL) was added to the resulting suspension to form a solution. This was filtered through Celite® to remove catalyst, the Celite was washed with methanol (50 mL), solvent was removed under reduced pressure, and the residue dried in vacuo to provide compound 17 (483 mg, 97.4%). $^1$H NMR (300 MHz, CDCl$_3$): δ=3.23 (m, 4H, CH$_2$NC=O), 2.79 (t, 4H, CH$_2$N), 1.31 (s, 6H, CH$_3$), 1.20 (s, 3H, CH$_3$). $^{13}$C NMR (300 MHz, CDCl$_3$): δ=156.4, 79.9, 51.0, 41.1, 28.7. FTMS pESI: calculated for C$_9$H$_{22}$N$_3$O$_2$ [MH]$^+$, 204.1707. found, 204.1703.

Benzyl and tert-butyloxycarbonyl-protected mono-macrocycle 42. A solution of N,N''-bis[1-benzyloxy-2-(2-mercaptothiazoleamido)-6-benzoyl]-N'-[2-[2-(2-methoxyethoxy)ethoxy]ethoxy]-bis(2-aminoethyl)amine 9 (1.214 g, 1.26 mmol) in dichloromethane (45 mL) and triethylamine (529 µL) and a solution of N'-tert-butyloxycarbonyl-bis(2-aminoethyl)amine 17 (257 mg, 1.26 mmol) in methanol (45 mL) and triethylamine (529 µL) were added dropwise to dichloromethane (1 L) over a period of four days using two syringe pumps at a rate of 0.5 mL/hr. After an additional two days of reaction, solvent was removed under reduced pressure, and the crude product was purified by silica gel chromatography using 0.1% triethylamine, 2-5% methanol in dichloromethane as eluents. Fractions containing product were combined, solvent was removed under reduced pressure, and the residue dried in vacuo to provide the protected mono-macrocycle 42 (776 mg, 66.3%). $^1$H NMR (600 MHz, MeOD): δ=7.66-7.17 (m, 16H, PhH, ArH), 4.62 (s, 4H, PhCH$_2$O), 3.54-3.31 (m, 14H, CH$_2$O, CH$_2$NC=O), 3.32 (s, 3H, OCH$_3$), 2.63 (m, 6H, CH$_2$N), 1.41 (s, 9H, CH$_3$). $^{13}$C NMR (600 MHz, MeOD): δ=168.0, 153.9, 131.7, 128.6, 128.3, 128.2, 124.3, 80.1, 77.6, 71.5, 70.0, 69.8, 68.8, 57.7, 53.6, 52.6, 39.4, 37.9. FTMS pESI: calculated for C$_{50}$H$_{65}$N$_6$O$_{11}$ [M+H]$^+$, 925.4706. found, 925.4684.

Mono-macrocycle 43. Protected mono-macrocycle 42 (50 mg, 54 µmol) was dissolved in dichloromethane (500 µL) and dichloroacetic acid (500 µL) was added. After 3 hr, the reaction mixture was transferred to three microcentrifuge tubes and diethyl ether (ca. 1.5 mL/tube) was added. The tubes were stored at 4° C. for 30 minutes, centrifuged at 12,000 rpm for 3 minutes, and decanted. The pellets were washed with ether (ca. 1.5 mL) and allowed to air dry. The pellets were dried in vacuo to provide mono-macrocycle 43, dichloroacetate salt (15.4 mg, 30%). FTMS pESI: calculated for C$_{45}$H$_{57}$N$_6$O$_9$ [M+H]$^+$, 825.4182. found, 825.4186.

Di-macrocycle 120. Mono-macrocycle 43, dichloroacetate salt (75 mg, 79 µmol) and potassium carbonate (3 molar equivalents) are dried overnight in vacuo. Anhydrous acetonitrile (2 mL) and 1,3-diiodo-2-propanol (0.5 molar equivalents) are added and the resulting suspension is heated at reflux for 24 hr. Upon cooling, solvent is removed under reduced pressure, and the residue is dissolved in dichloromethane (ca. 10 mL) and washed with water (ca. 5 mL). Solvent is removed under reduced pressure, and the crude product is purified by silica gel chromatography using 0.1% triethylamine, methanol in dichloromethane as eluents. Fractions containing product are combined, solvent is removed under reduced pressure, and the residue dried in vacuo to provide di-macrocycle 120.

Di-macrocycle 121. Di-macrocycle 120 (50 mg, 29 μmol) is dissolved in anhydrous tetrahydrofuran (2 mL) and cooled in an ice bath. Sodium hydride (1 molar equivalent) is added, followed by 4-(Boc-amino) butyl bromide (1 molar equivalent). The reaction mixture is allowed to warm to ambient temperature, and after reaction is complete, solvent is removed under reduced pressure. The residue is dissolved in dichloromethane (ca. 10 mL) and washed with water (ca. 5 mL). Solvent is removed under reduced pressure, and the crude product is purified by silica gel chromatography using 0.1% triethylamine, methanol in dichloromethane as eluents. Fractions containing product are combined, solvent is removed under reduced pressure, and the residue dried in vacuo to provide di-macrocycle 121.

Di-macrocycle 122. Benzyl and tert-butyloxycarbonyl-protected di-macrocycle 121 (ca. 50 mg) is dissolved in 12N hydrochloric acid (1.0 mL) and glacial acetic acid (1.0 mL). The solution is stirred under inert atmosphere for ca. one day, whereupon HCl is removed with a stream of inert gas. Solvents are removed under reduced pressure and the residue is dried in vacuo. The residue is dissolved in methanol (600+300 μL) and transferred to two O-ring microcentrifuge tubes. Ether (ca. 1.5 mL) is added, and the tube is placed at 4° C. for 1 hr. The tubes are centrifuged at 12,000 rpm for 3 minutes, decanted, the pellets are washed with ether (ca. 1.5 mL) and allowed to air dry. The pellets are dried in vacuo to provide di-macrocycle 122, pentahydrochloride salt.

Example 24

Synthesis of an Octa-Coordinating Di-Macrocyclic Bifunctional Chelator (Scheme 20)

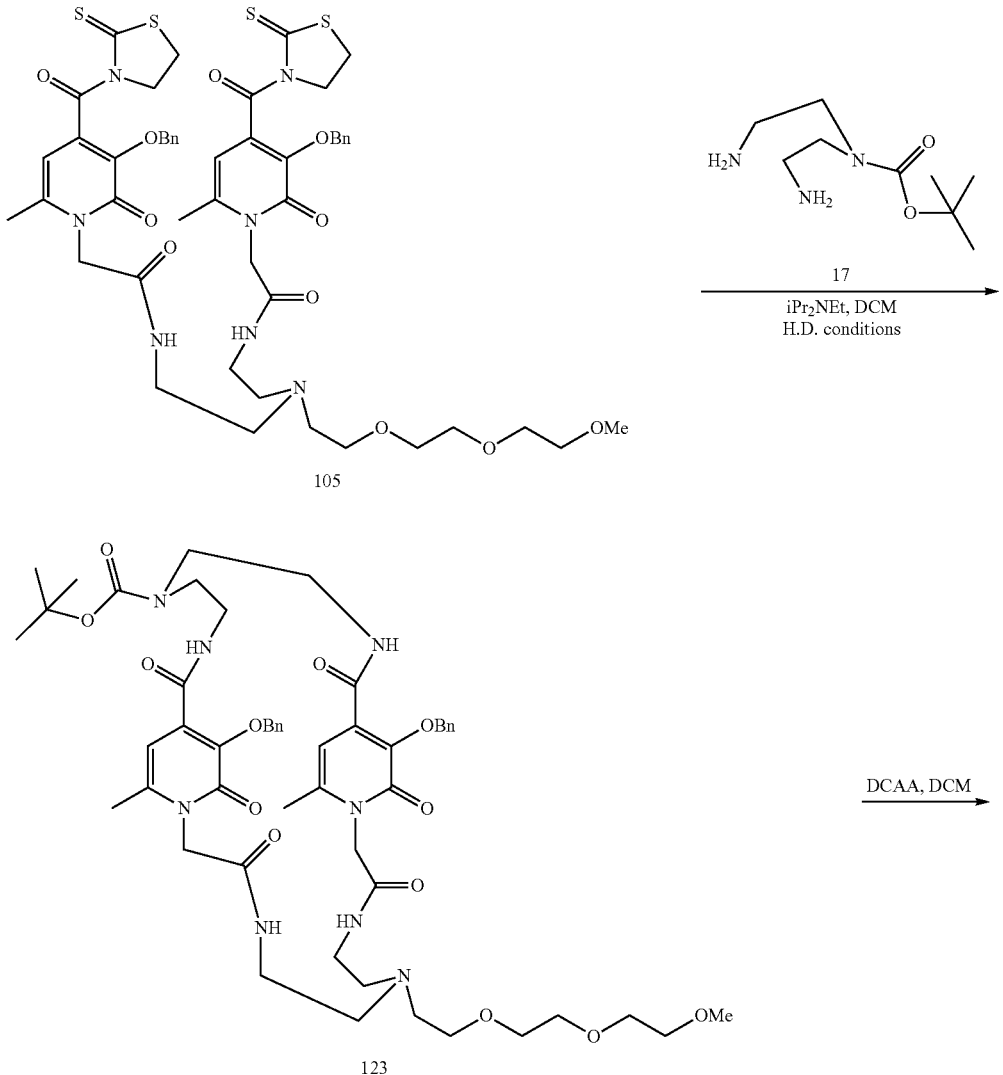

Scheme 20. Synthesis of di-macrocyclic bifunctional chelator 128.

-continued
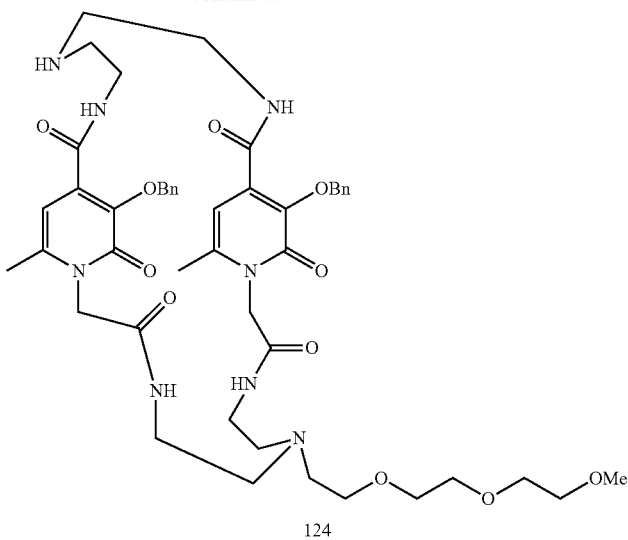
124
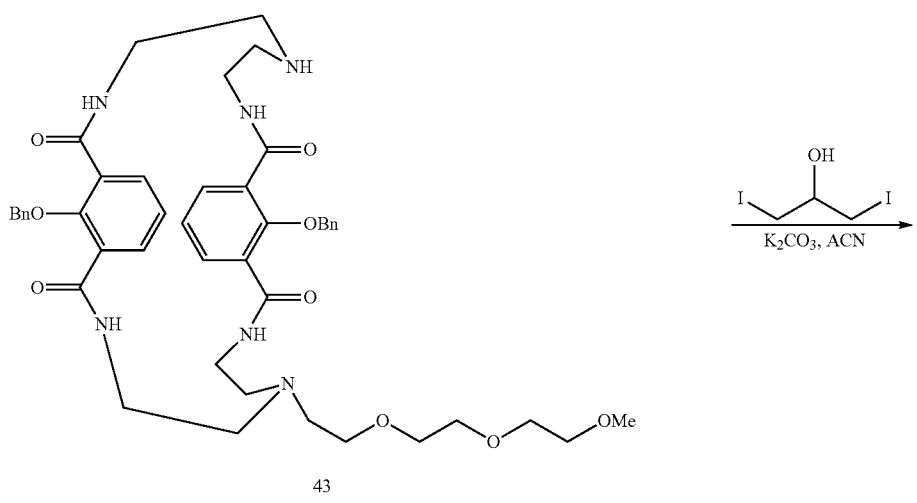
43
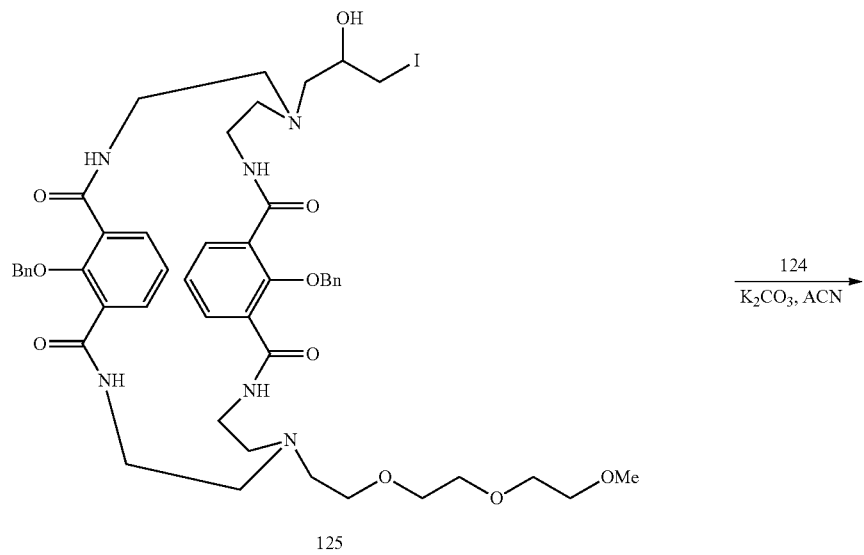
125

-continued
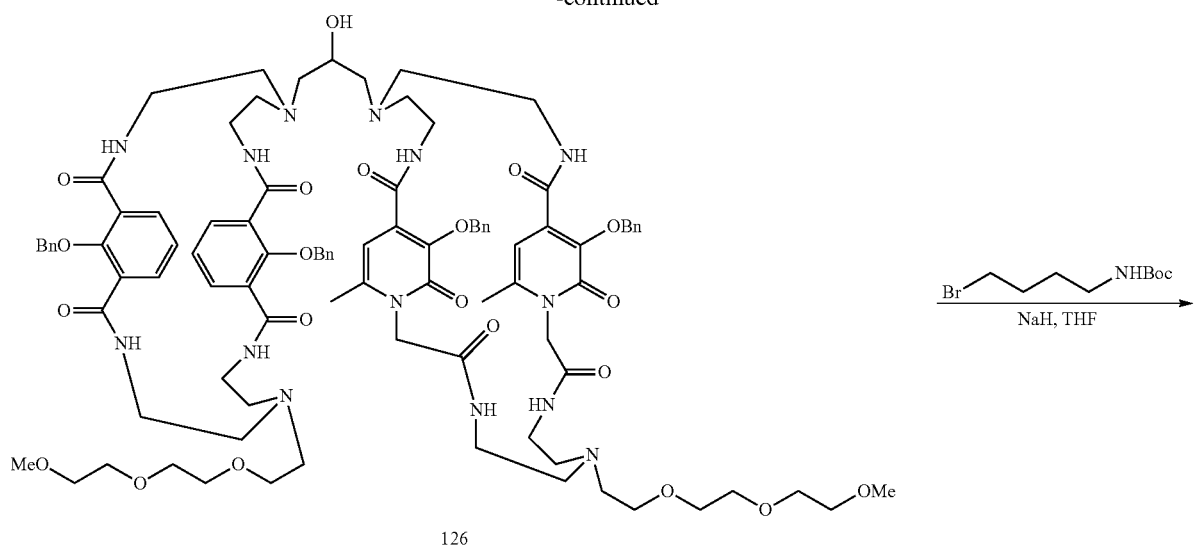
126
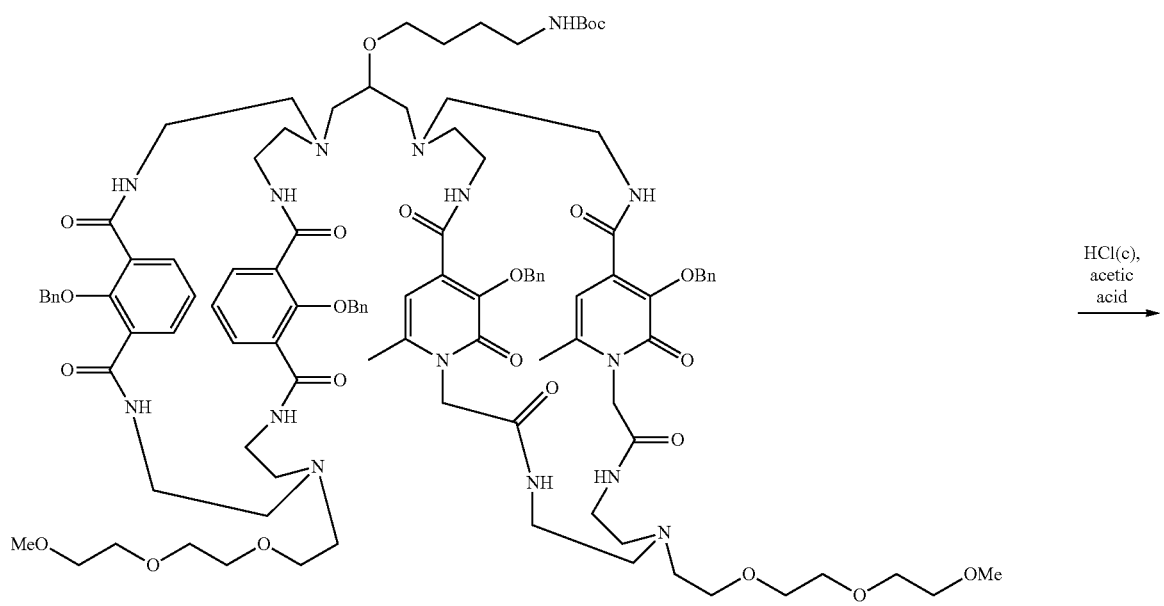
127

-continued

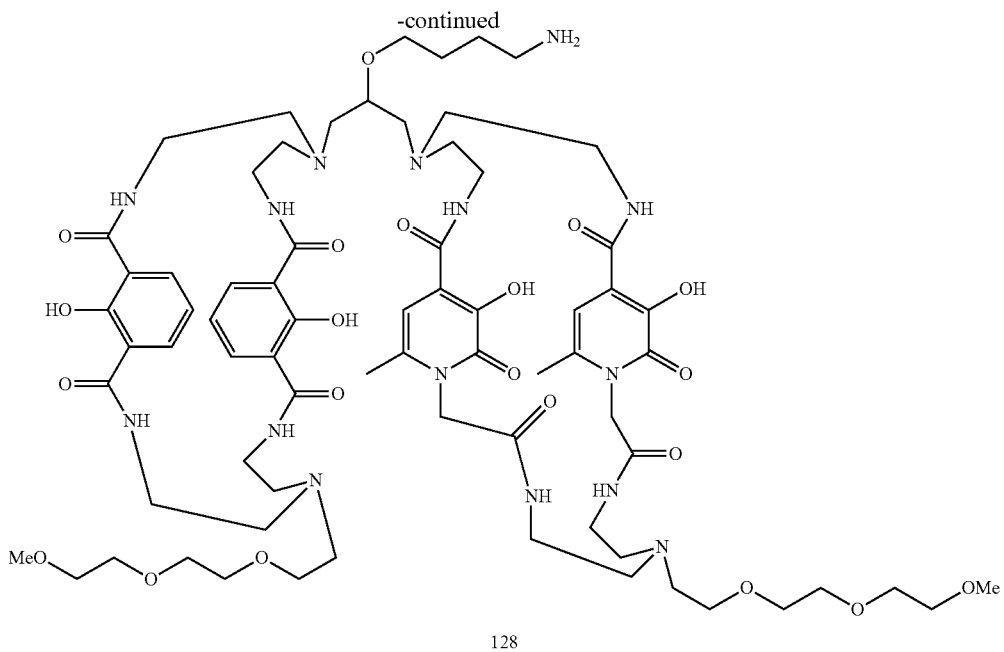

128

To one skilled in the art, it should be possible to use the methods disclosed above to prepare octa-coordinating di-macrocyclic bifunctional chelators that combine dissimilar coordinating groups. One example of such as synthesis is shown in Scheme 20, wherein the di-macrocyclic chelator 128, which contains two isophthalamide and two 3-hydroxy-pyridin-2-one coordinating groups, is described. Dithiazolide 105 is condensed with N'-tert-butyloxycarbonyl-bis(2-aminoethyl)amine 17 to provide protected mono-macrocycle 123. This is converted to the secondary amine 124 using acidic conditions. Mono-macrocycle 43 is reacted with an excess of 1,3-diiodo-2-propanol to provide the iodide 125. Iodide 125 is used to alkylate the secondary amine 124 under basic conditions to form di-macrocycle 126. Di-macrocycle 126 may be alkylated to form ether 127, and protective groups are removed under acidic conditions to provide di-macrocycle 128 as the penta-hydrochloride salt. Similar syntheses to prepare di-macrocyclic chelators bearing alternative coordinating groups are envisioned. Such approaches may yield bifunctional chelators that combine advantageous properties of the individual coordinating groups, such as luminescence in the presence of certain lanthanide ions (to help assess, for example, biodistribution) with strong metal cation binding properties or more facile kinetics of metalation.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

We claim:
1. A di-macrocycle having the structure:

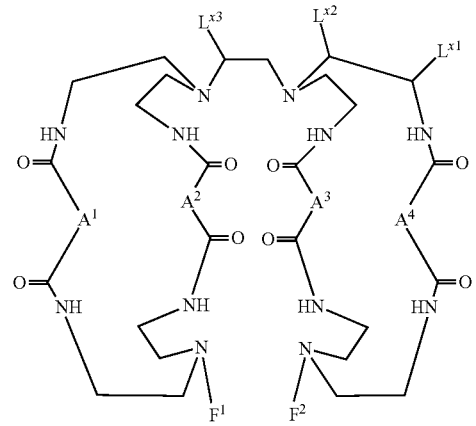

wherein
$A^1, A^2, A^3$ and $A^4$ are members independently selected from:

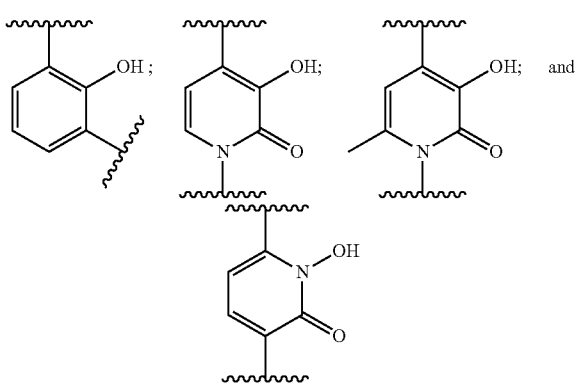

$F^1$ and $F^2$ are independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, a peptide and a nucleic acid; and $L^{x1}$, $L^{x2}$ and $L^{x3}$ are independently selected from H and a linker.

2. The di-macrocycle according to claim 1, the structure:

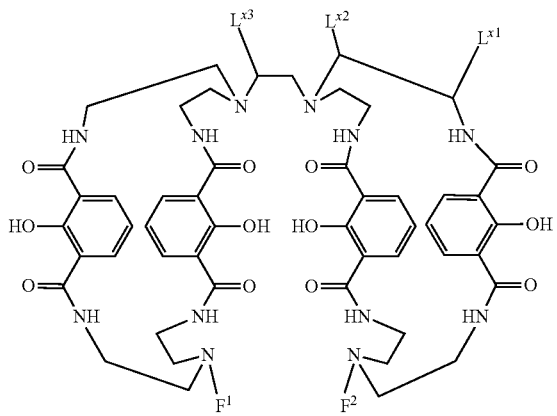

3. The di-macrocycle according to claim 1, wherein $F^1$ and $F^2$ are independently selected from a substituted or unsubstituted polyether and a peptide.

4. A complex comprising a di-macrocycle according to claim 1 and a metal ion.

5. The complex according to claim 4, wherein said metal ion is $^{227}$Th(IV) or $^{89}$Zr(IV).

6. The complex according to claim 4, wherein said metal is a member selected from $^{177}$Lu, $^{166}$Ho, $^{153}$Sm, $^{90}$Y, $^{86}$Y, $^{166}$Dy, $^{165}$Dy, $^{169}$Er, $^{175}$Yb, $^{225}$Ac, $^{149}$Tb, $^{153}$Gd, and $^{230}$U.

7. The complex according to claim 4, wherein said metal is a member selected from $^{111}$In, $^{67}$Ga, $^{67}$Cu, $^{64}$Cu, $^{186}$Re, $^{188}$Re, $^{111}$Ag, $^{109}$Pd, $^{212}$Pb, $^{203}$Pb, $^{212}$Bi, $^{213}$Bi, $^{195m}$Pt, $^{201}$Tl, $^{55}$Co, and $^{99m}$Tc.

8. The complex according to claim 4, wherein said metal is Tb.

9. The complex according to claim 4, wherein said metal is a lanthanide.

10. The di-macrocycle according to claim 1, wherein $F^1$, $F^2$ are independently selected from a polyether substituted with an estradiol moiety, a peptide and an oligonucleotide.

11. The di-macrocycle according to claim 1, wherein one or both $F^1$ and $F^2$ are independently selected from:

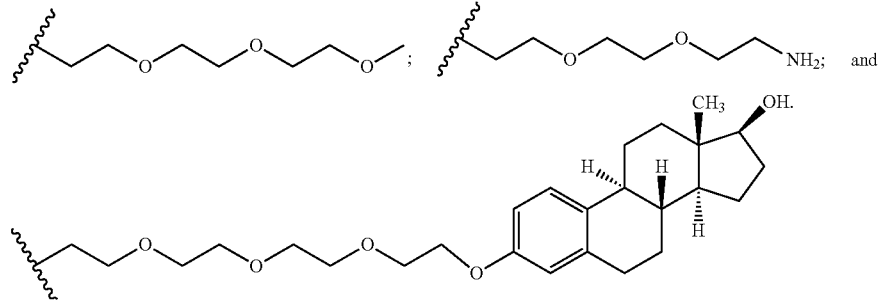

12. The di-macrocycle according to claim 1, wherein $F^1$ and $F^2$ both are a peptide.

13. The di-macrocycle according to claim 12, wherein $F^1$, $F^2$ or both are:

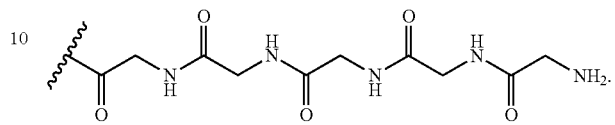

14. The di-macrocycle according to claim 1, wherein $F^1$ and $F^2$ each comprise an oligonucleotide.

15. The di-macrocycle according to claim 14, wherein the oligonucleotide of $F^1$ is complementary to the oligonucleotide of $F^2$.

16. A di-macrocycle having the structure:

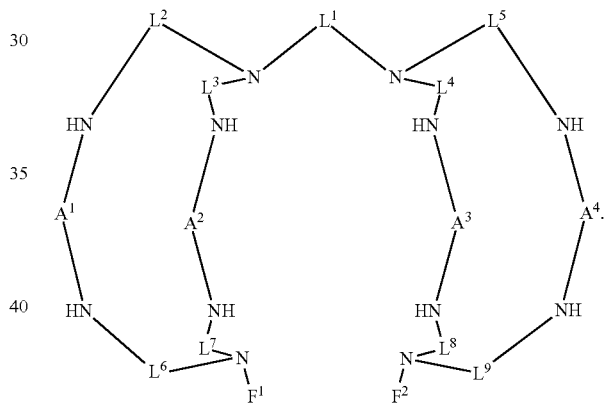

wherein each of $A^1$, $A^2$, $A^3$ and $A^4$ is independently selected from:

(1) 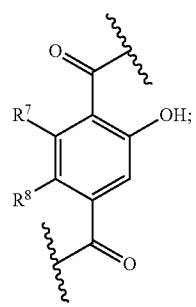
(2) 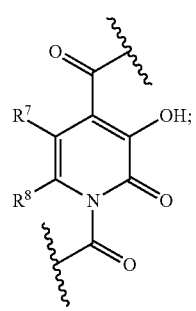
(3) 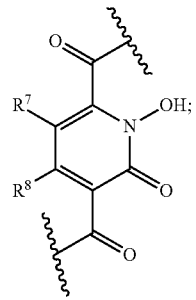
(4) 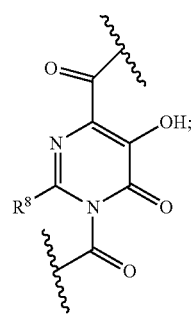
(5) 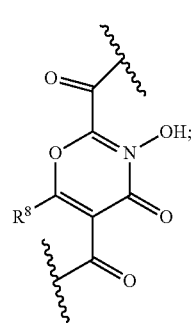
(6) 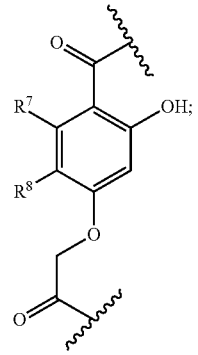
(7) 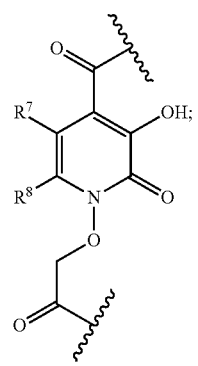
(8) 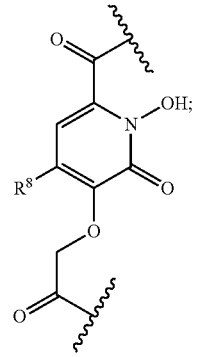
(9) 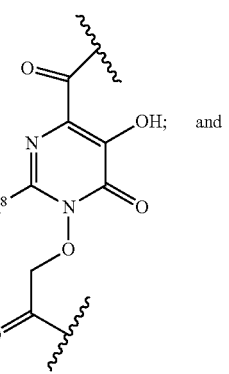
and -continued

(10)
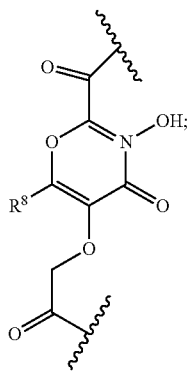

wherein
$L^1, L^2, L^3, L^4, L^5, L^6, L^7, L^8$, and $L^9$ are independently selected from $C_1$, $C_2$, $C_3$, and $C_4$ substituted or unsubstituted alkyl; and
$F^1$ and $F^2$ are independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, a peptide and a nucleic acid
each $R^7$, and $R^8$, $R^9$ is independently selected from H, substituted or unsubstituted alkyl, substituted or unsubstituted heteroalkyl, halogen, CN, $CF_3$, —C(O)$R^{17}$, —SO$_2$NR$^{17}$R$^{18}$, —NR$^{17}$R$^{18}$, —OR$^{17}$, —S(O)$_2$R$^{17}$, —COOR$^{17}$, —S(O)$_2$OR$^{17}$, —OC(O)R$^{17}$, —C(O)NR$^{17}$R$^{18}$, —NR$^{17}$C(O)R$^{18}$, —NR$^{17}$SO$_2$R$^{18}$, and —NO$_2$,
wherein
$R^7$, and $R^8$, together with the atoms to which they are attached, are optionally joined to form a ring system selected from substituted or unsubstituted cycloalkyl, substituted or unsubstituted heterocycloalkyl, substituted or unsubstituted aryl and substituted or unsubstituted heteroaryl;
$R^{17}$ and $R^{18}$ are independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl; and
$R^{17}$ and $R^{18}$, together with the atoms to which they are attached, are optionally joined to form a 5-, 6- or 7-membered ring.

17. The di-macrocycle according to claim 16, wherein each of $A^1$, $A^2$, $A^3$ and $A^4$ is independently selected from:

(1)
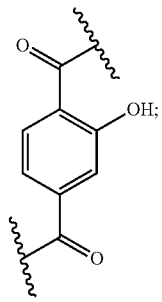

(2)
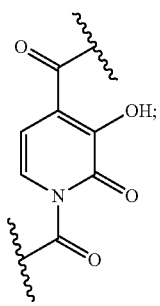

(3)
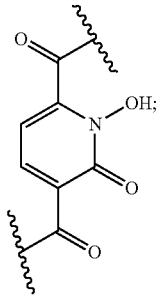

(4)
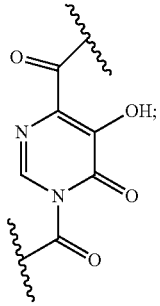

(5)
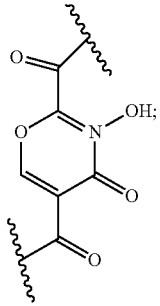

(6)
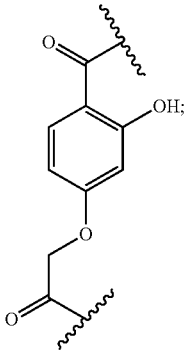

-continued

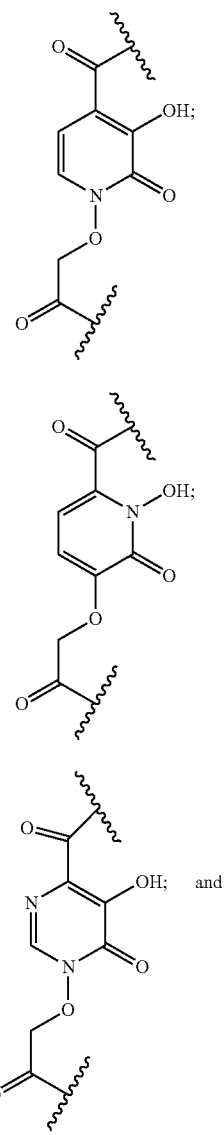

(7)

(8)

(9)

-continued

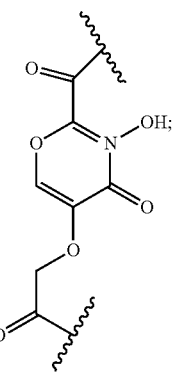

(10)

18. A metal ion complex comprising a di-macrocycle according to claim 16 and a metal ion.

19. The metal ion complex according to claim 18, wherein said metal ion is $^{227}$Th(IV) or $^{89}$Zr(IV).

20. The metal ion complex according to claim 18, wherein said metal is a member selected from $^{177}$Lu, $^{166}$Ho, $^{153}$Sm, $^{90}$Y, $^{86}$Y, $^{166}$Dy, $^{165}$Dy, $^{169}$Er, $^{175}$Yb, $^{225}$Ac, $^{149}$Tb, $^{153}$Gd, and $^{230}$U.

21. The metal ion complex according to claim 18, wherein said metal is a member selected from $^{111}$In, $^{67}$Ga, $^{67}$Cu, $^{64}$Cu, $^{186}$Re, $^{188}$Re, $^{111}$Ag, $^{109}$Pd, $^{212}$Pb, $^{203}$Pb, $^{212}$Bi, $^{213}$Bi, $^{195m}$Pt, $^{201}$Tl, $^{55}$Co, and $^{99m}$Tc.

22. The metal ion complex according to claim 18, wherein said metal is Tb.

23. The metal ion complex according to claim 18, wherein said metal is a lanthanide.

* * * * *